(12) United States Patent
Lücking et al.

(10) Patent No.: US 7,825,128 B2
(45) Date of Patent: Nov. 2, 2010

(54) SULFOXIMINE-SUBSTITUTED PYRIMIDINES, PROCESSES FOR PRODUCTION THEREOF AND USE THEREOF AS DRUGS

(75) Inventors: Ulrich Lücking, Berlin (DE); Duy Nguyen, Berlin (DE); Arne Von Bonin, Glienicke-Nordbahn (DE); Oliver Von Ahsen, Berlin (DE); Martin Krüger, Berlin (DE); Hans Briem, Bremen (DE); Georg Kettschau, Berlin (DE); Olaf Prien, Berlin (DE); Anne Mengel, Berlin (DE); Krolikiewicz Konrad, Berlin (DE); Ulf Boemer, Glienicke/Nordbahn (DE); Ulrich Bothe, Berlin (DE); Ingo Hartung, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 747 days.

(21) Appl. No.: 11/642,961

(22) Filed: Dec. 21, 2006

(65) Prior Publication Data
US 2007/0232632 A1    Oct. 4, 2007

Related U.S. Application Data

(60) Provisional application No. 60/757,859, filed on Jan. 11, 2006, provisional application No. 60/818,501, filed on Jul. 6, 2006.

(30) Foreign Application Priority Data

Dec. 22, 2005 (DE) .................. 10 2005 062 742
Jun. 30, 2006 (DE) .................. 10 2006 031 224

(51) Int. Cl.
| | | |
|---|---|---|
| C07D 239/47 | (2006.01) | |
| C07D 239/48 | (2006.01) | |
| C07D 403/04 | (2006.01) | |
| C07D 403/14 | (2006.01) | |
| C07D 409/04 | (2006.01) | |
| C07D 409/14 | (2006.01) | |
| C07D 401/04 | (2006.01) | |
| C07D 405/04 | (2006.01) | |
| C07D 413/04 | (2006.01) | |
| C07D 417/04 | (2006.01) | |
| A61K 31/505 | (2006.01) | |
| A61K 31/506 | (2006.01) | |
| A61P 19/02 | (2006.01) | |
| A61P 35/00 | (2006.01) | |

(52) U.S. Cl. ............... 514/269; 514/272; 544/319; 544/323; 544/332; 544/334

(58) Field of Classification Search ............... 544/319, 544/323, 332, 334; 514/269, 272
See application file for complete search history.

(56) References Cited

U.S. PATENT DOCUMENTS

| 2004/0063737 A1 | 4/2004 | Luecking et al. |
| 2005/0176743 A1 | 8/2005 | Luecking et al. |

FOREIGN PATENT DOCUMENTS

| DE | 10212100 | 10/2003 |
| DE | 10349423 | 6/2005 |
| WO | WO 00/39101 | 7/2000 |
| WO | WO 2005/037800 | 4/2005 |
| WO | WO 2005/113548 | 12/2005 |

OTHER PUBLICATIONS

Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Dermer et al., Bio/Technology, 1994, 12:320.*
Freshney et al., Culture of Animal Cells, A Manual of Basic Technique, Alan R. Liss, Inc., 1983, New York, p. 4.*
Golub et al., Science, 286, 531-537, 1999.*
Mass, R. D., Int. J. Radiation Oncology Bio. Phys. vol. 58(3): 932-940, 2004.*
Fabbro et al. Pharmacology & therapeutics 93, 7.*
Powell et al., British Journal of Dermatology, 141: 802-810, 1999.*

* cited by examiner

*Primary Examiner*—Venkataraman Balasubramanian
(74) *Attorney, Agent, or Firm*—Millen, White, Zelano, Branigan, P.C.

(57) ABSTRACT

The invention relates to sulfoximine-substituted pyrimidines of the general formula I

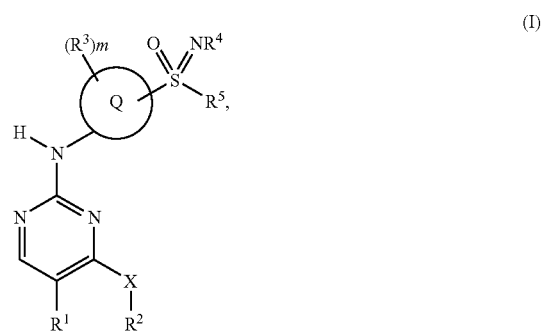

processes for the preparation thereof and their use as drugs.

18 Claims, No Drawings

SULFOXIMINE-SUBSTITUTED PYRIMIDINES, PROCESSES FOR PRODUCTION THEREOF AND USE THEREOF AS DRUGS

This application claims the benefit of the filing date of U.S. Provisional Application Ser. No. 60/757,859 filed Jan. 11, 2006 and U.S. Provisional Application Ser. No. 60/818,501 filed Jul. 6, 2006.

The invention relates to sulfoximine-substituted pyrimidines, processes for the production thereof and the use thereof as drugs.

STATE OF THE TECHNOLOGY

From the state of the technology WO 2005/037800, sulfoximines of the general formula (a)

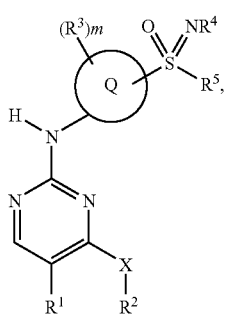

(a)

wherein $R^1$ stands for hydrogen, halogen, $C_1$-$C_6$ alkyl, $CF_3$, CN, nitro or for the group —$COR^8$ or —O—$C_1$-$C_6$ alkyl, are known.

The properties of the compounds of the state of the technology still merit improvement, so that the task still remained that of finding compounds which are active as kinase inhibitors.

It has now been found that sulfoximines of the general formula I, wherein $R^1$ stands for an optionally substituted heteroaryl residue or an optionally substituted aryl residue, act as kinase inhibitors and are suitable for use in oncology or as inflammation inhibitors.

An aspect of the present invention are compounds which are suitable for use in oncology or as inflammation inhibitors.

The present invention therefore relates to compounds of the general formula (I),

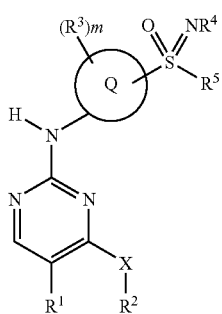

(I)

wherein $R^1$ means an optionally partly or fully saturated, optionally substituted mono- or bicyclic heteroaryl group or an optionally substituted aryl group, $R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_8$ heterocyclyl group, an aryl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, perfluoro ($C_1$-$C_6$)alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO) $C_1$-$C_6$ alkyl, —COO—($C_1$-$C_6$)alkyl-O—($C_1$-$C_6$)alkyl, $C_1$-$C_6$ alkyl(CO)O—, $C_3$-$C_{10}$ cycloalkyl, =N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)$C_1$-$C_6$ alkylene-NH—(CO)aryl, —NH(CO)(($C_1$-$C_6$)alkylene)aryl, —NH—(CH$_2$)$_n$—$C_3$-$C_{10}$ cycloalkyl, —(CH$_2$)$_n$aryl, —(CH$_2$)$_n$—O-aryl, —(CH$_2$)$_n$ heteroaryl, —(CH$_2$)$_n$—($C_3$-$C_8$) heterocyclyl, —$CF_3$, —$OCF_3$, —$NR^7$—C(O)—O$C_1$-$C_3$ alkyl, —$NR^7$—C(O)—$NR^8R^9$ or —$NR^7$—$SO_2$—$R^{10}$, wherein, if the $C_3$-$C_{10}$ cycloalkyl group, the (CH$_2$)$_n$—($C_3$-$C_8$) heterocyclyl group, the (CH$_2$)$_n$ aryl- or the (CH$_2$)$_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—(CH$_2$)$_o$—O—, halogen($C_1$-$C_4$) alkoxy, —(CH$_2$)$_n$aryl, $NR^8R^9$, $COOR^7$ or $SO_2NR^8R^9$, and/or the ring of any $C_3$-$C_{10}$ cycloalkyl group, $C_3$-$C_8$ heterocyclyl group and the $C_1$-$C_{10}$ alkyl group can optionally contain one or several —$NR^8$, oxygen and/or sulphur atoms and/or can optionally contain one or several —C(O)— groups in the ring and/or optionally one or several possible double bonds can be contained in the ring, n means 0-6, o means 1-4, $R^3$ hydroxy, halogen, nitro, cyano, —(CO)$NR^8R^9$, —(CS)$NR^8R^9$, $CF_3$, $OCF_3$, —$R^9N(CO)NR^8R^9$, —$R^7N(CO)R^8$, —$R^7NS(O)_2R^8$, the group —$NR^8R^9$ or a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —C(O)O—$R^{10}$, —C(O)—$R^{10}$, —C(O)—$NR^8R^9$, —C(S)—$NR^8R^9$, $NO_2$, —Si($R^{15}R^{16}R^{17}$), —$R^{18}$—Si($R^{15}R^{16}R^{17}$), —$SO_2$—$R^{18}$—Si($R^{15}R^{16}R^{17}$) group or an —$SO_2R^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CSR^6$, —$CF_3$, —$OCF_3$ or —$NR^8R^9$ or an optionally substituted —(CH$_2$)$_n$-aryl or —(CH$_2$)$_n$-heteroaryl group or $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, $R^4$ and $R^5$ together form a 5 to 8-membered ring of the formula

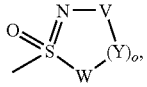

where
V, W and Y
each independently of one another stands for a —$CH_2$ group which is optionally substituted one or more times, identically or differently with hydroxy, $C_1$-$C_{10}$ alkyl, $C_1$-$C_{10}$ alkoxy or —$NR^8R^9$,
where
the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$
and/or the ring
can be interrupted by one or several —C(O)— groups
and/or
optionally can contain one or several double bonds, and
$R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with hydroxy, $C_1$-$C_6$ alkoxy, $C_3$-$C_{10}$ cycloalkyl, halogen, cyano, —$CF_3$, —$OCF_3$ or the group —$NR^8R^9$,
an aryl group or heteroaryl group which is optionally substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, —$COR^6$, $COOR^7$, —$NR^8R^9$, CN, $NO_2$, or $SO_2NR^8R^9$
X an oxygen atom, a sulphur atom or a —$NR^8$— group
or
X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$— group,
Q $C_6$-$C_{10}$ arylene, heteroarylene with 5-10 ring atoms
m 0-4
$R^6$ a hydrogen atom or a hydroxy, benzyloxy or $NR^8R^9$ group
or
a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, $C_6$-$C_{10}$-aryl group or heteroaryl group with 5 or 6 ring atoms, which is optionally substituted one or more times, identically or differently with hydroxy, —$NR^8R^9$, cyano, halogen, —$CF_3$, $C_1$-$C_6$ alkyl, $C_1$-$C_6$ alkoxy or —$OCF_3$
$R^7$ a hydrogen atom or a $C_1$-$C_6$ alkyl group,
$R^8$, $R^9$ independently of one another mean a hydrogen atom, ($C_1$-$C_6$)alkoxy group, a ($C_1$-$C_6$)alkyl group, hydroxy($C_1$-$C_6$)alkyl group, dihydroxy($C_1$-$C_6$)alkyl group, ($C_3$-$C_7$)cycloalkyl, $(CH_2)_n$—$NR^{11}R^{12}$, $NR^{11}R^{12}$, —(CO)—($C_1$-$C_6$) alkyl, —(CO)-phenyl, —(CO)—($C_1$-$C_6$)alkyl-NH—(CO)aryl, —(CO)benzyl, —(CO)O($C_1$-$C_6$)alkyl,
a —$(CH_2)_n$—($C_6$-$C_{10}$)aryl group or a heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$,
or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$,
$R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or an aryl group, which is optionally substituted one or more times, identically or differently with halogen, hydroxy, $C_1$-$C_6$ alkyl, $C_1$-$C_6$ alkoxy, cyano, —$CF_3$, —$OCF_3$, —$NR^8R^9$ or with the group —$SiR^{15}R^{16}R^{17}$,
$R^{11}$, $R^{12}$ independently of one another mean a hydrogen atom, a $C_1$-$C_6$ alkyl, $C_1$-$C_6$ alkoxy-, hydroxy($C_1$-$C_6$) alkyl, dihydroxy($C_1$-$C_6$) alkyl, (CO)—($C_1$-$C_6$) alkyl, (CO)-phenyl, or a benzyl group, which is optionally substituted one or more times, identically or differently with hydroxy, cyano, halogen, —$CF_3$, $C_1$-$C_6$ alkoxy and/or —$OCF_3$,
or $NR^{11}R^{12}$ forms a saturated or unsaturated 5-7-membered ring, in which up to two methylene groups can be replaced by —O—, —$NR^7$—, or —C(=O)—,
$R^{15}$, $R^{16}$ and $R^{17}$ independently of one another can be a $C_1$-$C_6$ alkyl group, and/or a phenyl group and
$R^{18}$ stands for a $C_1$-$C_3$ alkylene group
Another aspect of the present invention relates to compounds of the general formula I according to Claim 1, wherein
$R^1$ means an optionally partly or fully saturated mono- or bicyclic heteroaryl group, which is optionally substituted one or more times, identically or differently with
halogen, hydroxy, $NO_2$, $NR^8R^9$, $OCF_3$, $CF_3$, cyano, —$COR^6$, ($C_1$-$C_6$)alkyl, halogen($C_1$-$C_6$)alkyl, hydroxy($C_1$-$C_6$)alkyl, cyano($C_1$-$C_6$)alkyl-, $(NR^8R^9)(C_1$-$C_4)$alkyl, —NH(CO)($C_1$-$C_6$)alkylene-NH—(CO)aryl, —NH(CO)($C_1$-$C_6$)alkylene-aryl, $(R^6OC)(C_1$-$C_6)$alkyl-, [$(HR^8N(OC)]$—($C_1$-$C_6$) alkyl-, ($C_1$-$C_6$)-alkoxy, $(CH_2)_n$aryl, halogen($C_1$-$C_6$) alkoxy, $SO_2NR^8R^9$
or an aryl group
which is optionally substituted one or more times, identically or differently with a group selected from halogen, hydroxy, $C_1$-$C_5$alkyl, hydroxy($C_1$-$C_5$)alkyl, ($C_1$-$C_5$)alkoxy, —O-perfluoro($C_1$-$C_5$)alkyl, —($C_1$-$C_5$)-alkyl-O—($C_1$-$C_5$)-alkyl, —($C_1$-$C_5$)-alkyl-$COOR^7$, —O—$(CH_2)_o$O—, cyano, $CF_3$, nitro, $(CO)R^6$, $NR^8R^9$, —$NR^8$—(CO)—($C_1$-$C_4$)alkyl, —$NR^8$—$SO_2$—($C_1$-$C_4$)-alkyl, —($C_1$-$C_4$)alkyl-$NR^8$—(CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), phenyl, —(CO)-morpholino,
$R^2$ a hydrogen atom,
a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_8$ heterocyclyl group, an aryl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, perfluoro ($C_1$-$C_6$)alkyl,
$C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO) $C_1$-$C_6$ alkyl, $C_1$-$C_6$ alkyl(CO)O—, $C_3$-$C_{10}$ cycloalkyl, =N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)C$_1$-C$_6$ alkylene-NH—(CO)aryl, —NH(CO)((C$_1$-C$_6$)alkylene)aryl, —NH—(CH$_2$)$_n$—C$_3$-C$_{10}$ cycloalkyl, —(CH$_2$)$_n$aryl, —(CH$_2$)$_n$—O-aryl, —(CH$_2$)$_n$ heteroaryl, —(CH$_2$)$_n$—(C$_3$-C$_8$) heterocyclyl, —CF$_3$, —OCF$_3$, —NR$^7$—C(O)—OC$_1$-C$_3$ alkyl, —NR$^7$—C(O)—NR$^8$R$^9$ or —NR$^7$—SO$_2$—R$^{10}$, wherein, if the C$_3$-C$_{10}$ cycloalkyl group, the (CH$_2$)$_n$—(C$_3$-C$_8$) heterocyclyl group, the (CH$_2$)$_n$ aryl- or the (CH$_2$)$_n$-heteroaryl group are substituents of R$^2$, these themselves optionally can be substituted one or more times, identically or differently with halogen, hydroxy, C$_1$-C$_6$ alkyl, halogen-(C$_1$-C$_4$) alkyl, C$_1$-C$_6$ alkoxy, —O—(CH$_2$)$_o$—O—, halogen(C$_1$-C$_4$) alkoxy, —(CH$_2$)$_n$aryl, NR$^8$R$^9$, COOR$^7$ or SO$_2$NR$^8$R$^9$, and/or the ring of any C$_3$-C$_{10}$ cycloalkyl group, C$_3$-C$_8$ heterocyclyl group and the C$_1$-C$_{10}$ alkyl group can optionally contain one or several —NR$^8$, oxygen and/or sulphur atoms and/or can optionally contain one or several —C(O)— groups in the ring and/or optionally one or several possible double bonds can be contained in the ring, n means 0-6, o means 1-4, R$^3$ hydroxy, halogen, nitro, cyano, —(CO)NR$^8$R$^9$, —(CS)NR$^8$R$^9$, CF$_3$, OCF$_3$, —R$^9$N(CO)NR$^8$R$^9$, —R$^7$N(CO)R$^8$, —R$^7$NS(O)$_2$R$^8$, the group —NR$^8$R$^9$ or a C$_1$-C$_6$ alkyl group, a C$_3$-C$_7$ cycloalkyl group or a C$_1$-C$_6$ alkoxy group, which is optionally substituted one or more times, identically or differently with halogen, hydroxy, C$_1$-C$_6$ alkoxy or the group —NR$^8$R$^9$, R$^4$ a hydrogen atom, a —C(O)O—R$^{10}$, —C(O)—R$^{10}$, —C(O)—NR$^8$R$^9$, —C(S)—NR$^8$R$^9$, NO$_2$, —Si(R$^{15}$R$^{16}$R$^{17}$), —R$^{18}$—Si(R$^{15}$R$^{16}$R$^{17}$), —SO$_2$—R$^{18}$—Si(R$^{15}$R$^{16}$R$^{17}$) group or an —SO$_2$R$^{10}$ group or a C$_1$-C$_{10}$ alkyl, C$_3$-C$_{10}$ cycloalkyl, C$_2$-C$_{10}$ alkenyl, or a C$_2$-C$_{10}$ alkynyl group, which is optionally substituted one or more times, identically or differently with hydroxy, halogen, C$_1$-C$_6$ alkoxy, C$_1$-C$_6$ alkylthio, cyano, C$_3$-C$_{10}$ cycloalkyl, C$_1$-C$_6$ hydroxyalkyl, C$_2$-C$_6$ alkenyl, C$_2$-C$_6$ alkynyl, C$_1$-C$_6$ alkoxy-C$_1$-C$_6$ alkyl, C$_1$-C$_6$ alkoxy-C$_1$-C$_6$ alkoxy-C$_1$-C$_6$ alkyl, —COR$^6$, —CSR$^6$, —CF$_3$, —OCF$_3$ or —NR$^8$R$^9$ or an optionally substituted —(CH$_2$)$_n$-aryl or —(CH$_2$)$_n$-heteroaryl group or R$^3$ and R$^5$ together form a 5 to 7-membered ring, where the ring optionally can be substituted one or more times, identically or differently with hydroxy, C$_1$-C$_6$ alkyl, C$_1$-C$_6$ alkoxy, halogen or the group —NR$^8$R$^9$ and contain 1-2 double bonds and R$^3$ and the sulfoximine residue must be bound at neighbouring positions of Q, R$^4$ and R$^5$ together form a 5 to 8-membered ring of the formula

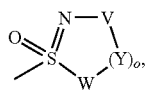

where

V, W and Y each independently of one another stands for a —CH$_2$ group which is optionally substituted one or more times, identically or differently with hydroxy, C$_1$-C$_{10}$ alkyl, C$_1$-C$_{10}$ alkoxy or —NR$^8$R$^9$, where the C$_1$-C$_{10}$ alkyl- or C$_1$-C$_{10}$ alkoxy group likewise can be substituted one or more times, identically or differently with hydroxy, C$_1$-C$_6$ alkoxy or NR$^8$R$^9$ and the ring can be interrupted by one or several —C(O)— groups and/or optionally can contain one or several double bonds, and R$^5$ a C$_1$-C$_6$ alkyl, C$_2$-C$_6$ alkenyl, C$_2$-C$_6$ alkynyl or C$_3$-C$_7$ cycloalkyl group which is optionally substituted one or more times, identically or differently with hydroxy, C$_1$-C$_6$ alkoxy, C$_3$-C$_{10}$ cycloalkyl, halogen, cyano, —CF$_3$, —OCF$_3$ or the group —NR$^8$R$^9$, an aryl group or heteroaryl group which is optionally substituted one or more times, identically or differently with halogen, hydroxy, C$_1$-C$_6$ alkyl, halogen-(C$_1$-C$_4$) alkyl, C$_1$-C$_6$ alkoxy, halogen(C$_1$-C$_4$) alkoxy, —COR$^6$, COOR$^7$, —NR$^8$R$^9$, CN, NO$_2$, or SO$_2$NR$^8$R$^9$ X an oxygen atom, a sulphur atom or a —NR$^8$— group or X and R$^2$ together form a 3 to 8-membered ring, which contains one or several hetero atoms, and which is optionally substituted one or more times, identically or differently with hydroxy, C$_1$-C$_6$ alkyl, C$_1$-C$_6$ alkoxy, halogen or the group —NR$^8$R$^9$, if X means a —NR$^8$— group Q C$_6$-C$_{10}$ arylene, heteroarylene with 5-10 ring atoms m 0-4

R$^6$ a hydrogen atom or a, hydroxy, benzyloxy, NR$^8$R$^9$ or a C$_1$-C$_6$ alkyl group, C$_2$-C$_6$ alkenyl group, C$_2$-C$_6$ alkynyl group, C$_1$-C$_6$ alkoxy group, C$_1$-C$_6$ alkylthio group, C$_3$-C$_7$ cycloalky group, C$_6$-C$_{10}$-aryl group or heteroaryl group with 5 or 6 ring atoms, which is optionally substituted one or more times, identically or differently with hydroxy, —NR$^8$R$^9$, cyano, halogen, —CF$_3$, C$_1$-C$_6$ alkyl, C$_1$-C$_6$ alkoxy or —OCF$_3$ R$^7$ a hydrogen atom or a C$_1$-C$_6$ alkyl group, R$^8$, R$^9$ independently of one another mean a hydrogen atom, (C$_1$-C$_6$)alkoxy group, a (C$_1$-C$_6$)alkyl group, hydroxy(C$_1$-C$_6$)alkyl group, dihydroxy(C$_1$-C$_6$)alkyl group, (C$_3$-C$_7$)cycloalkyl, (CH$_2$)$_n$—NR$^{11}$R$^{12}$, NR$^{11}$R$^{12}$, —(CO)—(C$_1$-C$_6$) alkyl, —(CO)-phenyl, —(CO)—(C$_1$-C$_6$)alkyl-NH—(CO) aryl, —(CO)benzyl, —(CO)O(C$_1$-C$_6$)alkyl, a —(CH$_2$)$_n$—(C$_6$-C$_{10}$)aryl group or a heteroaryl group with 5 or 6 ring atoms, which is optionally substituted one or more times, identically or differently with hydroxy, —NR$^{11}$R$^{12}$, cyano, halogen, —CF$_3$, C$_1$-C$_6$ alkyl, C$_1$-C$_6$ alkoxy, or —OCF$_3$, or R$^8$ and R$^9$ together form a saturated or unsaturated 5 to 7-membered ring, which optionally can contain 1-3 further hetero atoms selected from the group oxygen, sulphur, =N— or —NR$^{11}$— and which is optionally substituted one or more times, identically or differently with hydroxy, —NR$^{11}$R$^{12}$, cyano, halogen, —CF$_3$, C$_1$-C$_6$ alkoxy and/or —OCF$_3$, R$^{10}$ a C$_1$-C$_6$ alkyl, C$_2$-C$_6$ alkenyl, C$_2$-C$_6$ alkynyl, C$_3$-C$_7$ cycloalkyl, C$_3$-C$_{10}$ heterocyclyl, heteroaryl group with 5 or 6 ring atoms or aryl group, which is optionally substituted one or more times, identically or differently with halogen, hydroxy, C$_1$-C$_6$ alkyl, C$_1$-C$_6$ alkoxy, cyano, —CF$_3$, —OCF$_3$, —NR$^8$R$^9$ or with the group SiR$^{15}$R$^{16}$R$^{17}$, R$^{11}$, R$^{12}$ independently of one another mean a hydrogen atom, a C$_1$-C$_6$ alkyl group, C$_1$-C$_6$ alkoxy group, hydroxy (C$_1$-C$_6$) alkyl, dihydroxy(C$_1$-C$_6$) alkyl, (CO)—(C$_1$-C$_6$) alkyl, (CO)-phenyl, benzyl, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group and/or a phenyl group and $R^{18}$ stands for a $C_1$-$C_3$ alkylene group.

A further aspect of the present invention relates to compounds of the general formula I according to Claim 1 or 2, wherein $R^1$ means an optionally substituted mono- or bicyclic heteroaryl group or an optionally substituted aryl group.

Another aspect of the present invention relates to compounds of the general formula I according to Claims 1 to 3, wherein Q means phenylene.

A further aspect of the present invention relates to compounds of the general formula I according to Claims 1 to 4 wherein $R^1$ means an mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, ($C_1$-$C_6$)alkyl, halogen($C_1$-$C_6$)alkyl, hydroxy($C_1$-$C_6$)alkyl, cyano($C_1$-$C_6$)alkyl-, ($NR^8R^9$)($C_1$-$C_4$)alkyl, —NH(CO)($C_1$-$C_6$)alkylene-NH—(CO)phenyl, —NH(CO)($C_1$-$C_6$)alkylene-phenyl, ($R^6$OC)($C_1$-$C_6$)alkyl-, [(HR$^8$N(OC)]—($C_1$-$C_6$)alkyl-, ($C_1$-$C_6$)-alkoxy, ($CH_2$)$_n$phenyl, halogen($C_1$-$C_6$)alkoxy, $SO_2NR^8R^9$ or a phenyl group which is optionally substituted one or more times, identically or differently with a group selected from halogen, hydroxy, $C_1$-$C_5$alkyl, hydroxy($C_1$-$C_5$)alkyl, $C_1$-$C_5$alkoxy, —O-perfluoro($C_1$-$C_5$)alkyl, —($C_1$-$C_5$)-alkyl-O—($C_1$-$C_5$)-alkyl, —($C_1$-$C_5$)-alkyl-COOR$^7$, —O—($CH_2$)$_o$O—, cyano, $CF_3$, nitro, (CO)R$^6$, $NR^8R^9$, —$NR^8$—(CO)—($C_1$-$C_4$)alkyl, —$NR^8$—$SO_2$—$C_1$-$C_4$-alkyl, —($C_1$-$C_4$)alkyl-$NR^8$ (CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), phenyl, —(CO)-morpholino, $R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_8$ heterocyclyl group, an phenyl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, perfluoro($C_1$-$C_6$)alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, =N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)$C_1$-$C_6$ alkylene-NH—(CO)phenyl, —NH(CO)(($C_1$-$C_6$)alkylene)phenyl, —NH—($CH_2$)$_n$—$C_3$-$C_{10}$ cycloalkyl, —($CH_2$)$_n$aryl, —($CH_2$)$_n$—O-phenyl, —($CH_2$)$_n$ heteroaryl, —($CH_2$)$_n$—($C_3$-$C_8$) heterocyclyl, —$CF_3$, —$OCF_3$, —$NR^7$—C(O)—O$C_1$-$C_3$ alkyl, —$NR^7$—C(O)—$NR^8R^9$ or —$NR^7$—$SO_2$—$R^{10}$, wherein, if the $C_3$-$C_{10}$ cycloalkyl group, the ($CH_2$)$_n$—($C_3$-$C_8$) heterocyclyl group, the ($CH_2$)$_n$-phenyl- or the ($CH_2$)$_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—($CH_2$)$_o$—O—, halogen($C_1$-$C_4$) alkoxy, —($CH_2$)$_n$phenyl, $NR^8R^9$, $COOR^7$ or $SO_2NR^8R^9$, and/or the ring of any $C_3$-$C_{10}$ cycloalkyl group, $C_3$-$C_8$ heterocyclyl group and the $C_1$-$C_{10}$ alkyl group can optionally contain one or several —$NR^8$, oxygen and/or sulphur atoms and/or can optionally contain one or several —C(O)— groups in the ring and/or optionally one or several possible double bonds can be contained in the ring, n means 0-3, o means 1-2, $R^3$ halogen $R^4$ a hydrogen atom, a —C(O)O—$R^{10}$, —C(O)—$R^{10}$, —C(O)—$NR^8R^9$, —C(S)—$NR^8R^9$, or a $C_1$-$C_{10}$ alkyl, $C_3$-$C_{10}$ cycloalkyl, group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, or —$NR^8R^9$ or $R^5$ a $C_1$-$C_6$ alkyl, a $C_3$-$C_7$ cycloalkyl group or a phenyl group X an oxygen atom, a sulphur atom or a —$NR^8$— group Q phenylene, m 0-1

$R^6$ a hydrogen atom or a, hydroxy, benzyloxy, $NR^8R^9$, a $C_1$-$C_6$ alkyl group, $C_1$-$C_6$ alkoxy group, $C_1$-$C_6$ alkylthio group, a phenyl group, $R^7$ a hydrogen atom or a $C_1$-$C_6$ alkyl group, $R^8$, $R^9$ independently of one another mean a hydrogen atom, ($C_1$-$C_6$)alkoxy group, a ($C_1$-$C_6$)alkyl group, hydroxy($C_1$-$C_6$)alkyl group, dihydroxy($C_1$-$C_6$)alkyl group, ($C_3$-$C_7$)cycloalkyl, ($CH_2$)$_n$—$NR^{11}R^{12}$, $NR^{11}R^{12}$, —(CO)—($C_1$-$C_6$) alkyl, —(CO)-phenyl, —(CO)—($C_1$-$C_6$)alkyl-NH—(CO) phenyl, —(CO)benzyl, —(CO)O($C_1$-$C_6$)alkyl, a —($CH_2$)$_n$—($C_6$-$C_{10}$)phenyl group or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $R^{11}$, $R^{12}$ independently of one another mean a hydrogen atom, a $C_1$-$C_6$ alkyl group, $C_1$-$C_6$ alkoxy group, hydroxy ($C_1$-$C_6$) alkyl, dihydroxy($C_1$-$C_6$) alkyl, (CO)—($C_1$-$C_6$) alkyl, (CO)-phenyl, benzyl, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—.

Still a further aspect of the present invention relates to compounds of the general formula I according to Claims 1 to 5, wherein $R^1$ means an optionally one or more times substituted phenyl group whereby its substituents are selected from the group halogen, $C_1$-$C_5$alkyl, ($C_1$-$C_5$)alkoxy, —($C_1$-$C_5$)-alkyl-O—($C_1$-$C_5$)-alkyl, —($C_1$-$C_5$)-alkyl-COOR$^7$, —O—($CH_2$)$_o$ O—, cyano, $CF_3$, (CO)R$^6$, $NR^8R^9$, —$NR^8$—(CO)—($C_1$-$C_4$)alkyl, —$NR^8$—$SO_2$—$C_1$-$C_4$-alkyl, —($C_1$-$C_4$)alkyl-$NR^8$(CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), —(CO)-morpholino.

Still a further aspect of the present invention relates to compounds of the general formula I according to Claims 1 to 6,
wherein $R^1$ means an mono- or bicyclic heteroaryl group, which is optionally substituted one or more times, identically or differently with
halogen, hydroxy, $NO_2$, $NR^8R^9$, perfluoro($C_1$-$C_3$)alkyl, cyano, —$COR^6$, $COOR^7$, ($C_1$-$C_4$)alkyl, halogen($C_1$-$C_4$) alkyl, hydroxy($C_1$-$C_4$)alkyl, cyano($C_1$-$C_4$)alkyl, ($NR^8R^9$) ($C_1$-$C_4$)alkyl, ($C_1$-$C_6$)alkoxy, $(CH_2)_n$aryl, perfluoro($C_1$-$C_3$)alkoxy or $SO_2NR^8R^9$.

Still another aspect of the present invention relates to compounds of the general formula I according to Claims 1 to 7, wherein
$R^1$ means a mono- or bicyclic heteroaryl group, which is optionally substituted one or more times, identically or differently with
halogen (especially fluorine and chlorine), cyano, ($C_1$-$C_3$) alkyl, hydroxy($C_1$-$C_3$)alkyl, cyano($C_1$-$C_3$)alkyl, ($C_1$-$C_3$) alkoxy, —$(CH_2)_n$aryl,
or an aryl group
which is optionally substituted one or more times, identically or differently with a group selected from halogen, ($C_1$-$C_3$) alkyl, ($C_1$-$C_3$)alkoxy, —($C_1$-$C_3$)-alkyl-O—($C_1$-$C_3$)-alkyl, —$(CH_2)_3$—COO—($C_1$-$C_3$)-alkyl, —O—$(CH_2)_o$O—, cyano, $CF_3$, —NH—(CO)($C_1$-$C_3$)-alkyl, —(CO)($C_1$-$C_3$)-alkyl, —$NHSO_2$($C_1$-$C_3$)-alkyl, —($C_1$-$C_3$)-alkylen-NH—(CO)($C_1$-$C_3$)-alkyl, —(CO)(4-oxo-N-piperidyl), —(CO)NH—($C_1$-$C_3$)-alkyl, —NH(CO)NH—($C_1$-$C_5$)-alkyl, —(CO)-morpholine,
$R^2$ a $C_1$-$C_5$ alkyl group, a ($C_3$-$C_8$)cycloalkyl group, a ($C_3$-$C_8$) heterocyclyl group, a phenyl group, which is optionally substituted one or more times, identically or differently with a group selected from halogen, hydroxy, cyano, $CF_3$, $SO_2NH_2$, ($C_2$-$C_4$)alkynyl, ($C_1$-$C_3$)alkoxy, —$COR^6$, —COO—($C_1$-$C_4$)alkyl-O—($C_1$-$C_3$)alkyl, ($C_1$-$C_3$)alkyl (CO)O—, =N—OH, —$NR^8R^9$,
—NH(CO)($C_1$-$C_4$)alkyl, —NH(CO)($C_1$-$C_4$)alkylene-NH—(CO)phenyl,
—NH(CO)(($C_1$-$C_6$)alkylene)aryl, —$(CH_2)_n$phenyl, —$(CH_2)_n$—O-phenyl, —$(CH_2)_n$heteroaryl,
—$(CH_2)_n$—($C_3$-$C_8$)heterocyclyl,
wherein,
if the ($C_3$-$C_8$)cycloalkyl group, the $(CH_2)_n$—($C_3$-$C_7$)heterocyclyl group, the $(CH_2)_n$ aryl- or the $(CH_2)_n$-heteroaryl group are substituents of $R^2$,
these themselves optionally can be substituted one or more times, identically or differently with halogen, hydroxy, ($C_1$-$C_3$)alkyl, ($C_1$-$C_3$)alkoxy, —O—$(CH_2)_o$O—, hydroxy ($C_1$-$C_5$)alkyl, cyano, —$OCF_3$, $CF_3$, —N($C_1$-$C_3$ alkyl)$_2$, —$SO_2NH_2$, —$SO_2$—($C_1$-$C_4$)-alkyl, phenyl
and/or the ring of any ($C_3$-$C_8$)cycloalkyl group, ($C_3$-$C_8$)heterocyclyl group and the ($C_1$-$C_5$)alkyl group can optionally contain one —$NR^8$, oxygen and/or sulphur
atoms and/or can optionally contain one —C(O)— group can be contained in the ring,
n means 0-3,
o means 1-3,
$R^3$ halogen
$R^4$ a hydrogen atom, a —C(O)O—$R^{10}$, —C(O)—$NR^8R^9$, or a $C_1$-$C_6$ alkyl, which is optionally substituted one or more times, identically or differently with
hydroxy, ($C_1$-$C_3$)alkoxy, ($C_3$-$C_6$)cycloalkyl, or —$NR^8R^9$ or an optionally substituted —$(CH_2)_n$-aryl group or
$R^5$ a ($C_1$-$C_4$)alkyl or ($C_3$-$C_6$)cycloalkyl group or an aryl group X an oxygen atom, a sulphur atom or a —$NR^8$— group
Q phenylene
m 0, 1
$R^6$ a hydrogen atom or a hydroxy, or $NR^8R^9$ group
or
a ($C_1$-$C_6$)alkyl group, ($C_1$-$C_6$)alkoxy group
$R^7$ a hydrogen atom
$R^8$, $R^9$ independently of one another mean a hydrogen atom, a ($C_1$-$C_6$)alkyl group, ($C_3$-$C_7$)cycloalkyl, —(CO)O($C_1$-$C_6$)alkyl,
a —$(CH_2)_n$—($C_6$-$C_{10}$)aryl group, which is optionally substituted one or more times, identically or differently with hydroxy, —$NR^{11}R^{12}$, halogen, $C_1$-$C_6$ alkyl
or $R^8$ and $R^9$ together form a saturated 5 to 7-membered ring, which optionally can contain 1-3 further hetero atoms selected from the group oxygen, =N— or —$NR^{11}$,
$R^{10}$ a $C_1$-$C_6$ alkyl,
$R^{11}$, $R^{12}$ independently of one another mean a hydrogen atom, a ($C_1$-$C_3$)alkyl, Still another aspect of the present invention relates to compounds of the general formula I according to Claims 1 wherein
$R^1$ means a heteroaryl or phenyl group, optionally independently of one another substituted with 1 to 2 groups selected from $C_1$-$C_3$ alkyl, benzyl, cyano, $CF_3$, $C_1$-$C_3$ alkoxy, halogen, —O—$CH_2$—O—, —$(CH_2)_2$(CO)O($C_1$-$C_3$alkyl), —NH(CO)($C_1$-$C_3$ alkyl), —(CO)($C_1$-$C_3$ alkyl), —($C_3$-$C_8$) heterocyclyl,
$R^2$ a $C_3$-$C_6$ cycloalkyl group, an phenyl group or a $C_1$-$C_8$ alkyl group,
which optionally is identically or differently substituted with a group selected from
hydroxy, $(CH_2)_n$-phenyl-$SO_2NH_2$, —($C_3$-$C_8$) heterocyclyl, —($C_5$-$C_8$) heteroaryl, —NH(CO)$CH_2$—NH(CO)-phenyl, $NR^8R^9$, —$COR^6$, NH(CO)$CH_2$-phenyl or $SO_2R^8R^9$,
$R^3$ a hydrogen atom or a halogen atom,
$R^4$ a hydrogen atom, a $C_1$-$C_3$ alkyl group, a COO($C_1$-$C_6$) alkyl group, an phenyl group,
a —$(CH_2—)_n$—($C_3$-$C_6$) cycloalkyl group
$R^5$ a $C_1$-$C_3$ alkyl group, a $C_3$-$C_6$ cycloalkyl group or a phenyl group
X —NH—, —O—
Q phenylene a
m 0 or 1.

A further aspect of the present invention relates to compounds of the general formula I according to Claims 1 to 10, in the form of the salts with physiologically compatible anions.

The most preferred aspect of the present invention are the compounds of the examples themselves and the subcombinations of all residues as disclosed by the examples.

Therefore the preferred embodiment of the invention relates to compounds of the general formula I wherein
$R^1$ means an thienyl, thiazolyl, tetrazolyl, pyrrolyl, pyrazolyl, imidazolyl, oxazolyl, pyridyl, pyrimidyl, pyrazinyl, indolyl, group, which is optionally substituted one or more times, identically or differently with
methyl, hydroxymethyl, cyano, benzyl, cyanomethyl, methoxy, chlorine,
or a phenyl group
which is optionally substituted one or more times, identically or differently with a group selected from cyano, $CF_3$, methyl, ethyl, methoxy, ethoxy, fluorine, —O—$CH_2$—O—, NH(CO)NH—$C_4H_9$, —$(CH_2)_2$—$COOCH_3$, NH(CO)$CH_3$, (CO)$CH_3$, pyrrolidinyl, —(CO)(4-oxo-piperidinyl), —(CO)morpholino, $NHSO_2CH_3$, —$CH_2$—NH (CO)$CH_3$, —(CO)$NHC_2H_5$, —$CH_2$—O—$CH_3$, R² —CH₃, —(CH₂)₂CH₃, —(CH₂—)₂—OH, —(CH₂)₃—OH, —CH(CH₃)CH₂—OH, —C(CH₂—OH)—CH₂-phenyl, —(CH₂)—CH(CH₃)CH₂—OH, —(CH₂)—C(CH₃)₂—CH₂—OH, —CH(CH₂—CH₃)CH₂—OH, —CH[CH₂—CH(CH₃)₂CH₂—OH, —(CH₂)₂—C(OH)(CH₃)(CF₃), —(CH₂)₂C(=N—OH)(CH₃),
—(CH₂)₂—CN,
—CH(CH₃)CH₂—O—CH₃, —(CH₂)₂—O-phenyl, —(CH₂)₂—O—COCH₃, —(CH₂)₃—COO(CH₂)₂—O—CH₃, —(CH₂)₂CH(OH)—CH₂—COOC₂H₅,
—CH₂—C≡CH,
—CH₂—COOH, —(CH₂)₂—COOH, —(CH₂)₃—COOH, —CH₂—COOʳbutyl, —(CH₂)₂—COOʳbutyl, —(CH₂)₃—COOʳbutyl —(CH₂)₄—COOʳbutyl, —(CH₂)₂—COOCH₃,
—(CH₂)₂—CONH₂,
—(CH₂)N(CH₃)₂, —(CH₂)₂—N(CH₃)₂, —(CH₂)₃—N(CH₃)₂, —(CH₂)₂—NH-phenyl, —(CH₂)₂—N(C₂H₅)-(3-methyl)-phenyl
—CH₂—CH—N(C₂H₅)(3-tolyl)
—(CH₂)₂—CH(COOH)(NH₂),
cyclopentyl, cyclohexyl,
—CH₂-phenyl, —(CH₂)₂-phenyl, —(CH₂)₃-phenyl, —CH(CH₃)-phenyl, —CH-phenyl₂, CH₂-phenyl-phenyl, —CH₂-(methyl-phenyl), —CH₂-(4-methyl-phenyl), —CH₂—(CH₂—OH)—CH₂-phenyl, —(CH₂)₂-(4-methoxy-phenyl), —(CH₂)₂-(3-methoxy-phenyl), —(CH₂)₂-(2-methoxy-phenyl), —CH₂-(4-SO₂NH₂)phenyl, —(CH₂)₂-(4-SO₂NH₂)phenyl, —CH₂-(3-SO₂CH₃)phenyl, —CH₂-(4-SO₂CH₃)phenyl, —CH₂-(2-cyano-phenyl), —CH₂-(3-cyano-phenyl), CH₂-(4-cyano-phenyl), CH₂-(3-CF₃O-phenyl), CH₂-(4-CF₃-phenyl), CH₂-(2-CF₃-phenyl), CH₂-(4-hydroxymethyl-phenyl), CH₂—(N(CH₃)₂-phenyl), CH₂—(NH(CH₃)-phenyl), CH₂—(N(C₂H₅)-(3-methyl-phenyl)), —CH₂-(methoxy-phenyl), (CH₂)₂-hydroxyphenyl, (CH₂)₂-(3,4-methylendioxy)phenyl, —CH₂-(3-fluorine-phenyl), —(CH₂)₂(N-methyl)piperazine, —CH₂)₂—N-piperidine, —(CH₂)₃-morpholino, —(CH₂)₂-morpholino, —(CH₂)₃—N-imidazolyl, —(CH₂)₂-4-imidazolyl, —(CH₂)₃-1-imidazolyl, —(CH₂)₂-1-pyrazolyl, —(CH₂)₂-4-(5-methyl)pyrazolyl, —(CH₂)₃—N-pyrazolyl, —(CH₂)₂-pyrrolidinyl, —(CH₂)—(N-ethyl)pyrrolidinyl, —(CH₂)₃-1,3,4-triazolyl, —(CH₂)₃—NH(CO)—CH₂—NH(CO)para-tolyl, —CH₂-2-pyridyl, —CH₂-3-pyridyl, —CH₂-4-pyridyl, —(CH₂)₂-3-pyridyl, —CH₂—(N-benzyl)piperidinyl, —CH₂-2-(5-methyl)furanyl, —CH₂-tetrahydrofuranyl, (CH₂)₂-indolyl,
—(CH₂)₂—CH(NH₂)(COOʳbutyl)
—(CH₂)₂CH(COOʳbutyl)NH(COOʳbutyl)
—(CH₂)₃—NH(CO)—CH₂-phenyl
NH—SO₂-phenyl
tetrahydropyranyl,
2-oxo-azapan-3yl,
R³ bromine
R⁴ a hydrogen atom, a group —CH₂—CH₃, —(CH₂)₂—CH₃, CH₂)₂—O—CH₃, (CH₂)₂—OH, —(CH₂)₂—N(C₂H₅)₂, —CH₂-cyclopropyl, —(CH₂)₂—N-piperidyl, —(CH₂)₂—N-morpholino, —(CH₂)₂—N—(N-methy)-piperazinyl, I phenyl —C(O)O—C₂H₅, —(CO)NHCH₃, —(CO)NH—C₂H₅, —(CO)NH—CH(CH₃)₃, —(CO)NH-cyclopentyl, —(CO)NH-(4-methyl-phenyl), —(CO)NH-(4-Cl-phenyl), —(CO)NH-(3-Cl-phenyl), (CO)NH-(4-N(CH₃)₂-phenyl), —(CO)NH-(4-methoxyl-phenyl), —(CO)NH—CH₂-phenyl, —(CO)morpholino, —(CO)NH-3-pyridyl,
R⁵ methyl, ethyl, cyclopropyl, phenyl,
X an oxygen atom, a sulphur atom or a —NR⁸— group
Q phenylene,
m 0-1

Another preferred embodiment of the invention relates to compounds of the general formula I wherein
R¹ means an thienyl, thiazolyl, tetrazolyl, pyrrolyl, pyrazolyl, imidazolyl, oxazolyl, pyridyl, pyrimidyl, pyrazinyl, indolyl, group, which is optionally substituted one or more times, identically or differently with
methyl, benzyl, cyanomethyl, chlorine,
or a phenyl group
which is optionally substituted one or more times, identically or differently with a group selected from cyano, CF₃, methyl, ethyl, methoxy, ethoxy, fluorine, —O—CH₂—O—, NH(CO)NH—C₄H₉, —(CH₂)₂—COOCH₃, NH(CO)CH₃, (CO)CH₃, pyrrolidinyl, —(CO)(4-oxo-piperidinyl), —(CO)morpholino, NHSO₂CH₃, —CH₂—NH(CO)CH₃, —(CO)NHC₂H₅, —CH₂—O—CH₃,
R² —CH₃, —(CH₂)₂CH₃, —(CH₂—)₂—OH, —(CH₂)₃—OH, —CH(CH₃)CH₂—OH, —C(CH₂—OH)—CH₂-phenyl, —(CH₂)—CH(CH₃)CH₂—OH, —(CH₂)—C(CH₃)₂—CH₂—OH, —CH(CH₂—CH₃)CH₂—OH, —CH[CH₂—CH(CH₃)₂CH₂—OH,
—CH(CH₃)CH₂—O—CH₃, —(CH₂)₂—O-phenyl, —(CH₂)₂—O—COCH₃,
—CH₂—C≡CH,
—(CH₂)₂—COOH,
—CH₂—COOʳbutyl, —(CH₂)₂—COOʳbutyl, —(CH₂)₃—COOʳbutyl, —(CH₂)₄—COOʳbutyl, —(CH₂)₂—COOCH₃,
—(CH₂)₂—CONH₂,
—(CH₂)N(CH₃)₂, —(CH₂)₂—N(CH₃)₂, —(CH₂)₃—N(CH₃)₂, —(CH₂)₂—NH-phenyl, —(CH₂)₂—N(C₂H₅)-(3-methyl)-phenyl
—CH₂—CH—N(C₂H₅)(3-tolyl)
—(CH₂)₂—CH(COOH)(NH₂),
cyclopentyl, cyclohexyl,
—(CH₂)₂-phenyl, —CH(CH₃)-phenyl, CH₂-phenyl-phenyl, CH-phenyl₂, —CH₂-(methyl-phenyl), —(CH₂)₂-(3-methoxy-phenyl), —(CH₂)₂-(4-SO₂NH₂)phenyl, —CH₂-(methoxy-phenyl),
—(CH₂)₂(N-methyl)piperazine, —(CH₂)₃-morpholino, —(CH₂)₂-morpholino, —(CH₂)₂-4-imidazolyl, —(CH₂)₃-1-imidazolyl, —(CH₂)₂-1-pyrazolyl, —(CH₂)₂-pyrrolidinyl, —(CH₂)—(N-ethyl)pyrrolidinyl,
—(CH₂)₃—NH(CO)—CH₂—NH(CO)para-tolyl,
—(CH₂)₂—CH(NH₂)(COOʳbutyl)
—(CH₂)₂CH(COOʳbutyl)NH(COOʳbuty)l
—(CH₂)₃—NH(CO)—CH₂-phenyl
NH—SO₂-phenyl
tetrahydropyranyl,
2-oxo-azapan-3yl,
R³ bromine
R⁴ a hydrogen atom, a group —CH₂—CH₃, —(CH₂)₂—CH₃, (CH₂)₂—O—CH₃, —CH₂-cyclopropyl, —(CH₂)₂—N-piperidyl, —(CH₂)₂—N-morpholino, phenyl —C(O)O—C₂H₅, —(CO)NHCH₃, —(CO)NH—C₂H₅, —(CO)NH—CH(CH₃)₂, —(CO)NH-cyclopentyl, —(CO)NH-(4-methyl-phenyl), —(CO)NH-(4-Cl-phenyl), —(CO)NH-(3-C₁-phenyl), (CO)NH-(4-N(CH₃)₂-phenyl), —(CO)NH-(4-methoxy-phenyl), —(CO)NH—CH₂-phenyl, —(CO)morpholino, —(CO)NH-3-pyridyl,
R⁵ methyl, ethyl, cyclopropyl, phenyl,
X an oxygen atom, a sulphur atom or a —NR⁸— group
Q phenylene,
m 0-1

One embodiment of the present invention are compounds of the general formula (I)
wherein
$R^1$ means an optionally partly or fully saturated, optionally substituted mono- or bicyclic heteroaryl group or an optionally substituted aryl group, $R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, a ($C_3$-$C_8$) heterocyclyl, an aryl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, —$NR^8R^9$, —NH($C_1$-$C_6$) alkyl-N($C_1$-$C_6$ alkyl)$_2$, —NH(CO)$C_1$-$C_6$ alkyl, —N[(CO)($C_1$-$C_6$ alkyl)]$_2$, —NH—(CH$_2$)$_n$—$C_3$-$C_{10}$ cycloalkyl, —(CH$_2$)$_n$aryl, —(CH$_2$)$_n$ heteroaryl, —(CH$_2$)$_n$—($C_3$-$C_8$) heterocyclyl, —$CF_3$, —$OCF_3$, —$NR^7$—$SO_2$—$R^{10}$, —$NR^7$—C(O)—O$C_1$-$C_3$ alkyl, —$NR^7$—C(O)—$NR^8R^9$ or —$NR^7$—$SO_2$—$R^{10}$, where, if the $C_3$-$C_{10}$ cycloalkyl group, the (CH$_2$)$_n$—($C_3$-$C_8$) heterocyclyl group, the (CH$_2$)$_n$ aryl- or the (CH$_2$)$_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, $NR^8R^9$, $COOR^7$ or $SO_2NR^8R^9$, and/or the ring of the $C_3$-$C_{10}$ cycloalkyl group and the $C_1$-$C_{10}$ alkyl group can optionally be interrupted by one or several —$NR^8$, oxygen and/or sulphur atoms and/or can be interrupted by one or several —C(O)— groups in the ring and/or optionally one or several possible double bonds can be contained in the ring, n 0-6, $R^3$ hydroxy, halogen, nitro, cyano, —(CO)$NR^8R^9$, —(CS)$NR^8R^9$, $CF_3$, $OCF_3$, —$R^9$N(CO)$NR^8R^9$, —$R^7$N(CO)$R^8$, —$R^7$NS(O)$_2R^8$, the group —$NR^8R^9$ or a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —C(O)O—$R^{10}$, —C(O)—$R^{10}$, —C(O)—$NR^8R^9$, —C(S)—$NR^8R^9$, $NO_2$, —Si($R^{15}R^{16}R^{17}$), —$R^{18}$—Si($R^{15}R^{16}R^{17}$), —$SO_2$—$R^{18}$—Si($R^{15}R^{16}R^{17}$) group or an —$SO_2R^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —C(S)$R^6$, —$CF_3$, —$OCF_3$ or —$NR^8R^9$ or an optionally substituted —(CH$_2$)$_n$-aryl or —(CH$_2$)$_n$-heteroaryl group, or $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, or $R^4$ and $R^5$ together form a 5 to 8-membered ring of the formula

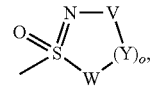

where
V, W and Y each independently of one another stands for a —CH$_2$ group which is optionally substituted one or more times, identically or differently with hydroxy, $C_1$-$C_{10}$ alkyl, $C_1$-$C_{10}$ alkoxy or —$NR^8R^9$, wherein the $C_1$-$C_{10}$ alkyl- or $C_1$-$C_{10}$ alkoxy group can likewise be substituted one or more times, identically or differently with hydroxy, $C_1$-$C_6$ alkoxy or $NR^8R^9$ and/or the ring can be interrupted by one or several —C(O)— groups and/or optionally can contain one or several double bonds, and o means 1-4, $R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with hydroxy, $C_1$-$C_6$ alkoxy, $C_3$-$C_{10}$ cycloalkyl, halogen, cyano, —$CF_3$, —$OCF_3$ or the group —$NR^8R^9$, an aryl group or heteroaryl group which is optionally substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, —$COR^6$, $COOR^7$, —$NR^8R^9$, CN, $NO_2$, or $SO_2NR^8R^9$, X and an oxygen atom, a sulphur atom or a —$NR^8$— group, or X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —NR— group, Q $C_6$-$C_{10}$ arylene or heteroarylene with 5-10 ring atoms, m 0-4, $R^6$ a hydrogen atom or a hydroxy, benzyloxy or $NR^8R^9$ group or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalkyl group, $C_6$-$C_{10}$ aryl group or heteroaryl group with 5 or 6 ring atoms, which is optionally substituted one or more times, identically or differently with hydroxy, $NR^8R^9$, cyano, halogen, —$CF_3$, $C_1$-$C_6$ alkyl, $C_1$-$C_6$ alkoxy or —$OCF_3$, $R^7$ a hydrogen atom or a $C_1$-$C_6$ alkyl group, $R^8$, $R^9$ independently of one another mean a hydrogen atom, $C_1$-$C_6$ alkoxy group, a $C_1$-$C_6$ alkyl group, hydroxy($C_1$-$C_6$) alkyl group, dihydroxy($C_1$-$C_6$) alkyl group, (CH$_2$)$_n$—$NR^{11}R^{12}$, $NR^{11}R^{12}$, —(CO)—($C_1$-$C_6$) alkyl, —(CO)-phenyl, —(CO)—($C_1$-$C_6$) alkyl-NH—(CO) aryl, —CObenzyl, (CO)O($C_1$-$C_6$) alkyl, or a $C_6$-$C_{10}$-aryl group, or a heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$, or $R^8$ and $R^9$ together form a saturated or unsaturated 5 to 7-membered ring, which optionally can contain 1-3 further hetero atoms selected from the group oxygen, sulphur, =N— or —$NR^{11}$— an which is optionally substituted one or more times, identically or differently with hydroxy, —NR$^{11}$R$^{12}$, cyano, halogen, —CF$_3$, C$_1$-C$_6$ alkoxy and/or —OCF$_3$, R$^{10}$ a C$_1$-C$_6$ alkyl, C$_2$-C$_6$ alkenyl, C$_2$-C$_6$ alkynyl, C$_3$-C$_7$ cycloalkyl, C$_3$-C$_{10}$ heterocyclyl, heteroaryl group with 5 or 6 ring atoms or an aryl group, which is optionally substituted one or more times, identically or differently with halogen, hydroxy, C$_1$-C$_6$ alkyl, C$_1$-C$_6$ alkoxy, cyano, —CF$_3$, —OCF$_3$, —NR$^8$R$^9$ or by the group —SiR$^{15}$R$^{16}$R$^{17}$, and R$^{11}$, R$^{12}$ independently of one another mean a hydrogen atom, a C$_1$-C$_6$ alkyl, C$_1$-C$_6$ alkoxy, hydroxy(C$_1$-C$_6$) alkyl, dihydroxy(C$_1$-C$_6$) alkyl, (CO)—(C$_1$-C$_6$) alkyl, (CO)-phenyl, or a benzyl group, which is optionally substituted one or more times, identically or differently with hydroxy, cyano, halogen, —CF$_3$, C$_1$-C$_6$ alkoxy and/or —OCF$_3$, or NR$^{11}$R$^{12}$ forms a saturated or unsaturated 5-7-membered ring, in which up to two methylene groups can be replaced by —O—, —NR$^7$—, or —C(=O)—, R$^{15}$, R$^{16}$ and R$^{17}$ independently of one another can be a C$_1$-C$_6$ alkyl group, and/or a phenyl group and R$^{18}$ stands for a C$_1$-C$_3$ alkylene group.

A further object of the invention are compounds of the general formula I wherein R$^1$ means an optionally partly or fully saturated mono- or bicyclic heteroaryl group, which is optionally substituted one or more times, identically or differently with halogen, hydroxy, NO$_2$, NR$^8$R$^9$, OCF$_3$, CF$_3$, cyano, —COR$^6$, C$_1$-C$_6$ alkyl, halogen(C$_1$-C$_6$) alkyl, hydroxy(C$_1$-C$_6$) alkyl, cyano (C$_1$-C$_6$ alkyl)-, (NR$^8$R$^9$)C$_1$-C$_4$ alkyl, —NH(CO)C$_1$-C$_6$ alkylene-NH—(CO)aryl, —NH(CO)C$_1$-C$_6$ alkylene aryl, (R$^6$OC)C$_1$-C$_6$ alkyl, [(HR$^8$N(OC)]C$_1$-C$_6$ alkyl, C$_1$-C$_6$ alkoxy, (CH$_2$)$_n$ aryl, halogen(C$_1$-C$_6$) alkoxy or SO$_2$NR$^8$R$^9$ or an optionally substituted aryl group.

R$^2$ a hydrogen atom, a C$_1$-C$_{10}$ alkyl group, a C$_2$-C$_{10}$ alkenyl group, a C$_2$-C$_{10}$ alkynyl group a C$_3$-C$_8$ cycloalkyl group, a (C$_3$-C$_8$) heterocyclyl group, an aryl or heteroaryl group, which is optionally substituted one or more times, identically or differently with a group selected from halogen, hydroxy, cyano, SO$_2$NR$^8$R$^9$, SO$_2$R$^{10}$, S(O)(NR$^8$)R$^9$, C$_1$-C$_6$ alkyl, C$_1$-C$_6$ hydroxyalkyl, C$_2$-C$_6$ alkenyl, C$_2$-C$_6$ alkynyl, C$_1$-C$_6$ alkoxy, C$_1$-C$_6$ alkoxy-(C$_1$-C$_6$) alkyl, C$_1$-C$_6$ alkoxy-(C$_1$-C$_6$) alkoxy-(C$_1$-C$_6$) alkyl, —COR$^6$, —C$_1$-C$_6$ alkylO(CO)C$_1$-C$_6$ alkyl, C$_1$-C$_6$ alkyl(CO)O—, C$_3$-C$_{10}$ cycloalkyl, —NR$^8$R$^9$, —NH(C$_1$-C$_6$) alkyl-N(C$_1$-C$_6$ alkyl)$_2$, —NH (CO)C$_1$-C$_6$ alkyl, —N[(CO)(C$_1$-C$_6$ alkyl)]$_2$, —NH— (CH$_2$)$_n$—C$_3$-C$_{10}$ cycloalkyl, —(CH$_2$)$_n$ aryl, —(CH$_2$)$_n$ heteroaryl, —(CH$_2$)$_n$—(C$_3$-C$_8$) heterocyclyl, —CF$_3$, —OCF$_3$, —NR$^7$—C(O)—OC$_1$-C$_3$ alkyl, —NR$^7$—C (O)—NR$^8$R$^9$ or —NR$^7$—SO$_2$—R$^{10}$, where, if the C$_3$-C$_{10}$ cycloalkyl group, the (CH$_2$)$_n$—(C$_3$-C$_8$) heterocyclyl group, the (CH$_2$)$_n$ aryl- or the (CH$_2$)$_n$-heteroaryl group are substituents of R$^2$, these themselves optionally can be substituted one or more times, identically or differently with halogen, hydroxy, C$_1$-C$_6$ alkyl, halogen-(C$_1$-C$_4$) alkyl, C$_1$-C$_6$ alkoxy, halogen(C$_1$-C$_4$) alkoxy, NR$^8$R$^9$, COOR$^7$ or SO$_2$NR$^8$R$^9$, and/or the ring of the C$_3$-C$_{10}$ cycloalkyl group and the C$_1$-C$_{10}$ alkyl group optionally can be interrupted by one or several —NR$^8$, oxygen and/or sulphur atoms and/or can be interrupted by one or several —C(O)— groups in the ring and/or optionally one or several possible double bonds can be contained in the ring, n means 0-6, R$^3$ hydroxy, halogen, nitro, cyano, —(CO)NR$^8$R$^9$, —(CS) NR$^8$R$^9$, CF$_3$, OCF$_3$—R$^9$N(CO)NR$^8$R$^9$, —R$^7$N(CO)R$^8$, —R$^7$NS(O)$_2$R$^8$ the group —NR$^8$R$^9$ or a C$_1$-C$_6$ alkyl group, a C$_3$-C$_7$ cycloalkyl group or a C$_1$-C$_6$ alkoxy group, which is optionally substituted one or more times, identically or differently with halogen, hydroxy, C$_1$-C$_6$ alkoxy or the group —NR$^8$R$^9$, R$^4$ a hydrogen atom, a —C(O)O—R$^{10}$, —C(O)—R$^{10}$, —C(O)—NR$^8$R$^9$, —C(S)—NR$^8$R$^9$, NO$_2$, —Si (R$^{15}$R$^{16}$R$^{17}$), —R$^{18}$—Si(R$^{15}$R$^{16}$R$^{17}$), —SO$_2$—R$^{18}$—Si (R$^{15}$R$^{16}$R$^{17}$) group or an —SO$_2$R$^{10}$ group or a C$_1$-C$_{10}$ alkyl, C$_3$-C$_{10}$ cycloalkyl, C$_2$-C$_{10}$ alkenyl, or a C$_2$-C$_{10}$ alkynyl group, which is optionally substituted one or more times, identically or differently with hydroxy, halogen, C$_1$-C$_6$ alkoxy, C$_1$-C$_6$ alkylthio, cyano, C$_3$-C$_{10}$ cycloalkyl, C$_1$-C$_6$ hydroxyalkyl, C$_2$-C$_6$ alkenyl, C$_2$-C$_6$ alkynyl, C$_1$-C$_6$ alkoxy-C$_1$-C$_6$ alkyl, C$_1$-C$_6$ alkoxy-C$_1$-C$_6$-alkoxy-C$_1$-C$_6$ alkyl, —COR$^6$, —CSR$^6$, —CF$_3$, —OCF$_3$ or —NR$^8$R$^9$ or an optionally substituted —(CH$_2$)$_n$-aryl- or —(CH$_2$)$_n$-heteroaryl group, or R$^3$ and R$^5$ together form a 5 to 7-membered ring, where the ring optionally can be substituted one or more times, identically or differently with hydroxy, C$_1$-C$_6$ alkyl, C$_1$-C$_6$ alkoxy, halogen or the group —NR$^8$R$^9$ and contain 1-2 double bonds and R$^3$ and the sulfoximine residue must be bound at neighbouring positions of Q, R$^4$ and R$^5$ together form a 5 to 8-membered ring of the formula

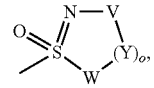

where

V, W and Y each independently of one another stands for a —CH$_2$ group which is optionally substituted one or more times, identically or differently with hydroxy, C$_1$-C$_{10}$ alkyl, C$_1$-C$_{10}$ alkoxy or —NR$^8$R$^9$, where the C$_1$-C$_{10}$ alkyl- or C$_1$-C$_{10}$ alkoxy group likewise can be substituted one or more times, identically or differently with hydroxy, C$_1$-C$_6$ alkoxy or NR$^8$R$^9$ and the ring can be interrupted by one or several —C(O)— groups and/or optionally can contain one or several double bonds, and o means 1-4, R$^5$ means a C$_1$-C$_6$ alkyl, C$_2$-C$_6$ alkenyl, C$_2$-C$_6$ alkynyl or C$_3$-C$_7$ cycloalkyl group which is optionally substituted one or more times, identically or differently with hydroxy, C$_1$-C$_6$ alkoxy, C$_3$-C$_{10}$ cycloalkyl, halogen, cyano, —CF$_3$, —OCF$_3$ or the group —NR$^8$R$^9$, an aryl group or heteroaryl group which is optionally substituted one or more times, identically or differently with halogen, hydroxy, C$_1$-C$_6$ alkyl, halogen-(C$_1$-C$_4$) alkyl, C$_1$-C$_6$ alkoxy, halogen(C$_1$-C$_4$) alkoxy, —COR$^6$, COOR$^7$, —NR$^8$R$^9$, CN, NO$_2$, or SO$_2$NR$^8$R$^9$, and X an oxygen atom, a sulphur atom or a —NR$^8$— group, or X and R$^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if $R^2$ means a —$NR^8$ group, Q $C_6$-$C_{10}$ arylene, or heteroarylene with 5-10 ring atoms, m 0-4, $R^6$ a hydrogen atom or a, hydroxy, benzyloxy, $NR^8R^9$ or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, $C_6$-$C_{10}$-aryl group or heteroaryl group with 5 or 6 ring atoms, which is optionally substituted one or more times, identically or differently with hydroxy, $NR^8R^9$, cyano, halogen, —$CF_3$, $C_1$-$C_6$ alkyl, $C_1$-$C_6$ alkoxy or —$OCF_3$, $R^7$ a hydrogen atom or a $C_1$-$C_6$ alkyl group, $R^8$, $R^9$ independently of one another mean a hydrogen atom, $C_1$-$C_6$ alkoxy group, a $C_1$-$C_6$ alkyl group, hydroxy($C_1$-$C_6$) alkyl group, dihydroxy ($C_1$-$C_6$) alkyl group, $(CH_2)_n$—$NR^{11}R^{12}$, $NR^{11}R^{12}$, (CO)—($C_1$-$C_6$) alkyl, (CO)-phenyl, —(CO)—($C_1$-$C_6$) alkyl-NH—(CO) aryl, —CObenzyl, (CO)O($C_1$-$C_6$) alkyl or a $C_6$-$C_{10}$ aryl group or heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$, or together form a saturated or unsaturated 5 to 7-membered ring, which optionally can contain 1-3 further hetero atoms selected from the group oxygen, sulphur, =N— or —$NR^{11}$— and which is optionally can substituted one or more times, identically or differently with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or aryl group, which is optionally substituted one or more times, identically or differently with halogen, hydroxy, $C_1$-$C_6$ alkyl, $C_1$-$C_6$ alkoxy, cyano, —$CF_3$, —$OCF_3$, —$NR^8R^9$ or with the group $SiR^{15}R^{16}R^{17}$, $R^{11}$, $R^{12}$ independently of one another mean a hydrogen atom, a $C_1$-$C_6$ alkyl group, $C_1$-$C_6$ alkoxy group, hydroxy ($C_1$-$C_6$) alkyl, dihydroxy($C_1$-$C_6$) alkyl, (CO)—($C_1$-$C_6$) alkyl, (CO)-phenyl or benzyl, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group and/or a phenyl group and $R^{18}$ stands for a $C_1$-$C_3$ alkylene group.

A further object of the invention are compounds of the general formula I wherein Q means phenylene.

An object of the invention are compounds of the general formula I wherein $R^1$ means an optionally partly or fully saturated mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, ($NR^8R^9$)$C_1$-$C_4$ alkyl, —NH(CO)$C_1$-$C_6$ alkylene-NH—(CO)aryl, —NH(CO) $C_1$-$C_6$ alkylene aryl, ($R^6OC$)$C_1$-$C_6$ alkyl, [($HR^8N(OC)$] $C_1$-$C_6$ alkyl, $C_1$-$C_6$ alkoxy, halogen($C_1$-$C_6$) alkoxy, $SO_2NR^8R^9$ or an optionally substituted phenyl group.

$R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, a ($C_3$-$C_8$) heterocyclyl, an aryl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, —$NR^8R^9$, —NH($C_1$-$C_6$) alkyl-N($C_1$-$C_6$ alkyl)$_2$, —NH(CO)$C_1$-$C_6$ alkyl, —N[(CO)($C_1$-$C_6$ is alkyl)]$_2$, —NH—$(CH_2)_n$—$C_3$-$C_{10}$ cycloalkyl, —$(CH_2)_n$-phenyl, —$(CH_2)_n$ heteroaryl, —$(CH_2)_n$—($C_3$-$C_8$) heterocyclyl, —$CF_3$, —$OCF_3$, —$NR^7$—C(O)—$OC_1$-$C_3$ alkyl, —$NR^7$—C (O)—$NR^8R^9$ or —$NR^7$—$SO_2$—$R^{10}$, where, if the $C_3$-$C_{10}$ cycloalkyl group, the $(CH_2)_n$—($C_3$-$C_8$) heterocyclyl group, the $(CH_2)_n$ aryl- or the $(CH_2)_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, $NR^8R^9$, $COOR^7$ or $SO_2NR^8R^9$, and/or the ring of the $C_3$-$C_{10}$ cycloalkyl group and the $C_1$-$C_{10}$ alkyl group optionally can be interrupted by one or several —$NR^8$, oxygen and/or sulphur atoms and/or can be interrupted by one or several —C(O)— groups in the ring and/or optionally one or several possible double bonds can be contained in the ring, n 0-6, $R^3$ hydroxy, halogen, nitro, cyano, —(CO)$NR^8R^9$, —(CS) $NR^8R^9$, $CF_3$, $OCF_3$, —$R^9N(CO)NR^8R^9$, —$R^7N(CO)R^6$, —$R^7NS(O)_2R^8$, the group —$NR^8R^9$ or a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —C(O)O—$R^{10}$, —C(O)—$R^{10}$, —C(O)—$NR^8R^9$, —C(S)—$NR^8R^9$, $NO_2$, —Si ($R^{15}R^{16}R^{17}$), —$R^{18}$—Si($R^{15}R^{16}R^{17}$), —$SO_2$—$R^{18}$—Si ($R^{15}R^{16}R^{17}$) group or a —$SO_2R^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CSR^6$, —$CF_3$, —$OCF_3$ or —$NR^8R^9$ or an optionally substituted —$(CH_2)_n$-phenyl- or —$(CH_2)_n$-heteroaryl group, or $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, $R^4$ and $R^5$ together form a 5 to 8-membered ring of the formula

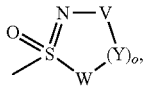

where
V, W and Y
each independently of one another stand for a —$CH_2$ group which is optionally substituted one or more times, identically or differently with hydroxy, $C_1$-$C_{10}$ alkyl, $C_1$-$C_{10}$ alkoxy or —$NR^8R^9$,
where
the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$ and the ring can be interrupted by one or several —C(O)— groups
and/or
optionally can contain one or several double bonds, and
o means 1-4,
$R^5$ a $C_1$—C alkyl, $C_2$-$C_6$ alkenyl, $C_2$-$C_6$ alkynyl or $C_3$-$C_7$ cycloalkyl group which is optionally substituted one or more times, identically or differently with hydroxy, $C_1$-$C_6$ alkoxy, $C_3$-$C_{10}$ cycloalkyl, halogen, cyano, —$CF_3$, —$OCF_3$ or the group —$NR^8R^9$,
a phenyl group or heteroaryl group which is optionally substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, —$COR^6$, $COOR^7$, —$NR^8R^9$, CN, $NO_2$, or $SO_2NR^8R^9$ and
X an oxygen atom, a sulphur atom or a —$NR^8$— group,
or
X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$ group
Q $C_6$-$C_{10}$ phenylene,
m 0-4,
$R^6$ a hydrogen atom or a, hydroxy, benzyloxy, $NR^8R^9$
or
a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$-cycloalkyl group, $C_6$-$C_{10}$ phenyl group or heteroaryl group with 5 or 6 ring atoms, which is optionally substituted one or more times, identically or differently with hydroxy, —$NR^8R^9$, cyano, halogen, —$CF_3$, $C_1$-$C_6$ alkyl, $C_1$-$C_6$ alkoxy or —$OCF_3$
$R^7$ a hydrogen atom or a $C_1$-$C_6$ alkyl group,
$R^8$, $R^9$ independently of one another mean a hydrogen atom, $C_1$-$C_6$ alkoxy group,
a $C_1$-$C_6$ alkyl group, hydroxy($C_1$-$C_6$) alkyl group, dihydroxy ($C_1$-$C_6$) alkyl group, $(CH_2)_n$—$NR^{11}R^{12}$, $NR^{11}R^{12}$, (CO)—($C_1$-$C_6$) alkyl, (CO)-phenyl, —(CO)—($C_1$-$C_6$) alkyl-NH—(CO)-phenyl, —(CO)benzyl, (CO)O($C_1$-$C_6$) alkyl or
a phenyl group or heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$,
or together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$,
$R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or phenyl group, which is optionally substituted one or more times, identically or differently with halogen, hydroxy, $C_1$-$C_6$ alkyl, $C_1$-$C_6$ alkoxy, cyano, —$CF_3$, —$OCF_3$, —$NR^8R^9$ or with the group $SiR^{15}R^{16}R^{17}$,
$R^{11}$, $R^{12}$ independently of one another mean a hydrogen atom, a $C_1$-$C_6$ alkyl group, $C_1$-$C_6$ alkoxy group, hydroxy ($C_1$-$C_6$) alkyl, dihydroxy($C_1$-$C_6$) alkyl, (CO)—($C_1$-$C_6$) alkyl, (CO)-phenyl or benzyl, which is substituted one or more times, identically or differently with hydroxy, cyano, halogen, —$CF_3$, $C_1$-$C_6$ alkoxy and/or —$OCF_3$,
or $NR^{11}R^{12}$ forms a saturated or unsaturated 5-7-membered ring, in which up to two methylene groups can be replaced by —O—, —$NR^7$—, or —C(=O)—,
$R^{15}$, $R^{15}$ and $R^{17}$ independently of one another can be a $C_1$-$C_6$ alkyl group,
and/or a phenyl group and
$R^{18}$ stands for a $C_1$-$C_3$ alkylene group.
A preferred object of the invention are compounds of the general formula I wherein $R^1$ means an optionally partly or fully saturated mono- or bicyclic heteroaryl group, which is optionally substituted one or more times, identically or differently with
halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, ($NR^8R^9$)$C_1$-$C_4$ alkyl, ($R^6OC$)$C_1$-$C_6$ alkyl, [($HR^8N(OC)$]$C_1$-$C_6$ alkyl, $C_1$-$C_6$ alkoxy, halogen ($C_1$-$C_6$) alkoxy or $SO_2NR^8R^9$.
A further preferred object are compounds of the general formula I, wherein $R^1$ is an optionally partly or fully saturated monocyclic 5-membered heteroaryl group,
which is optionally substituted one or more times, identically or differently with halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, ($NR^8R^9$)$C_1$-$C_4$ alkyl, ($R^6OC$)$C_1$-$C_6$ alkyl, [($HR^8N(OC)$]$C_1$-$C_6$ alkyl, $C_1$-$C_6$ alkoxy, halogen($C_1$-$C_6$) alkoxy or $SO_2NR^8R^9$.
A quite particular preferred object of the present invention are compounds, of the general formula I, of Claims 1-7, wherein $R^1$ is an aromatic monocyclic 5-membered heteroaryl group.
A particularly preferred object of the invention are compounds of the general formula I,
wherein
$R^1$ means a heteroaryl or phenyl group optionally independently of one another substituted with 1 to 2 groups selected from $C_1$-$C_3$ alkyl, benzyl, cyano, $CF_3$, $C_1$-$C_3$ alkoxy, halogen, —O—$CH_2$—O—, —$(CH_2)_2(CO)O(C_1$-$C_3$ alkyl), —NH(CO)($C_1$-$C_3$ alkyl), —(CO)($C_1$-$C_3$ alkyl) or —($C_3$-$C_8$) heterocyclyl,
$R^2$ a $C_3$-$C_6$ cycloalkyl group, an aryl group or a $C_1$-$C_8$ alkyl group,
which optionally is identically or differently substituted with a group selected from
hydroxy, $(CH_2)_n$ aryl-$SO_2NH_2$, —($C_3$-$C_8$) heterocyclyl, —($C_5$-$C_8$) heteroaryl, —NH(CO)$CH_2$—NH(CO)aryl, $NR^8R^9$, —$COR^6$, NH(CO)$CH_2$-aryl or $SO_2R^8R^9$,
$R^3$ a hydrogen atom or a halogen atom,
$R^4$ a hydrogen atom, a $C_1$-$C_3$ alkyl group, a $COO(C_1$-$C_6$) alkyl group, an aryl group, a —$(CH_2—)_n$—($C_3$-$C_6$) cycloalkyl group
$R^5$ a $C_1$-$C_3$ alkyl group, a $C_3$-$C_6$ cycloalkyl group or a phenyl group
X —NH—, —O—

Q phenylene and m 0 or 1.

A further object of the invention are compounds of the general formula I according to Claim 1 or 2, wherein $R^1$ means an optionally substituted aryl group, in particular a phenyl group.

This aryl group or the phenyl group can for example be substituted with one or several residues from the group hydroxy, halogen, $C_1$-$C_5$ alkyl, $C_1$-$C_5$ alkoxy, cyano, $CF_3$, nitro, $COR^8$, $COOR^8$ or $SO_2NR^9R^{10}$.

A further object of the invention are compounds of the general formula I according to claim 1 or 2, wherein $R^1$ means an optionally substituted heteroaryl group.

A further especially preferred object are compounds of the general formula I, according to all disclosed claims, wherein the monocyclic heteroaryl group $R^1$ is 5-membered and is neither wholly nor partly hydrogenated.

A further object of the invention are compounds of the general formula I wherein $R^1$ means an optionally partly or fully saturated mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, $C_1$-$C_6$ alkyl halogen($C_1$-$C_6$) alkyl, hydroxy($C_1$-$C_6$) alkyl, cyano($C_1$-$C_6$ alkyl), ($NR^8R^9$)$C_1$-$C_4$ alkyl, ($R^6OC$)$C_1$-$C_6$ alkyl, [($HR^8N(OC)$]$C_1$-$C_6$ alkyl, $C_1$-$C_6$ alkoxy, halogen ($C_1$-$C_6$) alkoxy or $SO_2NR^8R^9$ or a substituted aryl group, $R^2$ a hydrogen atom, a $C_1$-$C_{10}$ alkyl group, a $C_2$-$C_{10}$ alkenyl group or a $C_2$-$C_{10}$ alkynyl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, $C_2$-$C_6$ alkenyl, $C_2$-$C_6$ alkynyl, $C_1$-$C_6$ alkoxy, —$COR^6$, $C_1$-$C_6$ alkyl(CO)O—, $C_3$-$C_{10}$ cycloalkyl, —$NR^8R^9$, —$NH(C_1$-$C_6$) alkyl-$N(C_1$-$C_6$ alkyl)$_2$, —$NH(CO)C_1$-$C_6$ alkyl, —$N[(CO)(C_1$-$C_6$ alkyl)]$_2$, Aryl, Heteroaryl, ($C_3$-$C_8$) heterocyclyl, —$CF_3$, —$OCF_3$, —$NR^7$—$C(O)$—$OC_1$-$C_3$ alkyl, —$NR^7$—$C(O)$—$NR^8R^9$, or —$NR^7$—$SO_2$—$R^{10}$, where, if the $C_3$-$C_{10}$ cycloalkyl group, the ($CH_2$)$_n$—($C_3$-$C_8$) heterocyclyl group, the ($CH_2$)$_n$aryl- or the ($CH_2$)$_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, $NR^8R^9$, $COOR^7$ or $SO_2NR^8R^9$, and/or the ring of the $C_3$-$C_{10}$ cycloalkyl group and the $C_1$-$C_{10}$ alkyl group optionally can be interrupted by one or several —$NR^8$, oxygen and/or sulphur atoms and/or can be interrupted by one or several —$C(O)$— groups in the ring and/or optionally one or several possible double bonds can be contained in the ring, n 0-6, $R^3$ hydroxy, halogen, nitro, cyano, —$(CO)NR^8R^9$, —$(CS)NR^8R^9$, $CF_3$, $OCF_3$, —$R^9N(CO)NR^8R^9$, the group —$NR^8R^9$ or a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —$C(O)O$—$R^{10}$, —$C(O)$—$R^{10}$, —$C(O)$—$NR^8R^9$, —$C(S)$—$NR^8R^9$, $NO_2$, —$Si(R^{15}R^{16}R^{17})$, —$R^{18}$—$Si(R^{15}R^{16}R^{17})$, —$SO_2$—$R^{18}$—$Si(R^{15}R^{16}R^{17})$ group or a —$SO_2R^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, cyano, —$CF_3$, —$OCF_3$ or —$NR^8R^9$ or an aryl or heteroaryl group, or $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, $R^4$ and $R^5$ together form a 5 to 8-membered ring of the formula

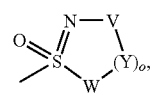

where

V, W and Y each independently of one another stand for a —$CH_2$ group which is optionally substituted one or more times, identically or differently with hydroxy, $C_1$-$C_{10}$ alkyl, $C_1$-$C_{10}$ alkoxy or —$NR^8R^9$, where the $C_1$-$C_{10}$ alkyl or $C_1$-$C_{10}$ alkoxy group likewise can be substituted one or more times, identically or differently with hydroxy, $C_1$-$C_6$ alkoxy or $NR^8R^9$ and/or the ring can be interrupted by one or several —$C(O)$— groups and/or optionally can contain one or several double bonds, and o means 1-4, $R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with hydroxy, $C_1$-$C_6$ alkoxy, $C_3$-$C_{10}$ cycloalkyl, halogen, cyano, —$CF_3$, —$OCF_3$ or the group —$NR^8R^9$, an aryl group or heteroaryl group which is optionally substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, —$COR^6$, $COOR^7$, —$NR^8R^9$, CN, $NO_2$, or $SO_2NR^8R^9$, and X an oxygen atom, a sulphur atom or a —NR— group, or X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$— group Q $C_6$-$C_{10}$ arylene, heteroarylene with 5-10 ring atoms, m 0-4, $R^6$ a hydrogen atom or a hydroxy, benzyloxy or $NR^8R^9$ group or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, $C_6$-$C_{10}$ aryl group or heteroaryl group with 5 or 6 ring atoms, which is optionally substituted one or more times, identically or differently with hydroxy, $NR^8R^9$, cyano, halogen, —$CF_3$, $C_1$-$C_6$ alkyl, $C_1$-$C_6$ alkoxy or —$OCF_3$ $R^7$ a hydrogen atom or a $C_1$-$C_6$ alkyl group, $R^8$, $R^9$ independently of one mean another a hydrogen atom, a $C_1$-$C_6$ alkyl group, $(CH_2)_n$—$NR^{11}R^{12}$, $NR^{11}R^{12}$, —(CO)-phenyl, —(CO)—$(C_1$-$C_6)$ alkyl, —CObenzyl, $(CO)O(C_1$-$C_6)$ alkyl, a $C_6$-$C_{10}$ aryl group or a heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$, or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $C_3C_2$-$C_6$ alkenyl, $C_2$-$C_6$ alkynyl, —$C_7$ cycloalkyl, $C_3$-$C_{10}$ heterocyclyl, heteroaryl group with 5 or 6 ring atoms or an aryl group, which is optionally substituted one or more times, identically or differently with halogen, hydroxy, $C_1$-$C_6$ alkoxy, cyano, —$CF_3$, —$OCF_3$ or —$NR^8R^9$, $R^{11}$, $R^{12}$ independently of one another mean a hydrogen atom or a $C_1$-$C_6$ alkyl group, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group, and/or a phenyl group and $R^{18}$ stands for a $C_1$-$C_3$ alkylene group.

A further object of the invention are compounds of the general formula I according to Claims 1-7, wherein $R^1$ means an optionally partly or fully saturated, optionally substituted mono- or bicyclic heteroaryl group, $R^2$ a hydrogen atom, a $C_1$-$C_{10}$ alkyl group, a $C_2$-$C_{10}$ alkenyl group, a $C_2$-$C_{10}$ alkynyl group or a $C_3$-$C_8$ cycloalkyl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-$(C_1$-$C_6)$ alkyl, $C_1$-$C_6$ alkoxy-$(C_1$-$C_6)$ alkoxy-$(C_1$-$C_6)$ alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, —$NR^8R^9$, —NH($C_1$-$C_6$) alkyl-N($C_1$-$C_6$ alkyl)$_2$, —NH (CO)$C_1$-$C_6$ alkyl, —N[(CO)($C_1$-$C_6$ alkyl)]$_2$, —NH—$(CH_2)_n$—$C_3$-$C_{10}$ cycloalkyl, —$(CH_2)_n$—$(C_3$-$C_8)$ heterocyclyl, —$CF_3$, —$OCF_3$, —$NR^7$—C(O)—O$C_1$-$C_3$ alkyl, —$NR^7$—C(O)—$NR^8R^9$, or —$NR^7$—$SO_2$—$R^{10}$, where, if the $C_3$-$C_{10}$ cycloalkyl group or the $(CH_2)_n$—$(C_3$-$C_8)$ heterocyclyl group are substituents of $R^2$, these themselves optionally can be substituted one or more times, identically or differently with halogen, hydroxy, $C_1$-$C_6$ alkyl, halogen-$(C_1$-$C_4)$ alkyl, $C_1$-$C_6$ alkoxy, halogen$(C_1$-$C_4)$ alkoxy, $NR^8R^9$, $COOR^7$ or $SO_2NR^8R^9$, and/or the ring of the $C_3$-$C_{10}$ cycloalkyl group and the $C_1$-$C_{10}$ alkyl group optionally can be interrupted by one or several —$NR^8$, oxygen and/or sulphur atoms and/or be interrupted by one or several —C(O)— groups in the ring and/or optionally one or several possible double bonds can be contained in the ring, n means 0-6, $R^3$ hydroxy, halogen, nitro, cyano, —(CO)$NR^8R^9$, —(CS) $NR^8R^9$, $CF_3$, $OCF_3$, —$R^9$N(CO)$NR^8R^9$, the group —$NR^8R^9$ or a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —C(O)O—$R^{10}$, —C(O)—$R^{10}$, —C(O)—$NR^8R^9$, —C(S)—$NR^8R^9$, $NO_2$, —Si $(R^{15}R^{16}R^{17})$, —$R^{18}$—Si$(R^{15}R^{16}R^{17})$, —$SO_2$—$R^{18}$—Si $(R^{15}R^{16}R^{17})$ group or a —$SO_2R^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$C(S)R^5$, —$CF_3$, —$OCF_3$ or —$NR^8R^9$, or $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, or $R^4$ and $R^5$ together form a 5 to 8-membered ring of the formula

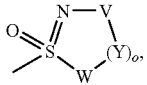

where

V, W and Y each independently of one another stands for a —$CH_2$ group which is optionally substituted one or more times, identically or differently with hydroxy, $C_1$-$C_{10}$ alkyl, $C_1$-$C_{10}$ alkoxy or —$NR^8R^9$, wherein the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$ and/or the ring can be interrupted by one or several —C(O)— groups and/or optionally can contain one or several double bonds, and o means 1-4, $R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with hydroxy, $C_1$-$C_6$ alkoxy, $C_3$-$C_{10}$ cycloalkyl, halogen, cyano, —$CF_3$, —$OCF_3$ or the group —$NR^8R^9$, and X an oxygen atom, a sulphur atom or a —$NR^8$— group, or X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$— group Q means $C_6$-$C_{10}$ arylene, m 0-4, $R^6$ a hydrogen atom or a hydroxy, benzyloxy or $NR^8R^9$ group or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, which is optionally substituted one or more times, identically or differently with hydroxy, $NR^8R^9$, cyano, halogen, $—CF_3$, $C_1$-$C_6$ alkyl, $C_1$-$C_6$ alkoxy or $—OCF_3$, $R^7$ a hydrogen atom or a $C_1$-$C_6$ alkyl group, $R^8$, $R^9$ independently of one another mean a hydrogen atom, $C_1$-$C_6$ alkoxy group, a $C_1$-$C_6$ alkyl group, hydroxy($C_1$-$C_6$) alkyl group, dihydroxy($C_1$-$C_6$) alkyl group, $(CH_2)_n$—$NR^{11}R^{12}$, $NR^{11}R^{12}$, —(CO)—($C_1$-$C_6$) alkyl, —(CO)-phenyl, —(CO)—($C_1$-$C_6$) alkyl-NH—(CO) aryl, —(CO)-benzyl, (CO)O($C_1$-$C_6$) alkyl, or, or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, which is optionally substituted one or more times, identically or differently with halogen, hydroxy, $C_1$-$C_6$ alkyl, $C_1$-$C_6$ alkoxy, cyano, —$CF_3$, —$OCF_3$, —$NR^8R^9$ or with the group —$SiR^{15}R^{16}R^{17}$, $R^{11}$, $R^{12}$ independently of one another mean a hydrogen atom, a $C_1$-$C_6$ alkyl, $C_1$-$C_6$ alkoxy-, hydroxy($C_1$-$C_6$) alkyl, dihydroxy($C_1$-$C_6$) alkyl, (CO)—($C_1$-$C_6$) alkyl, (CO)-phenyl, or a benzyl group, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group, and/or a phenyl group and $R^{18}$ stands for a $C_1$-$C_3$ alkylene group.

An object of the invention are compounds of the general formula I according to Claims 1-7, wherein $R^2$ means a hydrogen atom, a $C_1$-$C_{10}$ alkyl group, a $C_2$-$C_{10}$ alkenyl group, a $C_2$-$C_{10}$ alkynyl group or a $C_3$-$C_8$ cycloalkyl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, —$NR^8R^9$, —NH($C_1$-$C_6$) alkyl-N($C_1$-$C_6$ alkyl)$_2$, —NH(CO)$C_1$-$C_6$ alkyl, —N[(CO)($C_1$-$C_6$ alkyl)]$_2$, —NH—$(CH_2)_n$—$C_3$-$C_{10}$ cycloalkyl, —$(CH_2)_n$—($C_3$-$C_8$) heterocyclyl, —$CF_3$, —$OCF_3$, —$NR^7$—C(O)—$OC_1$-$C_3$ alkyl, —$NR^7$—C(O)—$NR^8R^9$ or —$NR^7$—$SO_2$—$R^{10}$, where, if the $C_3$-$C_{10}$ cycloalkyl group or the $(CH_2)_n$—($C_3$-$C_8$) heterocyclyl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, $NR^8R^9$, $COOR^7$ or $SO_2NR^8R^9$, and/or the ring of the $C_3$-$C_{10}$ cycloalkyl group and the $C_1$-$C_{10}$ alkyl group optionally can be interrupted by one or several —$NR^8$, oxygen and/or sulphur atoms and/or can be interrupted by one or several —C(O)— groups in the ring and/or optionally one or several possible double bonds can be contained in the ring.

A further object of the invention are compounds according to Claims 1-7, wherein m=0, 1, 2, 3 or 4, in particular if Q means $C_6$-$C_{10}$ arylene.

A further object of the invention are compounds of the general formula I according to Claims 1 to 7, wherein m=0, 1 or 2, preferably m=0 or 1.

A further object of the invention are compounds of the general formula I according to Claim 1-7, wherein o=1 or 2.

A further object of the invention are compounds of the general formula I according to Claim 1-7, wherein n=0-5, preferably 0-3 or 1-5, especially preferably 1-3.

A further object of the invention are compounds of the general formula I according to Claims 1-7, wherein $R^3$ and $R^5$ together form a 5 to 7-membered ring, where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, A further object of the invention are compounds of the general formula I according to of Claims 1-7, wherein $R^4$ and $R^5$ together form a 5 to 8-membered ring of the formula

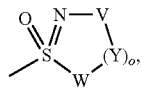

where

V, W and Y each independently of one another stand for a —$CH_2$ group which is optionally substituted one or more times, identically or differently with hydroxy, $C_1$-$C_{10}$ alkyl, $C_1$-$C_{10}$ alkoxy or —$NR^8R^9$, where the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$ and/or the ring can be interrupted by one or several —C(O)— groups and/or optionally can contain one or several double bonds.

A further object of the invention are compounds of the general formula I according to Claims 1-7, wherein $R^4$ means a hydrogen atom, a —$COR^6$ group, $NO_2$, a trimethylsilyl- (TMS), tert.-butyl-dimethylsilyl- (TBDMS), tert.-butyl-diphenylsilyl (TBDPS), triethylsilyl- (TES) or an —$SO_2R^{10}$ group or a $C_1$-$C_{10}$ alkyl, $C_3$-$C_{10}$ cycloalkyl group or aryl which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CF_3$, —$OCF_3$ or —$NR^8R^9$.

A particular object of the invention are compounds of the general formula I according to Claims 1-7, wherein $R^4$ means a hydrogen atom, a —$COR^6$ group, $NO_2$, a trimethylsilyl- (TMS), tert.-butyl-dimethylsilyl- (TBDMS), tert.-butyl-diphenylsilyl (TBDPS), triethylsilyl- (TES) or an —$SO_2R^{10}$ group or a $C_1$-$C_{10}$ alkyl- or $C_3$-$C_{10}$ cycloalkyl group which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CF_3$, —$OCF_3$ or —$NR^8R^9$.

A further object of the present invention are compounds of the general formula I, wherein
$R^1$ means a heteroaryl or phenyl group optionally independently of one another substituted with 1 to 2 groups selected from $C_1$-$C_3$ alkyl, benzyl, cyano, $CF_3$, $C_1$-$C_3$ alkoxy, halogen, —O—$CH_2$—O—, —$(CH_2)_2(CO)O(C_1$-$C_3$ alkyl), —$NH(CO)(C_1$-$C_3$ alkyl), —$(CO)(C_1$-$C_3$ alkyl) or —($C_3$-$C_8$) heterocyclyl,
$R^2$ $C_3$-$C_6$ cycloalkyl group, an aryl group or a $C_1$-$C_8$ alkyl group,
which is optionally identically or differently substituted with a group selected from
hydroxy, $(CH_2)_n$ aryl-$SO_2NH_2$, —($C_3$-$C_8$) heterocyclyl, —($C_5$-$C_8$) heteroaryl, —$NH(CO)CH_2$—$NH(CO)$aryl, $NR^8R^9$, —$COR^6$, $NH(CO)CH_2$-aryl or $SO_2R^8R^9$,
$R^3$ a hydrogen atom or a halogen atom,
$R^4$ a hydrogen atom, a $C_1$-$C_3$ alkyl group, a $COO(C_1$-$C_6)$ alkyl group, an aryl group, a —$(CH_2$—$)_n$—($C_3$-$C_6$) cycloalkyl group
$R^5$ a $C_1$-$C_3$ alkyl group, a $C_3$-$C_6$ cycloalkyl group or a phenyl group
X —NH—, —O—
Q phenylene and
m 0 or 1.

A further object of the present invention are compounds of the general formula I, wherein
$R^1$ means a thienyl, tetrazolyl, pyrazolyl, imidazolyl, pyridyl, pyrimidinyl, oxazolyl, thiazolyl, pyrrolyl, pyrazinyl, or phenyl group optionally independently of one another substituted with 1 to 2 groups selected from $C_1$-$C_3$ alkyl, benzyl, cyano, $CF_3$, $C_1$-$C_3$ alkoxy, halogen, —O—$CH_2$—O—, —$(CH_2)_2(CO)O(C_1$-$C_3$ alkyl), —$NH(CO)(C_1$-$C_3$ alkyl), —$(CO)(C_1$-$C_3$ alkyl) or pyrrolyl,
$R^2$ $C_3$-$C_6$ cycloalkyl group, a phenyl group or a $C_1$-$C_8$ alkyl group,
which optionally is identically or differently substituted with a group selected from
hydroxy, $(CH_2)_n$ aryl-$SO_2NH_2$, —($C_3$-$C_8$) heterocyclyl, —($C_5$-$C_8$) heteroaryl, —$NH(CO)CH_2$—$NH(CO)$aryl, $NR^8R^9$, —$COR^6$, $NH(CO)CH_2$-phenyl or $SO_2R^8R^9$,
$R^3$ a hydrogen atom or a halogen atom,
$R^4$ a hydrogen atom, a $C_1$-$C_3$ alkyl group, a $COO(C_1$-$C_3$) alkyl group, a phenyl group, a —$CH_2$—($C_3$-$C_6$) cycloalkyl group
$R^5$ a $C_1$-$C_3$ alkyl group, a $C_3$-$C_6$ cycloalkyl group or a phenyl group
X —NH—, —O—,
Q phenylene and
m 0 or 1.

A special object of the present invention are compounds of the general formula I,
wherein
$R^1$ means a thienyl, tetrazolyl, pyrazolyl, imidazolyl, pyridyl, pyrimidinyl, oxazolyl, thiazolyl, pyrrolyl, pyrazinyl, or phenyl group optionally independently of one another substituted with 1 to 2 groups selected from methyl, benzyl, cyano, $CF_3$, methoxy, fluorine, chlorine, —O—$CH_2$—O—, —$(CH_2)_2(CO)OC_2H_5$, —$NH(CO)CH_3$, —$(CO)CH_3$ or pyrrolyl,
$R^2$ cyclohexyl group, a phenyl group or a $C_1$-$C_6$ alkyl group, which optionally is identically or differently substituted with a group selected from hydroxy, phenyl-4-($SO_2$—$NH_2$), piperidinyl, morpholino, $NH(CO)CH_2$—$NH(CO)$(4-methylphenyl), $NH_2$, —COO (tert.-butyl), $NH(CO)CH_2$-phenyl, imidazolyl, $SO_2NH_2$, pyrazolyl, or tetrahydropyranyl,
$R^3$ a hydrogen atom or a bromine atom,
$R^4$ a hydrogen atom, a $C_1$-$C_3$ alkyl group, a $COO(C_1$-$C_2)$ alkyl group, a phenyl group, a —$CH_2$-cyclopropyl group
$R^5$ a $C_1$-$C_3$ alkyl group, a cyclopropyl group or a phenyl group
X —NH—
Q phenylene and
m 0 or 1.

One special aspect of the invention are the residues as disclosed in the examples and all combinations thereof.

Another aspect of the invention are compounds of general formula I,

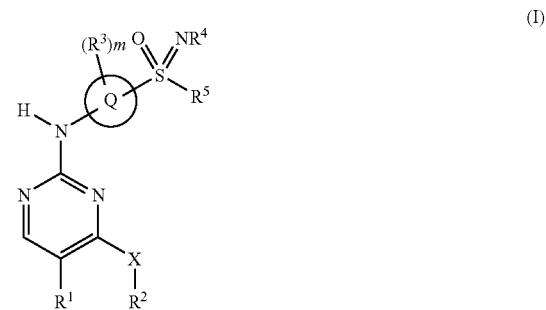

wherein
$R^1$ means an optionally partly or fully saturated, optionally substituted mono- or bicyclic heteroaryl group or an optionally substituted aryl group,
$R^2$ a hydrogen atom,
a $C_1$-$C_{10}$ alkyl group, a $C_2$-$C_{10}$ alkenyl group, a $C_2$-$C_{10}$ alkynyl group, a $C_3$-$C_8$ cycloalkyl group, an aryl or heteroaryl group, which is optionally substituted one or more times identically or differently with a group selected from halogen, hydroxy, cyano, $SO_2NR^8R^9$, $SO_2R^{10}$, $S(O)(NR^8)R^9$, $C_1$-$C_6$-alkyl, $C_1$-$C_6$-hydroxyalkyl, $C_2$-$C_6$-alkenyl, $C_2$-$C_6$-alkinyl, $C_1$-$C_6$-alkoxy, $C_1$-$C_6$-alkoxy-($C_1$-$C_6$)-alkyl, $C_1$-$C_6$-alkoxy-($C_1$-$C_6$)-alkoxy-($C_1$-$C_6$)-alkyl, —$COR^6$, —$C_1$-$C_6$-alkylO(CO)$C_1$-$C_6$-alkyl, $C_1$-$C_6$-alkyl(CO)O—, $C_3$-$C_{10}$-cycloalkyl, —$NR^8R^9$, —$NH(C_1$-$C_6)$-alkyl-, —$N(C_1$-$C_6$-alkyl)$_2$, —$NH(CO)C_1$-$C_6$-alkyl, —$N[(CO)(C_1$-$C_6$-alkyl)]$_2$, —$NH$—$(CH_2)$, —$C_3$-$C_{10}$-cycloalkyl, —$(CH_2)_n$-aryl, —$(CH_2)_n$-heteroaryl, —$(CH_2)_n$—($C_3$-$C_8$)-heterocyclyl, —$CF_3$, —$OCF_3$, —$NR^7$—$C(O)$—$OC_1$-$C_3$-Alkyl, —$NR^7$—$C(O)$—$NR^8R^9$, —$NR^7$—$SO_2$—$R^{10}$,
whereby,
if the $C_3$-$C_{10}$ cycloalkyl group, the $(CH_2)_n$—($C_3$-$C_8$) heterocyclyl group, the $(CH_2)_n$ aryl- or the $(CH_2)_n$-heteroaryl group are substituents of $R^2$,
these themselves optionally can be substituted one or more times identically or differently with a group selected from halogen, hydroxy, $C_1$-$C_6$-alkyl, halogen-($C_1$-$C_4$)alkyl, $C_1$-$C_6$-alkoxy, halogen($C_1$-$C_4$)alkoxy, $NR^8R^9$, $COOR^7$ order $SO_2NR^8R^9$,
and/or the ring of the $C_3$-$C_{10}$ cycloalkyl group and the $C_1$-$C_{10}$ alkyl group can optionally be interrupted by one or several —$NR^8$, oxygen and/or sulphur atoms and/or can be interrupted by one or several —$C(O)$— groups in the ring and/or optionally one or several possible double bonds can be contained in the ring,
n 0-6, $R^3$ hydroxy, halogen, nitro, cyano, —(CO)NR$^8$R$^9$, —(CS)NR$^8$R$^9$, CF$_3$, OCF$_3$, —R$^9$N(CO)NR$^8$R$^9$, the group —NR$^8$R$^9$ or a C$_1$-C$_6$-alkyl group, a C$_3$-C$_7$-cycloalkyl group or a C$_1$-C$_6$-alkoxy group, which is optionally substituted one or more times identically or differently with halogen, hydroxy, C$_1$-C$_6$-alkoxy or the group —NR$^8$R$^9$, $R^4$ a hydrogen atom, a group —C(O)O—R$^{10}$, —C(O)—R$^{10}$, —C(O)—NR$^8$R$^9$, —C(S)—NR$^8$R$^9$, NO$_2$, —Si(R$^{15}$R$^{16}$R$^{17}$), —R$^{18}$—Si(R$^{15}$R$^{16}$R$^{17}$), —SO$_2$—R$^{18}$—Si(R$^{15}$R$^{16}$R$^{17}$) or a —SO$_2$R$^{10}$— group or a C$_1$-C$_{10}$-alkyl-, C$_3$-C$_{10}$-cycloalkyl-, C$_2$-C$_{10}$-alkenyl-, or a C$_2$-C$_{10}$-alkinylgruppe, which is optionally substituted one or more times identically or differently with hydroxy, halogen, C$_1$-C$_6$-alkoxy, C$_1$-C$_6$-alkylthio, cyano, C$_3$-C$_{10}$-cycloalkyl, C$_1$-C$_6$-hydroxyalkyl, C$_2$-C$_6$-alkenyl, C$_2$-C$_6$-alkinyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —COR$^6$, —CSR$^6$, —CF$_3$, —OCF$_3$ or —NR$^8$R$^9$ or an optionally substituted —(CH$_2$)$_n$-aryl- or —(CH$_2$)$_n$-heteroaryl group or $R^3$ and $R^5$ together form a 5 to 7-membered ring, where the ring optionally can be singly or multiply, identically or differently substituted with hydroxy, C$_1$-C$_6$ alkyl, C$_1$-C$_6$ alkoxy, halogen or the group —NR$^8$R$^9$ and contain 1-2 double bonds and R$^3$ and the sulphoximine residue must be bound at neighbouring positions of Q, $R^4$ und $R^5$ together form a 5 to 8-membered ring of the formula

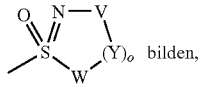 bilden, where

V, W and Y each independently of one another stands for a —CH$_2$ group which is optionally substituted one or more times, identically or differently with hydroxy, C$_1$-C$_{10}$ alkyl, C$_1$-C$_{10}$ alkoxy or —NR$^8$R$^9$, where the C$_1$-C$_{10}$ alkyl- or C$_1$-C$_{10}$ alkoxy group likewise can be substituted one or more times, identically or differently with hydroxy, C$_1$-C$_6$ alkoxy or NR$^8$R$^9$ and/or the ring can be interrupted by one or several —C(O)— groups and/or optionally can contain one or several double bonds, and o 1-4 bedeutet, $R^5$ a C$_1$-C$_6$ alkyl, C$_2$-C$_6$ alkenyl, C$_2$-C$_6$ alkynyl or C$_3$-C$_7$ cycloalkyl group which is optionally substituted one or more times identically or differently with hydroxy, C$_1$-C$_6$-alkoxy, C$_3$-C$_{10}$-cycloalkyl, halogen, cyano, —CF$_3$, —OCF$_3$ or the group —NR$^8$R$^9$, an aryl group or heteroaryl group optionally which si substituted one or more times identically or differently with halogen, hydroxy, C$_1$-C$_6$ alkyl, halogen-(C$_1$-C$_4$) alkyl, C$_1$-C$_6$ alkoxy, halogen(C$_1$-C$_4$) alkoxy, —COR$^6$, COOR$^7$, —NR$^8$R$^9$, CN, NO$_2$, or SO$_2$NR$^8$R$^9$ X an oxygen atom, a sulphur atom or an —NR$^8$— group or X und $R^2$ together form a 3 to 8-membered ring, which contains one or several hetero atoms, and optionally can be substituted one or more times identically or differently with hydroxy, C$_1$-C$_6$-alkyl, C$_1$-C$_6$-alkoxy, halogen or the group —NR$^8$R$^9$, Q C$_6$-C$_{10}$-arylen, heteroarylen with 5-10 ring atoms m 0-4

$R^6$ a hydrogen atom or a hydroxy-, benzyloxy-, or NR$^8$R$^9$— group or a C$_1$-C$_6$-alkyl group, C$_2$-C$_6$-alkenyl group, C$_2$-C$_6$-alkinyl group, C$_1$-C$_6$-alkoxy group, C$_1$-C$_6$-alkylthio group, C$_3$-C$_7$-cycloalky group, C$_6$-C$_{10}$-aryl group or a heteroaryl group with 5 or 6 ring atoms, which is optionally substituted one or more times with hydroxy, —NR$^8$R$^9$, cyano, halogen, —CF$_3$, C$_1$-C$_6$-alkyl, C$_1$-C$_6$-alkoxy or —OCF$_3$ $R^7$ a hydrogen atom or a C$_1$-C$_6$-alkyl group, $R^8$, $R^9$ independently of one another mean a hydrogen atom, C$_1$-C$_6$-alkoxy group, a C$_1$-C$_6$-alkyl group, hydroxy(C$_1$-C$_6$)-alkyl group, dihydroxy (C$_1$-C$_6$)-alkyl group, (CH$_2$)$_n$—NR$^{11}$R$^{12}$, NR$^{11}$R$^{12}$, —(CO)—(C$_1$-C$_6$)-alkyl, —(CO)-phenyl, —(CO)—(C$_1$-C$_6$)alkyl-NH—(CO)-aryl, —CObenzyl, (CO)O(C$_1$-C$_6$)-alkyl, a C$_6$-C$_{10}$-aryl group or a heteroaryl group with 5 or 6 ring atoms, which optionally can be substituted one or more times identically or differently with hydroxy, —NR$^{11}$R$^{12}$, cyano, halogen, —CF$_3$, C$_1$-C$_6$-alkyl, C$_1$-C$_6$-alkoxy, or —OCF$_3$, or $R^8$ and $R^9$ together form a saturated or unsaturated 5 to 7-membered ring, which optionally can contain 1-3 further hetero atoms selected from the group oxygen, sulphur, =N— or —NR$^{11}$— and which optionally can be singly or multiply, identically or differently substituted with hydroxy, —NR$^{11}$R$^{12}$, cyano, halogen, —CF$_3$, C$_1$-C$_6$ alkoxy and/or —OCF$_3$, $R^{10}$ a C$_1$-C$_6$ alkyl, C$_2$-C$_6$ alkenyl, C$_2$-C$_6$ alkynyl, C$_3$-C$_7$ cycloalkyl, C$_3$-C$_{10}$ heterocyclyl, heteroaryl group with 5 or 6 ring atoms or an aryl group, which is optionally substituted one or more times, identically or differently with halogen, hydroxy, C$_1$-C$_6$ alkyl, C$_1$-C$_6$ alkoxy, cyano, —CF$_3$, —OCF$_3$, —NR$^8$R$^9$ or with the group —SiR$^{15}$R$^{16}$R$^{17}$, $R^{11}$, $R^{12}$ independently of one another mean a hydrogen atom, a C$_1$-C$_6$ alkyl, C$_1$-C$_6$ alkoxy-, hydroxy(C$_1$-C$_6$) alkyl, dihydroxy(C$_1$-C$_6$) alkyl, (CO)—(C$_1$-C$_6$) alkyl, (CO)-phenyl, or a benzyl group, which optionally can be singly or multiply, identically or differently substituted with hydroxy, cyano, halogen, —CF$_3$, C$_1$-C$_6$ alkoxy and/or —OCF$_3$, or NR$^{11}$R$^{12}$ forms a saturated or unsaturated 5-7-membered ring, in which up to two methylene groups can be replaced by —O—, —NR$^7$—, or —C(=O)—, $R^{15}$, $R^{16}$ und $R^{17}$ independently of one another can be a C$_1$-C$_6$ alkyl group, and/or a phenyl group and $R^{18}$ stands for a C$_1$-C$_3$ alkylene group.

Another embodiment are compounds of the general formula I according to the preceeding embodiment wherein $R^1$ means an optionally partly or fully saturated mono- or bicyclic heteroaryl group, which is substituted one or more times identically or differently with halogen, hydroxy, NO$_2$, NR$^8$R$^9$, OCF$_3$, CF$_3$, cyano, —COR$^6$, C$_1$-C$_6$-alkyl, halogen(C$_1$-C$_6$)-alkyl-, hydroxy(C$_1$-C$_6$)-alkyl-, cyano(C$_1$-

$C_6$-alkyl)-, $(NR^8R^9)C_1$-$C_4$-alkyl-, $(R^6OC)C_1$-$C_6$-alkyl, [(HR$^8$N(OC)]C$_1$-C$_6$-alkyl, C$_1$-C$_6$-alkoxy, halogen(C$_1$-C$_6$) alkoxy, SO$_2$NR$^8$R$^9$ or an optionally substituted aryl group, $R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, an aryl or heteroaryl group, which is optionally substituted one or more times identically or differently with a group selected from halogen, hydroxy, cyano, SO$_2$NR$^8$R$^9$, SO$_2$R$^{10}$, S(O)(NR$^8$)R$^9$, $C_1$-$C_6$-alkyl, $C_1$-$C_6$-hydroxyalkyl, $C_2$-$C_6$-alkenyl, $C_2$-$C_6$-alkinyl, $C_1$-$C_6$-alkoxy, $C_1$-$C_6$-alkoxy-($C_1$-$C_6$)-alkyl, $C_1$-$C_6$-alkoxy-($C_1$-$C_6$)-alkoxy-($C_1$-$C_6$)-alkyl, —COR$^6$, —$C_1$-$C_6$-alkylO(CO)C$_1$-C$_6$-alkyl, C$_1$-C$_6$-alkyl(CO)O—, $C_3$-$C_{10}$-cycloalkyl, —NR$^8$R$^9$, —NH(C$_1$-C$_6$)-alkyl-N(C$_1$-C$_6$-alkyl)$_2$, —NH(CO)C$_1$-C$_6$-alkyl, —N[(CO)(C$_1$-C$_6$-alkyl)]$_2$, —NH—(CH$_2$)$_n$—C$_3$-C$_{10}$-cycloalkyl, —(CH$_2$)$_n$-Aryl, —(CH$_2$)$_n$-heteroaryl, —(CH$_2$)$_n$—(C$_3$-C$_8$)-heterocyclyl, —CF$_3$, —OCF$_3$, —NR$^7$—C(O)—OC$_1$-C$_3$-Alkyl, —NR$^7$—C(O)—NR$^8$R$^9$, —NR$^7$—SO$_2$—R$^{10}$, where, if the $C_3$-$C_{10}$ cycloalkyl group, the (CH$_2$)$_n$—(C$_3$-C$_8$) heterocyclyl group, the (CH$_2$)$_n$ aryl- or the (CH$_2$)$_n$-heteroaryl group are substituents of $R^2$, these themselves optionally can be substituted one or more times, identically or differently with halogen, hydroxy, $C_1$-$C_6$ alkyl, halogen-(C$_1$-C$_4$) alkyl, C$_1$-C$_6$ alkoxy, halogen (C$_1$-C$_4$) alkoxy, NR$^8$R$^9$, COOR$^7$ or SO$_2$NR$^8$R$^9$, and/or the ring of the $C_3$-$C_{10}$ cycloalkyl group and the $C_1$-$C_{10}$ alkyl group optionally can be interrupted by one or several —NR$^8$, oxygen and/or sulphur atoms and/or can be interrupted by one or several —C(O)— groups in the ring and/or optionally one or several possible double bonds can be contained in the ring, n 0-6, $R^3$ hydroxy, halogen, nitro, cyano, —(CO)NR$^8$R$^9$, —(CS)NR$^8$R$^9$, CF$_3$, OCF$_3$, —R$^9$N(CO)NR$^8$R$^9$, the group —NR$^8$R$^9$ or a $C_1$-$C_6$-alkyl group, a $C_3$-$C_7$-cycloalkyl group or a $C_1$-$C_6$-alkoxy group, which is optionally substituted one or more times identically or differently with halogen, hydroxy, $C_1$-$C_6$-alkoxy or the group —NR$^8$R$^9$, $R^4$ a hydrogen atom, a —C(O)O—R$^{10}$, —C(O)—R$^{10}$, —C(O)—NR$^8$R$^9$, —C(S)—NR$^8$R$^9$, NO$_2$, —Si(R$^{15}$R$^{16}$R$^{17}$), —R$^{18}$—Si(R$^{15}$R$^{16}$R$^{17}$), —SO$_2$—R$^{18}$—Si(R$^{15}$R$^{16}$R$^{17}$) group or an —SO$_2$R$^{10}$ group or a $C_1$-$C_{10}$ alkyl, $C_3$-$C_{10}$ cycloalkyl, $C_2$-$C_{10}$ alkenyl, or a $C_2$-$C_{10}$ alkynyl group, which optionally is substituted one or more times identically or differently with hydroxy, halogen, $C_1$-$C_6$-alkoxy, $C_1$-$C_6$-alkylthio, cyano, $C_3$-$C_{10}$-cycloalkyl, $C_1$-$C_6$-hydroxyalkyl, $C_2$-$C_6$-alkenyl, $C_2$-$C_6$-alkinyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —COR$^6$, —CSR$^5$, —CF$_3$, —OCF$_3$ or —NR$^8$R$^9$ or an optionally substituted —(CH$_2$)$_n$-aryl or —(CH$_2$)$_n$-heteroaryl group or $R^3$ und $R^5$ together form a 5 to 7-membered ring, where the ring optionally can substituted one or more times, identically or differently with hydroxy, $C_1$-$C_6$ alkyl, $C_1$-$C_6$ alkoxy, halogen or the group —NR$^8$R$^9$ and contain 1-2 double bonds and $R^3$ and the sulphoximine residue must be bound at neighbouring positions of Q, $R^4$ und $R^5$ together form a 5 to 8-membered ring of the formula

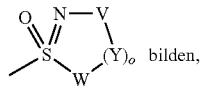 bilden, where

V, W and Y each independently of one another stands for a —CH$_2$ group optionally singly or multiply, identically or differently substituted with hydroxy, $C_1$-$C_{10}$ alkyl, $C_1$-$C_{10}$ alkoxy or —NR$^8$R$^9$, where the $C_1$-$C_{10}$ alkyl- or $C_1$-$C_{10}$ alkoxy group likewise can be singly or multiply, identically or differently substituted with hydroxy, $C_1$-$C_6$ alkoxy or NR$^8$R$^9$ and the ring can be interrupted by one or several —C(O)— groups and/or optionally can contain one or several double bonds, and o means 1-4, $R^5$ a $C_1$-$C_6$ alkyl, $C_2$-$C_6$ alkenyl, $C_2$-$C_6$ alkynyl or $C_3$-$C_7$ cycloalkyl group optionally is substituted one or more times, identically or differently with hydroxy, $C_1$-$C_6$ alkoxy, $C_3$-$C_{10}$ cycloalkyl, halogen, cyano, —CF$_3$, —OCF$_3$ or the group —NR$^8$R$^9$, an aryl group or heteroaryl group optionally singly or multiply, identically or differently substituted with halogen, hydroxy, $C_1$-$C_6$ alkyl, halogen-($C_1$-$C_4$) alkyl, $C_1$-$C_6$ alkoxy, halogen($C_1$-$C_4$) alkoxy, —COR$^6$, COOR$^7$, —NR$^8$R$^9$, CN, NO$_2$, or SO$_2$NR$^8$R$^9$ X an oxygen atom, a sulphur atom or an —NR$^8$— group or X und $R^2$ together form a 3 to 8-membered ring, which contains one or several hetero atoms, and optionally can be substituted one or more times, identically or differently with hydroxy, $C_1$-$C_6$ alkyl, $C_1$-$C_6$ alkoxy, halogen or the group —NR$^8$R$^9$, if X means a —NR$^8$— group Q $C_6$-$C_{10}$ arylene, heteroarylene with 5-10 ring atoms m 0-4

$R^6$ a hydrogen atom or a, hydroxy, benzyloxy, NR$^8$R$^9$ or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, $C_6$-$C_{10}$-aryl group or heteroaryl group with 5 or 6 ring atoms, which optionally can be singly or multiply, identically or differently substituted with hydroxy, —NR$^8$R$^9$, cyano, halogen, —CF$_3$, $C_1$-$C_6$ alkyl, $C_1$-$C_6$ alkoxy or —OCF$_3$ $R^7$ a hydrogen atom or a $C_1$-$C_6$ alkyl group, $R^8$, $R^9$ independently of one another mean a hydrogen atom, $C_1$-$C_6$-alkoxy group, eine $C_1$-$C_6$-alkyl group, hydroxy($C_1$-$C_6$)-alkyl group, dihydroxy($C_1$-$C_6$)-alkylgruppe, (CH$_2$)$_n$—NR$^{11}$R$^{12}$, NR$^{11}$R$^{12}$, (CO)—(C$_1$-C$_6$)-alkyl, (CO)-phenyl, —(CO)—(C$_1$-C$_6$)alkyl-NH—(CO)-aryl, —CObenzyl, (CO)O(C$_1$-C$_6$)-alkyl, $C_6$-$C_{10}$-aryl group, or heteroaryl group with 5 or 6 ring atoms, which is optionally substituted one or more times identically or differently with hydroxy, —NR$^{11}$R$^{12}$, cyano, halogen, —CF$_3$, $C_1$-$C_6$-alkyl, $C_1$-$C_6$-alkoxy, or —OCF$_3$ or together form a saturated or unsaturated 5 to 7-membered ring, which optionally can contain 1-3 further hetero atoms selected from the group oxygen, sulphur, =N— or —NR$^{11}$— and which optionally can be singly or multiply, identically or differently substituted with hydroxy, —NR$^{11}$R$^{12}$, cyano, halogen, —CF$_3$, C$_1$-C$_6$ alkoxy and/or —OCF$_3$, R$^{10}$ a C$_1$-C$_6$ alkyl, C$_2$-C$_6$ alkenyl, C$_2$-C$_6$ alkynyl, C$_3$-C$_7$ cycloalkyl, C$_3$-C$_{10}$ heterocyclyl, heteroaryl group with 5 or 6 ring atoms or aryl group, which optionally can be singly or multiply, identically or differently substituted with halogen, hydroxy, C$_1$-C$_6$ alkyl, C$_1$-C$_6$ alkoxy, cyano, —CF$_3$, —OCF$_3$, —NR$^8$R$^9$ or with the group SiR$^{15}$R$^{16}$R$^{17}$, R$^{11}$, R$^{12}$ independently of one another mean a hydrogen atom, a C$_1$-C$_6$ alkyl group, C$_1$-C$_6$ alkoxy group, hydroxy (C$_1$-C$_6$) alkyl, dihydroxy(C$_1$-C$_6$) alkyl, (CO)—(C$_1$-C$_6$) alkyl, (CO)-phenyl, benzyl, which optionally can be singly or multiply, identically or differently substituted with hydroxy, cyano, halogen, —CF$_3$, C$_1$-C$_6$ alkoxy and/or —OCF$_3$, or NR$^{11}$R$^{12}$ forms a saturated or unsaturated 5-7-membered ring, in which up to two methylene groups can be replaced by —O—, —NR$^7$—, or —C(=O)—, R$^{15}$, R$^{16}$ und R$^{17}$ independently of one another can be a C$_1$-C$_6$ alkyl group and/or a phenyl group and R$^{18}$ stands for a C$_1$-C$_3$ alkylene group.

Another embodiment are compounds of the general formula I according to the preceeding two embodiments wherein Q means phenylene.

Still a further embodiment of the invention are compounds of the general formula I according to the three embodiments above, wherein R$^1$ means an optionally partly or fully saturated mono- or bicyclic heteroaryl group, which is optionally substituted one or more times, identically or differently with halogen, hydroxy, NO$_2$, NR$^8$R$^9$, OCF$_3$, CF$_3$, cyano, —COR$^6$, C$_1$-C$_6$-alkyl, halogen(C$_1$-C$_6$)-alkyl-, hydroxy(C$_1$-C$_6$)-alkyl-, cyano(C$_1$-C$_6$-alkyl)-, (NR$^8$R$^9$)C$_1$-C$_4$-alkyl-, (R$^6$OC)C$_1$-C$_6$-alkyl, [(HR$^8$N(OC)]C$_1$-C$_6$-alkyl, C$_1$-C$_6$-alkoxy, halogen(C$_1$-C$_6$)alkoxy, SO$_2$NR$^8$R$^9$ or an optionally substituted phenyl group.

R$^2$ a hydrogen atom, a C$_1$-C$_{10}$ alkyl group, a C$_2$-C$_{10}$ alkenyl group, a C$_2$-C$_{10}$ alkynyl group, a C$_3$-C$_8$ cycloalkyl group, a —(C$_3$-C$_8$) heterocyclyl, an aryl or heteroaryl group which is substituted one or more times identically or differently, with a group selected from halogen, hydroxy, cyano, SO$_2$NR$^8$R$^9$, SO$_2$R$^{10}$, S(O)(NR$^8$)R$^9$, C$_1$-C$_6$-alkyl, C$_1$-C$_6$-hydroxyalkyl, C$_2$-C$_6$-alkenyl, C$_2$-C$_6$-alkinyl, C$_1$-C$_6$-alkoxy, C$_1$-C$_6$-alkoxy-(C$_1$-C$_6$)-alkyl, C$_1$-C$_6$-alkoxy-(C$_1$-C$_6$)-alkoxy-(C$_1$-C$_6$)-alkyl, —COR$^6$, —C$_1$-C$_6$-alkylO(CO)C$_1$-C$_6$-alkyl, C$_1$-C$_6$-alkyl(CO)O—, C$_3$-C$_{10}$-cycloalkyl, —NR$^8$R$^9$, —NH(C$_1$-C$_6$)alkyl-N(C$_1$-C$_6$-alkyl)$_2$, —NH(CO)C$_1$-C$_6$-alkyl, —N[(CO)(C$_1$-C$_6$-alkyl)]$_2$, —NH—(CH$_2$)$_n$—C$_3$-C$_{10}$-cycloalkyl, —(CH$_2$)$_n$-phenyl, —(CH$_2$)$_n$-heteroaryl, —(CH$_2$)$_n$—(C$_3$-C$_8$)-heterocyclyl, —CF$_3$, —OCF$_3$, —NR$^7$—C(O)—OC$_1$-C$_3$-alkyl, —NR$^7$—C(O)—NR$^8$R$^9$, —NR$^7$—SO$_2$—R$^{10}$, where, if the C$_3$-C$_{10}$ cycloalkyl group, the (CH$_2$)$_n$—(C$_3$-C$_8$) heterocyclyl group, the (CH$_2$)$_n$ aryl- or the (CH$_2$)$_n$-heteroaryl group are substituents of R$^2$, these themselves optionally can be substituted one or more times, identically or differently with halogen, hydroxy, C$_1$-C$_6$ alkyl, halogen-(C$_1$-C$_4$) alkyl, C$_1$-C$_6$ alkoxy, halogen (C$_1$-C$_4$) alkoxy, NR$^8$R$^9$, COOR$^7$ or SO$_2$NR$^8$R$^9$, and/or the ring of the C$_3$-C$_{10}$ cycloalkyl group and the C$_1$-C$_{10}$ alkyl group optionally can be interrupted by one or several —NR$^8$, oxygen and/or sulphur atoms and/or can be interrupted by one or several —C(O)— groups in the ring and/or optionally one or several possible double bonds can be contained in the ring, n 0-6, R$^3$ hydroxy, halogen, nitro, cyano, —(CO)NR$^8$R$^9$, —(CS)NR$^8$R$^9$, CF$_3$, OCF$_3$, —R$^9$N(CO)NR$^8$R$^9$, the group —NR$^8$R$^9$ or a C$_1$-C$_6$-alkyl group, a C$_3$-C$_7$-cycloalkyl group or a C$_1$-C$_6$-alkoxy group, which is optionally substituted one or more times identically or differently with halogen, hydroxy, C$_1$-C$_6$-alkoxy or the group —NR$^8$R$^9$, R$^4$ a hydrogen atom, a group —C(O)O—R$^{10}$, —C(O)—R$^{10}$, —C(O)—NR$^8$R$^9$, —C(S)—NR$^8$R$^9$, NO$_2$, —Si (R$^{15}$R$^{16}$R$^{17}$), —R$^{18}$—Si(R$^{15}$R$^{16}$R$^{17}$), —SO$_2$—R$^{18}$—Si (R$^{15}$R$^{16}$R$^{17}$) or a —SO$_2$R$^{10}$— group or a C$_1$-C$_{10}$ alkyl, C$_3$-C$_{10}$ cycloalkyl, C$_2$-C$_{10}$ alkenyl, or a C$_2$-C$_{10}$ alkynyl group, which optionally can be substituted one or more times identically or differently with hydroxy, halogen, C$_1$-C$_6$-alkoxy, C$_1$-C$_6$-alkylthio, cyano, C$_3$-C$_{10}$-cycloalkyl, C$_1$-C$_6$-hydroxyalkyl, C$_2$-C$_6$-alkenyl, C$_2$-C$_6$-alkinyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —COR$^6$, —CSR$^6$, —CF$_3$, —OCF$_3$ or —NR$^8$R$^9$ an optionally substituted —(CH$_2$)$_n$-phenyl or —(CH$_2$)$_n$-heteroaryl group or R$^3$ und R$^5$ together form a 5 to 7-membered ring, where the ring optionally be singly or multiply, identically or differently substituted with hydroxy, C$_1$-C$_6$ alkyl, C$_1$-C$_6$ alkoxy, halogen or the group —NR$^8$R$^9$ and can contain 1-2 double bonds and R$^3$ and the sulphoximine residue must be bound at neighbouring positions of Q, R$^4$ and R$^5$ together form a 5 to 8-membered ring of the formula

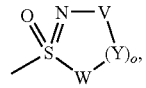

where

V, W and Y each independently of one another stands for a —CH$_2$ group optionally singly or multiply, identically or differently substituted with hydroxy, C$_1$-C$_{10}$ alkyl, C$_1$-C$_{10}$ alkoxy or —NR$^8$R$^9$, where the C$_1$-C$_{10}$ alkyl- or C$_1$-C$_{10}$ alkoxy group likewise can be singly or multiply, identically or differently substituted with hydroxy, C$_1$-C$_6$ alkoxy or NR$^8$R$^9$ and the ring can be interrupted by one or several —C(O)— groups and/or optionally can contain one or several double bonds, and o means 1-4, R$^5$ a C$_1$—C alkyl, C$_2$-C$_6$ alkenyl, C$_2$-C$_6$ alkynyl or C$_3$-C$_7$ cycloalkyl group which is optionally substituted one or more times identically or differently with, hydroxy, C$_1$-C$_6$-alkoxy, C$_3$-C$_{10}$-cycloalkyl, halogen, cyano, —CF$_3$, —OCF$_3$ or the group —NR$^8$R$^9$ or differently substituted with halogen, hydroxy, C$_1$-C$_6$ alkyl, halogen-(C$_1$-C$_4$) alkyl, C$_1$-C$_6$ alkoxy, halogen(C$_1$-C$_4$) alkoxy, —COR$^6$, COOR$^7$, —NR$^8$R$^9$, CN, NO$_2$, or SO$_2$NR$^8$R$^9$ X an oxygen atom, a sulphur atom or an —NR$^8$— group or X und $R^2$ together form a 3 to 8-membered ring, which contains one or several hetero atoms, and optionally can be singly or multiply, identically or differently substituted with hydroxy, $C_1$-$C_6$ alkyl, $C_1$-$C_6$ alkoxy, halogen or the group —$NR^8R^9$, if X means a —$NR^8$— group Q $C_6$-$C_{10}$-phenylene, m 0-4

$R^6$ a hydrogen atom or a, hydroxy, benzyloxy, $NR^8R^9$ or a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalky group, $C_6$-$C_{10}$-phenyl group or heteroaryl group with 5 or 6 ring atoms, which optionally can be singly or multiply, identically or differently substituted with hydroxy, —$NR^8R^9$, cyano, halogen, —$CF_3$, $C_1$-$C_6$ alkyl, $C_1$-$C_6$ alkoxy or —$OCF_3$ $R^7$ a hydrogen atom or a $C_1$-$C_6$ alkyl group, $R^8$, $R^9$ independently of one another mean a hydrogen atom, $C_1$-$C_6$-alkoxy group, a $C_1$-$C_6$-alkyl group, hydroxy($C_1$-$C_6$)-alkylgruppe, dihydroxy($C_1$-$C_6$)-alkylgruppe, $(CH_2)_n$—$NR^{11}R^{12}$, $NR^{11}R^{12}$, (CO)—($C_1$-$C_6$)-alkyl, (CO)-phenyl, —(CO)—($C_1$-$C_6$)alkyl-NH—(CO)-phenyl, —(CO)benzyl, (CO)O($C_1$-$C_6$)-alkyl, phenyl group, or heteroaryl group with 5 or 6 ring atoms, which optionally can be singly or multiply, identically or differently substituted with hydroxy, —$NR^{11}R^{12}$ cyano, halogen, —$CF_3$, $C_1$-$C_6$ alkyl, $C_1$-$C_6$ alkoxy, or —$OCF_3$ or together form a saturated or unsaturated 5 to 7-membered ring, which optionally can contain 1-3 further hetero atoms selected from the group oxygen, sulphur, =N— or —$NR^{11}$— and which optionally can be singly or multiply, identically or differently substituted with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or phenyl group, which optionally can be singly or multiply, identically or differently substituted with halogen, hydroxy, $C_1$-$C_6$ alkyl, $C_1$-$C_6$ alkoxy, cyano, —$CF_3$, —$OCF_3$, —$NR^8R^9$ or with the group $SiR^{15}R^{16}R^{17}$, $R^{11}$, $R^{12}$ independently of one another mean a hydrogen atom, a $C_1$-$C_6$ alkyl group, $C_1$-$C_6$ alkoxy group, hydroxy($C_1$-$C_6$) alkyl, dihydroxy($C_1$-$C_6$) alkyl, (CO)—($C_1$-$C_6$) alkyl, (CO)-phenyl, benzyl, which optionally can be singly or multiply, identically or differently substituted with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ und $R^{17}$ and $R^{17}$ independently of one another can be a $C_1$-$C_6$ alkyl group, and/or a phenyl group and $R^{18}$ stands for a $C_1$-$C_3$ alkylene group.

bedeutet.

Another embodiment are compounds according to one of the previous four embodiments, wherein $R^1$ means an optionally partly or fully saturated mono- or bicyclic heteroaryl group, which optionally can be substituted one or more times, identically or differently with halogen, hydroxy, $NO_2$, $NR^8R^9$, $OCF_3$, $CF_3$, cyano, —$COR^6$, $C_1$-$C_6$-alkyl, halogen($C_1$-$C_6$)-alkyl-, hydroxy($C_1$-$C_6$)-alkyl-, cyano($C_1$-$C_6$-alkyl)-, ($NR^8R^9$)$C_1$-$C_4$-alkyl-, ($R^6$OC)$C_1$-$C_6$-alkyl, [(HR$^8$N(OC)]$C_1$-$C_6$-alkyl, $C_1$-$C_6$-alkoxy, halogen($C_1$-$C_6$)alkoxy, $SO_2NR^8R^9$.

Another embodiment are compounds of the general formula I according to one of the previous five embodiments, characterized in that $R^1$ is an optionally partly or fully saturated monocyclic 5-membered heteroaryl group, which optionally can be substituted one or more times, identically or differently with halogen, hydroxy, $NO_2$, $NR^8R^9$, $OCF_3$, $CF_3$, cyano, —$COR^6$, $C_1$-$C_6$-alkyl, halogen($C_1$-$C_6$)-alkyl-, hydroxy($C_1$-$C_6$)-alkyl-, cyano($C_1$-$C_6$-alkyl)-, ($NR^8R^9$)$C_1$-$C_4$-alkyl-, ($R^6$OC)$C_1$-$C_6$-alkyl, [(HR$^8$N(OC)]$C_1$-$C_6$-alkyl, $C_1$-$C_6$-alkoxy, halogen($C_1$-$C_6$)alkoxy, $SO_2NR^8R^9$.

Another embodiment are compounds of the general formula I according to one of the previous six embodiments wherein $R^1$ is an optionally substituted heteroaryl- or an optionally substituted phenyl group, $R^2$ a $C_1$-$C_6$-hydroxyalkyl group or a group $(CH_2)_2$—NH(CO)—($C_1$-$C_3$)alkyl, $C_3$-$C_{10}$-cycloalkyl group $R^3$ a hydrogen atom or a halogen atom, $R^4$ a hydrogen atom, a $C_1$-$C_{10}$-alkyl group, a (CO)($C_1$-$C_{10}$)-alkyl group or a COO($C_1$-$C_3$)alkyl group, $R^5$ a $C_1$-$C_6$-alkyl group, a $C_3$-$C_7$-cycloalkyl-group or a phenyl group

X —NH—

Q phenylen and m means 0 or 1.

As well as the compounds of the general formula I, according to one of the preceeding 7 embodiments, in the form of the salts with physiologically compatible anions, and The use of the compounds according to one of the previous 7 embodiments for the preparation of a drug, the use of the compounds for the preparation of a drug for the treatment of inflammatory diseases, the use of the compounds for the preparation of a drug for the treatment of tumours or metastases, the use of the compounds for the preparation of pharmaceutical preparations containing at least one compound according to the preceeding embodiments or mixtures thereof and pharmaceutically acceptable carriers, the use of the compounds of the general formula I for the preparation of a drug for the treatment of cancer, angiofribroma, arthritis, eye diseases, autoimmune diseases, chemotherapeutic agent-induced alopecia and mucositis, Crohn's disease, endometriosis, fibrotic diseases, haemangioma, cardiovascular diseases, infectious diseases, nephrological diseases, chronic and acute neurodegenerative diseases, and of damage to the nerve tissue and viral infections and for the prevention of the reocclusion of blood vessels after balloon catheter treatment, in vascular prosthesis or after the use of mechanical devices for keeping blood vessels open, such as for example stents, and as immunosuppressants, and for the support of scar-free wound healing, and in senile keratitis and in contact dermatitis. psoriasis and atopic dermatitis.

DEFINITIONS

Aryl groups in the sense of the invention are aromatic or partly aromatic carbocyclic groups with 3 to 16 carbon atoms, preferably 5-10 carbon atoms, particularly preferably 6-10 carbon atoms, which have a ring, such as for example phenyl or several condensed rings such as for example naphthyl or anthranyl, quite particularly preferably phenyl and naphthyl. As examples, phenyl, indanyl, indenyl, naphthyl, tetralinyl, azulenyl, fluorenyl and anthranyl may be mentioned.

A preferred group of aryl groups is phenyl, indanyl, indenyl, naphthyl and tetralinyl especially preferred is phenyl.

The aryl groups can be substituted at any suitable site which leads to a stable compound, with one or several residues from the group halogen, hydroxy, $C_1$-$C_5$alkyl, hydroxy ($C_1$-$C_5$)alkyl, ($C_1$-$C_5$)alkoxy, perfluoro($C_1$-$C_5$)alkoxy, —($C_1$-$C_5$)-alkyl-O—($C_1$-$C_5$)-alkyl, —($C_1$-$C_5$)-alkyl-COOR$^7$, —O—(CH$_2$)$_o$O—, cyano, CF$_3$, nitro, (CO)R$^6$, NR$^8$R$^9$, —NR$^8$—(CO)—($C_1$-$C_4$)alkyl, —NR$^8$—SO$_2$—($C_1$-$C_4$)alkyl, —($C_1$-$C_4$)alkyl-NR$^8$—(CO)—($C_1$-$C_4$)-alkyl, —(CO)NR$^8$—($C_1$-$C_4$)alkyl, —NH(CO)NH—($C_1$-$C_4$)-alkyl, —(CO)piperidinon, phenyl, —(CO)-morpholino.

Preferred substituents for aryl groups are halogen, hydroxy, ($C_1$-$C_4$)-alkyl, hydroxy($C_1$-$C_4$)alkyl, ($C_1$-$C_4$)-alkoxy, —O-perfluoro($C_1$-$C_4$)alkyl, —($C_1$-$C_4$)-alkyl-O—($C_1$-$C_4$)-alkyl, —($C_1$-$C_4$)-alkyl-COOH, —($C_1$-$C_4$)-alkyl-COO[($C_1$-$C_4$)alkyl], —O—(CH$_2$)$_o$O—, cyano, CF$_3$, NR$^8$R$^9$, —NR$^8$—(CO)—($C_1$-$C_4$)alkyl, —NR$^8$—SO$_2$—($C_1$-$C_4$)-alkyl, —($C_1$-$C_4$)alkyl-NR$^8$(CO)($C_1$-$C_4$)-alkyl, —(CO)NR$^8$—($C_1$-$C_4$)alkyl, —NH(CO)NH—($C_1$-$C_4$)-alkyl, —SO$_2$—($C_1$-$C_4$)-alkyl, —SO$_2$NH$_2$, —(CO)piperidinon, —(CO)-morpholine, phenyl.

More preferred substituents for aryl groups are halogen, hydroxy, ($C_1$-$C_3$)alkyl, ($C_1$-$C_3$)alkoxy, —CH$_2$—O—CH$_3$, —OCF$_3$, hydroxy($C_1$-$C_3$)alkyl, —(CH$_2$)$_3$—COOCH$_3$, —O—(CH$_2$)$_1$O—, cyano, CF$_3$, —N(CH$_3$)$_2$, —NH(ethyl), —NH—(CO)CH$_3$, —(CO)CH$_3$, —NHSO$_2$CH$_3$, —CH$_2$—NH—(CO)CH$_3$, —(CO)(4-oxo-N-piperidyl), —(CO)NH(C$_2$H$_5$), —NH(CO)NH—C$_4$H$_9$, —(CO)-morpholine, phenyl, —SO$_2$—CH$_3$, SO$_2$NH$_2$.

In one embodiment of the invention R$^1$ means an optionally one or more times substituted phenyl group whereby its substituents are selected from the group halogen, ($C_1$-$C_5$)-alkyl, ($C_1$-$C_5$)alkoxy, —($C_1$-$C_5$)alkyl-O—($C_1$-$C_5$)alkyl, —($C_1$-$C_5$) alkyl-COOR$^7$, —O—(CH$_2$)$_o$O—, cyano, CF$_3$, (CO)R$^6$, NR$^8$R$^9$, —NR$^8$—(CO)—($C_1$-$C_4$)alkyl, —NR$^8$—SO$_2$—$C_1$-$C_4$-alkyl, —($C_1$-$C_4$)alkyl-NR$^8$ (CO)—($C_1$-$C_4$)-alkyl, —(CO)NR$^8$—($C_1$-$C_5$)alkyl, —NH(CO)NH—($C_1$-$C_5$)-alkyl, —(CO)piperidinon, phenyl, —(CO)-morpholine.

In a preferred embodiment the substituents for the aryl group in R$^1$ are halogen, ($C_1$-$C_3$)alkyl, ($C_1$-$C_3$)alkoxy, —($C_1$-$C_3$)-alkyl-O—($C_1$-$C_3$)-alkyl, —(CH$_2$)$_3$—COO—($C_1$-$C_3$)-alkyl, —O—(CH$_2$)$_o$O—, cyano, CF$_3$, —NH—(CO)($C_1$-$C_3$)-alkyl, —(CO)($C_1$-$C_3$)-alkyl, —NHSO$_2$($C_1$-$C_3$)-alkyl, —($C_1$-$C_3$)-alkylen-NH—(CO)($C_1$-$C_3$)-alkyl, —(CO)(4-oxo-N-piperidyl), —(CO)NH—($C_1$-$C_3$)-alkyl, —NH(CO)NH—($C_1$-$C_5$)-alkyl, —(CO)-morpholine.

Most preferred as substituents for the aryl group in R$^1$ are methyl, ethyl, methoxy, ethoxy, fluorine, —(CH$_2$)$_3$—COOCH$_3$, —O—(CH$_2$)$_1$O—, cyano, CF$_3$, —NH—(CO)CH$_3$, —(CO)CH$_3$, —NHSO$_2$CH$_3$, —CH$_2$—NH—(CO)CH$_3$, —(CO)(4-oxo-N-piperidyl), —(CO)NH(C$_2$H$_5$), —NH(CO)NH—C$_4$H$_9$, phenyl, —(CO)-morpholine, —CH$_2$—O—CH$_3$.

In one embodiment of the invention the aryl group R$^1$ can be substituted at any suitable site which leads to a stable compound, with one or several residues from the group halogen, hydroxy, $C_1$-$C_5$ alkyl, $C_1$-$C_5$ alkoxy, cyano, CF$_3$, nitro, (CO)R$^6$, SO$_2$(NR$^8$R$^9$), SO$_2$R$^{10}$, (C$_2$-$C_{10}$) alkenyl, (C$_2$-$C_{10}$) alkynyl, COOR$^7$ or —S(O)(NR$^8$)R$^9$. The optionally substituted phenyl group is preferred.

In one embodiment of the invention the $C_1$-$C_{10}$ alkyl group, $C_2$-$C_{10}$ alkenyl group, $C_2$-$C_{10}$ alkynyl group, $C_3$-$C_8$ cycloalkyl group, $C_3$-$C_8$ heterocyclyl group, the group aryl- and heteroaryl group in R$^2$ may be optionally substituted one or more times, identically or differently with halogen, hydroxy, cyano, SO$_2$NR$^8$R$^9$, SO$_2$R$^{10}$, S(O)(NR$^8$)R$^9$, $C_1$-$C_6$ alkyl, perfluoro($C_1$-$C_6$)alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —COR$^6$, —$C_1$-$C_6$ alkylO(CO)$C_1$-$C_6$ alkyl, $C_1$-$C_6$ alkyl(CO)O—, $C_3$-$C_{10}$ cycloalkyl, =N—OH, —NR$^8$R$^9$, —NH($C_1$-$C_6$) alkyl, —N($C_1$-$C_6$ alkyl)$_2$, —NH(CO)$C_1$-$C_6$ alkyl, —N[(CO) ($C_1$-$C_6$ alkyl)]$_2$, —NH(CO)$C_1$-$C_6$ alkylene-NH—(CO)aryl, —NH(CO)(($C_1$-$C_6$)alkylene)aryl, —NH—(CH$_2$)$_n$—$C_3$-$C_{10}$ cycloalkyl, —(CH$_2$)$_n$aryl, —(CH$_2$)$_n$—O-aryl, —(CH$_2$)$_n$ heteroaryl, —(CH$_2$)$_n$—($C_3$-$C_8$) heterocyclyl, —CF$_3$, —OCF$_3$, —NR$^7$—C(O)—OC$_1$-$C_3$ alkyl, —NR$^7$—C(O)—NR$^8$R$^9$ or —NR$^7$—SO$_2$—R$^{10}$, and if the $C_3$-$C_{10}$ cycloalkyl group, the (CH$_2$)$_n$—($C_3$-$C_8$) heterocyclyl group, the (CH$_2$)$_n$ aryl- or the (CH$_2$)$_n$-heteroaryl group are substituents of R$^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—(CH$_2$)$_q$—O—, halogen($C_1$-$C_4$) alkoxy, —(CH$_2$)$_n$aryl, NR$^8$R$^9$, COOR$^7$ or SO$_2$NR$^8$R$^9$, and/or the ring of any $C_3$-$C_{10}$ cycloalkyl group, $C_3$-$C_8$ heterocyclyl group and the $C_1$-$C_{10}$ alkyl group can optionally contain one or several —NR$^8$, oxygen and/or sulphur atoms and/or can optionally contain one or several —C(O)— groups in the ring and/or optionally one or several possible double bonds can be contained in the ring.

In a preferred embodiment the substituents for the aryl groups in R$^2$ are halogen, hydroxy, ($C_1$-$C_3$)alkyl, ($C_1$-$C_3$) alkoxy, —O—(CH$_2$)$_o$O—, hydroxy($C_1$-$C_5$)alkyl, cyano, —OCF$_3$, CF$_3$, —N($C_1$-$C_3$ alkyl)$_2$, —SO$_2$NH$_2$, —SO$_2$—($C_1$-$C_4$)-alkyl, phenyl.

Most preferred as substituents for the aryl groups in R$^2$ are fluorine, hydroxy, methyl, methoxy, —O—(CH$_2$)$_1$O—, hydroxymethyl, cyano, —OCF$_3$, —CF$_3$, —N(CH$_3$)$_2$, —SO$_2$NH$_2$, —SO$_2$CH$_3$, phenyl, no matter whether the group R$^2$ itself is an aryl group or another group R$^2$ has an aryl substituent, the preferred substituents mentioned above cover both.

As aryl groups in the sense of the present invention the optionally substituted phenyl group is preferred. Particularly preferred are phenyl groups with 0 to 1 substituent.

Should an aryl group occur within a chain, and still be named an "aryl" group, an arylene group is meant thereby.

If the groups —(CH$_2$)$_n$-aryl- or —(CH$_2$)$_n$-heteroaryl are defined as substituents of the residue R$^4$, they can optionally be substituted one or more times, identically or differently with hydroxy, —NR$^8$R$^9$, cyano, halogen, —CF$_3$, $C_1$-$C_6$ alkoxy, —OCF$_3$ and/or $C_1$-$C_6$ alkyl.

The aryl group R$^5$ preferably contains 5-10 ring atoms, particularly preferably 6-10, quite particularly preferably 6 ring atoms.

Arylene groups are aryl groups which are bound into the basic skeleton via two positions. In particular here, the optionally substituted phenylene group may be mentioned. Possible substituents are the same substituents as for the aryl group. Phenylene groups which bear 0-1 substituents (m=0-1) are preferred.

The substituents sulfoximine and aminopyrimidine on the group Q are preferably meta or para to one another.

The heteroaryl group in each case contains 5-10 ring atoms and can instead of a carbon atom contain one or several, identical or different hetero atoms such as oxygen, nitrogen or sulphur in the ring, and can be mono- or bicyclic, and can also in each case be benzo-condensed.

As examples, thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl and benzo derivatives thereof, such as for example benzofuranyl, benzothienyl, benzothiazolyl, benzoxazolyl, benzimidazolyl, indazolyl, indolyl, isoindolyl, and pyridyl, pyridazinyl, pyrimidinyl, pyrazinyl, triazinyl, and benzo derivatives thereof, such as for example quinolyl and isoquinolyl, may be mentioned.

A preferred group of heteroaryl groups are thiazolyl, furanyl, thienyl, triazolyl, tetrazolyl, pyrrolyl, pyrazolyl, imidazolyl, oxazolyl, pyridyl, pyrimidinyl, pyrazinyl, indolyl.

The linkage of the heteroaryl group with the pyrimidine in the case of $R^1$ or with other positions of the general formula I or residues thereof can occur both via any carbon atom and also via a nitrogen atom. The same is possible for all other kind of rings within the scope of the invention having at least one nitrogen atom within the ring e.g. heterocyclyl, partly or fully saturated heteroaryl. All resulting regio isomers are an aspect of the present invention.

Partly or fully saturated heteroaryl groups in the sense of the invention can be for example: tetrahydropyranyl, tetrahydrofuranyl, 2H-pyranyl, 4H-pyranyl, piperidyl, tetrahydropyridyl, dihydropyridyl, 1H-pyridin-2-onyl, 1H-pyridin-4-onyl, 4-amino-pyridyl, 1H-pyridin-4-ylidenaminyl, chromanyl, isochromanyl, chromenyl, isochromenyl, thiochromanyl, decahydroquinolinyl, tetrahydroquinolinyl, dihydroquinolinyl, 5,6,7,8-tetrahydro-1H-quinolin-4-onyl, decahydroisoquinolinyl, tetrahydroisoquinolinyl, dihydroisoquinolinyl, 3,4-dihydro-2H-benz[1,4]oxazinyl, 1,2-dihydro[1,3]benzoxazin-4-onyl, 3,4-dihydrobenz[1,4]oxazin-4-onyl, 3,4-dihydro-2H-benzo[1,4]thiazinyl, 4H-benzo[1,4] thiazinyl, 1,2,3,4-tetrahydroquinoxalinyl, 1H-cinnolin-4-onyl, 3H-quinazolin-4-onyl, 1H-quinazolin-4-onyl, 3,4-dihydro-1H-quinoxalin-2-onyl, 2,3-1,2,3,4-tetrahydro[1,5] naphthyridinyl, dihydro-1H-[1,5]naphthyridyl, 1H-[1,5] naphthyrid-4-onyl, 5,6,7,8-tetrahydro-1H-naphthyridin-4-onyl, 1,2-dihydropyrido[3,2-d][1,3]oxazin-4-onyl, octahydro-1H-indolyl, 2,3-dihydro-1H-indolyl, octahydro-2H-isoindolyl, 1,3-dihydro-2H-isoindolyl, 1,2-dihydroindazolyl, 1H-pyrrolo[2,3-b]pyridyl, 2,3-dihydro-1H-pyrrolo[2,3-b]pyridyl or 2,2-dihydro-1H-pyrrolo[2,3-b]pyridin-3-onyl; tetrahydropyranyl, tetrahydrofuranyl, piperidyl are preferred.

Possible substituents for the heteroaryl groups are halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano ($C_1$-$C_6$ alkyl)-, $(NR^8R^9)C_1$-$C_4$ alkyl, —NH(CO)$C_1$-$C_6$ alkylene-NH—(CO)aryl, —NH(CO)$C_1$-$C_6$ alkylene aryl, $(R^6OC)C_1$-$C_6$ alkyl, $[(HR^8N(OC)]C_1$-$C_6$ alkyl, $C_1$-$C_6$ alkoxy, $(CH_2)_n$aryl, halogen($C_1$-$C_6$) alkoxy, $SO_2NR^8R^9$ or an optionally substituted aryl group.

In general the term "optionally substituted" includes compounds having no, one, two or more substituent(s).

In a preferred embodiment of the invention compounds according to any one of the claims having an heteroaryl substituent have none, one or two substituents.

In a more preferred embodiment the heteroaryl group $R^1$ is not substituted or has one substitutent.

In one embodiment of the invention $R^1$ means an optionally partly or fully saturated mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, $(NR^8R^9)C_1$-$C_4$ alkyl, $(R^6OC)C_1$-$C_6$ alkyl, $[(HR^8N(OC)]C_1$-$C_6$ alkyl, $C_1$-$C_6$ alkoxy, halogen ($C_1$-$C_6$) alkoxy or $SO_2NR^8R^9$.

In one embodiment of the invention $R^1$ means a mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, $(NR^8R^9)C_1$-$C_4$ alkyl, $(R^6OC)C_1$-$C_6$ alkyl, $[(HR^8N(OC)]C_1$-$C_6$ alkyl, $C_1$-$C_6$ alkoxy, halogen ($C_1$-$C_6$) alkoxy or $SO_2NR^8R^9$.

Another embodiment of the invention are compounds wherein $R^1$ is an optionally partly or fully saturated monocyclic 5-membered heteroaryl group, which is optionally substituted one or more times, identically or differently with halogen, hydroxy, $NO_2$, $NR^8R^9$, $OCF_3$, $CF_3$, cyano, —$COR^6$, $C_1$-$C_6$ alkyl, halogen($C_1$-$C_6$) alkyl, hydroxy($C_1$-$C_6$) alkyl, cyano($C_1$-$C_6$ alkyl)-, $(NR^8R^9)C_1$-$C_4$ alkyl, $(R^6OC)C_1$-$C_6$ alkyl, $[(HR^8N(OC)]C_1$-$C_6$ alkyl, $C_1$-$C_6$ alkoxy, halogen($C_1$-$C_6$) alkoxy or $SO_2NR^8R^9$.

For compounds as claimed having a mono- or bicyclic heteroaryl group $R^1$ preferred substituents of said heteroaryl group are halogen, hydroxy, $NO_2$, $NR^8R^9$, perfluoro($C_1$-$C_4$) alkyl, cyano, —$COR^6$, $COOR^7$, ($C_1$-$C_4$)alkyl, halo($C_1$-$C_4$) alkoxy, $(CH_2)_n$aryl, perfluoro($C_1$-$C_4$)alkoxy or $SO_2NR^8R^9$.)

In a more preferred embodiment, the substituents for the heteroaryl groups $R^1$ are halogen (especially fluorine and chlorine), cyano, ($C_1$-$C_3$)alkyl, hydroxy($C_1$-$C_3$)alkyl, cyano ($C_1$-$C_3$)alkyl, ($C_1$-$C_3$)alkoxy, —$(CH_2)_n$aryl.

Most preferred is independent substitution of the heteroaryl group $R^1$, one or more times same or different with chlorine, cyano, methyl, methoxy, hydroxymethyl, cyanomethyl, and benzyl.

A particular embodiment of the invention are compounds according to the Claims 1-7, wherein $R^1$ means an unsubstituted heteroaryl group.

A further embodiment of the invention are compounds according to Claims 1-7, wherein $R^1$ means an aromatic optionally substituted heteroaryl group.

A further embodiment are compounds of the general formula I according to Claims 1-7, wherein $R^1$ means a substituted aryl or more preferred a phenyl group.

An embodiment of the present invention comprises compounds of the general formula I according to Claims 1-7, wherein the heteroaryl group $R^1$ means a 5- or 6-membered ring.

A quite particular embodiment are compounds according to Claims 1-7, wherein the heteroaryl group $R^1$ stands for a 5-membered ring.

A particular embodiment are compounds according to Claims 1-7, wherein the heteroaryl group $R^1$ stands for a 6-membered ring.

A particular embodiment are compounds according to Claims 1-7, wherein the heteroaryl group $R^1$ stands for a bicyclic ring.

The groups —$(CH_2)_n$-aryl and —$(CH_2)_n$-heteroaryl for $R^2$ and $R^4$ can themselves optionally be substituted one or more times, identically or differently with halogen, hydroxy, $C_1$-$C_6$ alkyl, halogen-($C_1$-$C_4$) alkyl $C_1$-$C_6$ alkoxy, halogen($C_1$-$C_4$) alkoxy, $NR^8R^9$, $COOR^7$ or $SO_2NR^8R^9$.

The heteroarylene group, analogously to the arylene group, is a divalent heteroaryl group, bound into the basic skeleton at two different positions, for example the heteroarylene group Q, which is bound at one position to the sulfoximine residue and at another position to the aminopyrimidine, for which all definitions stated under the definition for heteroaryl group likewise apply.

Monocyclic heteroarylene groups are preferred.

In one embodiment of the invention, these are 5-membered heteroarylene groups.

A further embodiment relates to 6-membered heteroarylene groups, in particular pyridinediyl.

Heterocyclyl groups are cycloalkyl groups which contain one or several hetero atoms, such as oxygen, sulphur and/or nitrogen instead of the carbon atoms. Preferred are those heterocyclyl groups with 3 to 8 ring atoms and 1-4 hetero atoms, wherein for the different ring sizes different maximum numbers of hetero atoms are allowed, in order to exclude nonsensical chemical compounds:

For the 3-membered ring heterocyclyl group, only one hetero atom selected from the aforesaid group is allowed.

For the 4-membered ring heterocyclyl group, an oxygen- or sulphur atom or 1-2 nitrogen atoms or 2 hetero atoms selected from oxygen, sulphur or nitrogen, wherein two oxygen- and/or sulphur atoms must not be simultaneously contained, are allowed, For the 5-membered ring heterocyclyl group, maximally one oxygen or sulphur atom, or up to four nitrogen atoms are allowed, as well as a total of 1-3 hetero atoms, where one hetero atom thereof is oxygen or sulphur and the other hetero atoms are nitrogen atoms.

For 6-membered ring heterocyclyl groups, those with 1-2 hetero atoms are preferred, where the hetero atoms are to be selected from the group oxygen, sulphur or nitrogen.

Depending on ring size, the heterocyclyl groups can contain 1-2 double bonds. As examples, piperidinyl, morpholino, thiomorpholino, piperazinyl, tetrahydrofuranyl, tetrahydrothienyl, dihydrofuranyl, dihydrothienyl, imidazolidinyl, dihydrotetrazolyl or a pyrrolidinyl group may be mentioned. Preferred heterocyclic rings in the sense of the present invention are tetrahydrofuranyl, tetrahydropyranyl, pyrrolidinyl, morpholino, piperidinyl.

The heterocyclyl group can be substituted one or more times. Possible substituents are for example substituents from the group optionally substituted $C_1$-$C_6$ alkyl group, $C_1$-$C_6$ alkoxy group, hydroxy, $NR^8R^9$, halogen, CN, CO, $COOR^7$, $SO_2NR^8R^9$ or $COR^6$. The substituents can optionally also be bound to the nitrogen atom; then N-oxides are also included in the definition. These rings may be connected to the rest of the molecule via a carbon atom or a nitrogen atom.

Even when they themselves are substituents, the alkyl and the alkoxy group can optionally be substituted with halogen, hydroxy or CO.

The alkyl groups can be linear or branched and for example mean methyl, ethyl, n-propyl, n-butyl, n-pentyl, n-hexyl, n-heptyl, n-octyl, iso-propyl, iso-butyl, sec-butyl, tert-butyl, iso-pentyl, neo-pentyl, 2-methylpentyl, 2,2-dimethylbutyl, 2,3-dimethylbutyl, 2-methylhexyl, 2,2-dimethylpentyl, 2,2, 3-trimethylbutyl or 2,3,3-trimethylbutyl group.

They can themselves independently of one another be substituted one or more times with substituents such as for example halogen, hydroxy, amino, cyano, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, ($C_1$-$C_6$)alkoxy-($C_1$-$C_6$) alkyl, $C_1$-$C_6$ alkoxy-($C_1$-$C_6$)alkoxy-($C_1$-$C_6$)alkyl, —$COR^6$, COO—($C_1$-$C_6$)alkylO—($C_1$-$C_6$) alkyl, —($C_1$-$C_6$)alkylO(CO)($C_1$-$C_6$)alkyl, ($C_1$-$C_6$)alkyl(CO)O—, $COOR^7$, ($C_3$-$C_{10}$)cycloalkyl, a =N—OH group, —$NR^8R^9$, —NH($C_1$-$C_6$) alkyl, —N[($C_1$-$C_6$)alkyl]$_2$, —NH(CO)($C_1$-$C_6$)alkyl, —N[(CO)($C_1$-$C_6$ alkyl)]$_2$, —NH(CO)$C_1$-$C_6$ alkylene-NH—(CO)aryl, —NH—(CH$_2$)$_n$—($C_3$-$C_{10}$)cycloalkyl, $SO_2NR^8R^9$, —(CH$_2$)$_n$-aryl, —(CH$_2$)$_n$-heteroaryl or —(CH$_2$)$_n$—($C_3$-$C_8$)-heterocyclyl.

Preferred substituents are halogen, hydroxyl, cyano, $CF_3$, $COR^6$, —$NR^8R^9$, ($C_1$-$C_6$)alkoxy-($C_1$-$C_6$)alkyl, COO—$C_1$-$C_6$ alkylO—$C_1$-$C_6$alkyl, $SO_2NR^8R^9$, —($C_3$-$C_{10}$)cycloalkyl, —(CH$_2$)$_n$—($C_3$-$C_8$)-heterocyclyl, —NH(CO)($C_1$-$C_6$)alkyl, —(CH$_2$)$_n$-aryl and a =N—OH group.

When it is chemically possible for the substituents, then all variations via which they can be bound to the chain are also part of the invention, thus for example, a heterocyclyl group which contains a nitrogen atom can be bound to the alkyl chain via a nitrogen atom or via a carbon atom.

For the alkylene group, the same definitions apply as for the alkyl groups with the single difference that they are divalent.

Hydroxyalkyl groups should be understood to mean linear or branched alkyl groups which contain 1-3 hydroxy groups at any positions in the chain. Dihydroxyalkyl groups can bear the two hydroxy groups at any positions in the chain.

Cyanoalkyl groups should be understood to mean linear or branched alkyl groups which contain 1-3 cyano groups at any positions in the chain.

Halogen, halo or halogen atom should be understood to mean fluorine, chlorine, bromine and iodine. Fluorine, chlorine and bromine are preferred. Especially preferred are the halogen atoms for each residue as disclosed in the examples.

Haloalkyl groups should be understood to mean linear or branched alkyl groups which contain 1-3 identical or different halogen atoms at any positions in the chain.

Perfluoro($C_1$-$C_6$) alkyl for example stands for $CF_3$, $C_2F_5$, or linear or branched residues $C_3F_7$, $C_4F_9$, $C_5F_{11}$; the $CF_3$ group is preferred.

The alkenyl groups can be linear or branched such as for example vinyl, allyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl. They can themselves be substituted with substituents such as for example halogen, hydroxy, amino, cyano, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $COOR^7$, $C_3$-$C_{10}$ cycloalkyl, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH—(CH$_2$)$_n$—$C_3$-$C_{10}$ cycloalkyl, —(CH$_2$)$_n$-aryl, —(CH$_2$)$_n$-heteroaryl or —(CH$_2$)$_n$—($C_3$-$C_8$) heterocyclyl.

The alkynyl groups can be linear or branched and for example mean C≡C, —CH$_2$—C≡CH, —C≡C—CH$_3$, —CH(CH$_3$)—C≡CH, —C≡C—CH$_2$(CH$_3$), —C(CH$_3$)$_2$—C≡CH, —C≡C—CH(CH$_3$)$_2$—, —CH(CH$_3$)—C≡C—CH$_3$, or —CH$_2$—C≡C—CH$_2$(CH$_3$).

They can themselves be substituted with substituents such as for example halogen, hydroxy, amino, cyano, $C_1$-$C_6$ alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $COOR^7$, $C_3$-$C_{10}$ cycloalkyl, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH—(CH$_2$)$_n$—$C_3$-$C_{10}$ cycloalkyl, —(CH$_2$)$_n$-aryl, —(CH$_2$)$_n$-heteroaryl or —(CH$_2$)$_n$—($C_3$-$C_8$) heterocyclyl.

Cycloalkyl should be understood to mean monocyclic alkyl rings such as cyclopropyl, cyclobutyl, cyclopentyl, cyclohexyl or cycloheptyl, cyclooctyl, cyclononyl or cyclodecyl, but also bicyclic and tricyclic rings. They can themselves be substituted with substituents such as for example halogen, hydroxy, $C_1$-$C_6$ alkyl, $C_1$-$C_6$ alkoxy, —$NR^8R^9$, $COOR^7$, perfluoro($C_1$-$C_6$) alkyl $SO_2NR^8R^9$, or —O-perfluoro($C_1$-$C_6$) alkyl. Like the alkyl group, the cycloalkyl group can also be interrupted by one or several —$NR^8$— groups and/or oxygen and/or sulphur atoms and/or contain one or several (CO) groups and/or double bonds. The term "and/or" means that either both or also only one of the two groups can be contained in the ring: sulphur atom and/or oxygen atom both includes cycloalkyl groups with only one sulphur atom or only one oxygen atom and also cycloalkyl groups with one sulphur atom and one oxygen atom. The cycloalkyl ring optionally contains 1-3 hetero atoms.

If the groups —(CH$_2$)$_n$aryl, —(CH$_2$)$_n$heteroaryl or —(CH$_2$)$_n$heterocyclyl are themselves substituted, then the substituent can both be located on the ring and also on the chain.

The alkoxy groups can be linear or branched and stand for a methoxy, ethoxy, n-propoxy, iso-propoxy, n-butoxy, iso-butoxy, tert.-butoxy or n-pentoxy, 2,2-dimethylpropoxy, 2-methylbutoxy or 3-methylbutoxy group.

A methoxy or ethoxy group is preferred.

Possible substituents for the alkoxy groups are hydroxy, NR$^8$R$^9$, cyano, halogen, CF$_3$, C$_1$-C$_6$ alkoxy, NR$^7$—(CO)O (C$_1$-C$_3$) alkyl, —NR$^7$—(CO)—NR$^8$R$^9$ or —NR$^7$—SO$_2$— (C$_1$-C$_3$), which independently of one another can optionally occur one or several times.

The perfluoroalkoxy group —O-perfluoro(C$_1$-C$_6$)alkyl for example stands for OCF$_3$, OC$_2$F$_5$, or linear or branched residues OC$_3$F$_7$, OC$_4$F$_9$ or OC$_5$F$_{11}$; the OCF$_3$ group is preferred.

The alkylthio groups can be linear or branched and stand for a methylthio, ethylthio, n-propylthio, iso-propylthio, n-butylthio, iso-butylthio, tert.-butylthio or n-pentylthio, 2,2-dimethylpropylthio, 2-methylbutylthio or 3-methylbutylthio group.

A methylthio or ethylthio group is preferred.

In the case of the group NR$^8$R$^9$, if R$^8$ and R$^9$ together with the nitrogen atom form a ring which contains 1-3 further hetero atoms, then those rings which contain several oxygen and/or sulphur atoms directly adjacent to one another are excluded. Piperidine, pyrrolidine, morpholine and piperazine are preferred. For X according to the invention the NH group is preferred.

The ring which is formed from X and R$^2$ can contain hetero atoms such as for example oxygen, sulphur or —NR$^8$ and be bound to the pyrimidine ring via a nitrogen atom. If X means oxygen or sulphur, no ring formation is possible. The ring can optionally be substituted one or more times, identically or differently with hydroxy, C$_1$-C$_6$ alkyl, C$_1$-C$_6$ alkoxy, halogen or the group —NR$^8$R$^9$.

If R$^4$ and R$^5$ form a ring, this ring can be 5-8-membered, preferably 5-6-membered. The ring can be substituted one or more times, identically or differently. Possible substituents are hydroxy, C$_1$-C$_{10}$ alkyl, C$_1$-C$_{10}$ alkoxy or NR$^8$R$^9$. 0-2 substituents are preferred. The ring can contain 1-2 double bonds.

An embodiment of the invention are compounds of the general formula I according to Claims 1-7, wherein R$^4$ and R$^5$ do not form a ring but have the other meanings stated above.

The following groups used for the meaning of R$^4$ are often abbreviated by the skilled person with a letter code which can be seen below brackets: a trimethylsilyl group (TMS), tert.-butyl-dimethylsilyl group (TBDMS), tert.-butyl-diphenylsilyl group (TBDPS) or triethylsilyl group (TES).

Q can mean arylene or heteroarylene. In a particular embodiment of the invention, Q means arylene, preferably phenylene. Possible substituents are a hydrogen atom, hydroxy, halogen, CF$_3$, OCF$_3$ or the group —NR$^8$R$^9$ or a C$_1$-C$_6$ alkyl group, C$_3$-C$_6$ cycloalkyl group or C$_1$-C$_6$ alkoxy group which is optionally substituted one or more times, identically or differently with halogen, hydroxy, C$_1$-C$_6$ alkoxy or the group —NR$^8$R$^9$.

Q can bear 0-4 substituents, which can be the same or different.

0-2 substituents, preferably 0-1, are preferred for Q.

In one embodiment of the invention Q is an unsubstituted phenylene moiety.

Should Q bear a substituent, then halogen, especially bromine is most preferred

The present invention also includes the salts of the compounds according to the invention with physiologically compatible acids or bases.

If an acidic function is present, the physiologically compatible salts of organic and inorganic bases are suitable as salts, for example the readily soluble alkali metal and alkaline earth metal salts and also N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base or 1-amino-2,3,4-butanetriol.

If a basic function is present, the physiologically compatible salts of organic and inorganic acids such as hydrochloric acid, sulphuric acid, phosphoric acid, citric, acid, tartaric acid as well as salts like pivalate, maleate, fumarate, tartrate, benzoate, mesylate, or succinate and the like are suitable.

All possible forms in which the compounds according to the invention can occur, such as for example solvates, hydrates and N-oxides are likewise objects of the present invention.

Owing to the presence of at least one asymmetric centre, the compounds according to the invention of the general formula I occur as stereoisomers. All possible enantiomers, and if several asymmetric centres are present all possible diastereomers (e.g.: RR, RS, SR, SS), both in enantiomerically pure form and also as racemates, both as pure diastereomers and also as diastereomer mixtures, are objects of the present invention.

Prodrugs are defined as compounds that are cleaved into the compounds that are claimed by metabolism in the organism or by contact with the organism.

The prodrugs are subject to at least one biotransformatory step until the claimed compounds are released, which then exert their pharmacological effect. Prodrugs of the presently claimed compounds are also an aspect of the invention.

Biological Background

The compounds according to the invention are for example suitable as inhibitors of the kinases CDK, Aurora A, Aurora B, Aurora C, Tie-2, ITK and Tyk-2.

In eukaryotic cells, many biological processes such as for example DNA replication, energy metabolism, and cell growth or differentiation are regulated by reversible phosphorylation of proteins. The phosphorylation level of a protein inter alia has an influence on the function, location or stability of proteins. The protein kinase and protein phosphatase enzyme families are respectively responsible for the phosphorylation and dephosphorylation of proteins.

The Aurora kinases, the cyclin-dependent kinases (CDK) and the checkpoint kinases (Chk) are enzyme families which play an important part in the regulation of the cell cycle and thus represent particularly interesting targets for the development of small inhibitory molecules. Inhibitors of the Aurora, CDK or Chk kinases can be used for the treatment of cancer or other diseases which are caused by disorders of cell proliferation.

Receptor tyrosine kinases and their ligands are decisively involved in a large number of cellular processes which are involved in the regulation of the growth and the differentiation of cells. Of particular interest here are the vascular endothelial growth factor (VEGF)/VEGF receptor system, the kit ligand/kit system and the Tie ligand/Tie system. In pathological situations which are associated with intensified new growth of blood vessels (neovascularisation), such as for example tumour diseases, increased expression of angiogenic growth factors and their receptors was found. Inhibitors of the VEGF/VEGF receptor system and of the Tie ligand/Tie system can inhibit the formation of a blood vessel system in tumours, hence cut the tumour off from the oxygen and nutrient supply and thus inhibit the tumour growth. The receptor tyrosine kinase c-kit is a proto-oncogen, which is expressed in mutated form in many malignant tumours such as for example gastrointestinal stromal tumours, mast cell leukaemias, myeloid leukaemias and ovarian carcinoma. The tumour-promoting action of c-kit is caused by activating mutations, so that even without binding of the ligand to c-kit, growth signals are constantly given to the tumour cells.

Cell Cycle Kinases

The eukaryotic cell division cycle ensures the duplication of the genome and its distribution to the daughter cells, in that it passes through a coordinated and regulated sequence of events. The cell cycle is divided into four consecutive phases: the G1 phase represents the time before the DNA replication, in which the cell grows and is receptive to external stimuli. In the S phase, the cell replicates its DNA and in the G2 phase it prepares for entry into mitosis. In the mitosis (M phase) the replicated DNA is separated and cell division completed. In the control and regulation of the cell cycle, members of the kinase enzyme class play an important part, in particular the CDK kinases, the Aurora kinases and the Chk kinases.

Commensurately with the exceptional importance of the cell division cycle, the operation of the cycle is strictly regulated and controlled. The enzymes which are necessary for progression through the cycle must be activated at the right time point, and also switched off again as soon as the relevant phase has been passed through.

Appropriate control points ("checkpoints") arrest the progression through the cell cycle if DNA damage is detected, or the DNA replication or the formation of the spindle apparatus is not yet finished. The activity of the CDK is directly controlled by various mechanisms, such as synthesis and degradation of the cyclin, complexing of the CDK with the various cyclins, phosphorylation and dephosphorylation of regulatory threonine and tyrosine residues, and the binding of natural inhibitory proteins. While the quantity of the CDK protein in a proliferating cell is relatively constant, the quantity of the individual cyclins oscillates with passage through the cycle. Thus for example the expression of CycD during the early G1 phase is stimulated by growth factors, and the expression of CycE after the "restriction point" has been passed is induced by the activation of the transcription factors of the E2F type. The cyclins themselves are degraded by ubiquitin-mediated proteolysis. Activating and inactivating phosphorylations regulate the activity of the CDKs, for example CDK-activating kinases (CAKs) phosphorylate Thr160/161 of CDK1, whereas the Wee1/Myt1 kinase family inactivate CDK1 by phosphorylation of Thr14 and Tyr15. These inactivating phosphorylations can be abolished again by cdc25 phosphatases. The regulation of the activity of the CDK/Cyc complex by two families of natural CDK inhibitor proteins (CKIs), the protein products of the p21 gene family (p21, p27, p57) and the p16 gene family (p15, p16, p18, p19) is of great significance. Members of the p21 family bind to cyclin complexes of the CDKs 1, 2, 4 and 6, but only inhibit complexes which contain CDK1 or CDK2. Members of the p16 family are specific inhibitors of the CDK4 and CDK6 complexes.

Above this complex, direct regulation of the activity of the CDKs lies the checkpoint regulation level. Checkpoints allow the cell to track the orderly progress of the individual phases during the cell cycle. The most important checkpoints lie at the transition from G1 to S and from G2 to M. The G1 check-point ensures that the cell does not start DNA synthesis unless it is appropriately nourished, is interacting correctly with other cells or the substrate, and its DNA is intact. The G2/M checkpoint ensures the complete replication of the DNA and the formation of the mitotic spindle, before the cell goes into mitosis. The G1 checkpoint is activated by the gene product of the p53 tumour suppressor gene. p53 is activated after detection of changes in the metabolism or the genomic integrity of the cell and can trigger either stoppage of the cell cycle progression or apoptosis. In this, the transcriptional activation of the expression of the CDK inhibitor protein p21 by p53 plays a decisive part. A second branch of the G1 checkpoint comprises the activation of the ATM and Chk1 kinases after DNA damage due to UV light or ionising radiation and finally the phosphorylation and the subsequent proteolytic degradation of the cdc25A phosphatase (Mailand N. et al. (2000). Rapid destruction of human cdc25A in response to DNA damage. *Science* 288, 1425-1429). This results in arrest of the cell cycle, since the inhibitory phosphorylation of the CDK is not removed. After activation of the G2/M checkpoint due to damage to the DNA, both mechanisms are similarly involved in stopping progression through the cell cycle.

Loss of the regulation of the cell cycles and loss of the function of the checkpoints are characteristics of tumour cells. The CDK-Rb signal path is affected by mutations in over 90% of human tumour cells. These mutations, which finally lead to the inactivating phosphorylation of the RB, include the overexpression of D and E cyclins due to gene amplification or chromosomal translocations, inactivating mutations or deletions of CDK-inhibitors of the p16 type, and increased (p27) or decreased (CycD) protein degradation. The second group of genes, which are affected by mutations in tumour cells, codes for components of the checkpoints. Thus p53, which is essential for the G1 and G2/M checkpoints, is the most commonly mutated gene in human tumours (ca. 50%). In tumour cells which express p53 without mutation, it is often inactivated owing to greatly increased protein degradation. Similarly, the genes of other proteins necessary for the function of the checkpoints are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2 and the transcriptional repression of CDK2 expression by antisense oligonucleotides cause a stoppage of the cell cycle progression. (2) The inactivation of the CycA gene in mice is lethal. (3) The disturbance of the function of the CDK2/CycA complex in cells by means of cell-permeable peptides led to tumour cell-selective apoptosis (Chen Y. N. P. et al. (1999). Selective killing of transformed cells by cyclin/cyclin-dependent kinase 2 antagonists. *Proc. Natl. Acad. Sci. USA* 96, 4325-4329).

Changes in cell cycle control are not only involved in cancer diseases. The cell cycle is activated by a number of viruses, both transforming and nontransforming, in order to enable the proliferation of the viruses in the host cell. The erroneous entry of normally post-mitotic cells into the cell cycle is linked with various neurodegenerative diseases.

The mechanisms of cell cycle regulation, changes in these in diseases and a large number of approaches to the development of inhibitors of the cell cycle progression and especially of the CDKs have already been exhaustively described in summary in several publications (Sielecki T. M. et al. (2000). Cyclin-dependent kinase inhibitors: useful targets in cell cycle regulation. *J. Med. Chem.* 43, 1-18; Fry D. W. & Garrett M. D. (2000). Inhibitors of cyclin-dependent kinases as therapeutic agents for the treatment of cancer. *Curr. Opin. Oncol. Endo. Metab. Invest. Drugs* 2, 40-59; Rosiania G. R. & Chang Y. T. (2000). Targeting hyperproliferative disorders with cyclin dependent kinase inhibitors. *Exp. Opin. Ther. Patents* 10, 215-230; Meijer L. et al. (1999). Properties and potential applications of chemical inhibitors of cyclin-dependent kinases. *Pharmacol. Ther.* 82, 279-284; Senderowicz A. M. & Sausville E. A. (2000). Preclinical and clinical development of cyclin-dependent kinase modulators. *J. Natl. Cancer Inst.* 92, 376-387).

Accordingly, compounds according to the invention can inhibit cyclin-dependent kinases, such as CDK1, CDK2, CDK3, CDK4, CDK5, CDK6, CDK7, CDK8 and CDK9, cyclin-dependent kinases. This action contributes to the fact that the compounds according to the invention can be used in the treatment of cancer, angiofribroma, arthritis, eye diseases, autoimmune diseases, chemotherapeutic agent-induced alopecia and mucositis, Crohn's disease, endometriosis, fibrotic diseases, haemangioma, cardiovascular diseases, infectious diseases, nephrological diseases, chronic and acute neurodegenerative diseases, and of damage to the nerve tissue, viral infections, for the inhibition of the reocclusion of blood vessels after balloon catheter treatment, in vascular prosthesis or after the use of mechanical devices for keeping blood vessels open, such as for example stents, as immuno-suppressants, for the support of scar-free wound healing, in senile keratosis and in contact dermatitis, wherein cancer should be understood to mean solid tumours, tumour or metastasis growth, Kaposi's sarcoma, Hodgkin's disease and leukaemia, arthritis to mean rheumatoid arthritis, eye diseases to mean diabetic retinopathy and neovascular glaucoma, autoimmune diseases to mean psoriasis, alopecia and multiple sclerosis, fibrotic diseases to mean liver cirrhosis, mesangial cell proliferative diseases and arteriosclerosis, infectious diseases to mean diseases caused by unicellular parasites, cardiovascular diseases to mean stenoses, such as for example stent-induced restenosis, arterioscleroses and restenoses, nephrological diseases to mean glomerulonephritis, diabetic nephropathy, malignant nephrosclerosis, thrombotic microangiopathic syndrome, transplantation rejections and glomerulopathy, chronic neurodegenerative diseases to mean Huntington's disease, amyotrophic lateral sclerosis, Parkinson's disease, AIDS dementia and Alzheimer's disease, acute neurodegenerative diseases to mean ischaemias of the brain and neural traumata, and viral infections to mean cytomegalus infections, herpes, hepatitis B or C, and HIV diseases.

CDK-Kinases

The cyclin-dependent kinases (CDK) are an enzyme family which plays an important part in the regulation of the cell cycle and thus represents an interesting target. Selective inhibitors of the CDKs (such as for example CDK1, CDK2, CDK3, CDK4, CDK5, CDK6, CDK7, CDK8 and CDK9) can be used for the treatment of cancer or other diseases which are caused by cell proliferation disorders.

Accordingly, compounds according to the invention can inhibit cyclin-dependent kinases, such as CDK1, CDK2, CDK3, CDK4, CDK5, CDK6, CDK7, CDK8 and CDK9, or cyclin-dependent kinases. Hence the compounds according to the invention can be used for the treatment of cancer, angiofribroma, arthritis, eye diseases, autoimmune diseases, chemotherapeutic agent-induced alopecia and mucositis, Crohn's disease, endometriosis, fibrotic diseases, haemangioma, cardiovascular diseases, infectious diseases, nephrological diseases, chronic and acute neurodegenerative diseases, and of damage to the nerve tissue, viral infections, for the inhibition of the reocclusion of blood vessels after balloon catheter treatment, in vascular prosthesis or after the use of mechanical devices for keeping blood vessels open, such as for example stents, as immuno-suppressants, for the support of scar-free healing, in senile keratosis and in contact dermatitis, wherein cancer should be understood to mean solid tumours, tumour or metastasis growth, Kaposi's sarcoma, Hodgkin's disease and leukaemia, arthritis to mean rheumatoid arthritis, eye diseases to mean diabetic retinopathy and neovascular glaucoma, autoimmune diseases to mean psoriasis, alopecia and multiple sclerosis, fibrotic diseases to mean liver cirrhosis, mesangial cell proliferative diseases and arteriosclerosis, infectious diseases to mean diseases caused by unicellular parasites, cardiovascular diseases to mean stenoses, such as for example stent-induced restenosis, arterioscleroses and restenoses, nephrological diseases to mean glomerulonephritis, diabetic nephropathy, malignant nephrosclerosis, thrombotic microangiopathic syndrome, transplantation rejections and glomerulopathy, chronic neurodegenerative diseases to mean Huntington's disease, amyotrophic lateral sclerosis, Parkinson's disease, AIDS dementia and Alzheimer's disease, acute neurodegenerative diseases to mean ischaemias of the brain and neural traumata, and viral infections to mean cytomegalus infections, herpes, hepatitis B or C, and HIV diseases.

Aurora Kinases

In the human organism, the Aurora kinase family consists of three members: Aurora-A, Aurora-B and Aurora-C. Functional orthologues are known in all eukaryotic organisms, such as for example *Xenopus laevis, Drosophila* and *Saccharomyces Cerevisiae* (see also: Marumoto et al. 2005, Carmena & Earnshaw, 2003; Katayama et al., 2003; Giet et al. 2005; Meraldi et al. 2004; Andrews et al. 2003; Keen & Taylor 2004; Mortlock et al. 2005).). All Aurora kinases are expressed in dividing body cells predominantly during mitosis, and Aurora-C in particular is strongly expressed in the testis.

The Aurora kinases regulate important processes during cell division (mitosis), inter alia the condensation and orientation of the chromosomes, the formation of the mitotic spindle apparatus, the interactions between the mitotic spindles and the chromosomes and the final division of the parent cell into two daughter cells in the last step of mitosis, cytokinesis. The three members of the Aurora family, Aurora-A, B and C possess a variable protein domain at the N-terminus, a conserved catalytic kinase domain and a short region at the C-terminal end. The variable N-terminus presumably controls the localisation via the interaction with other proteins, the catalytic kinase domains phosphorylate the respective substrate proteins and the C-terminal part mediates the proteolytic degradation of the Aurora kinases after the mitosis. The latter restricts the expression of the Aurora kinases to the mitosis phase in the cell cycle.

The activation of the Aurora kinases takes place on the one hand by phosphorylation of a conserved threonine residue in the activation loop and on the other hand via the binding of other proteins, such as for example TPX2 or Ajuba to Aurora-A (Bayliss et al. 2003), or INCENP to Aurora-B or -C (Sessa et al. 2005).

Aurora-A is located on the centrosomes and the spindle microtubuli, where it phosphorylates various substrate proteins, inter alia the kinesin Eg5, TACC, PP1. The exact mechanisms of the genesis of the spindle apparatus and the role of Aurora-A in this are however still largely unclear.

Aurora-B is part of a multiprotein complex, which is located on the centrosome structure of the chromosomes and as well as Aurora-B inter alia contains INCENP, survivin and borealin/dasra B (Vagnarelli & Earnshaw 2004). The kinase activity of Aurora-B ensures that before the division of the chromosome pair all linkages to the microtubulin spindle apparatus are correct (so-called spindle checkpoint). Substrates of Aurora-B here are inter alia histone H3 and MCAk. After separation of the chromosomes, Aurora-B changes its location and during the last mitosis phase (cytokinesis) can be found at the still remaining linking bridge between the two daughter cells. By phosphorylation of its substrates MgcRac-GAP, vimentin, desmin, the light regulatory chain of myosin, and others, Aurora-B regulates the sealing off of the daughter cells.

From its amino acid sequence, location, substrate specificity and function, Aurora-C is very similar to Aurora-B (Li et al. 2004, Sasai et al. 2004, Chen et al. 2005, Yan et al. 2005). The main difference between Aurora-B and Aurora-C is the strong overexpression of Aurora-C in the testis (Tseng et al. 1998, Bernard et al. 1998).

The essential function of the Aurora kinases in mitosis makes them interesting target proteins for the development of small inhibitory molecules for the treatment of cancer or other diseases which are caused by cell proliferation disorders. Convincing experimental data indicate that inhibition of the Aurora kinases in vitro and in vivo prevents the progression of cellular proliferation and triggers programmed cell death (apoptosis). This could be demonstrated by means of (1) siRNA technology or (2) overexpression of a dominant negative Aurora kinase, and also (3) with small chemical molecules which specifically inhibit Aurora kinases (Hirota et al. 2003; Du & Hannon 2004; Yokoyama et al. 2005, Honda et al. 2003, Sasai et al. 2004; Hauf et al. 2003; Ditchfield et al. 2003; Harrington et al. 2004).

The inactivation of Aurora kinases has the result that (1) the mitotic spindle apparatus is not formed, or is formed incorrectly (mainly in case of Aurora-A inhibition) and/or that (2) through blocking of the spindle checkpoint no separation or incorrect separation of the sister chromatids takes place (mainly in case of Aurora-B/-C inhibition) and/or that (3) the separation of the daughter cells is not completed (mainly in case of Aurora-B/-C inhibition). Finally, these consequences (1-3) of the inactivation of Aurora kinases individually or in combinations lead to aneuploidy and/or polyploidy and finally immediately or after repeated mitoses to a non-viable state or to the programmed cell death of the proliferating cells (mitotic catastrophe).

Use 1

The compounds according to the invention inhibit Aurora kinases, which is also the basis of their action for example against cancer, such as solid tumours and leukaemia, autoimmune diseases such as psoriasis, alopecia, and multiple sclerosis, chemotherapeutic agent-induced alopecia and mucositis, cardiovascular diseases, such as stenoses, arteriosceroses and restenoses, infectious diseases, for example caused by unicellular parasites, such as trypanosoma, toxoplasma or plasmodium, or by fungi, nephrological diseases, such as for example glomerulonephritis, chronic neurodegenerative diseases, such as Huntington's disease, amyotrophic lateral sclerosis, Parkinson's disease, AIDS dementia and Alzheimer's disease, acute neurodegenerative diseases, such as ischaemias of the brain and neural traumata, viral infections, such as for example cytomegalus infections, herpes, hepatitis B and C, and HIV diseases.

Use 2

These actions contribute to the fact that the compounds according to the invention can be used in the treatment of cancer, angiofribroma, arthritis, eye diseases, autoimmune diseases, chemotherapeutic agent-induced alopecia and mucositis, Crohn's disease, endometriosis, fibrotic diseases, haemangioma, cardiovascular diseases, infectious diseases, nephrological diseases, chronic and acute neurodegenerative diseases, and of damage to the nervous tissue, viral infection, for the inhibition of the reocclusion of blood vessels after balloon catheter treatment, in vascular prosthesis or after the use of mechanical devices for keeping blood vessels open, such as for example stents, as immuno-suppressants, for the support of scar-free healing, in senile keratosis and in contact dermatitis, wherein cancer should be understood to mean-solid tumours, tumour or metastasis growth, Kaposi's sarcoma, Hodgkin's disease and leukaemia, arthritis to mean rheumatoid arthritis, eye diseases to mean diabetic retinopathy and neovascular glaucoma, autoimmune diseases to mean psoriasis, alopecia and multiple sclerosis, fibrotic diseases to mean liver cirrhosis, mesangial cell proliferative diseases and arteriosclerosis, infectious diseases to mean diseases caused by unicellular parasites, cardiovascular diseases to mean stenoses, such as for example stent-induced restenosis, arterioscleroses and restenoses, nephrological diseases to mean glomerulonephritis, diabetic nephropathy, malignant nephrosclerosis, thrombotic microangiopathic syndrome, transplantation rejections and glomerulopathy, chronic neurodegenerative diseases to mean Huntington's disease, amyotrophic lateral sclerosis, Parkinson's disease, AIDS dementia and Alzheimer's disease, acute neurodegenerative diseases to mean ischaemias of the brain and neural traumata, and viral infections to mean cytomegalus infections, herpes, hepatitis B or C, and HIV diseases.

ITK (T-Cell Inducible Kinase)

Itk belongs to the TEC kinase family (Schwartzberg et al. 2005. Tec-Family kinases: Regulators of T-helper cell differentiation. Nature Immunol Reviews, 5:284). As well as ITK (also described as EMT or TSK), BTK, RLK, BMX and TEC itself are grouped into this family (Smith et al. 2001. The TEC family of cytoplasmic tyrosine kinases: mammalian Btk, Bmx, Itk, Tec, Txk and homologues in other species. Bioassays, 23:436). Kinases, like other signal-transducing molecules, also possess a modular protein structure, which allows classification into different (protein) families. TEC kinases are characterized by a conserved domain structure: they possess an N-terminal pleckstrin homology domain (PH domain), which is followed by a TEC homology domain with one to two proline-rich segments. In addition, all TEC kinases express at least one SH2 and one SH3 domain, which is followed by the catalytic (kinase) domain (Berg et al. 2005. TEC family kinases in T lymphocyte development and function. Annu. Rev. Immunol. 23:549).

After binding of the T cell receptor to the MHC-bound antigenic peptide on the antigen-presenting cell, as one of the first steps the tyrosine kinase LCK is activated, which phosphorylates the ζ-chain of the TZR complex. A further tyrosine kinase—ZAP-70—binds to the phosphorylated ζ-chain. ZAP-70 induces a whole cascade of different tyrosine phosphorylations (inter alia the adaptor proteins LAT and SLP-76) at the end of which stands the activation of phospholipase C-γ1 (PLC-γ1) (Samelson, L. E. 2002. Signal transduction mediated by the T cell antigen receptor: the role of adaptor proteins. Annu. Rev. Immunol. 20:371; Kane et al. 2000. Signal transduction by the TCR for antigen. Curr. Opin. Immunol. 12:242). PLC-γ1 is a central enzyme for the mobilisation of $Ca^{2+}$ and the activation of MAP kinases and transcription factors (Rhee et al. 1997. Regulation of phosphoinositide-specific phospholipase C isozymes. J. Biol. Chem., 272:15045). ITK is phosphorylated in T cells by the SRC kinase LCK. Phosphorylated ITK is then capable of associating with the adaptor molecules SLP and LAT and is thus brought into the spatial vicinity of PLC-γ1. It has since been unambiguously shown that ITK thereupon phosphorylates PLC-γ1 on tyrosine residues and thus activates it, i.e. ITK is indirectly involved in the release of the "second messenger" molecules diacylglycerine and 1,4,5-triphosphate and thus plays an important part in the regulation of a T cell-dominated immune response (Villar et al. 1999. Regulated Association between the tyrosine kinase Emt/Itk/Tsk and Phosphlipase-Cγ1 in human T lymphocytes. J. Immunol, 163:6435). Thus for example ITK "knockout" mice express markedly less tyrosine-phosphorylated PLC-γ1, display a decreased influx of $Ca^{2+}$ and, directly coupled with this, a markedly decreased release of T cell-specific cytokines such as for example IL-2 or even IFN-γ (Schaeffer et al. 1999. Requirements for Tec kinases Rlk an Itk in T cell receptor signaling and immunity. Science, 284:638).

As well as the regulation of PLC-γ1 dependent signal paths by ITK, ITK also plays an important part in the reorganisation of the cytoskeleton (Finkelstein et al. 2004. Tec kinases: shaping T cell-activation trough actin. Trends Cell. Biol., 14:443). When T cells are activated by antigen-presenting cells, there is a rapid redistribution of F-actin at the site of the TZR "clustering". This structure is also described as an immunological synapse. Through the interaction of ITK with VAV (a nucleotide exchange factor), ITK is directly involved in the formation of this synapse and contributes to the productive activation of T cells, which can then also be measured for example in cellular proliferation (Tybulewicz et al. 2003. Vav1: a key signal transducer downstream of the TCR. Immunol. Rev. 192:42).

ITK appears to play a special part in the stimulation of T cells, since both RLK and also TEC "knockout" mice in contrast to ITK "knockout" mice show no pronounced T cell phenotype (Liao et al. 1995. Altered T cell receptor signaling and disrupted T cell development in mice lacking Itk. Immunity, 3:757). Although it has not so far been possible to link any human pathological disease with mutations of ITK, ITK "knockout" mice have shown that the modulation of ITK results in defects in Th2 controlled diseases and a reduced pathology in allergic asthma model systems (Mueller et al. 2003. Attenuation of immunological symptoms of allergic asthma in mice lacking the tyrosine kinase Itk. J. Immunol., 170:5056). On the other hand, the expression of ITK is significantly elevated in patients with atopic dermatitis, a Th2 dependent disease, (Matsumoto et al. 2002. Identification of highly expressed genes in peripheral blood T cells from patients with atopic dermatitis. Int. Arch. Allergy Immunol. 129:327).

Hence inhibitors of ITK are particularly suitable for the treatment of diseases which are accompanied by inflammatory, allergic and/or proliferative processes, in particular of T cell-mediated skin diseases.

On account of their anti-inflammatory and additional anti-allergic, immuno-suppressant and anti-proliferative action, the compounds according to the invention of the general formula I can be used as drugs for the treatment or prophylaxis of the following disease conditions in mammals and man, in particular for local application:

(i) Pulmonary diseases which are accompanied by inflammatory, allergic and/or proliferative processes:
  Chronic obstructive pulmonary diseases of any origin, in particular bronchial asthma
  Bronchitis of various origin
  Adult respiratory distress syndrome (ARDS), acute dyspnoea syndrome
  Bronchiectases
    All forms of restrictive pulmonary disease, in particular allergic alveolitis,
  Pulmonary oedema, in particular allergic
  Sarcoidoses and granulomatoses, in particular Boeck disease (ii) Rheumatic diseases/autoimmune diseases/arthoses which are accompanied by inflammatory, allergic and/or proliferative processes:
  All forms of rheumatic disease, in particular rheumatoid arthritis, acute rheumatic fever, polymyalgia rheumatica, Behcet disease
  Reactive arthritis
  Inflammatory soft tissue diseases of other origin
  Arthritic symptoms in generative joint diseases (arthroses)
    Vitiligo
    Collagenoses of any origin, e.g. systemic lupus erythematodes, Scleroderma, polymyositis, dermatomyositis-Sjögren syndrome, Still syndrome, Felty syndrome
  Sarcoidoses and granulomatoses
  Soft tissue rheumatism (iii) Allergies or pseudoallerg. diseases which are accompanied by inflammatory, and/or proliferative processes:
  All forms of allergic reaction, e.g. Quincke oedema, hay fever, insect bite, allergic reactions to drugs, blood derivatives, contrast agents, etc., anaphylactic shock, urticaria, allergic and irritative contact dermatitis, allergic vascular diseases
  Vasculitis allergica (iv) Vascular inflammation (vasculitis)
  Panarteriitis nodosa, Arteriitis temporalis, Erythema nodosum
  Polyarteritis nodosa
  Wegner granulomatosis.
  Giant cell arteritis (v) Dermatological diseases which are accompanied by inflammatory, allergic and/or proliferative processes:
  Atopic dermatitis (mainly in children)
  All forms of eczema such as for example atopic eczema (mainly in children)
  Exanthema of any origin or dermatoses
  Psoriasis and parapsoriasis group
  Pityriasis rubra pilaris
  Erythematous diseases, triggered by various noxious agents, e.g. radiation, chemicals, burns, etc.
  Bullous dermatoses such as for example autoimmune Pemphigus vulgaris, bullous pemphigoid
  diseases of the lichenoid group,
  Pruritus (e.g. of allergic origin)
  Rosacea group Erythema exsudativum multiforme
Manifestation of vascular diseases
Hair loss such as Alopecia areata
Cutaneous lymphomas
(vi) Renal diseases which are accompanied by inflammatory, allergic and/or proliferative processes:
Nephrotic syndrome
All nephrites, e.g. glomerulonephritis
(vii) Hepatic diseases which are accompanied by inflammatory, allergic and/or proliferative processes:
acute hepatitis of various origin
chronic aggressive and/or chronic intermittent hepatitis
(viii) Gastrointestinal diseases which are accompanied by inflammatory, allergic and/or proliferative processes:
regional enteritis (Crohn's disease)
Ulcerative colitis
Gastroenteritis of other origin, e.g. indigenous sprue
(ix) Eye diseases which are accompanied by inflammatory, allergic and/or proliferative processes:
allergic keratitis, uveitis, iritis,
Conjunctivitis
Blepharitis
Neuritis nervi optici
Chorioiditis
Ophthalmia sympathica
(x) Diseases of the ear-nose-throat region which are accompanied by inflammatory, allergic and/or proliferative processes:
allergic rhinitis, hay fever
Otitis externa, e. g. caused by contact eczema
(xi) Neurological diseases which are accompanied by inflammatory, allergic and/or proliferative processes:
cerebral oedema, in particular allergic cerebral oedema
multiple sclerosis
acute encephalomyelitis
Meningitis, in particular allergic
Guillain-Barre syndrome
Alzheimer's disease
(xii) Blood diseases which are accompanied by inflammatory, allergic and/or proliferative processes such as for example: Hodgkin's disease or non-Hodgkin lymphoma, thrombocytaemias, erythrocytoses
Acquired haemolytic anaemia
Idiopathic thrombocytopaenia
Idiopathic granulocytopaenia
(xiii) Tumour diseases which are accompanied by inflammatory, allergic and/or proliferative processes
Acute lymphatic leukaemia
Malignant lymphomas
Lymphogranulomatoses
Lymphosarcomas
(xiv) Endocrine diseases which are accompanied by inflammatory, allergic and/or proliferative processes such as for example:
Endocrine orbitopathy
de Quervain thyroiditis
Hashimoto thyroiditis
Basedow disease
Granulomatous thyroiditis
Struma lymphomatosa
Autoimmune adrenalitis
diabetes mellitus, in particular type 1 diabetes
(xv) Organ and tissue transplantations, graft-versus-host-disease
(xvi) Severe shock conditions, e.g. anaphylactic shock, systemic inflammatory response syndrome (SIRS)

An object of the invention is the use of the compounds according to the invention of the general formula I for the preparation of a drug.

A further object of the invention is the use of the compounds according to the invention for the treatment of diseases which are accompanied or caused by inflammatory, allergic and/or proliferative processes.

A further object of the invention is the use of the compounds according to the invention for preparation of a medicament for the treatment of diseases which are accompanied by inflammatory, allergic and/or proliferative processes.

A further object of the invention is the use of the compounds according to the invention for the preparation of a medicament for the treatment and/or therapy of oncological diseases, in particular cancer.

A further object of the invention is the use of the compounds according to the invention for preparation of a medicament for the treatment and/or therapy of oncological diseases.

A further object of the invention is the use of the compounds of Claims for the preparation of a medicament for the treatment of tumours or metastases.

A further aspect of the invention is the Use of the compounds of the general formula I for the preparation of a medicament for the treatment of cancer, angiofribroma, arthritis, eye diseases, autoimmune diseases, chemotherapeutic agent-induced alopecia and mucositis, Crohn's disease, endometriosis, fibrotic diseases, haemangioma, cardiovascular diseases, infectious diseases, nephrological diseases, chronic and acute neurodegenerative diseases, and of damage to the nerve tissue and viral infections and for the prevention of the reocclusion of blood vessels after balloon catheter treatment, in vascular prosthesis or after the use of mechanical devices for keeping blood vessels open, such as for example stents, and as immunosuppressants, and for the support of scar-free wound healing, and in senile keratitis and in contact dermatitis. psoriasis and atopic dermatitis.

A further object of the invention is a method for the treatment of oncological diseases, in particular cancer with the compounds according to the invention.

A further object of the invention is the a method of treatment of tumours or metastases with the compounds according to the invention.

A further object of the invention a method for the treatment of diseases which are accompanied by inflammatory, allergic and/or proliferative processes with the compounds according to the invention.

The formulation of the pharmaceutical preparations on the basis of the new compounds is effected in a manner known per se, in that the active substance is processed with the carrier substances, fillers, disintegration modifiers, binders, moisture retainers, lubricants, absorbents, diluents, flavour correctors, colorants and the like usual in pharmacology and converted into the desired administration form. Here reference should be made to Remington's Pharmaceutical Science, 15th ed. Mack Publishing Company, East Pennsylvania (1980).

For the use of the compounds according to the invention as drugs, these are brought into the form of a pharmaceutical preparation which as well as the active substance contains pharmaceutical, organic or inorganic inert carrier materials suitable for enteral or parenteral administration, such as for example water, gelatine, gum arabic, lactose, starch, magnesium stearate, talc, vegetable oils, polyalkylene glycols and the like.

The invention also includes the pharmaceutical preparations containing one or several compounds according to the invention of the general formula I and, if necessary, pharmaceutically compatible carriers and/or usual additives.

Preparation of the Compounds According to the Invention

One of the most important methods of preparation of sulfoximines is the reaction of a sulfoxide with hydrazoic acid, which is generated in situ e.g. from the reaction of sodium azide and conc. sulphuric acid (M. Reggelin, C. Zur, *Synthesis* 2000, 1, 1). The reaction can be performed in an organic solvent, such as chloroform. Further methods for the synthesis of sulfoximines are for example the reaction of sulfoxides with a) $TsN_3$ ((a) R. Tanaka, K. Yamabe, *J. Chem. Soc. Chem. Commun.* 1983, 329;
(b) H. Kwart, A. A. Kahn, *J. Am. Chem. Soc.* 1967, 89, 1959)).
b) N-tosylimino phenyl iodinane and catalytic amounts of Cu(I) triflate (J. F. K. Müller, P. Vogt, *Tetrahedron Lett.* 1998, 39, 4805)
c) Boc-azide and catalytic amounts of iron(II) chloride (T. Bach, C. Korber, *Tetrahedron Lett.* 1998, 39, 5015) or
d) o-Mesitylensulphonylhydroxylamine (MSH) (C. R. Johnson, R. A. Kirchhoff, H. G. Corkins, *J. Org. Chem.* 1974, 39, 2458).
e) [N-(2-(trimethylsilyl)ethanesulphonyl)imino]phenyliodinane (PhI=NSes) (S. Cren, T. C. Kinahan, C. L. Skinner and H. Tye, *Tetrahedron Lett.* 2002, 43, 2749).
f) Trifluoracetamide or sulphonylamides in combination with iodobenzene diacetate, magnesium oxide and catalytic amounts of rhodium(II) acetate dimer (H. Okamura, C. Bolm, *Organic Letters* 2004, 6, 1305.
g) Sulphonylamides in combination with iodobenzene diacetate and catalytic amounts of a chelating ligand and silver salts (G. Y. Cho, C. Bolm, *Organic Letters* 2005, 7, 4983).
h) $NsNH_2$ and iodobenzene diacetate (G. Y. Cho, C. Bolm, *Tetrahedron Lett.* 2005, 46, 8007).

As regards structure and configuration, sulfoximines as a rule are highly stable (C. Bolm, J. P. Hildebrand, *J Org. Chem.* 2000, 65, 169). These properties of the functional group often allow even drastic reaction conditions and enable the simple derivatisation of the sulfoximines on the imine nitrogen and the α-carbon. Enantiomerically pure sulfoximines are also used as auxiliaries in diastereoselective synthesis ((a) S. G. Pyne, *Sulphur Reports* 1992, 12, 57; (b) C. R. Johnson, *Aldrichchimica Acta* 1985, 18, 3). The preparation of enantiomerically pure sulfoximines is for example described via racemate separation with enantiomerically pure camphor-10-sulphonic acid ((a) C. R. Johnson, C. W. Schroeck, *J. Am. Chem. Soc.* 1973, 95, 7418; (b) C. S. Shiner, A. H. Berks, *J. Org. Chem.* 1988, 53, 5543). A further method for the preparation of optically active sulfoximines consists in the stereoselective imination of optically active sulfoxides ((a) C. Bolm, P. Müller, K. Harms, *Acta Chem. Scand.* 1996, 50, 305; (b) Y. Tamura, J. Minamikawa, K. Sumoto, S. Fujii, M. Ikeda, *J. Org. Chem.* 1973, 38, 1239; (c) (H. Okamura, C. Bolm, *Organic Letters* 2004, 6, 1305).

Process Variation 1

Scheme 1

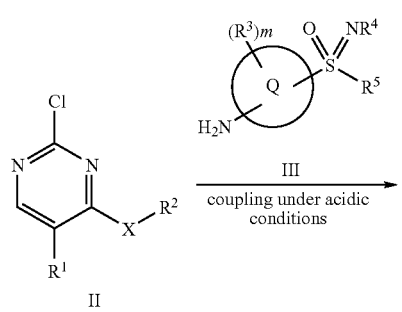

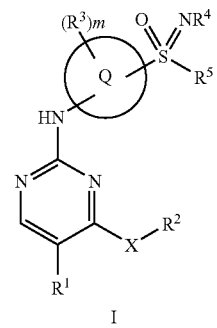

I

According to process variation 1, the compounds II and III are reacted under acidic conditions to give compounds of the type I. As the acid, for example hydrogen chloride is suitable. Various solvents/solvent mixtures can be used. Particularly suitable for example is the use of acetonitrile or acetonitrile/water. The reaction temperature can be varied in the range from room temperature to reflux depending on the reactivity of the compounds II and III, and of the acid used and of the solvent used. For acetonitrile and acetonitrile/water mixtures in combination with hydrogen chloride as acid, the temperature range from 60-90° C. is particularly suitable.

General Preparation of the Compounds of the Type II:

Scheme 2

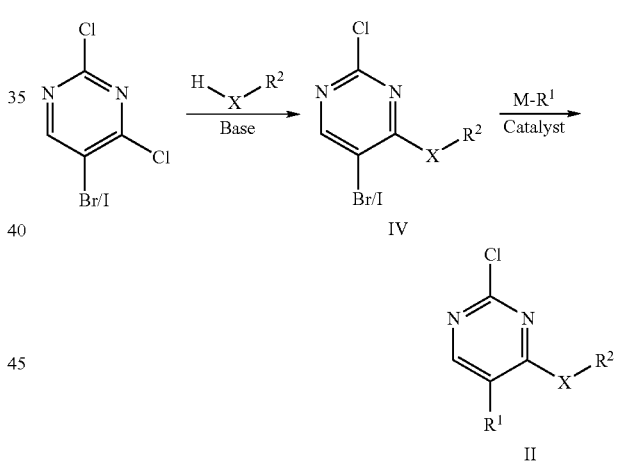

5-bromo-2,4-dichloropyrimidine or 2,4-dichloro-5-iodopyrimidine can be converted to compounds of the type IV by reaction with nucleophiles under basic conditions (see e.g.: a) U. Lücking, M. Krüger, R. Jautelat, G. Siemeister, WO 2005037800; b) U. Lücking, M. Krueger, R. Jautelat, O. Prien, G. Siemeister, A. Ernst, WO 2003076437; c) T. Brumby, R. Jautelat, O. Prien, M. Schäfer, G. Siemeister, U. Lücking, C. Huwe, WO 2002096888).

For N-nucleophiles ($X=NR^8$), acetonitrile is particularly suitable as the solvent and triethylamine as the base. The reaction preferably takes place at room temperature.

For O-nucleophiles (X=O), THF is particularly suitable as the solvent and sodium hydride as the base. The reaction preferably takes place at 0° C. to room temperature.

For S-nucleophiles (X=S), acetonitrile is particularly suitable as the solvent and triethylamine as the base. The reaction preferably takes place at −20° C. to room temperature.

The derivatives of the type IV obtained can then for example be reacted to give compounds of the type II by Suzuki coupling (see e.g.: a) F. Bellina, A. Carpita, R. Rossi, *Synthesis* 2004, 15, 2419; b) V. Wittmann, *Nachrichten aus der Chemie* 2002, 50, 1122; c) A. Herrmann, *Applied Homogeneous Catalysis with Organometallic Compounds* (2nd Edition) 2002, 1, 591; d) A. Suzuki in F. Thederich, P. J. Stang (Eds.) *Metal-catalyzed Cross-Coupling Reactions*, Wiley-VCH, New York, 1998, 47) with boronic acid derivatives (M=B(OH)$_2$ or B(OR)$_2$) or by Stille coupling (see e.g.: a) Oliver Reiser, *Chemie in unserer Zeit* 2001, 35, 94; b) V. Farina, V. Krishnamurthy, W. J. Scott, *Org. React* (N.Y.) 1997, 50, 1) with tin derivatives (M=SnR$_3$) or by Negishi-coupling (see e. g.: a) E. Negishi, X. Zeng,; *Metal-Catalyzed Cross-Coupling Reactions* (2nd Edition) 2004, 2, 815; b) E. Negishi, *Handbook of Organopalladium Chemistry for Organic Synthesis* 2002, 1, 229) with zinc derivatives.

General Preparation of the Compounds of the Type III:

Scheme 3

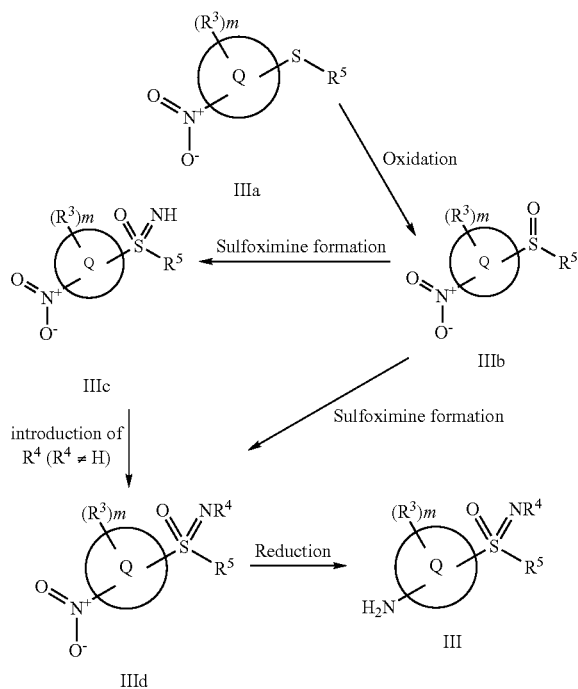

Compound IIIa is firstly oxidised to the sulfoxide IIIb. For the conversion of a thioether into a sulfoxide, many methods are available (see e.g.: a) M. H. Ali, W. C. Stevens, *Synthesis* 1997, 764; b) I. Fernandez, N. Khiar, *Chem. Rev.* 2003, 103, 3651). Particularly suitable for the preparation of IIIb is the described use of periodic acid/iron(III) chloride.

Compound IIIb can as described be converted to compound IIIc with the use of sodium azide/sulphuric acid (see also: M. Reggelin, C. Zur, *Synthesis* 2000, 1, 1). For the further N-functionalisation of the sulfoximine with formation of compounds of the type IIId various methods are available:

a) Alkylation (see e.g.: C. R. Johnson, *J. Org. Chem.* 1993, 58, 1922-1923); Reduction of acylsulfoximines [see b)b)].

b) Acylation (see e.g.: a) C. P. R. Hackenberger, G. Raabe, C. Bolm, *Chem. Europ. J.* 2004, 10, 2942-2952; b) C. Bolm, C. P. R. Hackenberger, O. Simic, M. Verrucci, D. Müller, F. Bienewald, *Synthesis* 2002, 7, 879-887; c) C. Bolm, G. Moll, J. D. Kahmann, *Chem. Europ. J.* 2001, 7, 1118-1128).

c) Arylation (see e.g.: a) C. Bolm, J. P. Hildebrand, *Tetrahedron Lett.* 1998, 39, 5731-5734; b) C. Bolm, J. P. Hildebrand, *J. Org. Chem.* 2000, 65, 169-175; c) C. Bolm, J. P. Hildebrand, J. Rudolph, *Synthesis* 2000, 7, 911-913; d) Y. C. Gae, H. Okamura, C. Bolm, *J. Org. Chem.* 2005, 70, 2346-2349).

d) Reaction with isocyanates/isothiocyanates (see e.g.: a) V. J. Bauer, W. J. Fanshawe, S. R. Safir, *J. Org. Chem.* 1966, 31, 3440-3441; b) C. R. Johnson, M. Haake, C. W. Schroeck, *J. Am. Chem. Soc.* 1970, 92, 6594-6598; c) S. Allenmark, L. Nielsen, W. H. Pirkle, *Acta Chem. Scand. Ser. B* 1983, 325-328)

e) Reaction with sulphonyl chlorides (see e.g.: a) D. J. Cram, J. Day, D. R. Rayner, D. M von Schriltz, D. J. Duchamp, D. C. Garwood. *J. Am. Chem. Soc.* 1970, 92, 7369-7384), b) C. R. Johnson, H. G. Corkins, *J. Org. Chem.* 1978, 43, 4136-4140; c) D. Craig, N. J. Geach, C. J. Pearson, A. M. Z. Slawin, A. J. P. White, D. J. Williams, *Tetrahedron* 1995, 51, 6071-6098).

f) Reaction with chloroformates or anhydrides (see e.g.: a) D. J. Cram, J. Day, D. R. Rayner, D. M von Schriltz, D. J. Duchamp, D. C. Garwood. *J. Am. Chem. Soc.* 1970, 92, 7369-7384), b) S. G. Pyne, Z. Dong, B. W. Skelton, A. H. Allan, *J. Chem. Soc. Chem. Commun.* 1994, 6, 751-752; c) C. R. Johnson, H. G. Corkins, *J. Org. Chem.* 1978, 43, 4136-4140; d) Y. C. Gae, H. Okamura, C. Bolm, *J. Org. Chem.* 2005, 2346-2349).

g) Silylation: (see e.g.: A. J. Pearson, S. L. Blystone, H. Nar, A. A. Pinkerton, B. A. Roden, J. Yoon, *J. Am. Chem. Soc.* 1989, 111, 134-144).

A further possibility for synthesising N-functionalised components of the type IIId is the direct reaction of the sulfoxide IIIb, for example with the use of the following reagents/methods:

a) TsN$_3$ ((a) R. Tanaka, K. Yamabe, *J. Chem. Soc. Chem. Commun.* 1983, 329; (b) H. Kwart, A. A. Kahn, *J. Am. Chem. Soc.* 1967, 89, 1959)).

b) N-tosylimino phenyl iodinane and catalytic amounts of Cu(I) triflate (J. F. K. Müller, P. Vogt, *Tetrahedron Lett.* 1998, 39, 4805)

c) Boc-azide and catalytic amounts of iron(II) chloride (T. Bach, C. Korber, *Tetrahedron Lett.* 1998, 39, 5015) or d) o-Mesitylensulphonylhydroxylamine (MSH) (C. R. Johnson, R. A. Kirchhoff, H. G. Corkins, *J. Org. Chem.* 1974, 39, 2458).

e) [N-(2-(trimethylsilyl)ethanesulphonyl)imino]phenyliodinane (PhI=NSes) (S. Cren, T. C. Kinahan, C. L. Skinner and H. Tye, *Tetrahedron Lett.* 2002, 43, 2749).

f) Trifluoracetamide or sulphonylamides in combination with iodobenzene diacetate, magnesium oxide and catalytic amounts of rhodium(II) acetate dimer (H. Okamura, C. Bolm, *Organic Letters* 2004, 6, 1305.

g) Sulphonylamides in combination with iodobenzene diacetate and catalytic amounts of a chelating ligand and silver salts (G. Y. Cho, C. Bolm, *Organic Letters* 2005, 7, 4983).

h) NsNH$_2$ and iodobenzene diacetate (G. Y. Cho, C. Bolm, *Tetrahedron Lett.* 2005, 46, 8007).

For the subsequent reduction of the aromatic nitro group in compounds of the type IIId to give compounds of the type III a range of reaction conditions is in principle available (see e.g.: R. C. Larock, *Comprehensive Organic Transformations*, VCH, New York, 1989, 411-415). Particularly suitable is the described use of titanium(III) chloride.

The preparation of compounds of the type III is also described in: U. Lücking, M. Krüger, R. Jautelat, G. Siemeister, WO 2005037800

Process Variation 2—Synthesis of 5-Tetrazole Derivatives

Scheme 4

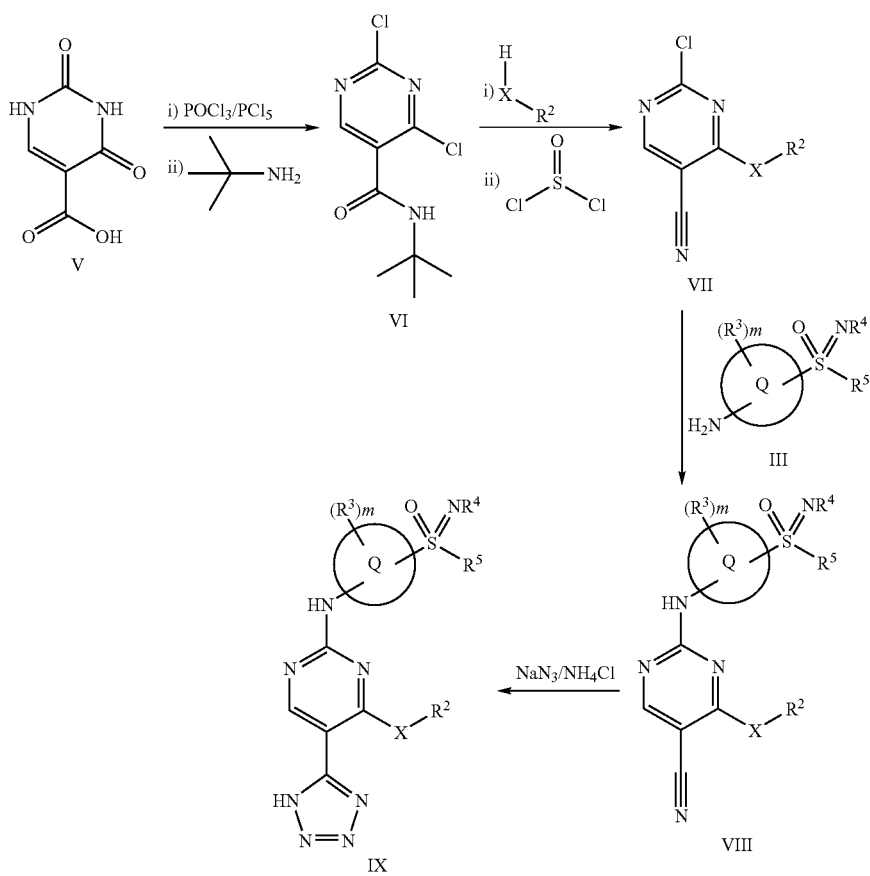

A further possibility for the synthesis of claimed compounds is shown in the above scheme. The commercial starting compound V is converted to VI by reaction with phosphorus oxychloride/phosphorus pentachloride followed by tert.-butylamine. Selective introduction of the side-chain at C4 and subsequent reaction with thionyl chloride leads to compounds of the type VII (see also e. g.: N. J. Newcombe, A. P. Thomas WO 2002096887). This is followed by the introduction of the aniline III in the 2 position of the pyrimidine under acidic conditions. By reaction with sodium azide/NH$_4$Cl, the tetrazole derivative IX is obtained.

Process Variation 3—Functionalisation of the 5-Tetrazole

Scheme 5

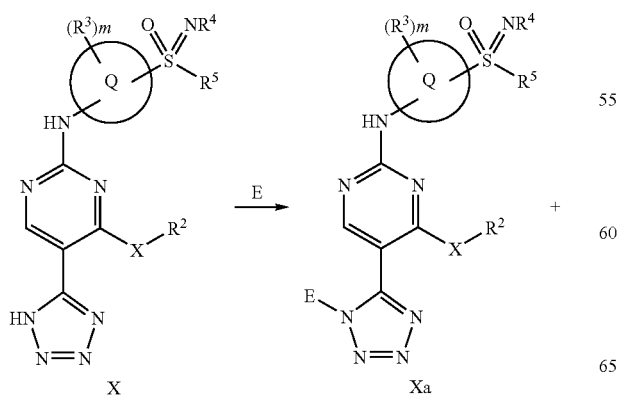

-continued

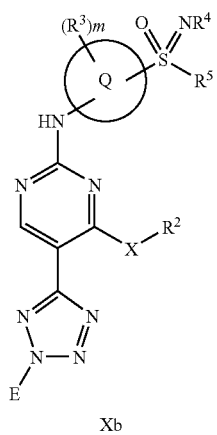

By reaction of X with suitable electrophiles (E), such as for example alkyl halides or alkylsulphonate esters, anhydrides or acid chlorides, epoxides, aziridines or α,β-unsaturated carbonyl compounds (Michael acceptors), suitable substituents on the tetrazole can be introduced (X a/b).

Process Variation 4

Scheme 6

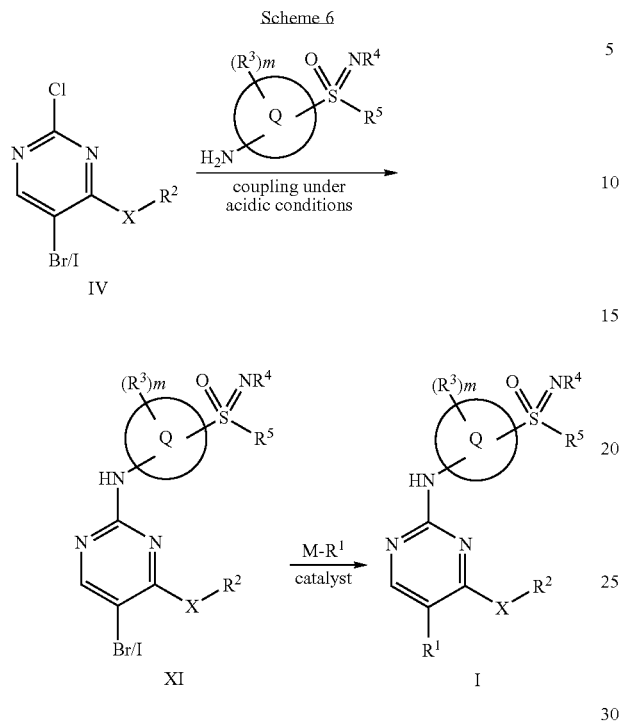

Process Variation 5:

Scheme 7

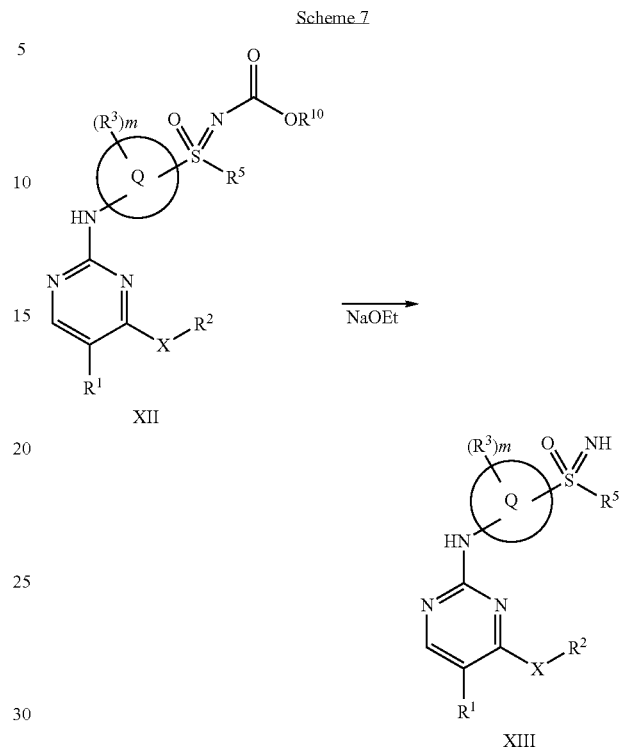

According to process variation 4, 5-bromo or 5-iodo derivatives of the type XI (for preparation, see also: a) U. Lücking, M. Krüger, R. Jautelat, G. Siemeister, WO 2005037800) are reacted by Suzuki coupling (see e.g.: a) F. Bellina, A. Carpita, R. Rossi. *Synthesis* 2004, 15, 2419; b) V. Wittmann, *Nachrichten aus der Chemie* 2002, 50, 1122; c) A. Herrmann, *Applied Homogeneous Catalysis with Organometallic Compounds* (2nd Edition) 2002, 1, 591; d) A. Suzuki in F. Thederich, P. J. Stang (Eds.) *Metal-catalyzed Cross-Coupling Reactions*, Wiley-VCH, New York, 1998, 47) with boronic acid derivatives (M=B(OH) or B(OR)$_2$) or by Stille coupling (see e.g.: a) Oliver Reiser, *Chemie in unserer Zeit* 2001, 35, 94; b) V. Farina, V. Krishnamurthy, W. J. Scott, *Org. React.* (*N.Y.*) 1997, 50, 1) with tin derivatives (M=SnR$_3$) or by Negishi-coupling (see e. g.: a) E. Negishi, X. Zeng,; *Metal-Catalyzed Cross-Coupling Reactions* (2nd Edition) 2004, 2, 815; b) E. Negishi *Handbook of Organopalladium Chemistry for Organic Synthesis* 2002, 1, 229-) with zinc derivatives or by Buchwald-Hartwig coupling (see e.g.: a) J. P. Wolfe, H. Tomori, J. P. Sadighi, J. Yin, S. L. Buchwald, *J. Org. Chem.* 2000, 65, 1158; b) A. Klapars, J. C. Antilla, X. Huang, S. L. Buchwald, *J. Am. Chem. Soc.* 2001, 123, 7727; c) G. Mann, J. F. Hartwig, M. S. Driver, C. Fernandez-Rivas, *J. Am. Chem. Soc.* 1998, 120, 827; d) D. W. Old, M. C. Harris, S. L. Buchwald, *Org. Lett.* 2000, 2, 1403; e) J. F. Hartwig, M. Kawatsura, S. I. Hauck, K. H. Shaughnessy, L. M. Alcazar-Roman, *J. Org. Chem.* 1999, 64, 5575; f) A. R. Muci, S. L. Buchwald, *Topics in Current Chemistry*, Volume 219, 2002: Cross-Coupling Reactions—a practical guide, p 131-209) with amines with palladium or copper catalysis.

Derivatives of the type XII, which bear a COOR$^{10}$ group on the nitrogen of the sulfoximine, can be converted e.g. under basic conditions to free sulfoximine derivatives of the type XIII. Particularly suitable is the described use of sodium ethanolate in ethanol at 60° C.

Process Variation 6

Scheme 8

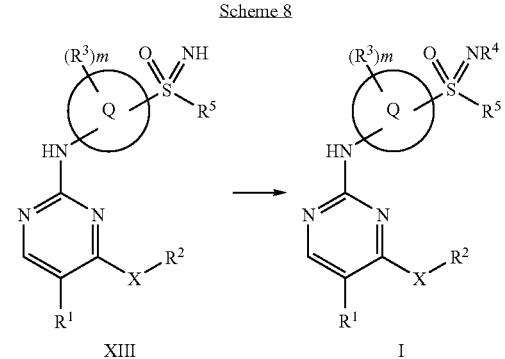

For the N-functionalisation of the sulfoximine with formation of compounds of the type I, various methods are available:
a) Alkylation (see e.g.: C. R. Johnson, *J. Org. Chem.* 1993, 58, 1922-1923); Reduction of acylsulfoximines [see b)b)].
b) Acylation (see e.g.: a) C. P. R. Hackenberger, G. Raabe, C. Bolm, *Chem. Europ. J.* 2004, 10, 2942-2952; b) C. Bolm, C. P. R. Hackenberger, O. Simic, M. Verrucci, D. Müller, F. Bienewald, *Synthesis* 2002, 7, 879-887; c) C. Bolm, G. Moll, J. D. Kahmann, *Chem. Europ. J.* 2001, 7, 1118-1128).

c) Arylation (see e.g.: a) C. Bolm, J. P. Hildebrand, *Tetrahedron Lett.* 1998, 39, 5731-5734; b) C. Bolm, J. P. Hildebrand, *J. Org. Chem.* 2000, 65, 169-175; c) C. Bolm, J. P. Hildebrand, J. Rudolph, *Synthesis* 2000, 7, 911-913; d) Y. C. Gae, H. Okamura, C. Bolm, *J. Org. Chem.* 2005, 70, 2346-2349).

d) Reaction with isocyanates/isothiocyanates (see e.g.: a) V. J. Bauer, W. J. Fanshawe, S. R. Safir, *J. Org. Chem.* 1966, 31, 3440-3441; b) C. R. Johnson, M. Haake, C. W. Schroeck, *J. Am. Chem. Soc.* 1970, 92, 6594-6598; c) S. Allenmark, L. Nielsen, W. H. Pirkle, *Acta Chem. Scand. Ser. B* 1983, 325-328)

e) Reaction with sulphonyl chlorides (see e.g.: a) D. J. Cram, J. Day, D. R. Rayner, D. M von Schriltz, D. J. Duchamp, D. C. Garwood. *J. Am. Chem. Soc.* 1970, 92, 7369-7384), b) C. R. Johnson, H. G. Corkins, *J. Org. Chem.* 1978, 43, 4136-4140; c) D. Craig, N. J. Geach, C. J. Pearson, A. M. Z. Slawin, A. J. P. White, D. J. Williams, *Tetrahedron* 1995, 51, 6071-6098).

f) Reaction with chloroformates or anhydrides (see e.g.: a) D. J. Cram, J. Day, D. R. Rayner, D. M von Schriltz, D. J. Duchamp, D. C. Garwood. *J. Am. Chem. Soc.* 1970, 92, 7369-7384), b) S. G. Pyne, Z. Dong, B. W. Skelton, A. H. Allan, *J. Chem. Soc. Chem. Commun.* 1994, 6, 751-752; c) C. R. Johnson, H. G. Corkins, *J. Org. Chem.* 1978, 43, 4136-4140; d) Y. C. Gae, H. Okamura, C. Bolm, *J. Org. Chem.* 2005, 2346-2349).

g) Silylation: (see e.g.: A. J. Pearson, S. L. Blystone, H. Nar, A. A. Pinkerton, B. A. Roden, J. Yoon, *J. Am. Chem. Soc.,* 1989, 111, 134-144).

Process Variation 7

Scheme 9

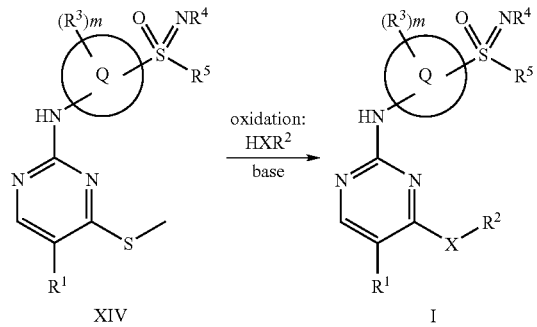

XIV    I

According to process variation 7 the compound XIV is reacted under oxidative conditions followed by substitution with HXR² under basic conditions. As the Oxidant meta-chlorobenzoic acid is suitable. Various nucleophiles (HXR²) can be used. Particularly suitable for example is the use of primary amines with triethylamine as base and N-methylpyrrolidin-2-one as solvent. The starting material can be prepared by various routes described e.g. in Scheme 2 (X=S) and 1 or in Scheme 6.

Thus the present invention thus also includes the processes described above for the preparation of the compounds according to the invention, in particular:

A:

a process for the preparation of the compounds of the general formula I, characterized in that compounds of the general formula II

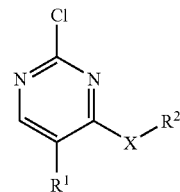

are reacted under acidic conditions with compounds of the general formula III

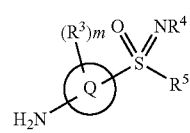

to give the compounds of the general formula I, wherein the residues $R^1$, $R^2$, $R^3$, $R^4$, $R^5$, and Q, X and m have the meanings stated in Claim 1.

B:

Furthermore, a process for the preparation of the compounds of the general formula I, characterized in that compounds of the general formula II

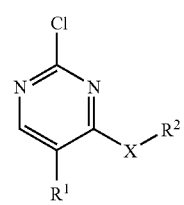

are reacted under acidic conditions with compounds of the general formula III

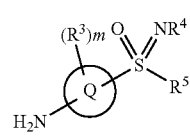

to give the compounds of the general formula I, wherein the residues $R^1$, $R^2$, $R^3$, $R^4$, $R^5$, and Q, X and m have the meanings stated in Claim 1, and

C:

a process for the preparation of the compounds of the general formula I, characterized in that compounds of the general formula IV

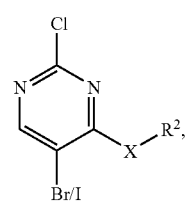

obtainable by reaction of 5-bromo-2,4-dichloropyrimidine or 5-iodo-2,4-dichloropyrimidine with R²—X—H under basic conditions, are reacted with compounds of the general formula III

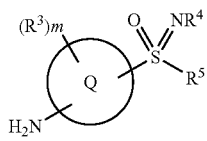

III under acidic conditions and the compounds of the general formula XI obtained are optionally with the use of a catalyst reacted with compounds of the general formula

M-R¹, where M means B(OH)$_2$, B(OR$^{19}$)(OR$^{20}$), wherein
R$^{19}$ and R$^{20}$ (C$_1$-C$_6$) alkyl, or can together form a ring of C$_1$-C$_{10}$ alkyl, or M means Sn(R$^{21}$)$_3$, wherein
R$^{21}$ means C$_1$-C$_6$ alkyl, or M means R$^{21}$MgR$^{22}$/Zn(R$^{22}$)$_2$ wherein R$^{21}$ means C$_1$-C$_6$ alkyl and R$^{22}$ halogen, to give compounds of the general formula I, wherein the residues R¹, R², R³, R⁴, R⁵, and Q, X and m have the meanings stated in Claim 1 and the intermediate products passed through, wherein the substituents thereof, if not otherwise necessary for the process, have the meanings stated in Claim 1, and D: a process for the preparation of the compounds of the general formula I characterized in that compounds of general formula XIV

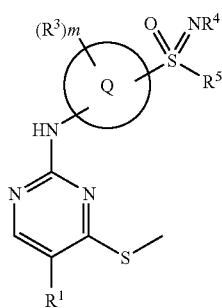

XIV wherein R¹, R³, m, R⁴ and R⁵ have the meanings as defined in claim 1 are reacted under oxidative conditions followed by substitution with

HX—R² wherein X and R² have the meaning as defined in claim 1, to result in compounds of general formula I and the intermediate products passed through, wherein the substituents thereof, if not otherwise necessary for the process, have the meanings stated in Claim 1.

The following examples illustrate the preparation of the compounds according to the invention, without wishing to restrict the range of the claimed compounds to these examples.

EXPERIMENTAL SECTION

1. Preparation of the Starting Materials 1.1. Preparation of the Aniline Derivatives (See Also Scheme 3)

1) (RS)—S-(4-aminophenyl)-N-(ethoxycarbonyl)-S-methylsulfoximide

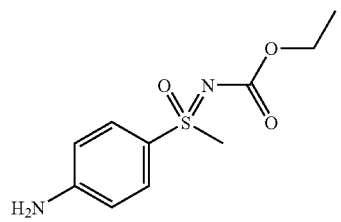

a) Preparation of (RS)-1-(methylsulphinyl)-4-nitrobenzene

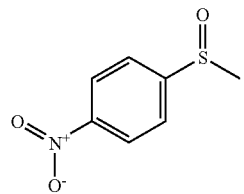

A suspension of 25.00 g (147.8 mmol) 1-methylsulphanyl-4-nitro-benzene and 0.69 g (4.2 mmol) iron(III) chloride (anhydrous) in 120 ml acetonitrile is treated with 36.0 g (158.1 mmol) periodic acid and stirred at room temperature. At the start of heat evolution, the mixture is transiently cooled with an ice-bath, so that the temperature does not rise above 30° C. After the heat evolution has subsided, the mixture is stirred at room temperature for a further 10 mins. The mixture is poured into a solution of 150 g sodium thiosulphate in 1000 ml ice-water and then extracted with DCM. The combined organic phases are washed with saturated NaCl solution, dried (Na$_2$SO$_4$), filtered and concentrated. The remaining residue is recrystallised from toluene. 23.6 g (128.0 mmol, corresponding to 86% of theor.) of the product is obtained.

¹H-NMR (DMSO): 8.41 (m, 2H), 7.97 (m, 2H), 2.86 (s, 3H).

ES: 186 (ES).

b) Preparation of (RS)—S-(4-nitrophenyl)-S-methylsulfoximide

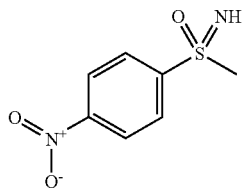

23.65 g (127.7 mmol) (RS)-1-(methylsulphinyl)-4-nitrobenzene in 130 ml chloroform are treated with 9.32 g (143.4 mmol) sodium azide. The mixture is slowly treated with 32.4 ml of concentrated sulphuric acid at 0° C. and then slowly heated to 45° C. After 16 hrs, the mixture is cooled to room temperature, treated with ice-water and extracted with chloroform. This organic phase is discarded. The aqueous phase is basified with 2N NaOH solution and extracted with DCM. The combined organic phases are washed with saturated NaCl solution, dried ($Na_2SO_4$), filtered and concentrated. 17.17 g (88.4 mmol, corresponding to 63% of theor.) of the product is obtained.

$^1$H-NMR (DMSO): 8.43 (m, 2H), 8.17 (m, 2H), 4.62 (s, 1H), 3.18 (s, 3H).

ES: 201 (ES).

c) Preparation of (RS)—N-(ethoxycarbonyl)-S-methyl-S-(4-nitrophenyl)sulfoximide

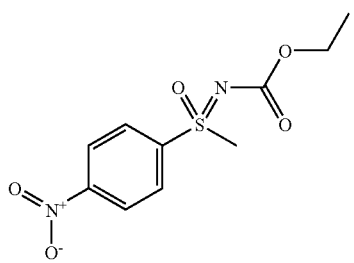

8.50 g (42.5 mmol) (RS)—S-(4-nitrophenyl)-S-methylsulfoximide in 400 ml pyridine are treated dropwise at room temperature with 18.8 ml (197.2 mmol) ethyl chloroformate. The mixture is stirred at room temperature for 4 hours and then poured into dilute NaCl solution. It is extracted with ethyl acetate. The combined organic phases are dried ($Na_2SO_4$), filtered and concentrated. The remaining residue is chromatographically purified (hexane/ethyl acetate 1:1). 8.94 g (32.8 mmol, corresponding to 77% of theor.) of the product is obtained.

$^1$H-NMR (DMSO-D6): 8.49 (m, 2H), 8.22 (m, 2H), 3.90 (m, 2H), 3.56 (s, 3H), 1.10 (tr, 3H).

d) Preparation of (RS)—S-(4-aminophenyl)-N-(ethoxycarbonyl)-S-methylsulfoximide

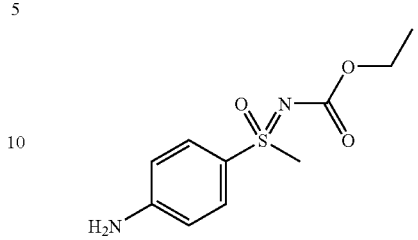

A solution of 8.70 g (32.0 mmol) (RS)—N-(ethoxycarbonyl)-S-methyl-S-(4-nitro-phenyl)sulfoximide in 650 ml THF is slowly treated at room temperature with 435 ml of a 10% solution of Ti(III)Cl in approximately 10% hydrochloric acid (Aldrich). The mixture is stirred at room temperature for 4 hours and then cooled to 0° C. 450 ml of a 32% NaOH solution are added dropwise. During this, the reaction mixture is periodically diluted by the addition of water and ethyl acetate. It is treated with 500 ml ethyl acetate and the organic phase is separated. The mushy aqueous phase is extracted with ethyl acetate. The combined organic phases are washed with dilute NaCl solution, dried ($Na_2SO_4$), filtered and concentrated. 8.05 g (ca. 32.0 mmol) of the product is obtained, which is used without further purification.

$^1$H-NMR (DMSO-D6): 7.52 (m, 2H), 6.66 (m, 2H), 6.17 (s, 2H), 3.91 (q, 2H), 3.30 (s, 3H), 1.12 (tr, 3H).

2) (RS)—S-(4-aminophenyl)-N-(ethoxycarbonyl)-S-ethylsulfoximide

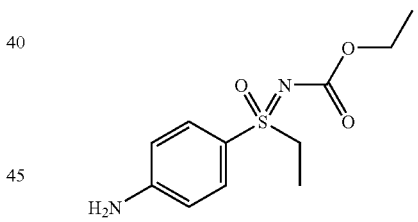

a) Preparation of (RS)-1-(ethylsulphinyl)-4-nitrobenzene

Preparation Analogously to Example 1a

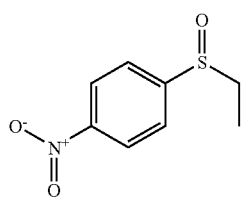

$^1$H-NMR (DMSO): 8.39 (m, 2H), 7.91 (m, 2H), 3.18 (m, 1H), 2.88 (m, 1H), 1.06 (tr, 3H).

b) Preparation of (RS)—S-(4-nitrophenyl)-S-ethylsulfoximide

Preparation Analogously to Example 1b

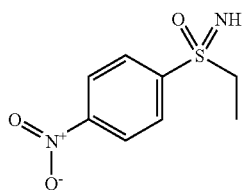

$^1$H-NMR (DMSO-D6): 8.42 (m, 2H), 8.13 (m, 2H), 4.59 (s, 1H), 3.23 (q, 2H), 1.10 (t, 3H).

c) Preparation of (RS)—N-(ethoxycarbonyl)-S-ethyl-S-(4-nitrophenyl)-sulfoximide Preparation Analogously to Example 1c

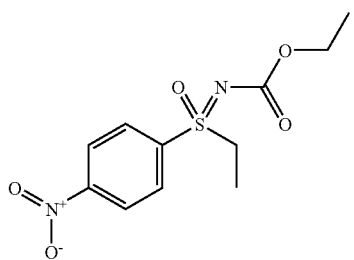

$^1$H-NMR (DMSO-D6): 8.48 (m, 2H), 8.15 (m, 2H), 3.92 (m, 2H), 3.69 (m, 2H), 1.12 (m, 6H).

d) Preparation of (RS)—S-(4-aminophenyl)-N-(ethoxycarbonyl)-S-ethyl-sulfoximide Preparation Analogously to Example 1d

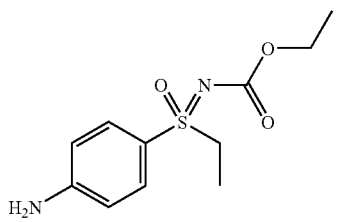

$^1$H-NMR (DMSO-D6): 7.47 (m, 2H), 6.67 (m, 2H), 6.20 (s, 2H), 3.90 (m, 2H), 3.42 (q, 2H), 1.10 (m, 6H).

3) (RS)—S-(4-aminophenyl)-N-(ethoxycarbonyl)-S-cyclopropylsulfoximide

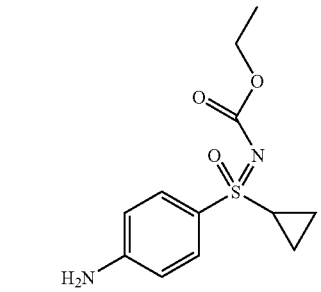

a) (RS)-1-(cyclopropylsulphinyl)-4-nitrobenzene

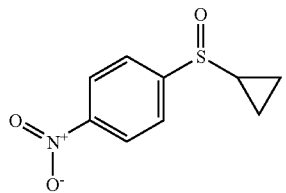

This compound is prepared as described in WO 2005/37800 on page 103.

b) Preparation of (RS)—S-(4-nitrophenyl)-S-cyclopropylsulfoximide

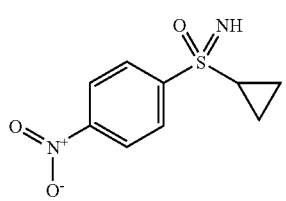

6.6 g (31.24 mmol) (RS)-1-(cyclopropylsulphinyl)-4-nitrobenzene, 7.77 g (68.74 mmol) trifluoroacetamide, 16.6 g (51.55 mmol) iodobenzene diacetate and 5.54 g (137.5 mmol) magnesium oxide are placed in 350 ml dichloromethane. The mixture is stirred for 5 minutes, treated with 0.69 g (1.56 mmol) rhodium(II) acetate dimer and stirred at room temperature for 12 hours. The suspension is diluted with 235 ml methanol, treated with 23.75 g potassium carbonate and stirred at room temperature for 4 hours. Next the mixture is treated with 400 ml water, and the organic phase is separated and filtered at the pump through Celite®. The aqueous phase is extracted several times with dichloromethane. The combined organic phases are washed with half-saturated sodium chloride solution and stirred with 100 ml 2N hydrochloric acid for 30 minutes. The aqueous phase is adjusted to pH 9 with concentrated sodium hydroxide solution with ice cooling. The crystallised product is aspirated dry, washed with water and dried. 4.7 g (66.5% of theor.) of the product is obtained.

¹H-NMR (DMSO-D6): 8.41 (m, 2H), 8.15 (m, 2H), 4.65 (s, 1H), 2.78 (m, 1H), 1.15 (m, 1H), 0.98 (m, 3H)

c) Preparation of (RS)—N-(ethoxycarbonyl)-S-cyclopropyl-S-(4-nitrophenyl)-sulfoximide Preparation Analogously to Example 1c

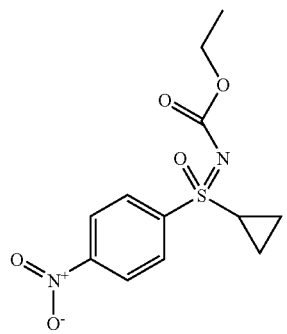

¹H-NMR (DMSO-D6): 8.46 (m, 2H), 8.18 (m, 2H), 3.88 (m, 2H), 3.22 (m, 1H), 1.40 (m, 1H), 1.28 (m, 1H), 1.07 (m, 5H)

d) Preparation of (RS)—S-(4-aminophenyl)-N-(ethoxycarbonyl)-S-cyclopropylsulfoximide Preparation Analogously to Example 1d

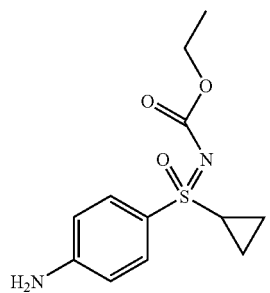

¹H-NMR (DMSO-D6): 7.45 (m, 2H), 6.66 (m, 2H), 6.16 (s, 2H), 3.87 (m, 2H), 2.86 (m, 1H), 1.19 (m, 1H), 1.11 (m, 1H), 1.08 (t, 3H), 0.93 (m, 2H)

4) (R)—S-(4-aminophenyl)-N-(ethoxycarbonyl)-S-cyclopropylsulfoximide

The enantiomerically pure compounds Example 4 and 5 are obtained by preparative chiral HPLC from the racemate Example 3:

| Analytical: | |
|---|---|
| Column: | Chiralpak AD-H 5μ 150 × 4.6 mm |
| Solvent: | hexane/ethanol 80:20 |
| Buffer: | — |
| Gradient: | isocratic |
| Flow: | 1.0 mL/min |
| Solution: | 1 mg/mL EtOH |
| Injection: | 20 μl |
| Detection: | PDA 254 nm |

| Peak | Retention Time | Area | Comment |
|---|---|---|---|
| 1 | 7.31 | 49.96% | Example 5 |
| 2 | 10.26 | 50.04% | Example 4 |

| Preparative: | |
|---|---|
| Column: | Chiralpak AD 20μ 250 × 60 mm |
| Solvent: | hexane/ethanol 80:20 |
| Buffer: | — |
| Gradient: | isocratic |
| Flow: | 80 mL/min |
| Solution: | 9200 mg/90 ml EtOH |
| Injection: | 15 × 6000 μl => 1 × ~610 mg |
| Reinjection: | 30 × ~200 mg/ml; 16X ~200 mg/ml; 8 × ~200 mg/ml; 4 × ~200 mg/ml |
| Detection: | UV 254 nm |

The assignment of the absolute stereochemistry was effected by Xray structural analysis. The enantiomer obtained as peak 2 possesses the R configuration at the sulphur atom.

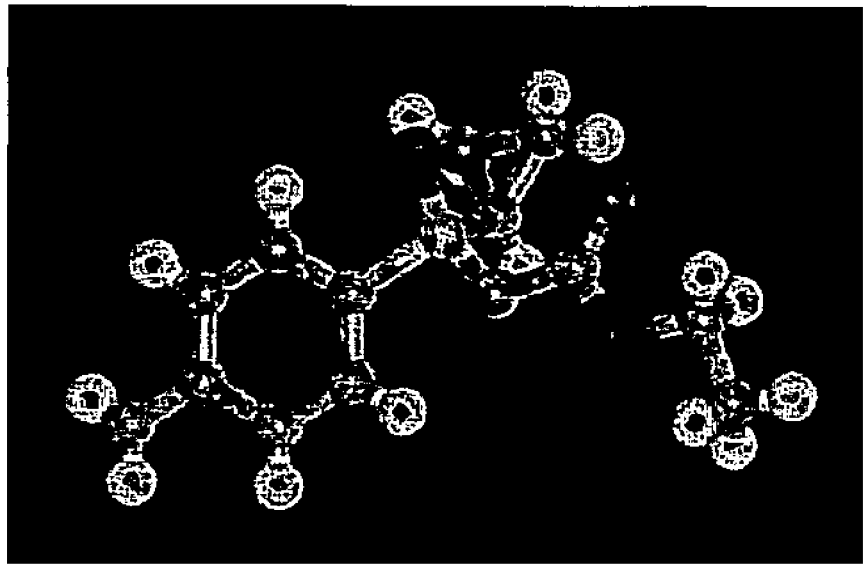

¹H-NMR (DMSO-D6): identical with Example 3

5) (S)—S-(4-aminophenyl)-N-(ethoxycarbonyl)-S-cyclopropylsulfoximide

As Described in Example 4

The Enantiomer Obtained as Peak 1 Possesses the S Configuration

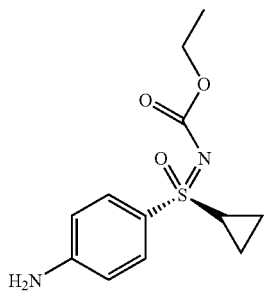

¹H-NMR (DMSO-D6): identical with Example 3

6) (RS)—S-(4-aminophenyl)-N-(ethoxycarbonyl)-S-phenylsulfoximide

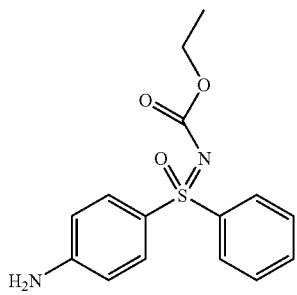

a) (RS)-1-(phenylsulphinyl)-4-nitrobenzene

Preparation Analogously to Example 1a from (4-nitrophenyl)-phenyl Sulphide (Aldrich, Acros etc.)

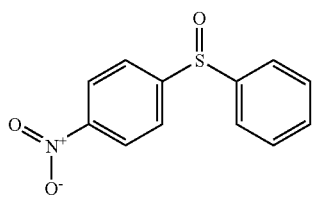

¹H-NMR (DMSO-D6): 8.35 (dm, 2H), 8.01 (dm, 2H), 7.82-7.78 (m, 2H), 7.60-7.52 (m, 3H)

b) (RS)—S-(4-nitrophenyl)-S-phenylsulfoximide

Preparation Analogously to Example 1b

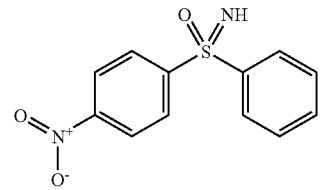

¹H-NMR (DMSO-D6): 8.35 (dd, 2H), 8.20 (dd, 2H), 8.01 (dm, 2H), 7.68-7.56 (m, 3H)

c) Preparation of (RS)—N-(ethoxycarbonyl)-S-phenyl-S-(4-nitrophenyl)-sulfoximide Preparation Analogously to Example 1c

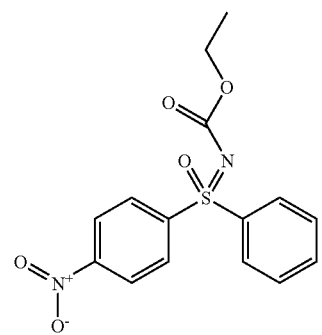

MS (ES+): 335 (M+1, 75%), 289 (100%), 263 (25%)

d) Preparation of (RS)—S-(4-aminophenyl)-N-(ethoxycarbonyl)-S-phenylsulfoximide

Preparation Analogously to Example 1d

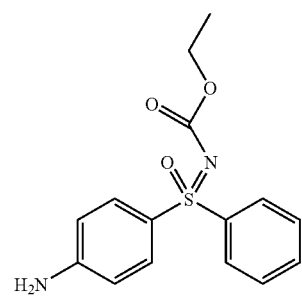

¹H-NMR (DMSO-D6): 7.83 (m, 2H), 7.65-7.54 (m, 5H), 6.63 (dm, 2H), 3.91 (qm, 2H), 1.07 (tm, 3H)

7) (RS)—S-(4-amino-2-bromophenyl)-N-(ethoxycarbonyl)-S-methyl-sulfoximide

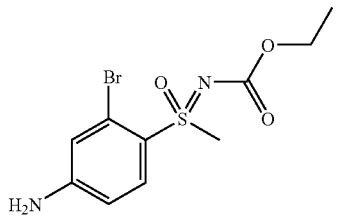

a) Preparation of 2-bromo-1-methylsulphanyl-4-nitro-benzene

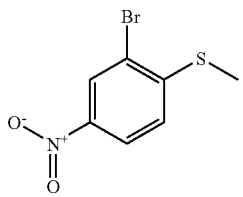

A solution of 25.7 g (120 mmol) 2-bromo-1-fluoro-4-nitrobenzene in 154 ml DMF is treated with 10.6 g (150 mmol) sodium thiomethylate and stirred for 5 hours at 60° C. The mixture is stirred at room temperature for 18 hours, again treated with 1.0 g sodium thiomethylate and stirred for a further 6 hours at 60° C. After cooling, the mixture is poured into ice-water and extracted with ethyl acetate (3×). The combined organic phases are washed with water, dried (Na$_2$SO$_4$), filtered and concentrated. The residue obtained is chromatographically purified (hexane/ethyl acetate 2:1). 20.4 g (82 mmol, corresponding to 70% of theor.) of the product is obtained.

$^1$H-NMR (DMSO-D6): 8.35 (m, 1H), 8.17 (m, 1H), 7.45 (m, 1H), 2.58 (s, 3H).

b) Preparation of 2-bromo-1-methanesulphinyl-4-nitro-benzene

Preparation Analogously to Example 1a

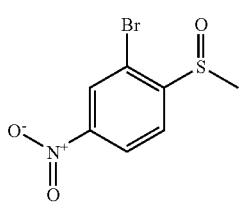

$^1$H-NMR (DMSO-D6): 8.52 (m, 2H), 8.04 (m, 1H), 2.88 (s, 3H).

c) Preparation of (RS)—S-(2-bromo-4-nitrophenyl)-S-ethylsulfoximide

Preparation Analogously to Example 1b

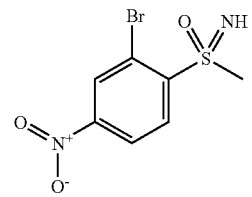

$^1$H-NMR (DMSO-D6): 8.52 (m, 1H), 8.38 (m, 1H), 8.32 (m, 1H), 4.85 (s, 1H), 3.28 (s, 3H).

d) Preparation of (RS)—N-(ethoxycarbonyl)-S-ethyl-S-(2-bromo-4-nitrophenyl)sulfoximide Preparation Analogously to Example 1c

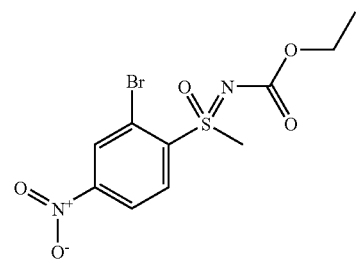

$^1$H-NMR (DMSO-D6): 8.61 (m, 1H), 8.45 (m, 1H), 8.32 (m, 1H), 3.86 (m, 2H), 3.57 (s, 3H), 1.02 (tr, 3H).

e) Preparation of (RS)—S-(4-amino-2-bromophenyl)-N-(ethoxycarbonyl)-S-ethylsulfoximide Preparation Analogously to Example 1d

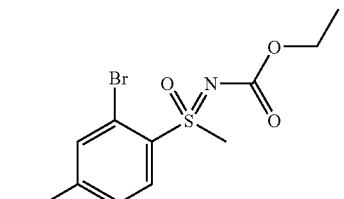

$^1$H-NMR (DMSO-D6): 7.69 (m, 1H), 6.95 (m, 1H), 6.67 (m, 1H), 6.41 (s, 2H), 3.89 (m, 2H), 3.41 (s, 3H), 1.06 (tr, 3H).

8) (RS)—S-(4-aminophenyl)-N,S-dimethylsulfoximide

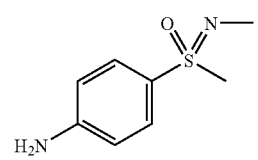

a) Preparation of (RS)—N,S-dimethyl-S-(4-nitrophenyl)sulfoximide

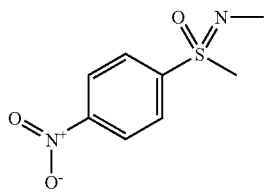

500 mg (2.5 mmol) (RS)—S-(4-nitrophenyl)-S-methylsulfoximide in 4 ml formaldehyde (aqueous, 37%) and 20 ml formic acid (98-100%) are stirred in the open flask at 100° C. After 22 hours, the solvent is evaporated, the mixture is treated again with 4 ml formaldehyde (aqueous, 37%) and 20 ml formic acid (98-100%) and stirred for a further 22 hours at 100° C. Residues of the solvent are removed on the rotary evaporator. The remaining residue is dissolved with 2N HCl and extracted with dichloromethane. The aqueous phase is basified with NaHCO$_3$ and extracted with dichloromethane. The combined organic phases are dried (Na$_2$SO$_4$), filtered and concentrated. 448 mg (2.1 mmol, corresponding to 85% of theor.) of the product is obtained.

$^1$H-NMR (DMSO-D6): 8.43 (m, 2H), 8.08 (m, 2H), 3.24 (s, 3H), 2.48 (s, 3H).

b) Preparation of (RS)—S-(4-aminophenyl)-N,S-dimethylsulfoximide

Preparation Analogously to Example 1d

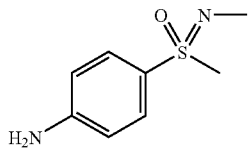

$^1$H-NMR (DMSO-D6): 7.48 (d, 2H), 6.62 (d, 2H), 5.95 (s, 2H), 2.95 (s, 3H), 2.41 (s, 3H).

9) (RS)—S-(4-aminophenyl)-N-propionyl-S-methylsulfoximide

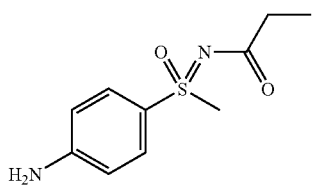

a) Preparation of (RS)—S-(4-nitrophenyl)-N-propionyl-S-methylsulfoximide

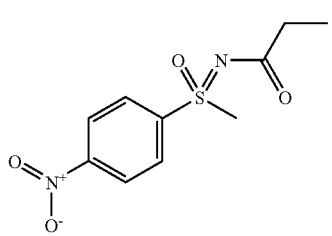

400 mg (2 mmol) (RS)—S-(4-nitrophenyl)-S-methylsulfoximide (Example 1b) are dissolved in 15 ml dichloromethane, cooled in the ice-bath and treated with 0.36 ml triethylamine. 185 mg (2 mmol) propionyl chloride are added dropwise with ice cooling. The mixture is stirred for 30 minutes in the ice-bath and for 15 hours at room temperature. After chromatographic purification (silica gel, hexane/ethyl acetate (0-50% ethyl acetate)), 489 mg (96%) of the desired product is obtained.

$^1$H-NMR (400 MHz, DMSO-D6): δ 0.95 (t, 3H), 2.28 (q, 2H), 3.51 (s, 3H), 8.20 (d, 2H), 8.46 (d, 2H)

b) Preparation of (RS)—S-(4-aminophenyl)-N-propionyl-S-methylsulfoximide

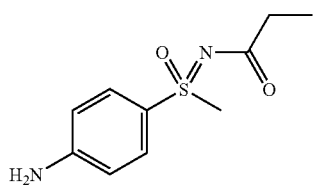

106 mg (0.41 mmol) (RS)—S-(4-nitrophenyl)-N-propionyl-S-methylsulfoximide is dissolved in 10 ml ethanol and treated with 20 mg palladium on activated charcoal (10% Pd). The mixture is stirred under hydrogen at normal pressure for 45 minutes at 23° C. The catalyst is filtered off and the solution concentrated. After chromatographic purification (silica gel, hexane/ethyl acetate (0-50% ethyl acetate)), 72 mg (77%) of the desired product is obtained.

$^1$H-NMR (400 MHz, DMSO-D6): δ 0.99 (t, 3H), 2.25 (q, 2H), 3.35 (s, 3H), 6.17 (s, 2H), 6.69 (d, 2H), 7.55 (d, 2H)

10) (RS)—S-(4-aminophenyl)-N-propyl-S-methylsulfoximide

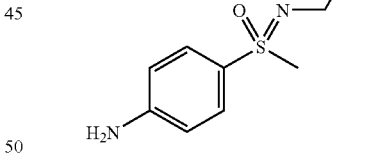

a) Preparation of (RS)—S-(4-nitrophenyl)-N-propyl-S-methylsulfoximide

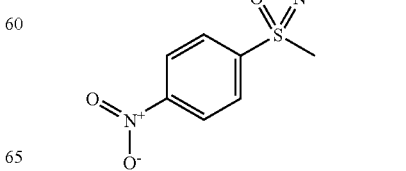

351 mg (1.37 mmol) (RS)—S-(4-nitrophenyl)-N-propionyl-S-methylsulfoximide (Example 9a) are dissolved in 15 ml dichloromethane and treated dropwise with borane-tetrahydrofuran complex (1.0 M solution in tetrahydrofuran, Aldrich) with ice-cooling. The mixture is stirred for 3 hours at 0° C. Next it is cautiously treated with ca. 10 ml water/methanol (1:1), stirred for 30 minutes and extracted with dichloromethane. The organic phase is dried over sodium sulphate and concentrated. After chromatographic purification (silica gel, hexane/ethyl acetate (0-50% ethyl acetate)), 146 mg (44%) of the desired product is obtained.

$^1$H-NMR (400 MHz, DMSO-D6): δ 0.82 (t, 3H), 1.41 (m, 2H), 2.65 (m, 2H), 2.94 (s, 3H), 5.94 (m, 2H), 6.64 (d, 2H), 7.43 (d, 2H)

b) Preparation of (RS)—S-(4-aminophenyl)-N-propyl-S-methylsulfoximide

Preparation Analogously to Example 1d

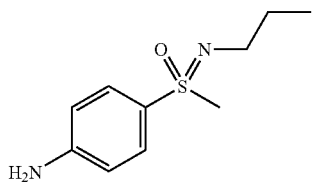

$^1$H-NMR (400 MHz, DMSO-D6): δ 0.82 (t, 3H), 1.41 (m, 2H), 2.65 (m, 2H), 2.94 (s, 3H), 5.94 (m, 2H), 6.64 (d, 2H), 7.43 (d, 2H)

11) (RS)—S-(3-aminophenyl)-N-(ethoxycarbonyl)-S-methylsulfoximide

Preparation Analogously to Example 1

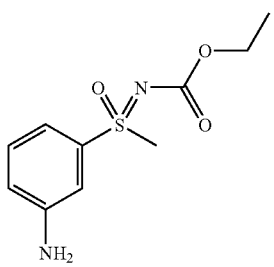

$^1$H-NMR (DMSO-D6): 7.27 (t, 1H), 7.09 (t, 1H), 6.99 (dd, 1H), 6.84 (dd, 1H), 5.71 (s, 2H), 3.91 (q, 2H), 3.33 (s, 3H), 1.10 (t, 3H)

12) (RS)—S-(4-aminophenyl)-N-(ethyl)-S-methylsulfoximide

Preparation Analogously to Example 10

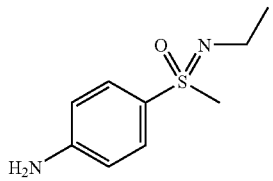

$^1$H-NMR (400 MHz, DMSO-D6): δ 1.02 (t, 3H), 2.70 (q, 1H), 2.78 (q, 1H), 2.95 (s, 3H), 5.94 (m, 2H), 6.64 (d, 2H), 7.43 (d, 2H)

13) (RS)—S-(4-aminophenyl)-N-(n-propyl)-S-cyclopropylsulfoximide

Preparation Analogously to Example 10

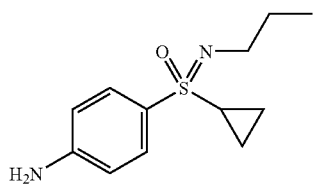

$^1$H-NMR (400 MHz, DMSO-D6): δ 0.75 (m, 2H), 0.83 (t, 3H), 0.94 (m, 1H), 1.06 (m, 1H), 1.41 (m, 2H), 2.50 (m, 1H), 2.68 (m, 1H), 2.76 (m, 1H), 5.93 (s, 2H), 6.63 (d, 2H), 7.38 (d, 2H)

14) (RS)—S-(4-aminophenyl)-N-(n-propyl)-S-phenylsulfoximide

Preparation Analogously to Example 10

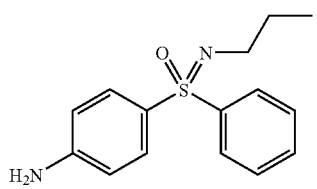

$^1$H-NMR (400 MHz, DMSO-D6): δ 0.89 (t, 3H), 1.51 (m, 2H), 2.81 (m, 2H), 5.99 (s, 2H), 6.59 (d, 2H), 7.52 (m, 5H), 7.80 (m, 2H)

15) (RS)—S-(4-aminophenyl)-N-(cyclopropylmethyl)-S-methylsulfoximide

Preparation Analogously to Example 10

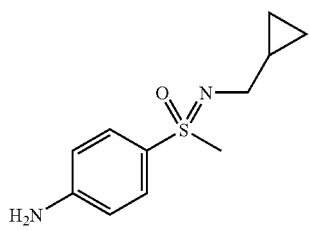

$^1$H-NMR (400 MHz, DMSO-D6): δ 0.04 (m, 2H), 0.32 (m, 2H), 0.85 (m, 1H), 2.53-2.68 (m, 2H), 2.95 (s, 3H), 5.94 (s, 2H), 6.63 (d, 2H), 7.42 (d, 2H)

16) (RS)—S-(4-aminophenyl)-N-(cyclopropylmethyl)-S-cyclopropyl-sulfoximide

Preparation Analogously to Example 10

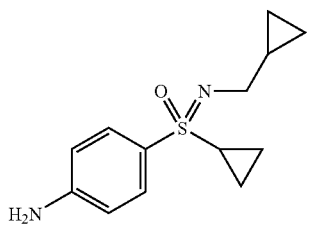

17) (RS)—S-(4-aminophenyl)-N-(cyclopropylmethyl)-S-phenylsulfoximide

Preparation Analogously to Example 10

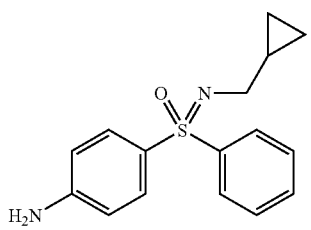

18) (RS)—S-(4-aminophenyl)-N-(phenyl)-S-methylsulfoximide

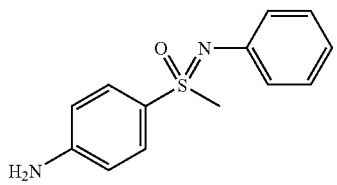

a) Preparation of (RS)—S-(4-nitrophenyl)-N-(phenyl)-S-methylsulfoximide

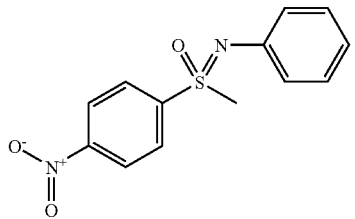

37 mg rac-BINAP and 23 mg bis-(dibenzylidenacetone)-palladium(0) are placed in an argon-flushed two-necked flask with septum. 10 ml toluene, 0.1 ml bromobenzene, 200 mg (RS)—S-(4-nitrophenyl)-S-methylsulfoximide and 365 mg caesium carbonate are added. The mixture is heated under reflux for 15 hours. The dark brown reaction solution is filtered at the pump over Celite, washed with methyl-tert.-butyl ether and the filtrate concentrated to dryness. After chromatographic purification (silica gel, hexane/ethyl acetate (0-50% ethyl acetate)), 230 mg (83%) of the desired product is obtained.

$^1$H-NMR (400 MHz, DMSO-D6): δ 3.50 (s, 3H), 6.84 (m, 3H), 7.09 (t, 2H), 8.19 (d, 2H), 8.41 (d, 2H)

b) Preparation of (RS)—S-(4-aminophenyl)-N-(phenyl)-S-methylsulfoximide

Preparation Analogously to Example 1d

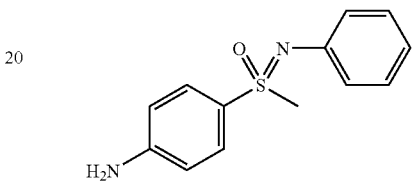

$^1$H-NMR (400 MHz, DMSO-D6): δ 3.20 (s, 3H), 6.04 (s, 2H), 6.60 (d, 2H), 6.75 (t, 1H), 6.82 (d, 2H), 7.05 (t, 2H), 7.50 (d, 2H)

19) (RS)—S-(4-aminophenyl)-N-(methylcarbamoyl)-S-methylsulfoximide

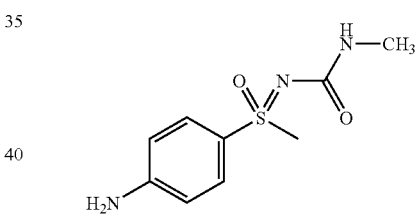

a) Preparation of (RS)—S-(4-nitrophenyl)-N-(methylcarbamoyl)-S-methylsulfoximide

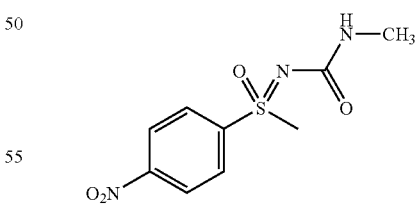

300 mg (1.5 mmol) (RS)—S-(4-nitrophenyl)-S-methylsulphoximide in 8 ml toluene and 4 ml petroleum ether 60/80 are treated with 0.097 ml (1.65 mmol) methyl isocyanate. The mixture is stirred in a pressure tube at 104° C. for 5 hours and at room temperature for 14 hours. The suspension is filtrated to give 302 mg (corresponding to 78% of theor.) of the product.

$^1$H-NMR (300 MHz, DMSO-D6): δ 2.46 (d, 3H), 3.43 (s, 3H), 6.97 (q, 1H), 8.17 (d, 2H), 8.45 (d, 2H)

b) Preparation of (RS)—S-(4-aminophenyl)-N-(methylcarbamoyl)-S-methylsulfoximide

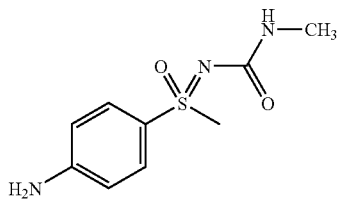

302 mg (1.17 mmol) (RS)—S-(4-nitrophenyl)-N-(methylcarbamoyl)-S-methylsulfoximide in 20 ml methanol is hydrogenated over 60 mg palladium (10% on carbon, 50% water wet) for 4 hours at 26° C. and 30 bar. The catalyst is filtered and the solvent evaporated to give 271 mg (corresponding to 100% of theor.) of the product.

$^1$H-NMR (300 MHz, DMSO-D6): δ 2.50 (3H), 3.26 (s, 3H), 6.08 (s br, 2H), 6.65 (d, 2H), 6.70 (m, 1H), 7.52 (d, 2H)

20) (RS)—S-(4-aminophenyl)-N-(ethylcarbamoyl)-S-methylsulfoximide

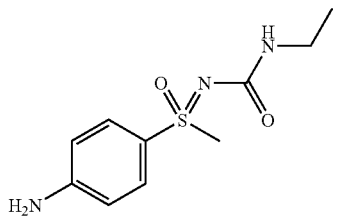

a) Preparation of (RS)—S-(4-nitrophenyl)-N-(ethylcarbamoyl)-S-methylsulfoximide

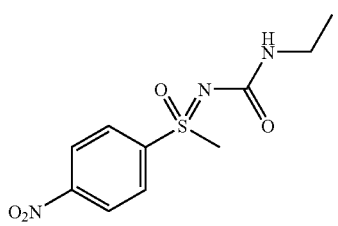

Preparation Analogous Example 19a $^1$H-NMR (300 MHz, DMSO-D6): δ 0.94 (t, 3H), 2.91 (q, 2H), 3.43 (s, 3H), 7.08 (m, 1H), 8.16 (d, 2H), 8.45 (d, 2H)

b) Preparation of (RS)—S-(4-aminophenyl)-N-(ethylcarbamoyl)-S-methylsulfoximide

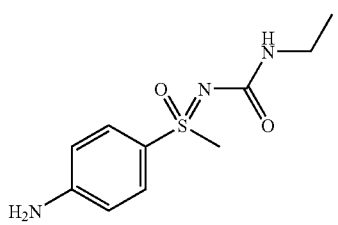

Preparation Analogous Example 19b $^1$H-NMR (300 MHz, DMSO-D6): δ 0:97 (t, 3H), 2.95 (q, 2H), 3.26 (s, 3H), 6.08 (s br, 2H), 6.64 (d, 2H), 6.78 (m, 1H), 7.52 (d, 2H)

21) (RS)—S-(4-aminophenyl)-N-(isopropylcarbamoyl)-S-methylsulfoximide

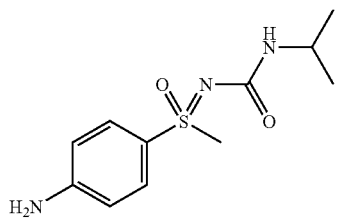

a) Preparation of (RS)—S-(4-nitrophenyl)-N-(isopropylcarbamoyl)-S-methylsulfoximide

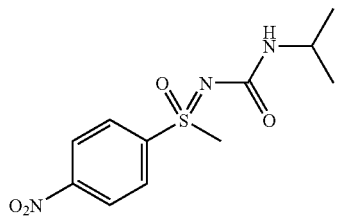

Preparation Analogous Example 19a $^1$H-NMR (300 MHz, DMSO-D6): δ 0.99 (m, 6H), 3.43 (s, 3H), 3.55 (m, 1H), 6.98 (m, 1H), 8.17 (d, 2H), 8.46 (d, 2H)

b) Preparation of (RS)—S-(4-aminophenyl)-N-(isopropylcarbamoyl)-S-methylsulfoximide

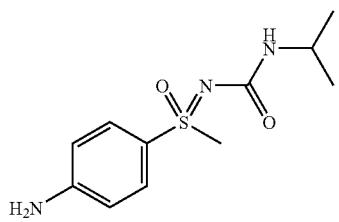

Preparation Analogous example 19b $^1$H-NMR (300 MHz, DMSO-D6): δ 1.01 (m, 6H), 3.26 (s, 3H), 3.62 (m, 1H), 6.07 (s br, 2H), 6.65 (d, 2H), 6.66 (d, 1H), 7.53 (d, 2H)

22) (RS)—S-(4-aminophenyl)-N-(cyclopentylcarbamoyl)-S-methylsulfoximide

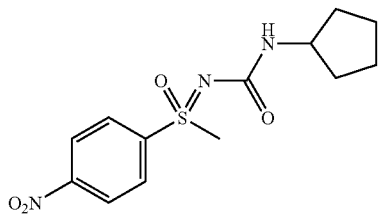

a) Preparation of (RS)—S-(4-nitrophenyl)-N-(cyclopentylcarbamoyl)-S-methylsulfoximide

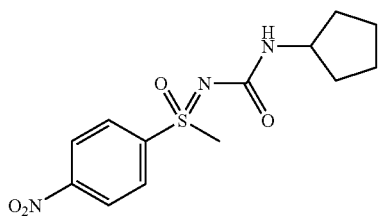

Preparation Analogous Example 19a $^1$H-NMR (300 MHz, DMSO-D6): δ 1.38 (m, 4H), 1.64 (m, 4H), 3.43 (s, 3H), 3.73 (m, 1H), 7.11 (m, 1H), 8.17 (d, 2H), 8.45 (d, 2H)

b) Preparation of (RS)—S-(4-aminophenyl)-N-(cyclopentylcarbamoyl)-S-methylsulfoximide

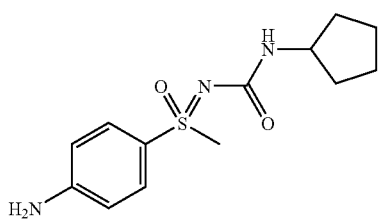

Preparation Analogous Example 19b $^1$H-NMR (300 MHz, DMSO-D6): δ 1.34 (m, 2H), 1.43 (m, 2H), 1.59 (m, 2H), 1.71 (m, 2H), 3.26 (s, 3H), 3.79 (q, 1H), 6.07 (s br, 2H), 6.64 (d, 2H), 6.79 (d, 1H), 7.52 (d, 2H)

23) (RS)—S-(4-aminophenyl)-N-(benzylcarbamoyl)-S-methylsulfoximide

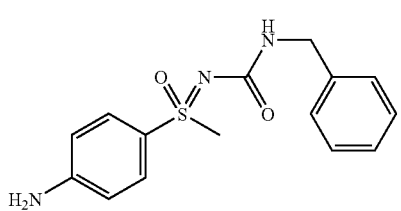

a) Preparation of (RS)—S-(4-nitrophenyl)-N-(benzylcarbamoyl)-S-methylsulfoximide

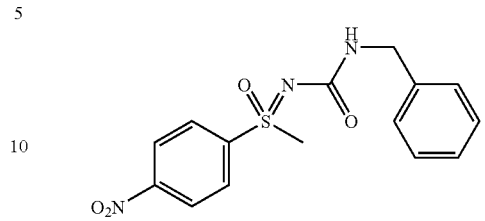

Preparation Analogous Example 19a $^1$H-NMR (300 MHz, DMSO-D6): δ 3.46 (s, 3H), 4.10 (d, 2H), 7.20 (m, 3H), 7.28 (m, 2H), 7.66 (t, 1H), 8.19 (d, 2H), 8.46 (d, 2H)

b) Preparation of (RS)—S-(4-aminophenyl)-N-(benzylcarbamoyl)-S-methylsulfoximide

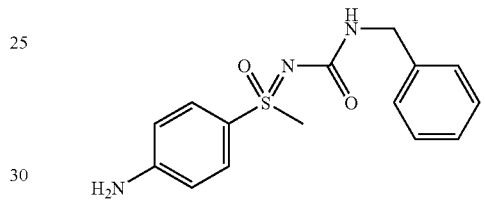

Preparation Analogous Example 19b $^1$H-NMR (300 MHz, DMSO-D6): δ 3.28 (s, 3H), 4.14 (d, 2H), 6.09 (s br, 2H), 6.65 (d, 2H), 7.20 (t, 1H), 7.23 (d, 2H), 7.29 (t, 2H), 7.37 (t, 1H), 7.54 (d, 2H)

24) (RS)—S-(4-aminophenyl)-N-(p-tolylcarbamoyl)-S-methylsulfoximide

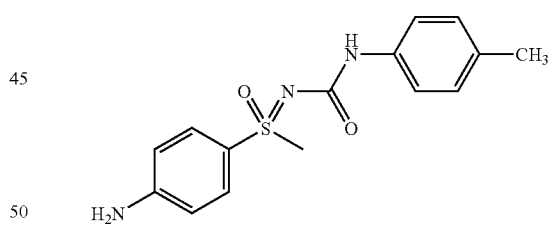

a) Preparation of (RS)—S-(4-nitrophenyl)-N-(p-tolylcarbamoyl)-S-methylsulfoximide

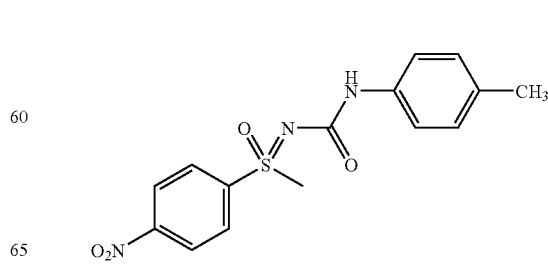

Preparation Analogous Example 19a

¹H-NMR (300 MHz, DMSO-D6): δ 2.19 (s, 3H), 3.55 (s, 3H), 6.99 (d, 2H), 7.34 (d, 2H), 8.25 (d, 2H), 8.48 (d, 2H), 9.42 (s br, 1H)

b) Preparation of (RS)—S-(4-aminophenyl)-N-(p-tolylcarbamoyl)-S-methylsulfoximide

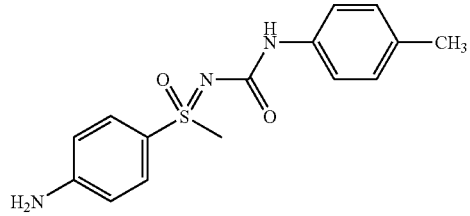

Preparation Analogous Example 19b

¹H-NMR (300 MHz, DMSO-D6): δ 2.20 (s, 3H), 3.36 (s, 3H), 6.14 (s br, 2H), 6.67 (d, 2H), 7.00 (d, 2H), 7.39 (d, 2H), 7.59 (d, 2H), 9.14 (s br, 1H)

25) (RS)—S-(4-aminophenyl)-N-(4-chloro-phenyl-carbamoyl)-S-methylsulfoximide

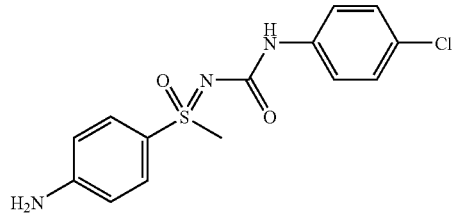

a) Preparation of (RS)—S-(4-nitrophenyl)-N-(4-chloro-phenylcarbamoyl)-S-methylsulfoximide

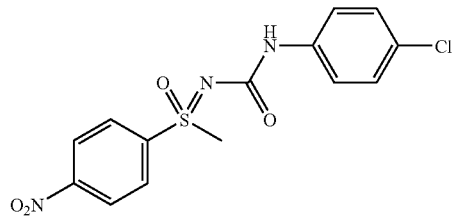

Preparation Analogous Example 19a

¹H-NMR (300 MHz, DMSO-D6): δ 3.57 (s, 3H), 7.24 (d, 2H), 7.49 (d, 2H), 8.25 (d, 2H), 8.48 (d, 2H), 9.68 (s br, 1H)

b) Preparation of (RS)—S-(4-aminophenyl)-N-(4-chloro-phenylcarbamoyl)-S-methylsulfoximide

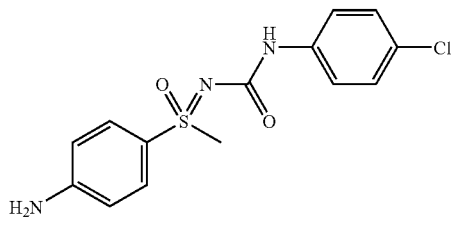

Preparation Analogous Example 19b

¹H-NMR (300 MHz, DMSO-D6): δ 3.37 (s, 3H), 6.14 (s br, 2H), 6.67 (d, 2H), 7.25 (d, 2H), 7.54 (d, 2H), 7.59 (d, 2H), 9.40 (s br, 1H)

26) (RS)—S-(4-aminophenyl)-N-(3-chloro-phenyl-carbamoyl)-S-methylsulfoximide

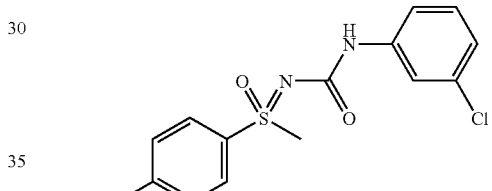

a) Preparation of (RS)—S-(4-nitrophenyl)-N-(3-chloro-phenylcarbamoyl)-S-methylsulfoximide

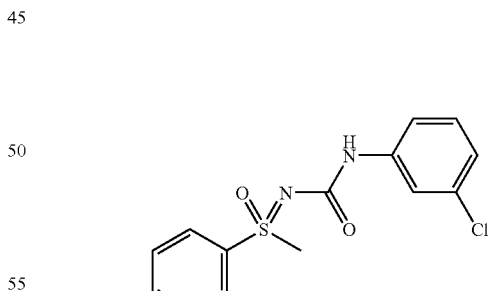

Preparation Analogous Example 19a

¹H-NMR (300 MHz, DMSO-D6): δ 3.58 (s, 3H), 6.95 (d, 1H), 7.21 (t, 1H), 7.35 (d, 1H), 7.64 (s, 1H), 8.25 (d, 2H), 8.49 (d, 2H), 9.75 (s br, 1H)

b) Preparation of (RS)—S-(4-aminophenyl)-N-(3-chloro-phenylcarbamoyl)-S-methylsulfoximide

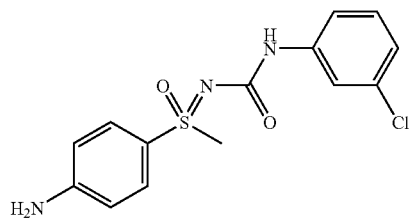

Preparation Analogous Example 19b

¹H-NMR (300 MHz, DMSO-D6): δ 3.38 (s, 3H), 6.15 (s br, 2H), 6.69 (d, 2H), 6.93 (d, 1H), 7.21 (t, 1H), 7.38 (d, 1H), 7.59 (d, 2H), 7.71 (s, 1H), 9.47 (s br, 1H)

27) (RS)—S-(4-aminophenyl)-N-(4-methoxy-phenylcarbamoyl)-S-methylsulfoximide

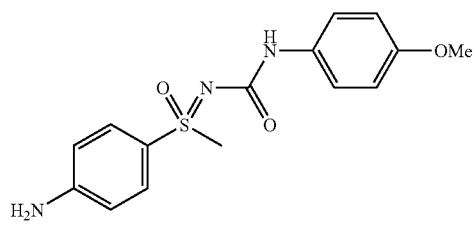

a) Preparation of (RS)—S-(4-nitrophenyl)-N-(4-methoxy-phenylcarbamoyl)-S-methylsulfoximide

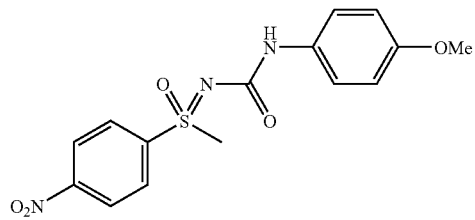

Preparation Analogous Example 19a

¹H-NMR (300 MHz, DMSO-D6): δ 3.54 (s, 3H), 3.67 (s, 3H), 6.77 (d, 2H), 7.36 (d, 2H), 8.24 (d, 2H), 8.48 (d, 2H), 9.36 (s br, 1H)

b) Preparation of (RS)—S-(4-aminophenyl)-N-(4-methoxy-phenylcarbamoyl)-S-methylsulfoximide

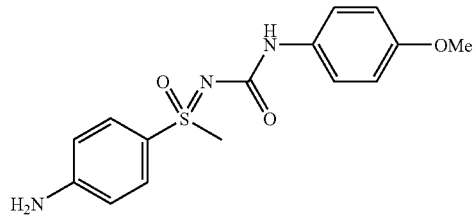

Preparation Analogous Example 19b

¹H-NMR (300 MHz, DMSO-D6): δ 3.35 (s, 3H), 3.67 (s, 3H), 6.13 (s br, 2H), 6.67 (d, 2H), 6.78 (d, 2H), 7.41 (d, 2H), 7.58 (d, 2H), 9.08 (s br, 1H)

28) (RS)—S-(4-aminophenyl)-N-(4-dimethylamino-phenylcarbamoyl)-S-methylsulfoximide

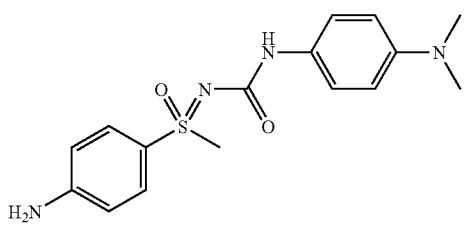

a) Preparation of (RS)—S-(4-nitrophenyl)-N-(4-dimethylamino-phenylcarbamoyl)-S-methylsulfoximide

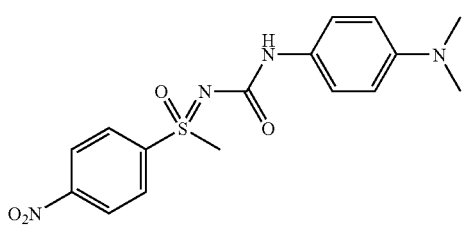

Preparation Analogous Example 19a

¹H-NMR (300 MHz, DMSO-D6): δ 2.79 (s, 6H), 3.52 (s, 3H), 6.61 (d, 2H), 7.27 (d, 2H), 8.24 (d, 2H), 8.48 (d, 2H), 9.19 (s br, 1H)

b) Preparation of (RS)—S-(4-aminophenyl)-N-(4-dimethylamino-phenylcarbamoyl)-S-methylsulfoximide

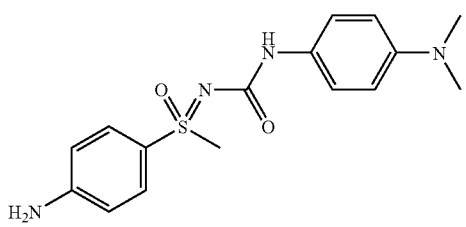

Preparation Analogous Example 19b

¹H-NMR (300 MHz, DMSO-D6): δ 2.79 (s, 6H), 3.34 (s, 3H), 6.13 (s br, 2H), 6.63 (d, 2H), 6.67 (d, 2H), 7.32 (d, 2H), 7.58 (d, 2H), 8.92 (s br, 1H)

29) (RS)—S-(4-aminophenyl)-N-(pyridin-3-ylcarbamoyl)-S-methylsulfoximide

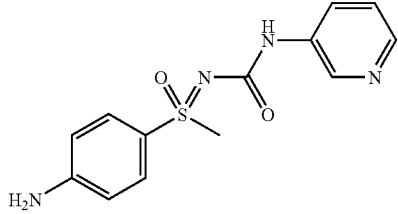

a) Preparation of (RS)—S-(4-nitrophenyl)-N-(pyridin-3-ylcarbamoyl)-S-methylsulfoximide

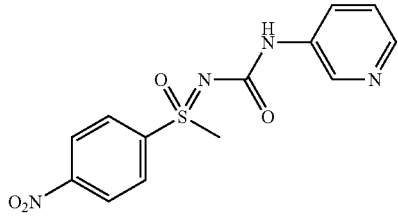

Preparation Analogous Example 19a $^1$H-NMR (300 MHz, DMSO-D6): δ 3.59 (s, 3H), 7.22 (dd, 1H), 7.88 (dm, 1H), 8.12 (dd, 1H), 8.27 (d, 2H), 8.49 (d, 2H), 8.61 (d, 1H), 9.73 (s br, 1H)

b) Preparation of (RS)—S-(4-aminophenyl)-N-(pyridin-3-ylcarbamoyl)-S-methylsulfoximide

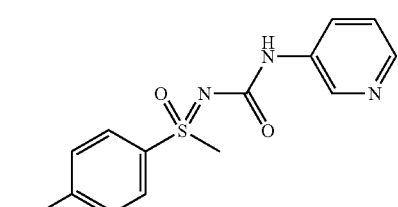

Preparation Analogous Example 19b $^1$H-NMR (300 MHz, DMSO-D6): δ 3.39 (s, 3H), 6.17 (s br, 2H), 6.68 (d, 2H), 7.23 (dd, 1H), 7.60 (d, 2H), 7.94 (dm, 1H), 8.10 (dd, 1H), 8.65 (d, 1H), 9.47 (s br, 1H)

30) (RS)—S-(4-aminophenyl)-N-(2-methoxy-ethyl)-S-methylsulphoximide

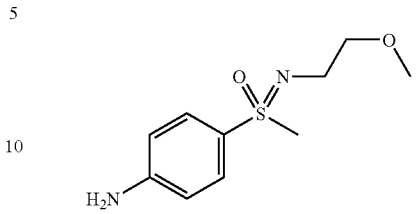

a) Preparation of (RS)—S-(4-nitrophenyl)-N-(2-methoxy-acetyl)-S-methylsulphoximide

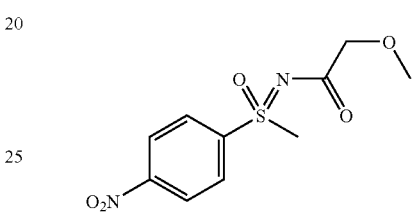

100 mg (0.5 mmol) (RS)—S-(4-nitrophenyl)-S-methylsulphoximide (Example 1b) are dissolved in 3.33 ml dichloromethane, cooled in the ice-bath and treated with 0.1 ml (0.75 mmol) triethylamine. 0.068 ml (0.75 mmol) 2-methoxy-acetyl chloride are added dropwise with ice cooling. The mixture is stirred for 30 minutes in the ice-bath and for 15 hours at room temperature. After chromatographic purification (silica gel, hexane/ethyl acetate (0-50% ethyl acetate)), 107 mg (79%) of the desired product is obtained.

$^1$H-NMR (400 MHz, DMSO-D6): δ 3.26 (s, 3H), 3.58 (s, 3H), 3.95 (m, 2H), 8.23 (d, 2H), 8.48 (d, 2H)

b) Preparation of (RS)—S-(4-aminophenyl)-N-(2-methoxy-acetyl)-S-methylsulphoximide

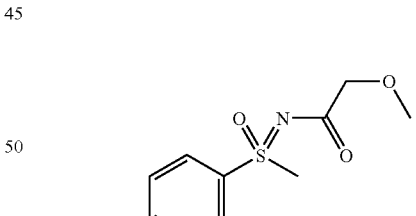

107 mg (0.39 mmol) (RS)—S-(4-nitrophenyl)-N-(2-methoxy-acetyl)-S-methylsulphoximide is dissolved in 13.6 ml ethanol and treated with 40 mg palladium on activated charcoal (10% Pd). The mixture is stirred under hydrogen at normal pressure for 60 minutes at 24° C. The catalyst is filtered off and the solution concentrated. After chromatographic purification (silica gel, hexane/ethyl acetate (0-50% ethyl acetate)), 50 mg (53%) of the desired product is obtained.

$^1$H-NMR (400 MHz, DMSO-D6): δ 3.27 (s, 3H), 3.35 (s, 3H), 3.89 (s, 2H), 6.19 (m, 2H), 6.67 (d, 2H), 7.54 (d, 2H)

c) Preparation of (RS)—S-(4-aminophenyl)-N-(2-methoxy-ethyl)-S-methylsulphoximide

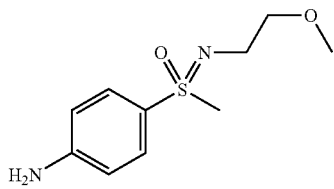

493 mg (2.03 mmol) (RS)—S-(4-aminophenyl)-N-(2-methoxy-acetyl)-S-methylsulphoximide is dissolved in 67.8 ml tetrahydrofuran, cooled in the ice-bath and treated dropwise with 6.13 ml (6.13 mmol) borane tetrahydrofuran complex. The mixture is stirred for 90 minutes and quenched with one drop of methanol and one drop of water. After chromatographic purification (silica gel, hexane/ethyl acetate (0-50% ethyl acetate)), 383 mg (82%) of the desired product is obtained.

¹H-NMR (400 MHz, DMSO-D6): δ 2.80 (q, 1H), 2.87 (q, 1H), 2.96 (s, 3H), 3.19 (s, 3H), 3.32 (t, 2H), 5.96 (s br, 2H), 6.65 (d, 2H), 7.44 (d, 2H)

31) (RS)—S-(4-aminophenyl)-N-(morpholine-4-carbonyl)-S-methylsulfoximide

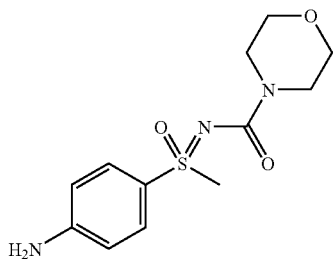

a) Preparation of (RS)—S-(4-nitrophenyl)-N-(morpholine-4-carbonyl)-S-methylsulfoximide

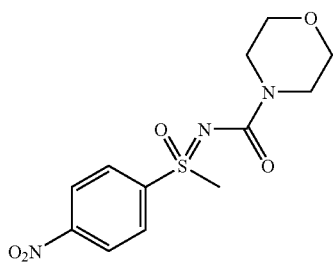

100 mg (0.5 mmol) (RS)—S-(4-nitrophenyl)-S-methylsulphoximide in 4 ml dimethylformamide are treated at room temperature with 23.97 mg sodium hydride (55%, 0.55 mmol). The mixture is stirred for 30 minutes at room temperature and for 30 minutes at 50° C. After cooling to room temperature 0.063 ml (0.55 mmol) 4-morpholinylcarbonyl chloride are added. The mixture is stirred for 30 minutes at room temperature and for 2 hours at 50° C. and finally quenched with methanol. After chromatographic purification (silica gel, hexane/ethyl acetate (0-50% ethyl acetate)), 87 mg (0.28 mmol, corresponding to 56% of theor.) of the desired product is obtained.

¹H-NMR (300 MHz, DMSO-D6): δ 3.13 (t, 4H), 3.50 (s, 3H), 3.55 (t, 4H), 8.19 (d, 2H), 8.46 (d, 2H)

b) Preparation of (RS)—S-(4-aminophenyl)-N-(morpholine-4-carbonyl)-S-methylsulfoximide

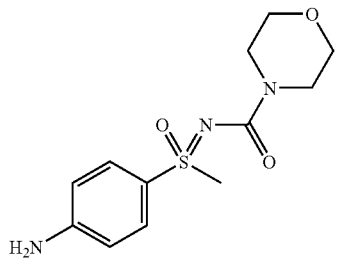

Preparation Analogous Example 1d

¹H-NMR (300 MHz, DMSO-D6): δ 3.13 (t, 4H), 3.32 (s, 3H), 3.55 (t, 4H), 6.12 (s br, 2H), 6.66 (d, 2H), 7.54 (d, 2H).

32) (RS)—S-(3-amino-phenyl)-N-(ethoxycarbonyl)-S-methyl-sulfoximide

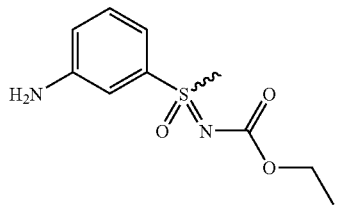

a) Preparation of 1-methanesulphinyl-3-nitro-benzene

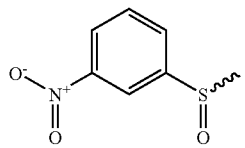

A solution of 3-nitro thioanisol (96 g, 568 mmol) in DCM (100 mL) is added dropwise to a cooled solution of sulfuryl chloride (96 g, 711 mmol) in DCM (600 mL) at −60° C. The mixture is stirred for 4 h at −20° C., then cooled to −60° C., and 350 mL of EtOH are carefully added. The reaction is then allowed to warm up to rt, subsequently, most of the solvent is evaporated, the residue is poured in sat. aq. NaHCO₃, and the solid product is filtered off and carefully washed with hexane on the filter, then air-dried to give the desired sulfoxide (95 g, 90% yield).

¹H-NMR (300 MHz, CDCl₃): 8.51 (s, 1H); 8.38 (d, 1H); 8.03 (d, 1H); 7.78 (t, 1H); 2.62 (s, 3H).

b) Preparation of (RS)—N-(ethoxycarbonyl)-S-methyl-S-(3-nitrophenyl)-sulfoximide

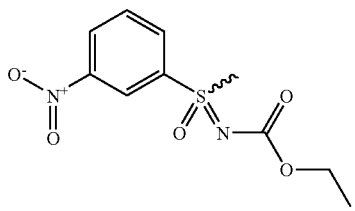

Step 1

In a 1000-mL three-necked flask equipped with reflux condenser, dropping funnel and mechanical stirrer, a mixture of 1-methanesulphinyl-3-nitro-benzene (95 g, 513 mmol), sodium azide (36 g, 553 mmol) and DCM (600 mL) is cooled to 0° C. Subsequently, conc. H₂SO₄ (130 mL) is slowly added. The mixture then is carefully warmed to 45° C. and stirred at this temperature for 24 h. After cooling to room temperature, the mixture is poured on ice and then basified to pH 11 by NaOH. The DCM layer is separated, and the aqueous solution is extracted three more times with DCM. The organic layers are combined, dried over sodium sulfate and evaporated. TLC indicate ~30% unreacted sulfoxide, LCMS analysis showed ~50% conversion to the target product. Further acylation is set up without purification.

Step 2

The crude product mixture from the previous stage (crude weight ~90 g) is dissolved in 300 mL of dry pyridine and treated with ethyl choroformiate (25 mL, 261 mmol) at room temperature. After 10 min, TLC indicates completion of the reaction. The mixture is poured into 1000 mL of water, acidified with aqueous hydrogen chloride to pH 3, extracted with ethyl acetate, dried over sodium sulfate and evaporated. The crude product is purified by column chromatography, followed by crystallisation from ethyl acetate and washing with hexane to give the desired product (72 g, 52% overall yield) and unreacted sulfoxide (23 g).

¹H-NMR (300 MHz, CDCl₃): 8.84 (s, 1H); 8.56 (d, 1H); 8.34 (d, 1H); 7.85 (t, 1H); 4.02-4.18 (m, 2H); 3.36 (s, 3H); 1.24 (t, 3H).

c) Preparation of (RS)—S-(3-aminophenyl)-N-(ethoxycarbonyl)-S-methylsulfoximide

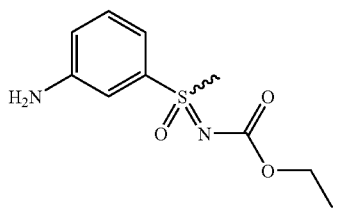

(RS)—S-(3-aminophenyl)-N-(ethoxycarbonyl)-S-methylsulfoximide is prepared from (RS)—N-(ethoxycarbonyl)-S-methyl-S-(3-nitrophenyl)-sulfoximide (4.8 g, 17.6 mmol, 1.0 equiv.) to give 4.2 g of the desired amine (98% yield) according to the following procedure: The respective nitro compound (1.0 eq) is added to a stirred mixture of powdered iron (12 eq) in 85% ethanol (5 mL per mmol nitro compound) and concentrated hydrochloric acid (10 µL per mmol nitro compound) at room temperature. Subsequently, the mixture is stirred at 60° C. until all starting material is consumed (typically after about 3 h). After cooling to room temperature, the mixture is filtered, and the filter cake is repeatedly washed with hot ethanol. The filtrate is evaporated and purified by column chromatography to give the desired amine.

¹H-NMR (300 MHz, CDCl₃): 7.24 (t, 1H); 7.03-7.08 (m, 1H); 6.95 (d, 1H); 6.81 (dd, 1H); 5.60-5.80 (m, 2H); 3.80-3.96 (m, 2H); 3.31 (s, 3H); 1.06 (t, 3H).

1.2. Preparation of 2-chloro-pyrimidine Derivatives (See Also Scheme 2)

General Procedures

Procedure 1—Preparation of 5-bromo-2,4-dichloro-pyrimidine or 2,4-dichloro-5-iodo-pyrimidine 5-bromo- or 5-iodouracil (1.0 equiv.) is suspended in N,N-dimethylaniline, treated with phosphorus oxychloride (10.0 equiv.) and stirred for 90 minutes at 125° C. After cooling to room temperature, excess phosphorus oxychloride is removed under vacuum. The residue is poured into ice-water. After 2 hours the crystals that have formed are filtered off at the pump and washed with water. Next, the crystals are dissolved in ethyl acetate. The organic phase is washed with saturated sodium hydrogen carbonate solution and saturated sodium sulphite solution and dried over sodium sulphate. After removal of the solvent the chromatographic purification is performed.

5-bromo-2,4-dichloro-pyrimidine is also commercially available (e. g.: Aldrich, Acros, Frontier).

2,4-dichloro-5-iodo-pyrimidine is likewise commercially available (Apin).

Procedure 2—Introduction of Amine in the 4 Position of the Pyrimidine 5-bromo-2,4-dichloro-pyrimidine or 2,4-dichloro-5-iodo-pyrimidine (1.0 equiv.) is dissolved in acetonitrile (62.0 equiv.) and treated with triethylamine (1.2 equiv.) and the amine component (1.1 equiv.). After 24 hours at room temperature, the mixture is diluted with ethyl acetate. The organic phase is washed with saturated sodium chloride solution, 10% aqueous citric acid solution and saturated sodium hydrogen carbonate solution. After drying over sodium sulphate and removal of the solvent, the purification is effected by chromatography.

The reaction of 5-bromo-2,4-dichloro-pyrimidine or 2,4-dichloro-5-iodo-pyrimidine with amines, alcohols or thiols is also described in: a) U. Lücking, M. Krüger, R. Jautelat, G. Siemeister, WO 2005037800; b) U. Lücking, M. Krueger, R. Jautelat, O. Prien, G. Siemeister, A. Ernst, WO 2003076437; c) T. Brumby, R. Jautelat, O. Prien, M. Schäfer, G. Siemeister, U. Lücking, C. Huwe, WO 2002096888).

Procedure 3—Functionalisation on C5 by Suzuki Coupling

Compound IV (1.0 equiv.), 1M sodium carbonate solution (1.6 equiv.), tri(2-furyl)phosphine (0.4 equiv.) and the appropriate R¹-boronic acid derivative (1.1 equiv.) are placed in dimethoxyethane (90 equiv.): After degassing, tetrakis-(triphenylphosphine)palladium (0.05 equiv.) is added and the mixture stirred for 5 hours at 100° C. under an argon atmosphere. After cooling to room temperature the mixture is diluted with water. It is extracted with ethyl acetate and the organic phase is dried over sodium sulphate. After removal of the solvent under vacuum the chromatographic purification is performed.

Procedure 4a—Introduction of Alcohols in the 4 Position of the Pyrimidine 5-bromo-2,4-dichloro-pyrimidine or 2,4-dichloro-5-iodo-pyrimidine (1.0 equiv.) is in dry methanol (85 equiv.) and added dropwise with stirring at −5 to 0° C. to methanolic-sodium ethanolate solution (1.05 equiv., 0.3 M). The reaction is warmed to RT and stirred for 18 hrs. The crude product precipitates from the solution and is recrystallised from methanol and then dried under vacuum over phosphorus pentoxide.

Procedure 4b—Introduction of Alcohols in the 4 Position of the Pyrimidine

A solution of 5-bromo-2,4-dichloro-pyrimidine or 2,4-dichloro-5-iodo-pyrimidine (1.0 eq) in dry acetonitrile (0.4 M) is treated by stirring at rt with a previously obtained suspension of sodium-alcoholate (1.05 eq) (from the corresponding alcohol (1.05 eq) and 60% w NaH (1.05 eq) in dry diethyl ether (0.11 M)). The reaction mixture is stirred overnight. Then the reaction mixture is poured in water and extracted with ethyl acetate (5 times). The combined extracts are dried over anhydrous sodium sulphate, filtered and evaporated in vacuum. The residue is purified by flash chromatography.

1) Preparation of 2,4-dichloro-5-iodopyrimidine

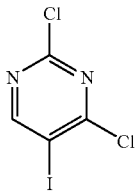

Starting from 5-iodouracil (10 g, 42 mmol)) and N,N-dimethylaniline (11.0 mL), the desired product is obtained according to procedure 1 in 92% yield (10.6 g) after chromatographic purification (silica gel, dichloromethane).
$^{1}$H-NMR (400 MHz, CDCl$_3$): δ 8.90 (s, 1H).

2) (R)-2-(2-chloro-5-iodopyrimidine-4-ylamino)propan-1-ol

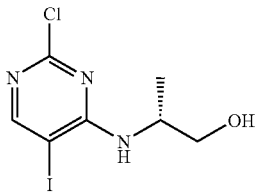

In the reaction of 2,4-dichloro-5-iodopyrimidine (3.0 g, 10.9 mmol) with (R)-2-amino-1-propanol (884 mg, 11.8 mmol) according to procedure 2, the desired product is obtained in 88% yield (1.6 g) after chromatographic purification (silica gel, dichloromethane/methanol (0% to 20% methanol)).
$^{1}$H-NMR (300 MHz, DMSO-D6): δ 1.10 (d, 3H), 3.35-3.45 (m, 2H), 4.05-4.15 (m, 1H), 4.86 (t, 1H), 6.56 (d, 1H), 8.30 (s, 1H).

3) (R)-2-(2-chloro-5-(2-thienyl)pyrimidine-4-ylamino)propan-1-ol

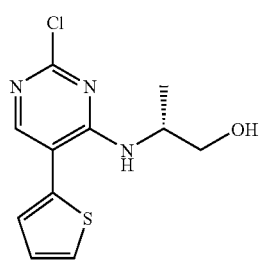

In the reaction of (R)-2-(2-chloro-5-iodopyrimidine-4-ylamino)propan-1-ol (400 mg, 1.3 mmol) with thiophen-2-boronic acid (e. g.: Aldrich, Acros, Apin) (179 mg, 1.4 mmol) according to procedure 3, the desired product is obtained in 70% yield (240 mg) after chromatographic purification (silica gel, ethyl acetate/hexane (0%-100% ethyl acetate)).
$^{1}$H-NMR (400 MHz, DMSO-D6): δ 1.10 (d, 3H), 3.35-3.42 (m, 2H), 4.10-4.20 (m, 1H), 4.82 (t, 1H), 6.65 (d, 1H), 7.18 (dd, 1H), 7.26 (d, 1H), 7.68 (d, 1H), 7.95 (s, 1H).

4) 2-(2-chloro-5-iodopyrimidine-4-ylamino)ethanol

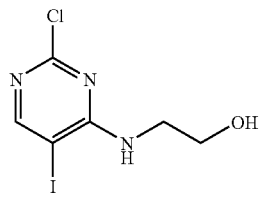

In the reaction of 2,4-dichloro-5-iodopyrimidine (2.0 g, 7.3 mmol) with 2-amino-ethanol (480 mg, 7.9 mmol) according to procedure 2, the desired product is obtained in 83% yield (1.8 g) after chromatographic purification (silica gel, dichloromethane/methanol (0% to 20% methanol)).
$^{1}$H-NMR (400 MHz, DMSO-D6): δ 3.35-3.40 (m, 2H), 3.45-3.54 (m, 2H), 4.80 (t, 1H), 7.12 (t, 1H), 8.33 (s, 1H).

5) 2-(2-chloro-5-(2-thienyl)pyrimidine-4-ylamino)ethanol

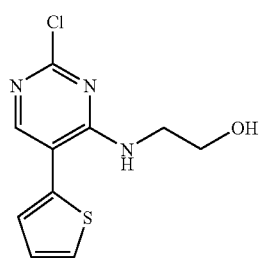

In the reaction of 2-(2-chloro-5-iodopyrimidine-4-ylamino)-ethanol (300 mg, 1.0 mmol) with thiophen-2-boronic acid (140 mg, 1.1 mmol) according to procedure 3, the desired product is obtained in 82% yield (210 mg) after chromatographic purification (silica gel, ethyl acetate/hexane (0%-100% ethyl acetate)).

$^1$H-NMR (300 MHz, DMSO-D6): δ 3.35-3.42 (m, 2H), 3.44-3.54 (m, 2H), 4.75 (t, 1H), 7.08 (t, 1H), 7.20 (dd, 1H), 7.28 (dd, 1H), 7.69 (d, 1H), 7.95 (s, 1H).

6) N-[2-(2-chloro-5-iodopyrimidine-4-ylamino)ethyl]acetamide

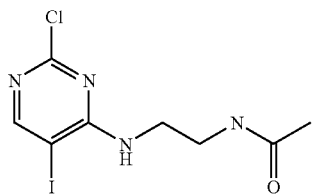

In the reaction of 2,4-dichloro-5-iodopyrimidine (1.0 g, 3.6 mmol) with N-(2-aminoethyl)acetamide (e. g. ABCR, Aldrich) (0.42 mL, 3.9 mmol) according to procedure 2, the desired product is obtained in 71% yield (878 mg) after trituration of the crystals obtained with diethyl ether.

$^1$H-NMR (300 MHz, DMSO-D6): δ 1.75 (s, 3H), 3.10-3.25 (m, 2H), 3.30-3.40 (m, 2H), 7.35 (t, 1H), 7.95 (t, 1H), 8.75 (s, 1H).

7) N-[2-(2-chloro-5-(2-thienyl)pyrimidine-4-ylamino)ethyl]acetamide

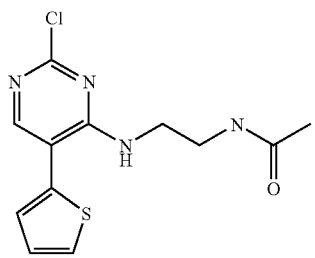

In the reaction of N-[2-(2-chloro-5-iodopyrimidine-4-ylamino)ethyl]-acetamide (870 mg, 2.6 mmol) with thiophen-2-boronic acid (359 mg, 2.8 mmol) according to procedure 3, the desired product is obtained in 79% yield (602 mg) after chromatographic purification (silica gel, ethyl acetate/hexane (0%-90% ethyl acetate)).

$^1$H-NMR (300 MHz, DMSO-D6): δ 1.75 (s, 3H), 3.15-3.25 (m, 2H), 3.30-3.40 (m, 2H), 7.18 (dd, 1H), 7.25-7.35 (m, 2H), 7.67 (dd, 1H), 7.90-8.00 (m, 2H).

8) (S)-2-(2-chloro-5-thiophen-3-yl-pyrimidine-4-ylamino)-4-methyl-pentan-1-ol

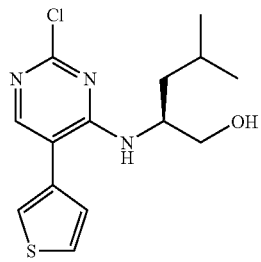

Preparation according to procedures 2 and 3 with the use of 2,4-dichloro-5-iodopyrimidine, L-leucinol (Aldrich) and thiophen-3-boronic acid (Aldrich).

9) (R)-2-(2-chloro-5-(2-thienyl)pyrimidine-4-ylamino)butan-1-ol

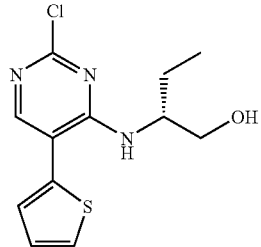

In the reaction of (R)-2-(2-chloro-5-bromopyrimidine-4-ylamino)butan-1-ol (18.17 g, 64.8 mmol) with thiophen-2-boronic acid (e. g.: Aldrich, Acros, Apin) (9.12 g, 128.0 mmol) according to procedure 3, the desired product is obtained in 71% yield (13.1 g) after chromatographic purification (silica gel, ethyl acetate/hexane (20%-50% ethyl acetate)).

$^1$H-NMR (400 MHz, CDCl$_3$): δ 0.98 (t, 3H), 1.52-1.77 (m, 2H), 2.56 (s, 1H), 3.63-3.82 (m, 2H), 4.20 (m, 1H), 5.75 (d, 1H), 7.18 (m, 2H), 7.48 (d, 1H), 8.00 (s, 1H).

10) 3-(2-chloro-5-iodopyrimidine-4-ylamino)propan-1-ol

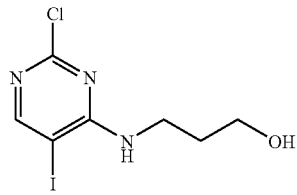

In accordance with procedure 2, 3-amino-1-propanol (0.38 ml, 5 mmol) and N-ethyldiisopropylamine (1.74 ml, 10 mmol) are dissolved in 100 ml acetonitrile under argon and cooled to −40° C. Next, the solution of 2,4-dichloro-5-iodopyrimidine (1.51, 5.5 mmol) in 50 ml acetonitrile is added dropwise at −40° C. internal temperature. The mixture is then stirred for 1 hr at −40° C., for a further 5 hrs at −37 to −25° C., slowly warmed to RT and stirred for 18 hrs at RT.

The reaction mixture is concentrated on the rotary evaporator. The residue is treated with 200 ml ethyl acetate and 75 ml sat. NaHCO₃ soln., well shaken, and the aqueous phase then extracted 2× with 75 ml portions of ethyl acetate. The ethyl acetate phase is dried over Na₂SO₄, filtered, concentrated and the residue dried at the oil pump: 1.76 g colourless crude product, which slowly crystallises at RT.

The crude product is purified by column chromatography (50 g column, mobile phase: gradient hexane: ethyl acetate 1:1 to 100% ethyl acetate), no separation of the isomers occurring (87:13)=1.49 g (95%).

¹H-NMR (400 MHz, DMSO-D6): δ 1.66 (m, 2H), 3.37 (q, 2H), 3.44 (q, 2H), 4.60 (t, 1H), 7.33 (t, 1H), 8.27 (s, 1H).

MS: 314 (MH+).

11) 3-(2-chloro-5-(2-thienyl)pyrimidine-4-ylamino)propan-1-ol

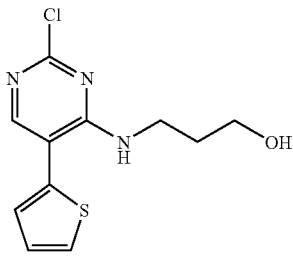

In accordance with procedure 3, 3-(2-chloro-5-iodopyrimidine-4-ylamino)propan-1-ol (1.38 g, 4.4 mmol) and 2-thiophenboronic acid (0.62 g, 4.87 mmol) are dissolved in 15 ml dimethoxyethane under argon, and tri(2-furyl)phosphine (104 mg, 0.45 mmol) and 1 molar Na₂CO₃ soln. (7.1 ml, 7.1 mmol) are added (the previously light yellow reaction mixture becomes almost colourless and turbid after the Na₂CO₃ addition). Argon is passed in for 15 mins. Tetrakis(triphenyl-phosphine)palladium (511 mg, 0.44 mmol) is then added and the reaction mixture is stirred for 18 hrs at 75° C. under argon (suspension). Dimethoxyethane is distilled off on the rotary evaporator, the residue treated with 250 ml ethyl acetate and 30 ml H₂O, stirred vigorously for 30 mins, and the undissolved substance filtered off at the pump on a G4 frit, and washed with H₂O and ethyl acetate: 372 mg residue.

Filtrate: the organic phase is separated, and the aqueous phase further extracted 3× with 50 ml portions of ethyl acetate. The combined organic phases washed 1× with sat. NaCl soln., dried over Na₂SO₄, filtered and concentrated: 1.54 g light brown, oily crude product.

For the chromatographic separation, it is dissolved in a little ethyl acetate and absorbed on Celite, dried and placed on a 20 g Flashmaster Si column. Chromatographed with hexane/ethyl acetate (0 to 100% ethyl acetate).

Fr. 15-19=679 mg (57%) almost colourless viscous oil (LCMS: 59% purity)

Fr. 20-28=253 mg (21%) almost colourless, crystallises slowly (LCMS: 92% purity).

| HPLC/MS: | Column: | ODSII 1.7μ 33 × 4.6 mm |
|---|---|---|
| | Solvent | A: H₂O B: acetonitrile |
| | Buffer: | 0.01% HCO₂H each |
| | Gradient: | 90% A + 10% B_10 -> 90% B(4.5') |
| | Flow: | 0.8 mL/min |
| | Solution: | 1 mg/mL MeOH |
| | Injection Volume: | 2 μl |

| -continued | |
|---|---|
| Detection: | DAD (200-350 nm) TAC; MS-ESI+ (160-800 m/z) TIC |
| Temperature: | Room temperature |
| Retention Time: | 1.70 min |
| Mass found: | 269 m/z |

12) (2-chloro-5-iodopyrimidine-4-yl)-(3-morpholin-4-yl-propyl)-amine

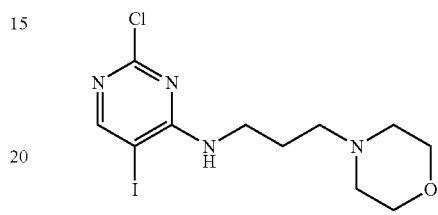

In accordance with procedure 2, 3-morpholin-4-yl-propylamine (0.73 ml, 5 mmol) and N-ethyldiisopropylamine (1.71 ml, 10 mmol) are dissolved in 100 ml acetonitrile under argon and cooled to −35° C. The solution of 2,4-dichloro-5-iodopyrimidine (1.37, 5.0 mmol) in 50 ml acetonitrile is then added dropwise at −35° C. internal temperature. Stirred 1 hr further at −30 to −20° C., then slowly warmed up to RT and stirred for 3 days at RT.

The reaction mixture is concentrated on the rotary evaporator. The residue is treated with 200 ml ethyl acetate and 75 ml sat. NaHCO₃ soln., well shaken and the aqueous phase further extracted 2× with 75 ml portions of ethyl acetate. The ethyl acetate phase is dried over Na₂SO₄ dried, filtered, concentrated and the residue dried at the oil pump: 1.92 g colourless and crystalline crude product. The crude product is purified by column chromatography (50 g column, mobile phase: gradient hexane: ethyl acetate 80% to 100% ethyl acetate): 1.66 g (97%).

¹H-NMR (400 MHz, DMSO-D6): δ 1.66 (m, 2H), 2.30 (m, 6H), 3.37 (m, 2H), 3.57 (m, 4H), 7.42 (t, 1H), 8.27 (s, 1H).

MS: 383 (MH+).

13) (2-chloro-5-thiophen-2-yl-pyrimidine-4-yl)-(3-morpholin-4-yl-propyl)-amine

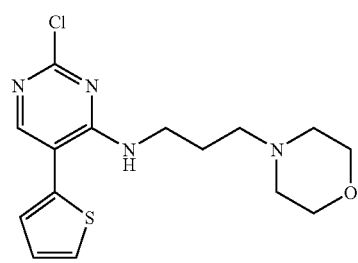

In accordance with procedure 3, (2-chloro-5-iodopyrimidine-4-yl)-(3-morpholin-4-yl-propyl)-amine (0.67 g, 1.75 mmol) and 2-thiophenboronic acid (0.246 g, 1.92 mmol) are dissolved in 20 ml dimethoxyethane under argon, and tri(2-furyl)phosphine (42.8 mg, 0.18 mmol) and 1 molar Na₂CO₃ soln. (2.8 ml, 2.8 mmol) are added (the previously light yellow reaction mixture becomes almost colourless and turbid after the Na$_2$CO$_3$ addition). Argon is introduced for 15 mins. Next, tetrakis(triphenylphosphine)palladium (204 mg, 0.18 mmol) is added and the reaction mixture stirred for 20 hrs at 75° C. under argon. Dimethoxyethane is distilled off on the rotary evaporator, the residue treated with 250 ml ethyl acetate and 30 ml H$_2$O, stirred vigorously for 30 mins, and the undissolved substance filtered off on a G4 frit at the pump, and washed with H$_2$O and ethyl acetate: 372 mg residue.

Filtrate: the organic phase is separated, and the aqueous phase further extracted 3× with 50 ml portions of ethyl acetate. The combined organic phases washed 1× with sat. NaCl soln., dried over Na$_2$SO$_4$ dried, filtered and concentrated: 790 mg dark brown, oily crude product.

For the chromatographic separation, it is dissolved in a little ethyl acetate and absorbed onto Celite, dried and placed on a 25 g Flashmaster Si column. Chromatographed with ethyl acetate/methanol (0 to 5% methanol).

Fr 10-14=318 mg (48%), brown oil; LC-MS 65.69%+ 34.31% triphenylphosphine oxide

Fr 15-28=295 mg (45%), pale brown-coloured oil, crystallises slowly; LC-MS 97.28%, +2.72% triphenylphosphine oxide $^1$H-NMR (400 MHz, DMSO-D6): δ 1.65 (m, 2H), 2.27 (m, 6H), 3.37 (m, 2H), 3.43 (t, 4H), 7.19 (dd, 1H), 7.27 (dd, 1H), 7.35 (t, 1H), 7.68 (dd, 1H), 7.92 (s, 1H).

MS: 339 (MH+).

14) (2-chloro-5-(2-thienyl)pyrimidine-4-yl)-methyl-amine

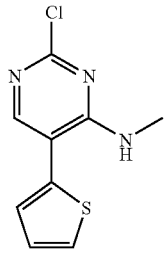

Preparation according to procedures 2 and 3 with the use of 2,4-dichloro-5-iodopyrimidine, methylamine and 4,4,5,5-tetramethyl-2-(2-thienyl)-1,3,2-dioxaborolane.

$^1$H-NMR (300 MHz, CDCl$_3$): δ 3.05 (s, 3H), 5.65 (s, 1H), 7.20 (m, 2H), 7.45 (m, 1H), 7.95 (s, 1H)

15) (2-chloro-5-(2-thienyl)pyrimidine-4-yl)-(2-piperidin-1-yl-ethyl)-amine

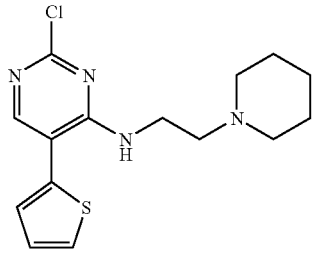

Preparation according to procedures 2 and 3 with the use of 2,4-dichloro-5-iodopyrimidine, 2-piperidin-1-yl-ethylamine and 4,4,5,5-tetramethyl-2-(2-thienyl)-1,3,2-dioxaborolane.

$^1$H-NMR (300 MHz, DMSO-D6): δ 1.45 (s, 6H), 2.40 (s, 4H), 2.55 (m, 2H), 3.45 (m, 2H), 6.70 (s, 1H), 7.20 (m, 2H), 7.45 (m, 1H), 8.00 (s, 1H)

16) 4-[(2-chloro-5-(2-thienyl)pyrimidine-4-ylamino)-methyl]-benzenesulphonamide

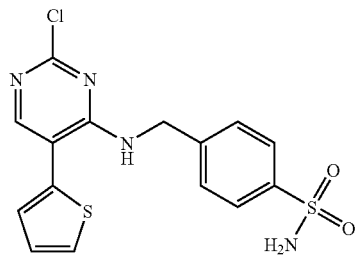

Preparation according to procedures 2 and 3 with the use of 2,4-dichloro-5-iodopyrimidine, 4-aminomethyl-benzenesulphonamide and 4,4,5,5-tetramethyl-2-(2-thienyl)-1,3,2-dioxaborolane.

$^1$H-NMR (300 MHz, DMSO-D6): δ 4.60 (m, 2H), 7.30 (m, 4H), 7.50 (m, 2H), 7.75 (m, 3H), 8.00 (m, 1H), 8.05 (s, 1H)

17) 3[2-chloro-5-(2H-pyrazol-3-yl)-pyrimidine-4-yl]-(3-morpholin-4-yl-propyl)-amine

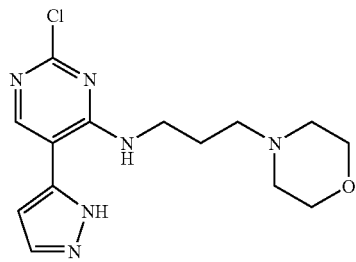

Preparation according to procedures 2 and 3 with the use of (2-chloro-5-iodo-pyrimidine-4-yl)-(3-morpholin-4-yl-propyl)-amine and 5-pyrazole.

$^1$H-NMR (300 MHz, DMSO-D6): δ 1.72 (m, 2H), 2.30 (m, 6H), 3.50 (m, 6H), 6.92 (m, 1H), 7.89 (m, 1H), 8.52 (s, 1H), 9.01 (m, 1H), 13.21 (s, 1H).

MS: 323 (MH+).

18) N-{[3-(2-chloro-5-thiophen-2-yl-pyrimidine-4-ylamino)-propyl-carbamoyl]-methyl}-4-methyl-benzamide

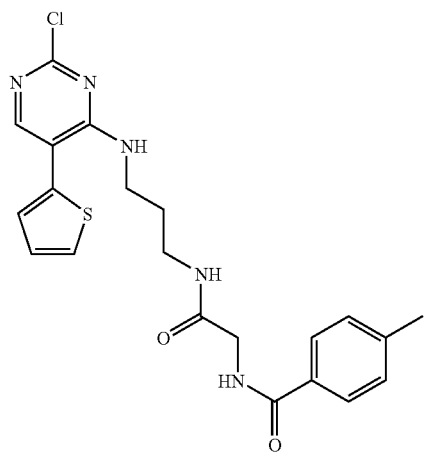

Preparation according to procedures 2 and 3 with the use of 2,4-dichloro-5-iodopyrimidine, N-[(3-amino-propylcarbamoyl)-methyl]-4-methyl-benzamide and 4,4,5,5-tetramethyl-2-(2-thienyl)-1,3,2-dioxaborolane.

$^1$H-NMR (300 MHz, DMSO-D6): δ 1.65 (m, 2H), 2.30 (s, 3H), 3.10 (m, 2H), 3.35 (m, 2H), 3.82 (m, 2H), 7.25 (m, 5H), 7.70 (m, 1H), 7.80 (m, 2H), 7.95 (m, 2H), 8.65 (bs, 1H).

MS: 444 (MH+).

19) (S)-2-tert-butoxycarbonylamino-4-(2-chloro-5-thiophen-2-yl-pyrimidine-4-ylamino)-butyric acid tert-butyl ester

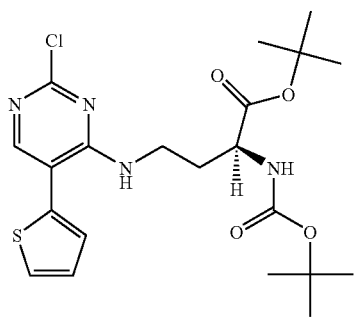

Preparation according to procedures 2 and 3 with the use of 2,4-dichloro-5-iodo-pyrimidine, (S)-2-tert-butoxycarbonylamino-4-methylaminobutyric acid tert-butyl ester and 2-thiophenboronic acid.

$^1$H-NMR (300 MHz, DMSO-D6): δ 1.32 (s, 9H), 1.34 (s, 9H), 1.88 (m, 2H), 3.35 (m, 2H), 3.85 (m, 1H), 7.11 (d, 1H), 7.18 (m, 1H), 7.25 (m, 2H), 7.69 (m, 1H), 7.93 (s, 1H).

MS: 469 (MH+).

20) 3(2-chloro-5-thiophen-2-yl-pyrimidine-4-yl)-(3-imidazol-1-yl-propyl)-amine

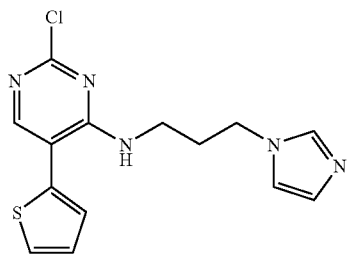

Preparation according to procedures 2 and 3 with the use of 2,4-dichloro-5-iodo-pyrimidine, 3-imidazol-1-yl-propylamine and 4,4,5,5-tetramethyl-2-(2-thienyl)-1,3,2-dioxaborolane.

$^1$H-NMR (300 MHz, DMSO-D6): δ 2.15 (m, 2H), 3.50 (m, 2H), 4.05 (m, 2H), 5.65 (bs, 1H), 6.88 (s, 1H), 7.02 (s, 1H), 7.12 (m, 1H), 7.20 (m, 1H), 7.46 (m, 2H), 8.00 (s, 1H).

MS: 320 (MH+).

21) (2-chloro-5-thiophen-2-yl-pyrimidine-4-yl)-[2-(1H-imidazol-4-yl)-ethyl]-amine

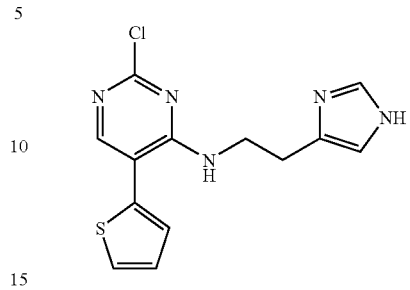

Preparation according to procedures 2 and 3 with the use of 2,4-dichloro-5-iodo-pyrimidine, 2-(1H-imidazol-4-yl)-ethylamine and 4,4,5,5-tetramethyl-2-(2-thienyl)-1,3,2-dioxaborolane.

$^1$H-NMR (300 MHz, DMSO-D6): δ 2.95 (t, 2H), 3.80 (m, 2H), 6.50 (bs, 1H), 6.85 (m, 1H), 7.15 (m, 2H), 7.28 (m, 1H), 7.40 (m, 1H), 7.55 (m, 1H), 7.98 (s, 1H).

MS: 306 (MH+).

22) N-[3-(2-chloro-5-thiophen-2-yl-pyrimidine-4-ylamino)-propyl]-2-phenyl-acetamide

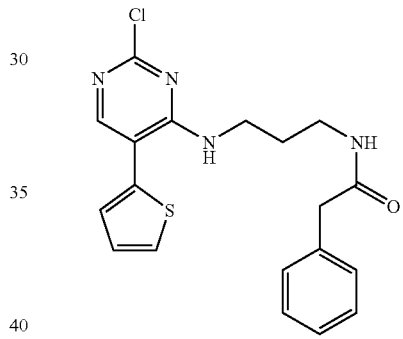

Preparation according to procedures 2 and 3 with the use of 2,4-dichloro-5-iodopyrimidine, N-(3-amino-propyl)-2-phenyl-acetamide and 4,4,5,5-tetramethyl-2-(2-thienyl)-1,3,2-dioxaborolane.

$^1$H-NMR (300 MHz, DMSO-D6): δ 1.65 (m, 2H), 3.08 (q, 2H), 3.35 (m, 4H), 7.20 (m, 8H), 7.70 (dd, 1H), 8.00 (m, 2H).

MS: 387 (MH+).

23) (2-chloro-5-(2-thiophen)pyrimidine-4-ylamino)-propane

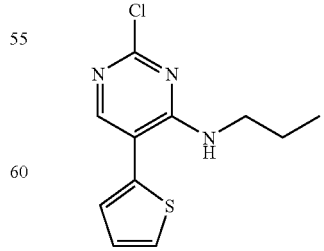

Preparation according to procedures 2 and 3 with the use of 2,4-dichloro-5-iodopyrimidine, 1-propylamine and 4,4,5,5-tetramethyl-2-(2-thienyl)-1,3,2-dioxaborolane.

¹H-NMR (300 MHz, DMSO-D6): δ 0.9 (t, 3H), 1.65 (m, 2H), 3.50 (m, 2H), 5.65 (bs, 1H), 7.20 (m, 2H), 7.48 (m, 1H), 7.98 (m, 1H).
MS: 254 (MH+).

24) 2-chloro-5-iodo-4-methoxy-pyrimidine

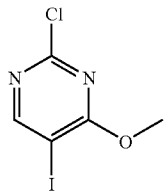

Methanolic sodium ethanolate solution (88.00 mL, 15.31 mmol—from 0.7 g sodium and 100 ml dry methanol) is added dropwise with stirring at −5 to 0° C. to a solution of 5-iodo-2,4-dichloropyrimidine (4.00 g, 14.55 mmol) in dry methanol (50 mL). The reaction solution is warmed to RT overnight, during which the crude product precipitates. The product is isolated by filtration and then stirred thoroughly with water (ca 50 mL) for 30 mins, recrystallised from methanol and dried over phosphorus pentoxide in the desiccator under vacuum: 2.18 g (8.06 mmol, 55.39%) of a white product.
¹H-NMR (300 MHz, CDCl₃): δ 4.08 (s, 3H), 8.60 (s, 1H).

25) 2-chloro-4-methoxy-5-thiophen-2-yl-pyrimidine

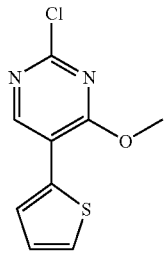

Preparation according to procedure 3 with the use of 2-chloro-5-iodo-4-methoxy-pyrimidine and 4,4,5,5-tetramethyl-2-(2-thienyl)-1,3,2-dioxaborolane for 36 hrs at 95° C. In this way, a yield of 54% is obtained.
¹H-NMR (300 MHz, CDCl₃): δ 4.15 (s, 3H), 7.15 (m, 1H), 7.45 (m, 1H), 7.55 (m, 1H), 8.63 (s, 1H).
MS: 227 (MH+).

26) 4-(2-chloro-5-thiophen-2-yl-pyrimidine-4-ylamino)-benzylsulphonamide

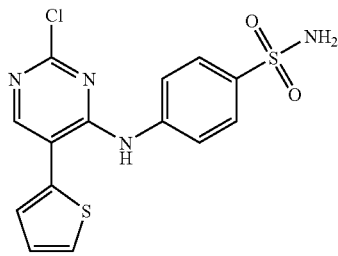

Preparation according to procedures 2 and 3 with the use of 2,4-dichloro-5-iodopyrimidine, 4-amino-phenyl-sulphonamide and 4,4,5,5-tetramethyl-2-(2-thienyl)-1,3,2-dioxaborolane.
¹H-NMR (300 MHz, DMSO-D6): δ 7.26 (m, 2H), 7.46 (m, 1H), 7.74 (m, 5H), 8.30 (s, 1H).
MS: 367 (MH+).

27) 2-chloro-5-thiophen-2-yl-pyrimidine-4-yl)-(2-pyrazol-1-yl-ethyl)-amine

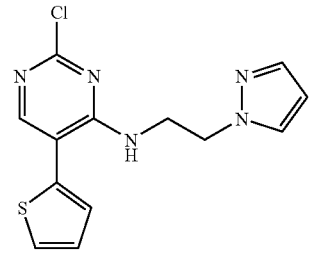

Preparation according to procedures 2 and 3 with the use of 2,4-dichloro-5-iodopyrimidine, 2-pyrazol-1-yl-ethylamine and 4,4,5,5-tetramethyl-2-(2-thienyl)-1,3,2-dioxaborolane.
¹H-NMR (300 MHz, DMSO-D6): δ 3.69 (q, 2H), 4.29 (t, 2H), 6.19 (m, 1H), 7.18 (m, 2H), 7.30 (t, 1H), 7.39 (m, 1H), 7.65 (d, 1H), 7.68 (t, 1H), 7.96 (s, 1H).
MS: 306 (MH+).

28) (5-bromo-2-chloro-pyrimidine-4-yl)-(tetrahydro-pyran-4-yl)-amine

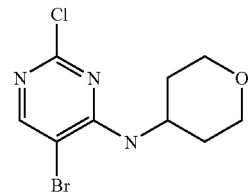

In the reaction of 5-bromo-2,4-dichloropyrimidine (300 mg, 1.32 mmol) with tetrahydropyran-4-ylamine (144 mg, 1.42 mmol) according to procedure 2, the desired product is obtained in 83% yield (320 mg) after chromatographic purification (silica gel, ethyl acetate/hexane with ethyl acetate: 0-100%).
¹HNMR (300 MHz, DMSO): δ 1.64-1.72 (m, 4H), 3.33-3.80 (m, 2H), 3.82-3.86 (m, 2H), 4.06-4.14 (m, 1H), 7.38 (d, 1H), 8.22 (s, 1H).

29) 3-(2-Chloro-5-thiophen-2-yl-pyrimidin-4-ylamino)-propionamide

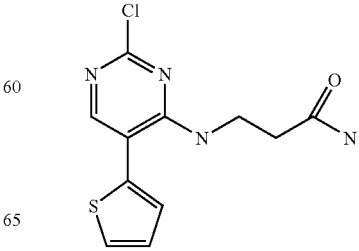

Preparation according to procedures 2 and 3 with the use of 2,4-dichloro-5-iodopyrimidine, 3-amino-propionicamide and 2-thienyl-boronic-acid.
¹H-NMR (400 MHz, DMSO-D$_6$): δ 2.35 (t, 2H), 3.51 (q, 2H), 6.87 (s, 1H), 7.18 (dd, 1H), 7.27 (dd, 1H), 7.32 (t, 1H), 7.36 (s, 1H), 7.68 (dd, 1H), 7.96 (s, 1H).
MS: 283 (MH+).

30) 2-Chloro-4-propoxy-5-thiophen-2-yl-pyrimidine

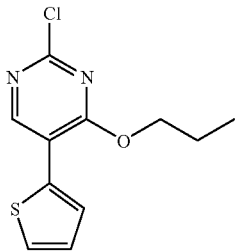

Preparation according to procedures 4a and 3 with the use of 2,4-dichloro-5-iodopyrimidine, n-propanol and 4,4,5,5-tetramethyl-2-(2-thienyl)-1,3,2-dioxaborolane.
¹H-NMR (300 MHz, CDCl$_3$): δ 1.15 (t, 3H), 1.95 (m, 2H), 4.50 (t, 2H), 7.15 (dd, 1H), 7.45 (dd, 1H), 7.58 (dd, 1H), 8.60 (s, 1H).

31) 4-[2-(2-Chloro-5-thiophen-2-yl-pyrimidin-4-yloxy)-ethyl]-morpholine

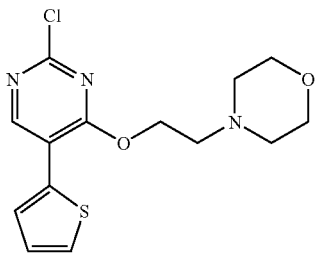

Preparation according to procedures 4b and 3 with the use of 2,4-dichloro-5-iodopyrimidine, N-morpholin-2-amino-ethanole and 4,4,5,5-tetramethyl-2-(2-thienyl)-1,3,2-dioxaborolane.
¹H-NMR (300 MHz, CDCl$_3$): δ 2.55 (m, 4H), 2.85 (t, 2H), 3.70 (m, 4H), 4.65 (t, 2H), 7.13 (dd, 1H), 7.45 (dd, 1H), 7.62 (dd, 1H), 8.65 (s, 1H).
MS: 326 (MH+).

32) 3-(2-Chloro-5-thiophen-2-yl-pyrimidin-4-yloxy)-2-methyl-propan-1-ol

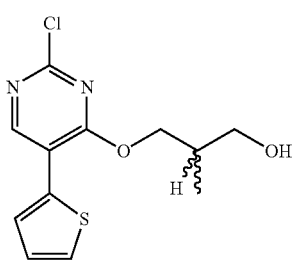

Preparation according to procedures 4b and 3 with the use of 2,4-dichloro-5-iodopyrimidine, 2-methyl-1,3-propandiol and 4,4,5,5-tetramethyl-2-(2-thienyl)-1,3,2-dioxaborolane.
¹H-NMR (300 MHz, DMSO-D$_6$): δ 1.05 (d, 3H), 2.10 (m, 1H), 3.50 (m, 2H), 4.35 (m, 1H), 4.45 (m, 1H), 4.65 (bs, 1H), 7.20 (m, 1H), 7.68 (m, 2H), 8.95 (s, 1H).
MS: 285 (MH+).

33) 4-(2-Chloro-5-thiophen-2-yl-pyrimidin-4-yloxy)-butan-1-ol

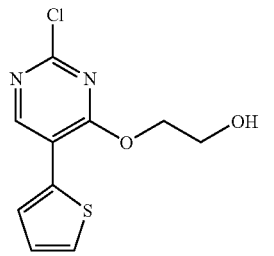

Preparation according to procedures 4b and 3 with the use of 2,4-dichloro-5-iodopyrimidine, 1,4-butandiol and 4,4,5,5-tetramethyl-2-(2-thienyl)-1,3,2-dioxaborolane.
¹H-NMR (300 MHz, DMSO-D$_6$): δ 1.65 (m, 2H), 1.85 (m, 2H), 3.50 (m, 2H), 4.50 (m, 3H), 7.21 (m, 1H), 7.77 (m, 2H), 8.95 (s, 1H).
MS: 285 (MH+).

34) 2-(2-Chloro-5-thiophen-2-yl-pyrimidin-4-yloxy)-ethanol

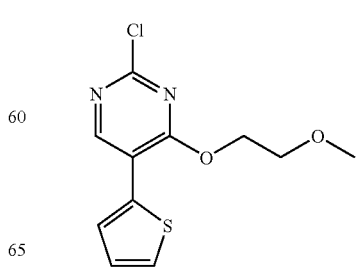

Preparation according to procedures 4b and 3 with the use of 2,4-dichloro-5-iodopyrimidine, 1,2-ethandiol and 4,4,5,5-tetramethyl-2-(2-thienyl)-1,3,2-dioxaborolane.
¹H-NMR (300 MHz, DMSO-D$_6$): δ 3.80 (m, 2H), 4.50 (m, 2H), 4.95 (m, 1H), 7.20 (t, 1H), 7.74 (d, 1H), 7.82 (d, 1H), 8.90 (s, 1H).
MS: 275 (MH+).

35) 2-Chloro-4-(2-methoxy-ethoxy)-5-thiophen-2-yl-pyrimidine

Preparation according to procedures 4b and 3 with the use of 2,4-dichloro-5-iodopyrimidine, 2-methoxy-ethanol and 4,4,5,5-tetramethyl-2-(2-thienyl)-1,3,2-dioxaborolane.

$^1$H-NMR (300 MHz, CDCl$_3$): δ 3.48 (s, 3H), 3.85 (m, 2H), 4.70 (m, 2H), 7.14 (m, 1H), 7.46 (m, 1H), 7.60 (m, 1H), 8.64 (s, 1H).

36) 2-Chloro-4-(tetrahydro-furan-2-ylmethoxy)-5-thiophen-2-yl-pyrimidine

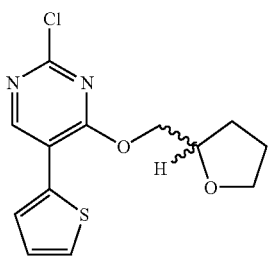

Preparation according to procedures 4b and 3 with the use of 2,4-dichloro-5-iodopyrimidine, 2-tetrahydrofuranyl-methanol and 4,4,5,5-tetramethyl-2-(2-thienyl)-1,3,2-dioxaborolane.

$^1$H-NMR (300 MHz, CDCl$_3$): δ 1.80 (m, 1H), 1.95 (m, 2H), 2.15 (m, 1H), 3.90 (m, 2H), 4.40 (m, 1H), 4.55 (m, 2H), 7.14 (t, 1H), 7.44 (d, 1H), 7.60 (d, 1H), 8.65 (s, 1H).

MS: 297 (MH+).

37) 3-(5-Bromo-2-chloro-pyrimidin-4-yloxy)-propionic acid tert-butyl ester

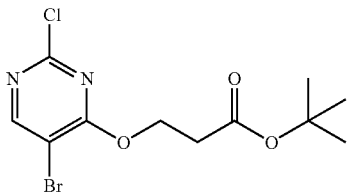

2,4-Dichloro-5-bromopyrimidine (7.98 g, 35 mmol) is dissolved in DMF (35 ml) and Cs$_2$CO$_3$ (11.4 g, 35 mmol) and 3-hydroxy-propionic acid tert-butyl-ester (5.12 g, 35 mmol) are added. The reaction mixture is stirred for 5 h at rt. The reaction mixture is diluted with brine and the extracted with ethyl acetate (3×). The organic layers are washed with brine, dried over sodiumsulfat and evaporated to dryness. The crude product is used for the following reaction without any further purification.

$^1$H-NMR (300 MHz, DMSO-D$_6$): δ 1.35 (s, 9H), 2.71 (t, 2H), 4.56 (t, 2H), 8.70 (s, 1H).

MS: 339 (MH+).

38) 3-(2-Chloro-5-thiophen-2-yl-pyrimidin-4-yloxy)-propionic acid tert-butyl ester

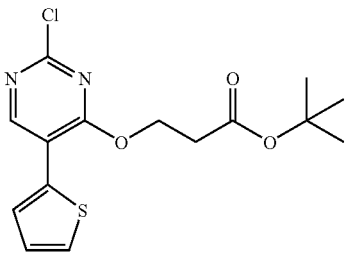

Preparation according to procedure 11a with the use of 3-(5-Bromo-2-chloro-pyrimidin-4-yloxy)-propionic acid tert-butyl ester and 2-thienyl-boronic-acid.

$^1$H-NMR (300 MHz, CDCl$_3$): δ 1.43 (s, 9H), 2.80 (t, 2H), 4.78 (t, 2H), 7.11 (dd, 1H), 7.42 (dd, 1H), 7.55 (dd, 1H), 8.61 (s, 1H).

MS: 341 (MH+).

2. Process Variation 1 (See Also Scheme 1)

General Procedures

Procedure 5a—Introduction of Anilines of the Type III in the 2 Position of the Pyrimidine II Compound II (1.1 equiv.) and the aniline III (1.0 equiv.) are dissolved in dioxan (210 equiv.), treated with a 4N solution of hydrogen chloride in dioxan (7.5 equiv.) and stirred for 5 hours at 120° C. After cooling to room temperature, the mixture is diluted with saturated sodium hydrogen carbonate solution. It is extracted with dichloromethane and the organic phase dried over sodium sulphate. After removal of the solvent under vacuum, the chromatographic purification is performed.

Procedure 5b—Introduction of Anilines of the type III in the 2 Position of the Pyrimidine II Compound II (1.0-1.1 equiv.) and the sulfoximine component III (1.0-1.05 equiv.) are dissolved in acetonitrile/water (10:1), treated with a 4 N-5 N solution of hydrogen chloride in dioxan (1.0 equiv.) and stirred for 18-24 hours at 50-60° C. After cooling to room temperature, the mixture is diluted with saturated sodium hydrogen carbonate solution. It is extracted with ethyl acetate and the combined organic layers dried over sodium sulphate. After removal of the solvent under vacuum, the purification is performed either by crystallization, prep. HPLC or column chromatography.

Procedure 5c—Introduction of Anilines of the Type III in the 2 Position of the Pyrimidine II Compound II (1.1 equiv.) and the sulfoximine component III (1.0 equiv.) are dissolved in butanol/methanol (10:1), treated with a few drops of a 4N solution of hydrogen chloride in dioxan and stirred for 6 hours at 70° C. After cooling, the mixture is concentrated and taken up in ethyl acetate. It is washed with saturated sodium hydrogen carbonate solution and dried over sodium sulphate. After removal of the solvent under vacuum, the chromatographic purification is performed.

Compounds which were Produced by Process Variation 1

Example 1.1

(RS)—N-(ethoxycarbonyl)-S-(4-{[4-{[(R)-2-hydroxy-1-methylethyl]amino}-5-(2-thienyl)pyrimidine-2-yl]amino}phenyl)-S-methylsulfoximide

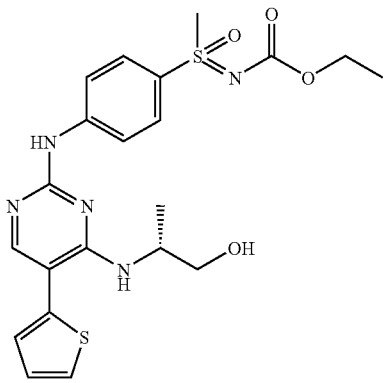

In the reaction of (R)-2-(2-chloro-5-(2-thienyl)pyrimidine-4-ylamino)propan-1-ol (178 mg, 0.7 mmol) with (RS)—S-(4-aminophenyl)-N-(ethoxycarbonyl)-S-methyl-sulfoximide (145 mg, 0.6 mmol) according to procedure 5a, the desired product is obtained in 27% yield (85 mg) after chromatographic purification (silica gel, ethyl acetate/hexane (0%-80% ethyl acetate)).

$^1$H-NMR (400 MHz, DMSO-D6): δ 1.07 (t, 3H), 1.15 (d, 3H), 3.40 (s, 3H), 3.45 (t, 2H), 3.83-3.92 (m, 2H), 4.20-4.30 (m, 1H), 6.20 (d, 1H), 7.12-7.20 (m, 2H), 7.55 (d, 1H), 7.75 (d, 2H), 7.97 (s, 1H), 8.05 (d, 2H), 9.85 (s, 1H).

Example 1.2

(RS)—N-(ethoxycarbonyl)-S-[4-({4-[(2-hydroxyethyl)amino]-5-(2-thienyl)-pyrimidine-2-yl}amino)phenyl]-S-methylsulfoximide

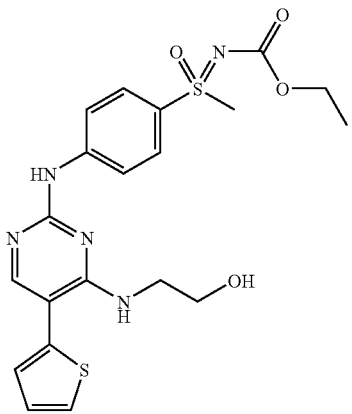

In the reaction of 2-(2-chloro-5-(2-thienyl)pyrimidine-4-ylamino)ethanol (200 mg, 0.8 mmol) with (RS)—S-(4-aminophenyl)-N-(ethoxycarbonyl)-S-methyl-sulfoximide (173 mg, 0.7 mmol) according to procedure 5a, the desired product is obtained in 37% yield (120 mg) after chromatographic purification (silica gel, dichloromethane/methanol (0%-20% methanol)).

$^1$H-NMR (300 MHz, DMSO-D6): δ 1.05 (t, 3H), 3.38 (s, 3H), 3.43-3.65 (m, 4H), 3.85-3.95 (m, 2H), 4.75 (t, 1H), 6.60 (t, 1H), 7.15-7.20 (m, 2H), 7.58 (dd, 1H), 7.77 (d, 2H), 7.93 (s, 1H), 8.03 (d, 2H), 9.85 (s, 1H).

Example 1.3

(RS)—S-(4-{[4-{[2-(acetylamino)ethyl]amino}-5-(2-thienyl)pyrimidine-2-yl]amino}phenyl)-N-(ethoxycarbonyl)-S-methylsulfoximide

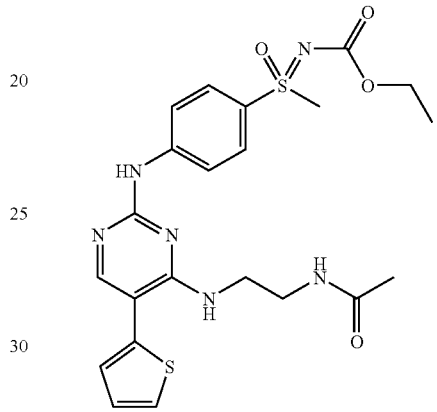

In the reaction of N-[2-(2-chloro-5-(2-thienyl)-pyrimidine-4-ylamino)ethyl]-acetamide (150 mg, 0.51 mmol) with (RS)—S-(4-aminophenyl)-N-(ethoxy-carbonyl)-S-methyl-sulfoximide (111 mg, 0.46 mmol) according to procedure 5a, the desired product is obtained in 11% yield (28 mg) after chromatographic purification (silica gel, dichloromethane/methanol (0%-10% methanol)).

$^1$H-NMR (300 MHz, DMSO-D6): δ 1.07 (t, 3H), 1.77 (s, 3H), 3.28-3.29 (m, 2H), 3.37 (s, 3H), 3.45-3.55 (m, 2H), 3.75-3.95 (m, 2H), 6.60 (t, 1H), 7.15 (dd, 1H), 7.20 (dd, 1H), 7.80 (d, 2H), 7.90-7.97 (m, 2H), 8.00 (d, 2H), 9.85 (s, 1H).

Example 1.4

(RS)—N-(ethoxycarbonyl)-S-(4-{[4-{[(S)-1-(hydroxymethyl)-3-methylbutyl]amino}-5-(3-thienyl)pyrimidine-2-yl]amino}phenyl)-S-methylsulfoximide

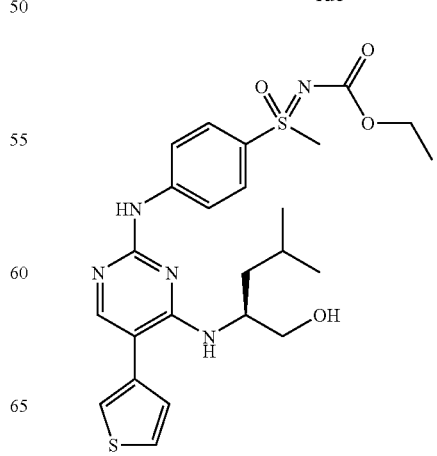

In the reaction (S)-2-(2-chloro-5-thiophen-3-yl-pyrimidine-4-ylamino)-4-methyl-pentan-1-ol (278 mg, 0.89 mmol) with (RS)—S-(4-amino-phenyl)-N-(ethoxycarbonyl)-S-methylsulfoximide (240 mg, 0.99 mmol) according to procedure 5b, the desired product is obtained in 42% yield (220 mg) after chromatographic purification (silica gel, dichloromethane/methanol (0%-10% methanol)).

¹H-NMR (300 MHz, DMSO-D6): δ 0.82 (m, 6H), 1.05 (t, 3H), 1.42 (m, 2H), 1.62 (m, 1H), 3.36 (s, 3H), 3.43 (m, 2H), 3.88 (m, 2H), 4.38 (m, 1H), 4.75 (m, 1H), 5.86 (d, 1H), 7.21 (m, 1H), 7.53 (m, 1H), 7.67 (m, 1H), 7.72 (m, 2H), 7.89 (s, 1H), 8.02 (m, 2H), 9.72 (s, 1H).

MS: 518 (ES+).

Example 1.5

(RS)—N-(ethoxycarbonyl)-S-ethyl-S-(4-{[4-{[(S)-1-(hydroxymethyl)-3-methyl-butyl]amino}-5-(3-thienyl)pyrimidine-2-yl]amino}phenyl)sulfoximide

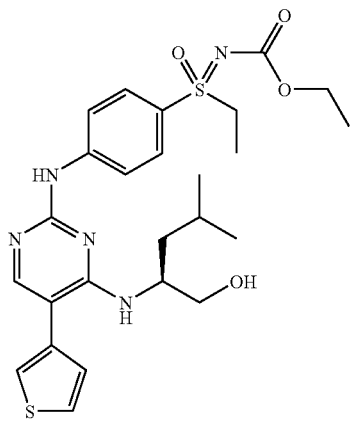

In the reaction (S)-2-(2-chloro-5-thiophen-3-yl-pyrimidine-4-ylamino)-4-methyl-pentan-1-ol (312 mg, 1.00 mmol) with (RS)—S-(4-amino-phenyl)-N-(ethoxycarbonyl)-S-ethylsulfoximide (231 mg, 0.90 mmol) according to procedure 5b, the desired product is obtained in 59% yield (282 mg) after chromatographic purification (silica gel, dichloromethane/methanol (0%-10% methanol)).

¹H-NMR (300 MHz, DMSO-D6): δ 0.81 (m, 6H), 1.06 (m, 6H), 1.41 (m, 2H), 1.62 (m, 1H), 3.45 (m, 4H), 3.87 (m, 2H), 4.36 (m, 1H), 4.74 (m, 1H), 5.86 (d, 1H), 7.21 (m, 1H), 7.56 (m, 1H), 7.68 (m, 3H), 7.90 (s, 1H), 8.02 (m, 2H), 9.71 (s, 1H).

Example 1.6

(RS)—S-{2-bromo-4-[(4-{[(R)-1-(hydroxymethyl)propyl]amino}-5-(3-thienyl)pyrimidine-2-yl)amino]phenyl}-N-(ethoxycarbonyl)-S-methylsulfoximide

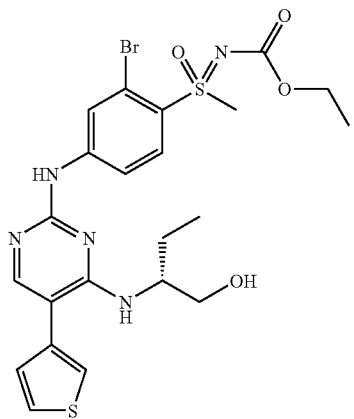

In the reaction of (R)-2-(2-chloro-5-thiophen-3-yl-pyrimidine-4-ylamino)-butan-1-ol (426 mg, 1.5 mmol) with (RS)—S-(4-amino-2-bromphenyl)-N-(ethoxycarbonyl)-S-methylsulfoximide (404 mg, 1.3 mmol) according to procedure 5b, the desired product is obtained in 30% yield (214 mg) after chromatographic purification (silica gel, dichloromethane/ethanol (0%-15% ethanol)).

¹H-NMR (DMSO): 10.65 (s, 1H), 8.38 (m, 1H), 8.02 (m, 1H), 7.95 (s, 1H), 7.88 (m, 1H), 7.75 (m, 1H), 7.68 (m, 1H), 7.25 (m, 1H), 7.00 (br, 1H), 4.18 (m, 1H), 3.83 (m, 2H), 3.52 (m, 2H), 3.45 (s, 3H), 1.60 (m, 2H), 1.03 (tr, 3H), 0.85 (tr, 3H).

MS: 568 (ES+).

Example 1.7

(RS)—S-{2-bromo-4-[(4-{[(R)-1-(hydroxymethyl)propyl]amino}-5-(2-thienyl)pyrimidine-2-yl)amino]phenyl}-N-(ethoxycarbonyl)-S-methylsulfoximide

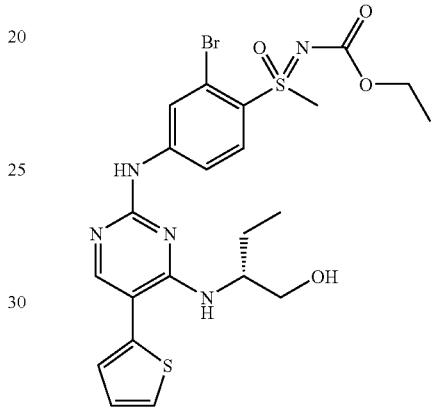

In the reaction of (R)-2-(2-chloro-5-thiophen-2-yl-pyrimidine-4-ylamino)-butan-1-ol (425 mg, 1.5 mmol) with (RS)—S-(4-amino-2-bromphenyl)-N-(ethoxycarbonyl)-S-methylsulfoximide (404 mg, 1.3 mmol) according to procedure 5b, the desired product is obtained in 47% yield (340 mg) after chromatographic purification (silica gel, dichloromethane/ethanol (0%-20% ethanol)).

¹H-NMR (DMSO): 10.50 (s, 1H), 8.38 (m, 1H), 7.95 (m, 3H), 7.62 (m, 1H), 7.20 (m, 2H), 6.75 (br, 1H), 4.13 (m, 1H), 3.83 (m, 2H), 3.51 (m, 2H), 3.45 (s, 3H), 1.60 (m, 2H), 1.03 (tr, 3H), 0.88 (tr, 3H).

MS: 568 (ES+).

Example 1.8

(R)—N-(ethoxycarbonyl)-S-(4-{[4-{[(R)-2-hydroxy-1-methylethyl]amino}-5-(2-thienyl)pyrimidine-2-yl]amino}phenyl)-S-cyclopropylsulfoximide

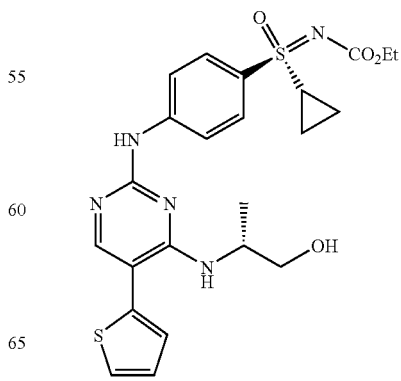

In the reaction of (R)-2-(2-chloro-5-(2-thienyl)pyrimidine-4-ylamino)propan-1-ol (185 mg, 0.7 mmol) with (R)—S-(4-aminophenyl)-N-(ethoxycarbonyl)-S-cyclo-propyl-sulfoximide (167 mg, 0.6 mmol) according to procedure 5a, the desired product is obtained in 26% yield (90 mg) after chromatographic purification (silica gel, dichloromethane/ethanol (0%-20% ethanol)).

¹H-NMR (400 MHz, DMSO-D6): δ 0.92-1.04 (m, 2H), 1.08 (t, 3H), 1.11-1.18 (m, 1H), 1.20 (d, 3H), 1.24-1.34 (m, 1H), 2.99 (m, 1H), 3.51 (t, 2H), 3.88 (m, 2H), 4.28 (m, 1H), 4.89 (t, 1H), 6.22 (d, 1H), 7.21 (m, 2H), 7.63 (d, 1H), 7.75 (d, 2H), 7.98 (s, 1H), 8.06 (d, 2H), 9.87 (s, 1H).

Example 1.9

(S)—N-(ethoxycarbonyl)-S-(4-{[4-{[(R)-2-hydroxy-1-methylethyl]amino}-5-(2-thienyl)pyrimidine-2-yl]amino}phenyl)-S-cyclopropylsulfoximide

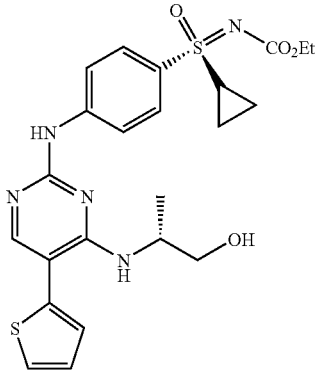

In the reaction of (R)-2-(2-chloro-5-(2-thienyl)pyrimidine-4-ylamino)propan-1-ol (267 mg, 1.0 mmol) with (S)—S-(4-aminophenyl)-N-(ethoxycarbonyl)-S-cyclo-propyl-sulfoximide (241 mg, 0.9 mmol) according to procedure 5c, the desired product is obtained in 50% yield (250 mg) after chromatographic purification (silica gel, dichloromethane/ethanol (0%-20% ethanol)).

¹H-NMR (400 MHz, DMSO-D6): δ 0.92-1.04 (m, 2H), 1.08 (t, 3H), 1.13-1.25 (m, 1H), 1.20 (d, 3H), 1.26-1.38 (m, 1H), 3.02 (m, 1H), 3.51 (t, 2H), 3.88 (m, 2H), 4.32 (m, 1H), 7.26 (m, 2H), 7.70 (d, 1H), 7.84 (d, 2H), 7.99 (d, 2H), 8.01 (s, 1H), 10.54 (s, 1H)

Example 1.10

(R)—N-(ethoxycarbonyl)-S-(4-{[4-{[(R)-1-(hydroxymethyl)propyl]amino}-5-(2-thienyl)pyrimidine-2-yl]amino}phenyl)-S-cyclopropylsulfoximide

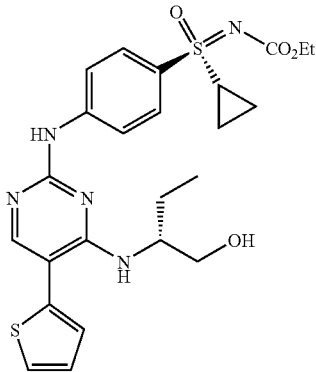

In the reaction of (R)-2-(2-chloro-5-(2-thienyl)pyrimidine-4-ylamino)butan-1-ol (270 mg, 0.95 mmol) with (R)—S-(4-aminophenyl)-N-(ethoxycarbonyl)-S-cyclo-propyl-sulfoximide (224 mg, 0.83 mmol) according to procedure 5c, the desired product is obtained in 40% yield (170 mg) after chromatographic purification (silica gel, dichloromethane/ethanol (0%-20% ethanol)).

¹H-NMR (400 MHz, DMSO-D6): δ 0.93 (t, 3H), 1.00 (m, 2H), 1.08 (t, 3H), 1.16 (m, 1H), 1.29 (m, 1H), 1.54-1.70 (m, 2H), 3.00 (m, 1H), 3.46-3.60 (m, 2H), 3.88 (m, 2H), 4.13 (m, 1H), 4.85 (t, 1H), 6.17 (d, 1H), 7.21 (m, 2H), 7.63 (d, 1H), 7.73 (d, 2H), 7.98 (s, 1H), 8.05 (d, 2H), 9.88 (s, 1H).

Example 1.11

(S)—N-(ethoxycarbonyl)-S-(4-{[4-{[(R)-1-(hydroxymethyl)propyl]amino}-5-(2-thienyl)pyrimidine-2-yl]amino}phenyl)-S-cyclopropylsulfoximide

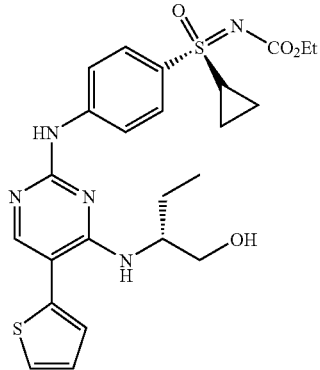

In the reaction of (R)-2-(2-chloro-5-(2-thienyl)pyrimidine-4-ylamino)butan-1-ol (300 mg, 1.06 mmol) with (S)—S-(4-aminophenyl)-N-(ethoxycarbonyl)-S-cyclo-propyl-sulfoximide (258 mg, 0.96 mmol) according to procedure 5c, the desired product is obtained in 47% yield (256 mg) after chromatographic purification (silica gel, dichloromethane/ethanol (0%-20% ethanol)).

¹H-NMR (400 MHz, DMSO-D6): δ 0.90 (t, 3H), 1.01 (m, 2H), 1.07 (t, 3H), 1.19 (m, 1H), 1.32 (m, 1H), 1.52-1.71 (m, 2H), 3.04 (m, 1H), 3.46-3.61 (m, 2H), 3.88 (m, 2H), 4.16 (m, 1H), 7.26 (m, 2H), 7.73 (d, 1H), 7.85 (d, 2H), 7.97 (d, 2H), 8.03 (s, 1H), 10.82 (s, 1H).

Example 1.12

(RS)—N-(ethoxycarbonyl)-S-(4-{[4-{[(R)-2-hydroxy-1-methylethyl]amino}-5-(2-thienyl)pyrimidine-2-yl]amino}phenyl)-S-cyclopropylsulfoximide

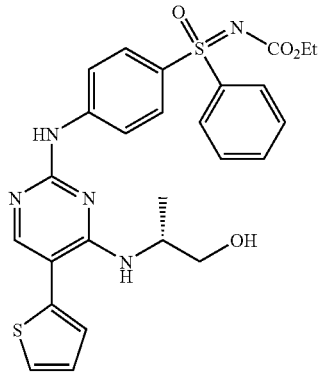

In the reaction of (R)-2-(2-chloro-5-(2-thienyl)pyrimidine-4-ylamino)propan-1-ol (155 mg, 0.57 mmol) with (RS)—S-(4-aminophenyl)-N-(ethoxycarbonyl)-S-phenylsulfoximide (159 mg, 0.52 mmol) according to procedure 5c, the desired product is obtained in 43% yield (120 mg) after chromatographic purification (silica gel, dichloromethane/ethanol (0%-20% ethanol)).

¹H-NMR (400 MHz, DMSO-D6): δ 1.09 (t, 3H), 1.18 (d, 3H), 3.49 (t, 2H), 3.94 (m, 2H), 4.26 (m, 1H), 4.88 (t, 1H), 6.22 (d, 1H), 7.20 (m, 2H), 7.58-7.70 (m, 4H), 7.86 (d, 2H), 7.94 (d, 2H), 7.96 (s, 1H), 8.03 (d, 2H), 9.90 (s, 1H).

Example 1.13

(RS)—N-(ethoxycarbonyl)-S-(4-{[4-{[(R)-1-(hydroxymethyl)propyl]amino}-5-(2-thienyl)pyrimidine-2-yl]amino}phenyl)-S-cyclopropylsulfoximide

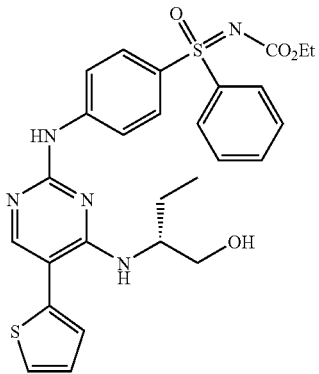

In the reaction of (R)-2-(2-chloro-5-(2-thienyl)pyrimidine-4-ylamino)butan-1-ol (151 mg, 0.53 mmol) with (RS)—S-(4-aminophenyl)-N-(ethoxycarbonyl)-S-phenylsulfoximide (147 mg, 0.48 mmol) according to procedure 5c, the desired product is obtained in 49% yield (130 mg) after chromatographic purification (silica gel, dichloromethane/ethanol (0%-20% ethanol)).

¹H-NMR (400 MHz, DMSO-D6): δ 0.90 (t, 3H), 1.09 (t, 3H), 1.51-1.72 (m, 2H), 3.44-3.60 (m, 2H), 3.94 (m, 2H), 4.10 (m, 1H), 4.82 (t, 1H), 6.16 (d, 1H), 7.20 (m, 2H), 7.58-7.70 (m, 4H), 7.85 (d, 2H), 7.94 (d, 2H), 7.96 (s, 1H), 8.03 (d, 2H), 9.89 (s, 1H).

Example 1.14

(RS)—N-(ethoxycarbonyl)-S-[4-({4-[(3-hydroxypropyl)amino]-5-(2-thienyl-)pyrimidine-2-yl}amino)phenyl]-S-methylsulfoximide

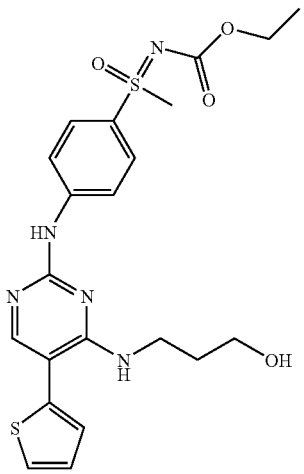

In the reaction of 3-(2-chloro-5-(2-thienyl)pyrimidine-4-ylamino)propanol (154 mg, 0.57 mmol) with (RS)—S-(4-aminophenyl)-N-(ethoxycarbonyl)-S-methyl-sulfoximide (127 mg, 0.53 mmol) according to procedure 5b, the desired product is obtained in 29% yield (80 mg) after chromatographic purification (silica gel, hexane/ethyl acetate (50%-100% ethyl acetate)) and subsequent purification by HPLC.

¹H-NMR (300 MHz, DMSO-D6): δ 1.07 (t, 3H), 1.73 (m, 2H), 3.41 (s, 3H), 3.47 (m, 4H), 3.88 (m, 2H), 4.40 (m, 1H), 7.21 (m, 2H), 7.67 (d, 1H), 7.77 (bs, 1H), 7.86 (d, 2H), 7.97 (m, 3H), 10.49 (bs, 1H).

MS: 476 (MH+).

Example 1.15

(RS)—N-(ethoxycarbonyl)-S-[4-({4-[(3-N-morpholinopropyl)amino]-5-(2-thienyl)-pyrimidine-2-yl}amino)phenyl]-S-methylsulfoximide

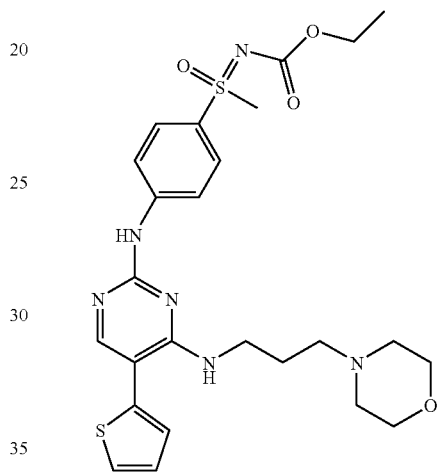

In the reaction of (2-chloro-5-thiophen-2-yl-pyrimidine-4-yl)-(3-morpholin-4-yl-propyl)-amine (281 mg, 0.83 mmol) with (RS)—S-(4-aminophenyl)-N-(ethoxy-carbonyl)-S-methylsulfoximide (201 mg, 0.83 mmol) according to procedure 5b, the desired product is obtained in 71% yield (327 mg) after chromatographic purification (silica gel, ethyl acetate/methanol (0%-5% methanol)).

¹H-NMR (300 MHz, DMSO-D6): δ 1.07 (t, 3H), 1.73 (m, 2H), 2.30 (m, 6H), 3.37 (s, 3H), 3.41 (m, 3H), 3.47 (m, 3H), 3.89 (m, 2H), 6.87 (t, 1H), 7.17 (m, 2H), 7.58 (dd, 1H), 7.77 (d, 2H), 7.90 (s, 1H), 8.04 (d, 2H), 9.82 (s, 1H).

MS: 545 (MH+).

Example 1.16

(RS)—N-(ethoxycarbonyl)-S-(3-{[4-{[(R)-2-hydroxy-1-methylethyl]amino}-5-(2-thienyl)pyrimidine-2-yl]amino}phenyl)-S-methylsulfoximide

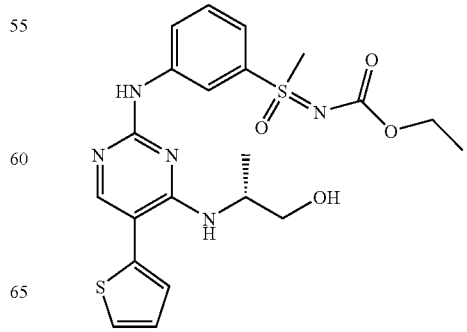

Preparation by Procedure 5c $^1$H-NMR (400 MHz, DMSO-D6): δ 1.09 (t, 3H), 1.18 (d, 3H), 3.42 (s, 3H), 3.50 (m, 2H), 3.87-3.96 (m, 2H), 4.30-4.38 (m, 1H), 4.85 (q, 1H), 6.18 (t, 1H), 7.21 (m, 2H), 7.44 (d, 1H), 7.54 (t, 1H), 7.61 (d, 1H), 7.92 (d, 2H), 7.96 (s, 1H), 8.70 (s, 1H), 9.78 (s, 1H)

Example 1.17

(RS)—N-(ethoxycarbonyl)-S-(4-{(4-methylamino)-5-(2-thienyl)pyrimidine-2-yl]amino}phenyl)-S-methylsulfoximide

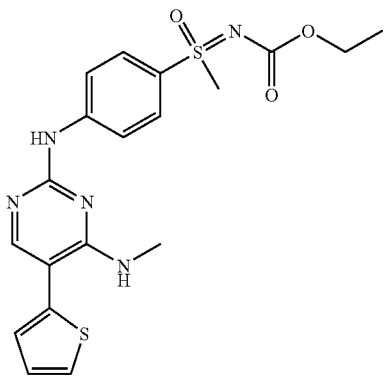

Preparation by Procedure 5c $^1$H-NMR (400 MHz, DMSO-D6): δ 1.11 (t, 3H), 2.93 (d, 3H), 3.41 (s, 3H), 3.92 (m, 2H), 6.83 (q, 1H), 7.19 (m, 2H), 7.61 (m, 1H), 7.81 (d, 2H), 7.93 (s, 1H), 8.09 (d, 2H), 9.87 (s, 1H)

Example 1.18

(RS)—N-(ethoxycarbonyl)-S-(4-{(4-(2-piperidin-1-yl-ethylamino)-5-(2-thienyl)pyrimidine-2-yl]amino}phenyl)-S-methylsulfoximide

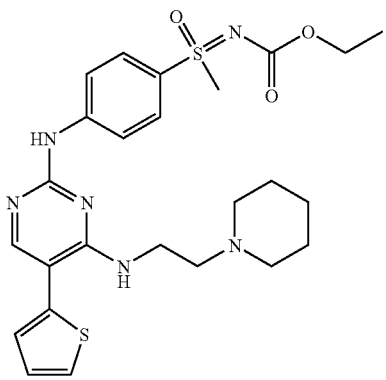

Preparation by Procedure 5c $^1$H-NMR (400 MHz, DMSO-D6): δ 1.11 (t, 3H), 1.38 (m, 1H), 1.64 (m, 3H), 1.79 (m, 2H), 2.92 (m, 2H), 3.32 (m, 2H), 3.42 (s, 3H), 3.54 (m, 2H), 3.78 (m, 2H), 3.93 (m, 2H), 7.24 (m, 2H), 7.67 (m, 1H), 7.87 (d, 2H), 7.99 (d, 2H), 8.04 (s, 1H), 10.13 (s, 1H)

Example 1.19

(RS)—N-(ethoxycarbonyl)-S-(4-{4-(4-sulphamoyl-benzylamino)-5-(2-thienyl)pyrimidine-2-yl]amino}phenyl)-S-methylsulfoximide

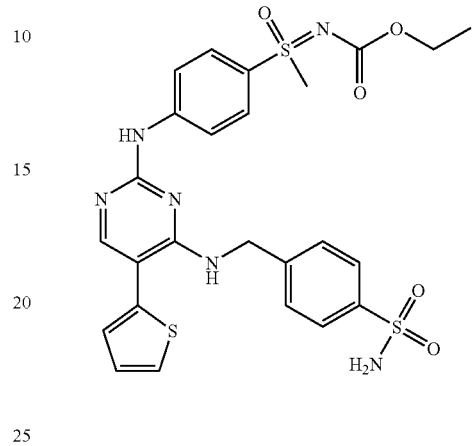

Preparation by Procedure 5c $^1$H-NMR (400 MHz, DMSO-D6): δ 1.10 (t, 3H), 3.40 (s, 3H), 3.92 (m, 2H), 4.71 (s, 2H), 7.27 (m, 2H), 7.55 (d, 2H), 7.65 (m, 1H), 7.72 (d, 2H), 7.77 (d, 2H), 7.88 (d, 2H), 7.99 (s, 1H)

Example 1.20

(RS)—N-(ethyl)-S-(4-{[4-{[(R)-2-hydroxy-1-methylethyl]amino}-5-(2-thienyl)-pyrimidine-2-yl]amino}phenyl)-S-methylsulfoximide

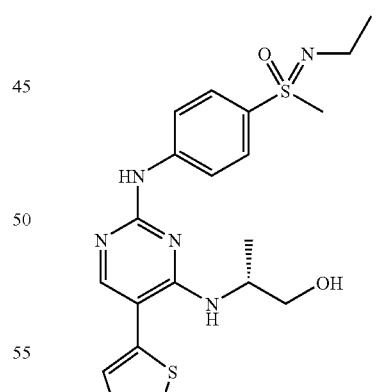

Preparation by Procedure 5c $^1$H-NMR (300 MHz, DMSO-D6): δ 1.04 (t, 3H), 1.20 (d, 3H), 3.05 (s, 3H), 3.40 (m, 2H), 3.51 (m, 2H), 4.28 (m, 1H), 4.88 (t, 1H), 6.17 (t, 1H), 7.14 (m, 2H), 7.61 (m, 1H), 7.70 (d, 2H), 7.97 (s, 1H), 8.02 (d, 2H), 9.76 (s, 1H)

Example 1.21

(RS)—N-(n-propyl)-S-(4-{[4-{[(R)-2-hydroxy-1-methylethyl]amino}-5-(2-thienyl)-pyrimidine-2-yl]amino}phenyl)-S-methylsulfoximide

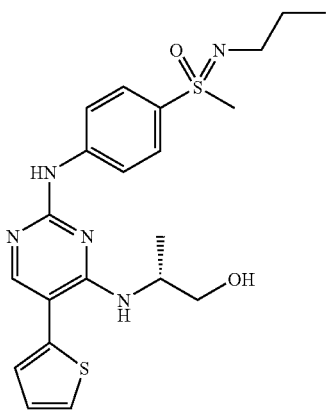

Preparation by Procedure 5c

¹H-NMR (300 MHz, DMSO-D6): δ 0.84 (t, 3H), 1.20 (d, 3H), 1.43 (m, 2H), 2.64 (m, 1H), 2.75 (m, 1H), 3.05 (s, 3H), 3.51 (m, 2H), 4.28 (m, 1H), 4.88 (t, 1H), 6.19 (d, 1H), 7.21 (m, 2H), 7.62 (m, 1H), 7.70 (d, 2H), 7.97 (s, 1H), 8.01 (d, 2H), 9.76 (s, 1H)

Example 1.22

(RS)—N-(n-propyl)-S-(4-{[4-{[(R)-2-hydroxy-1-methylethyl]amino}-5-(2-thienyl)-pyrimidine-2-yl]amino}phenyl)-S-cyclopropylsulfoximide

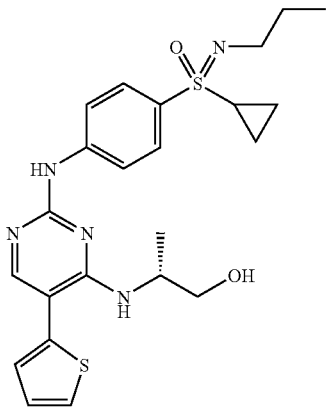

Preparation by Procedure 5c

¹H-NMR (300 MHz, DMSO-D6): δ 0.80 (m, 2H), 0.85 (t, 3H), 1.01 (m, 1H), 1.14 (m, 1H), 1.20 (d, 3H), 1.44 (m, 2H), 2.64 (m, 1H), 2.72 (m, 1H), 2.81 (m, 1H), 3.51 (m, 2H), 4.28 (m, 1H), 4.89 (t, 1H), 6.18 (d, 1H), 7.21 (m, 2H), 7.62 (m, 1H), 7.65 (d, 2H), 7.95 (s, 1H), 8.00 (d, 2H), 9.75 (s, 1H)

Example 1.23

(RS)—N-(n-propyl)-S-(4-{[4-{[(R)-2-hydroxy-1-methylethyl]amino}-5-(2-thienyl)-pyrimidine-2-yl]amino}phenyl)-S-phenylsulfoximide

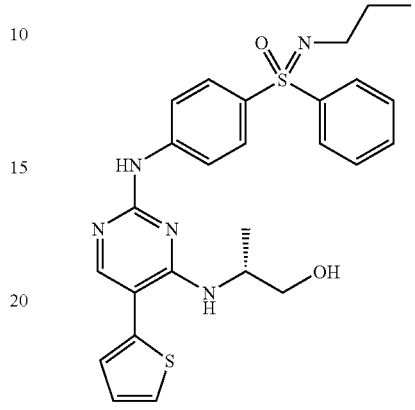

Preparation by Procedure 5c

¹H-NMR (300 MHz, DMSO-D6): δ 0.91 (t, 3H), 1.18 (d, 3H), 1.54 (m, 2H), 2.86 (m, 2H), 3.49 (m, 2H), 4.25 (m, 1H), 4.87 (t, 1H), 6.18 (d, 1H), 7.20 (m, 2H), 7.56 (m, 3H), 7.62 (m, 1H), 7.78 (d, 2H), 7.88 (m, 2H), 7.95 (s, 1H), 7.97 (d, 2H), 9.75 (s, 1H)

Example 1.24

(RS)—N-(cyclopropylmethyl)-S-(4-{[4-{[(R)-2-hydroxy-1-methylethyl]amino}-5-(2-thienyl)pyrimidine-2-yl]amino}phenyl)-S-methylsulfoximide

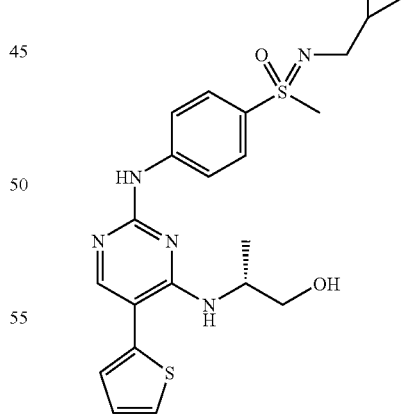

Preparation by Procedure 5c

¹H-NMR (300 MHz, DMSO-D6): δ 0.06 (m, 2H), 0.33 (m, 2H), 0.87 (m, 1H), 1.20 (d, 3H), 2.60 (m, 1H), 2.69 (m, 1H), 3.07 (s, 3H), 3.51 (m, 2H), 4.27 (m, 1H), 4.89 (t, 1H), 6.19 (d, 1H), 7.21 (m, 2H), 7.62 (m, 1H), 7.70 (d, 2H), 7.97 (s, 1H), 8.01 (d, 2H), 9.76 (s, 1H)

Example 1.25

(RS)—N-(cyclopropylmethyl)-S-(4-{[4-{[(R)-2-hydroxy-1-methylethyl]amino}-5-(2-thienyl)pyrimidine-2-yl]amino}phenyl)-S-cyclopropylsulfoximide

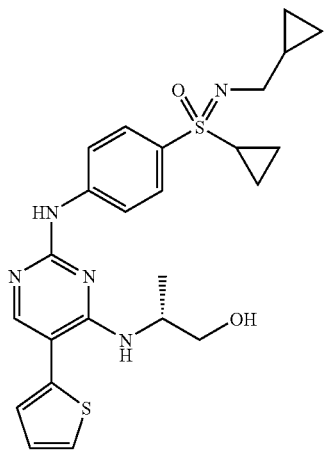

Preparation by Procedure 5c

| HPLC/MS: | Column: | XBrigde C18 3.5µ 100 × 4.6 mm |
|---|---|---|
| | Solvent: | A: H$_2$O B: acetonitrile |
| | Buffer: | A/0,2% NH$_3$ |
| | Gradient: | 95% A + 5% B__−> 95% B(7') |
| | Flow: | 1.0 mL/min |
| | Solution: | 1 mg/mL acetonitrile/H$_2$O 7:3 |
| | Injection Volume: | 20 µl |
| | Detection: | DAD (200-500 nm) TAC; MS-ESI+ (120-1000 m/z) TIC |
| | Temperature: | Room temperature |
| | Retention Time: | 5.90 min |
| | Mass found: | 483 m/z |

Example 1.26

(RS)—N-(cyclopropylmethyl)-S-(4-{[4-{[(R)-2-hydroxy-1-methylethyl]amino}-5-(2-thienyl)pyrimidine-2-yl]amino}phenyl)-S-phenylsulfoximide

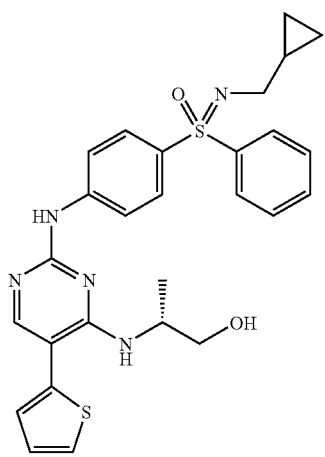

Preparation by Procedure 5c

| HPLC/MS: | Column: | XBrigde C18 3.5µ 100 × 4.6 mm |
|---|---|---|
| | Solvent: | A: H$_2$O B: acetonitrile |
| | Buffer: | A/0,2% NH$_3$ |
| | Gradient: | 95% A + 5% B_5 −> 95% B(7') |
| | Flow: | 1.0 mL/min |
| | Solution: | 1 mg/mL acetonitrile/H$_2$O 7:3 |
| | Injection Volume: | 20 µl |
| | Detection: | DAD (200-500 nm) TAC; MS-ESI+ (120-1000 m/z) TIC |
| | Temperature: | Room temperature |
| | Retention Time: | 6.94 min |
| | Mass found: | 519 m/z |

Example 1.27

(RS)—N-(phenyl)-S-(4-{[4-{[(R)-2-hydroxy-1-methylethyl]amino}-5-(2-thienyl)pyrimidine-2-yl]amino}phenyl)-S-methylsulfoximide

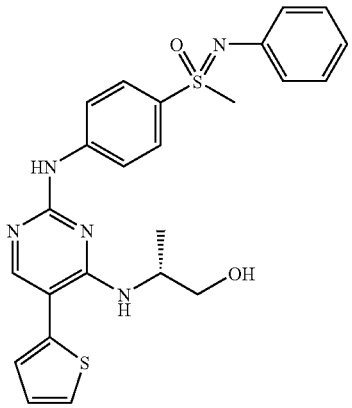

Preparation by Procedure 5c $^1$H-NMR (300 MHz, DMSO-D6): δ 1.18 (m, 3H), 3.32 (s, 3H), 3.49 (m, 2H), 4.26 (m, 1H), 4.88 (m, 1H), 6.19 (d, 1H), 6.77 (t, 1H), 6.85 (d, 2H), 7.07 (t, 2H), 7.20 (m, 2H), 7.62 (d, 1H), 7.78 (d, 2H), 7.95 (s, 1H), 7.99 (d, 2H), 9.79 (s, 1H)

Example 1.28

(RS)—N-(ethoxycarbonyl)-S-[4-({4-[(3-N-morpholinopropyl)amino]-5-(5-pyrazol)pyrimidine-2-yl}amino)phenyl]-S-methylsulfoximide and (RS)—S-[4-({4-[(3-N-morpholinopropyl)amino]-5-(5-pyrazol)pyrimidine-2-yl}amino)phenyl]-S-methylsulfoximide

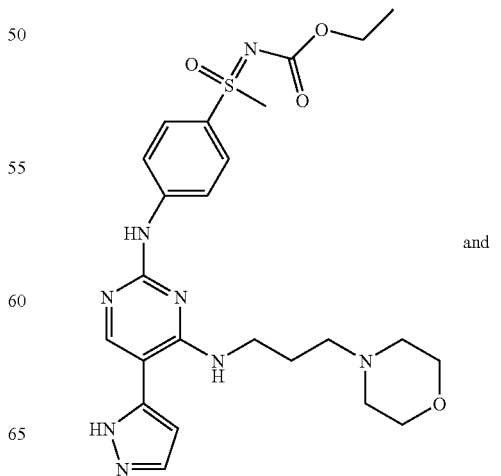

and

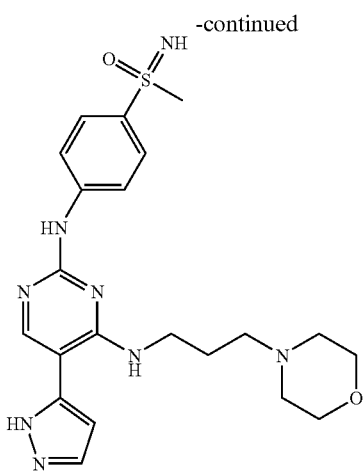

Preparation by Procedure 5b. Here both the desired product (12%) and also the deprotected form (36%) are formed.

¹H-NMR (300 MHz, DMSO-D6): δ 1.07 (m, 3H), 1.79 (m, 2H), 2.35 (m, 6H), 3.37 (s, 3H), 3.51 (m, 4H), 3.59 (m, 2H), 3.88 (m, 2H), 6.80 (m, 1H), 7.78 (m, 3H), 8.07 (d, 2H), 8.47 (s, 1H), 8.76 (t, 1H), 9.78 (s, 1H), 12.96 (s, 1H).

MS: 529 (MH+).

¹H-NMR (300 MHz, DMSO-D6): δ 1.78 (m, 2H), 2.32 (m, 6H), 2.98 (s, 3H), 3.51 (m, 6H), 3.92 (s, 1H), 6.79 (s, 1H), 7.75 (d, 2H), 7.81 (m, 1H), 7.99 (d, 2H), 8.45 (s, 1H), 8.73 (bs, 1H), 9.63 (s, 1H), 12.94 (s, 1H).

MS: 457 (MH+).

Example 1.29

(RS)—N-(ethoxycarbonyl)-S-[4-({4-[(-N-((4-methylbenzamido)-N-2-acetylamido)propylamino]-5-(2-thiophen) pyrimidine-2-yl}amino) phenyl]-S-methyl-sulfoximide

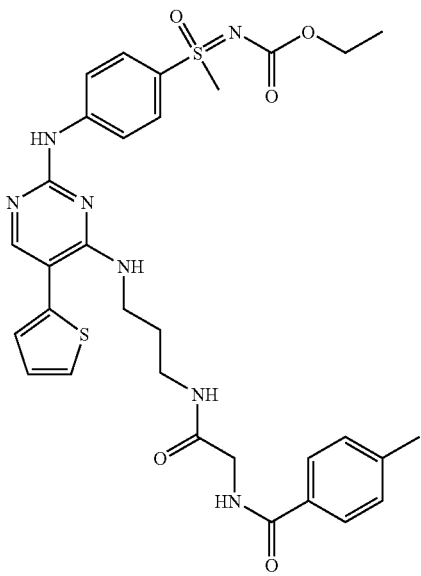

Preparation by Procedure 5b.

¹H-NMR (300 MHz, DMSO-D6): δ 1.06 (t, 3H), 1.71 (m, 2H), 2.31 (s, 3H), 3.13 (m, 2H), 3.37 (s, 3H), 3.42 (m, 2H), 3.77 (d, 2H), 3.88 (m, 2H), 6.85 (t, 1H), 7.13 (m, 1H), 7.18 (m, 1H), 7.23 (d, 2H), 7.56 (m, 1H), 7.74 (d, 2H), 7.78 (d, 2H), 7.91 (s, 1H), 7.93 (t, 1H), 8.03 (d, 2H), 8.60 (t, 1H), 9.83 (s, 1H).

MS: 650 (MH+).

Example 1.30

N-{5-(2-thienyl)-2-[(4-{(RS)—S-[ethoxycarbonyl]-S-methyl-sulfoximide}-phenyl)amino]pyrimidin-4-yl)}-4-amino-2-(S)-amino-butyric acid

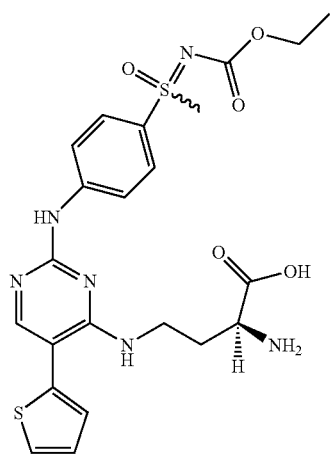

a) N-{5-(2-thienyl)-2-[(4-{(RS)—S-[ethoxycarbonyl]-S-methyl-sulfoximide}-phenyl)amino]pyrimidin-4-yl}-4-amino-2-(S)-amino-butyric acid tert-butyl ester and N-{5-(2-thienyl)-2-[(4-{(RS)—S-[ethoxycarbonyl]-S-methyl-sulfoximide}-phenyl)amino]pyrimidin-4-yl}-4-amino-2-(S)-[tert-butyloxycarbonyl]-amino-butyric acid tert-butyl ester

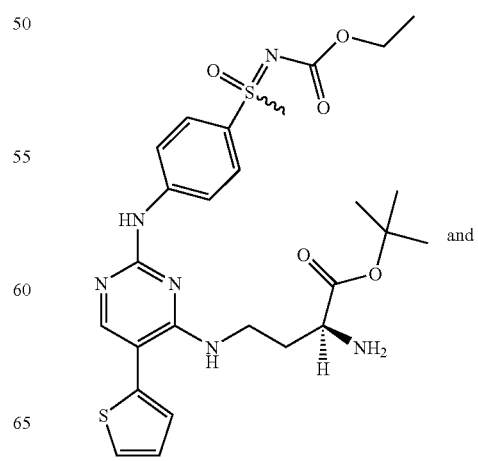

and

-continued

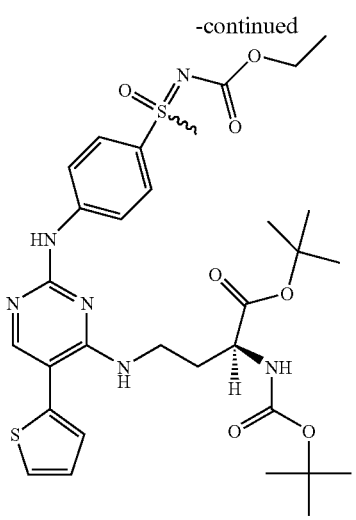

Preparation by procedure 5b. The Boc-protected and unprotected form can be isolated by column chromatography.

NH₂-Derivative:
¹H-NMR (300 MHz, DMSO-D6): δ 1.07 (t, 3H), 1.32 (s, 9H), 1.65 (m, 9H), 1.85 (m, 2H), 1.94 (m, 1H), 3.62 (m, 1H), 3.37 (s, 3H), 3.53 (m, 2H), 3.89 (m, 2H), 7.13 (m, 2H), 7.19 (m, 1H), 7.56 (dd, 1H), 7.78 (d, 2H), 7.91 (s, 1H), 8.04 (d, 2H), 9.82 (s, 1H).
MS: 575 (MH+).

Boc-Protected Derivative:
¹H-NMR (300 MHz, DMSO-D₆): δ 1.07 (t, 3H), 1.29 (s, 9H), 1.31 (s, 9H), 1.91 (m, 1H), 2.02 (m, 1H), 3.37 (m, 4H), 3.49 (m, 1H), 3.10 (m, 3H), 6.73 (bt, 1H), 7.19 (m, 3H), 7.58 (dd, 1H), 7.79 (d, 2H), 7.91 (s, 1H), 8.01 (d, 2H), 9.81 (s, 1H).
MS: 675 (MH+).

b) N-{5-(2-thienyl)-2-[(4-{(RS)—S-[ethoxycarbo-nyl]-S-methyl-sulfoximide}-phenyl)amino]pyrimi-din-4-yl}-4-amino-2-(S)-amino-butyric acid

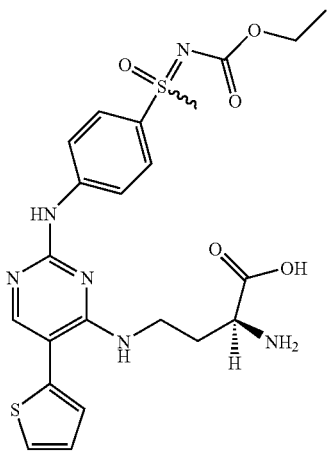

N-{5-(2-thienyl)-2-[(4-{(RS)—S-[ethoxycarbonyl]-S-methyl-sulfoximide}-phenyl)amino]pyrimidin-4-yl}-4-amino-2-(S)-amino-butyric acid tert-butyl ester (61 mg, 0.11 mmol) is dissolved in dioxane (2 ml) and HCl/dioxane (0.3 ml, 4 M) and water (0.3 ml) is added. The reaction mixture is stirred for 20 h at RT and further HCl/dioxane (0.6 ml, 4 M) is added. After 20 h at 40° C. the solvent is evaporated: 56 mg (95%).
¹H-NMR (300 MHz, DMSO-D₆): δ 1.06 (t, 3H), 2.11 (m, 1H), 2.20 (m, 1H), 3.42 (s, 3H), 3.63 (m, 2H), 3.89 (m, 3H), 7.19 (dd, 1H), 7.29 (d, 1H), 7.70 (d, 1H), 7.94 (m, 4H), 8.05 (s, 1H), 8.20 (bs, 1H), 8.51 (bs, 2H), 11.40 (bs, 1H).
MS: 519 (MH+).

Example 1.31

(RS)—N-(ethoxycarbonyl)-S-(4-{[4-{[3-N-imida-zol-propyl]amino}-5-(2-thiophen)-pyrimidine-2-yl}amino)phenyl]-S-methylsulfoximide

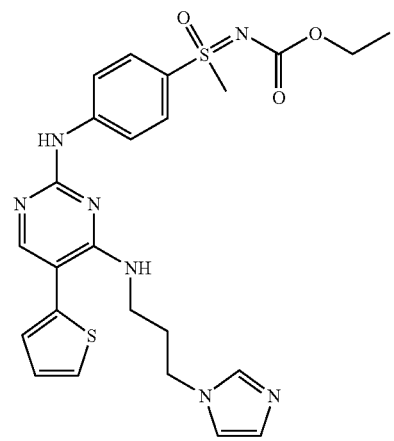

Preparation by Procedure 5b.
¹H-NMR (300 MHz, DMSO-D6): δ 1.12 (t, 3H), 2.09 (m, 2H), 3.43 (m, 5H), 3.93 (m, 2H), 4.06 (t, 2H), 6.89 (m, 2H), 7.20 (m, 3H), 7.63 (dd, 1H), 7.66 (s, 1H), 7.84 (d, 2H), 7.96 (s, 1H), 8.04 (d, 2H), 9.84 (s, 1H).
MS: 526 (MH+).

Example 1.32

(RS)—N-(ethoxycarbonyl)-S-(4-{[4-{[4-imidazol-2-ethan]amino}-5-(2-thiophen)-pyrimidine-2-yl}amino)phenyl]-S-methylsulfoximide

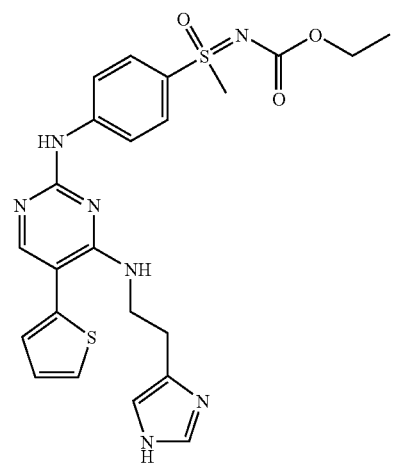

Preparation by Procedure 5b.

1H-NMR (300 MHz, DMSO-D6): δ 1.12 (t, 3H), 2.86 (t, 2H), 3.42 (s, 3H), 3.70 (q, 2H), 3.94 (m, 2H), 6.86 (bs, 1H), 6.98 (bs, 1H), 7.20 (d, 2H), 7.55 (s, 1H), 7.61 (t, 1H), 7.81 (d, 2H), 7.97 (s, 1H), 8.09 (d, 2H), 9.87 (s, 1H), 11.85 (bs, 1H).

MS: 512 (MH+).

Example 1.33

(RS)—N-(ethoxycarbonyl)-S-(4-{[4-{[3-benzylamido-propan]amino}-5-(2-thiophen)pyrimidine-2-yl}amino)phenyl]-S-methylsulfoximide

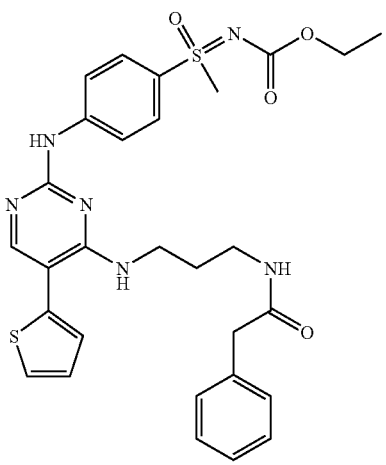

Preparation by Procedure 5b.

$^1$H-NMR (300 MHz, DMSO-D6): δ 1.06 (t, 3H), 1.71 (m, 2H), 3.10 (q, 2H), 3.34 (s, 2H), 3.36 (s, 3H), 3.40 (q, 2H), 3.89 (m, 2H), 6.81 (t, 1H), 7.18 (m, 7H), 7.58 (dd, 1H), 7.79 (d, 2H), 7.91 (s, 1H), 8.04 (m, 3H), 9.83 (s, 1H).

MS: 593 (MH+).

Example 1.34

(RS)—N-(ethoxycarbonyl)-S-(4-{[4-{propylamino}-5-(2-thiophen)-pyrimidine-2-yl}amino) phenyl]-S-methylsulfoximide

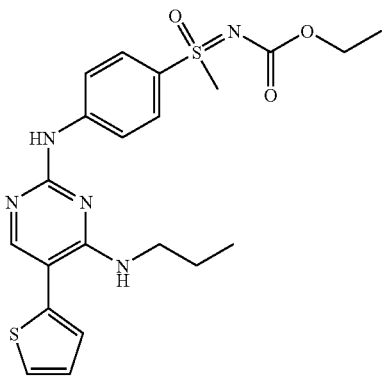

Preparation by Procedure 5b.

$^1$H-NMR (300 MHz, DMSO-D6): δ 0.89 (t, 3H), 1.07 (t, 3H), 1.59 (m, 2H), 3.38 (m, 5H), 3.88 (m, 2H), 6.79 (t, 1H), 7.16 (m, 2H), 7.58 (dd, 1H), 7.76 (d, 2H), 7.90 (s, 1H), 8.04 (d, 2H), 9.81 (s, 1H).

MS: 460 (MH+).

Example 1.35

(RS)—N-(ethoxycarbonyl)-S-(4-{[4-methoxy]-5-(2-thiophen)-pyrimidine-2-yl}amino)phenyl]-S-methylsulfoximide

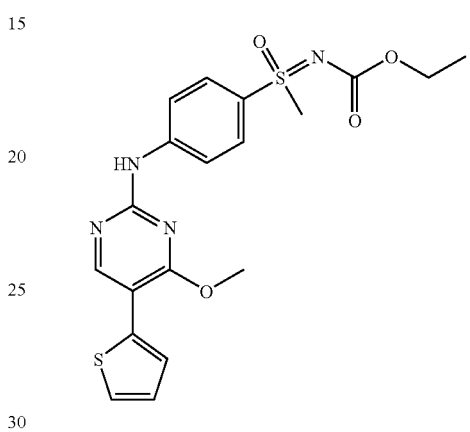

Preparation by Procedure 5b.

$^1$H-NMR (300 MHz, DMSO-D6): δ 3.17 (t, 3H), 3.39 (s, 3H), 3.89 (m, 2H), 4.08 (s, 3H), 7.10 (dd, 1H), 7.54 (m, 2H), 7.83 (d, 2H), 8.04 (d, 2H), 8.70 (s, 1H), 10.29 (s, 1H).

MS: 433 (MH+).

Example 1.36

(RS)—N-(ethoxycarbonyl)-S-(4-{[4-{[4-sulphonamid-phenyl]amino}-5-(2-thiophen)pyrimidine-2-yl}amino)phenyl]-S-methylsulfoximide

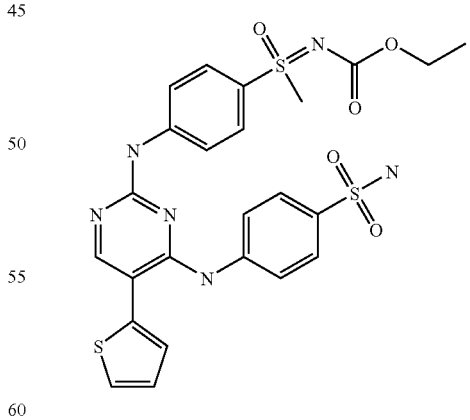

Preparation by Procedure 5b.

$^1$H-NMR (300 MHz, DMSO-D6): δ 1.07 (t, 3H), 3.38 (s, 3H), 3.89 (m, 2H), 7.19 (dd, 1H), 7.25 (s, 1H), 7.33 (dd, 1H), 7.65 (dd, 1H), 7.76 (m, 5H), 7.94 (d, 2H), 8.23 (s, 1H), 8.82 (s, 1H), 9.98 (s, 1H).

MS: 573 (MH+).

Example 1.37

(RS)—N-(ethoxycarbonyl)-S-(4-{[4-{[2-(1-pyrazol)-ethyl]amino}-5-(2-thiophen)pyrimidine-2-yl}amino)phenyl]-S-methylsulfoximide

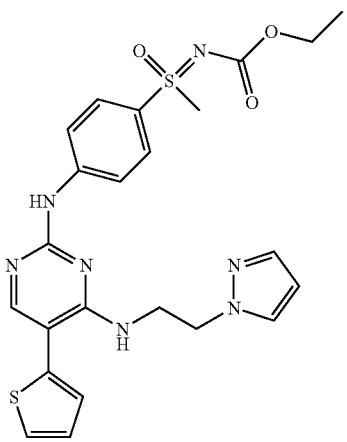

Preparation by Procedure 5b.

¹H-NMR (300 MHz, DMSO-D6): δ 1.07 (t, 3H), 3.38 (s, 3H), 3.80 (q, 2H), 2.89 (m, 2H), 4.36 (t, 2H), 6.21 (t, 1H), 6.85 (t, 1H), 7.10 (dd, 1H), 7.15 (dd, 1H), 7.42 (d, 1H), 7.57 (dd, 1H), 7.66 (d, 1H), 7.75 (d, 2H), 7.93 (s, 1H), 8.04 (d, 2H), 9.87 (s, 1H).

MS: 512 (MH+).

Example 1.38

(RS)—N-(methylcarbamoyl)-S-(4-{[4-{[(R)-2-hydroxy-1-methylethyl]amino}-5-(2-thienyl)pyrimidine-2-yl]amino}phenyl)-S-methylsulfoximide

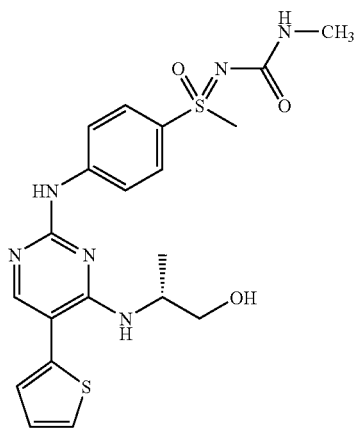

In the reaction of (R)-2-(2-chloro-5-(2-thienyl)pyrimidine-4-ylamino)propan-1-ol (164.5 mg, 0.61 mmol) with (RS)—S-(4-aminophenyl)-N-(methylcarbamoyl)-S-methyl-sulphoximide (126 mg, 0.55 mmol) according to procedure 5c, the desired product is obtained in 23.5% yield (60 mg) after chromatographic purification (silica gel, dichloromethane/ethanol (0%-20% ethanol)).

¹H-NMR (400 MHz, DMSO-D6): δ 2.50 (s, 3H), 1.21 (d, 3H), 3.34 (s, 3H), 3.51 (t, 2H), 4.23-4.33 (m, 1H), 4.90 (t, 1H), 6.21 (d, 1H), 6.79 (q, 1H), 7.18-7.24 (m, 2H), 7.62 (d, 1H), 7.78 (d, 2H), 7.98 (s, 1H), 8.03 (d, 2H), 9.83 (s, 1H).

Example 1.39

(RS)—N-(ethylcarbamoyl)-S-(4-{[4-{[(R)-2-hydroxy-1-methylethyl]amino}-5-(2-thienyl)pyrimidine-2-yl]amino}phenyl)-S-methylsulfoximide

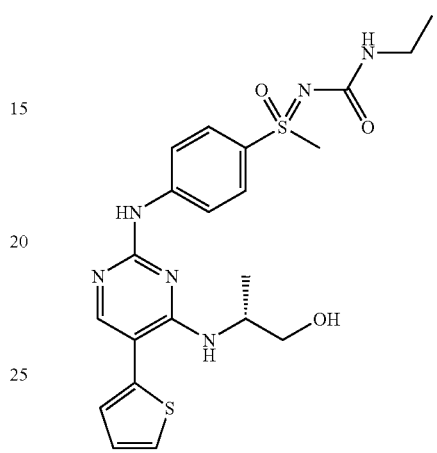

In the reaction of (R)-2-(2-chloro-5-(2-thienyl)pyrimidine-4-ylamino)propan-1-ol (296.3 mg, 1.1 mmol) with (RS)—S-(4-aminophenyl)-N-(ethylcarbamoyl)-S-methyl-sulphoximide (241 mg, 1 mmol) according to procedure 5c, the desired product is obtained in 26% yield (133 mg) after chromatographic purification (silica gel, dichloromethane/ethanol (0%-20% ethanol)).

¹H-NMR (400 MHz, DMSO-D6): δ 0.98 (t, 3H), 1.21 (d, 3H), 2.95 (m, 2H), 3.35 (s, 3H), 3.51 (t, 2H), 4.23-4.34 (m, 1H), 4.89 (t, 1H), 6.20 (d, 1H), 6.87 (m, 1H), 7.20 (dd, 1H), 7.23 (d, 1H), 7.62 (d, 1H), 7.79 (d, 2H), 7.98 (s, 1H), 8.04 (d, 2H), 9.82 (s, 1H).

Example 1.40

(RS)—N-(isopropylcarbamoyl)-S-(4-{[4-{[(R)-2-hydroxy-1-methylethyl]amino}-5-(2-thienyl)pyrimidine-2-yl]amino}phenyl)-S-methylsulfoximide

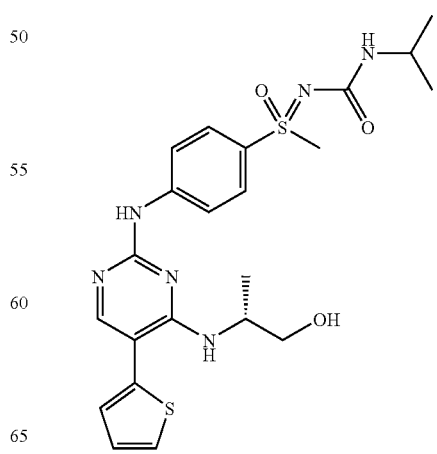

In the reaction of (R)-2-(2-chloro-5-(2-thienyl)pyrimidine-4-ylamino)propan-1-ol (291.7 mg, 1.08 mmol) with (RS)—S-(4-aminophenyl)-N-(isopropylcarbamoyl)-S-methylsulphoximide (251 mg, 0.98 mmol) according to procedure 5c, the desired product is obtained in 39% yield (186 mg) after chromatographic purification (silica gel, dichloromethane/ethanol (0%-20% ethanol)).

$^1$H-NMR (400 MHz, DMSO-D6): δ 1.00 (d, 3H), 1.02 (d, 3H), 1.20 (d, 3H), 3.35 (s, 3H), 3.51 (t, 2H), 3.61 (m, 1H), 4.28 (m, 1H), 4.89 (t, 1H), 6.21 (d, 1H), 6.77 (d, 1H), 7.20 (dd, 1H), 7.23 (d, 1H), 7.62 (d, 1H), 7.79 (d, 2H), 7.98 (s, 1H), 8.03 (d, 2H), 9.83 (s, 1H).

Example 1.41

(RS)—N-(cyclopentylcarbamoyl)-S-(4-{[4-{[(R)-2-hydroxy-1-methylethyl]amino}-5-(2-thienyl)pyrimidine-2-yl]amino}phenyl)-S-methylsulfoximide

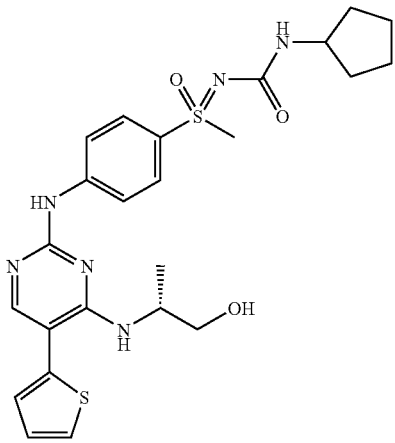

In the reaction of (R)-2-(2-chloro-5-(2-thienyl)pyrimidine-4-ylamino)propan-1-ol (103.4 mg, 0.38 mmol) with (RS)—S-(4-aminophenyl)-N-(cyclopentylcarbamoyl)-S-methylsulphoximide (98 mg, 0.35 mmol) according to procedure 5c, the desired product is obtained in 18% yield (33 mg) after chromatographic purification (silica gel, dichloromethane/ethanol (0%-20% ethanol)).

$^1$H-NMR (400 MHz, DMSO-D6): δ 1.21 (d, 3H), 1.41 (m, 4H), 1.60 (m, 2H), 1.72 (m, 2H), 3.35 (s, 3H), 3.51 (t, 2H), 3.80 (m, 1H), 4.28 (m, 1H), 4.89 (t, 1H), 6.20 (d, 1H), 6.88 (d, 1H), 7.20 (dd, 1H), 7.23 (d, 1H), 7.62 (d, 1H), 7.80 (d, 2H), 7.98 (s, 1H), 8.03 (d, 2H), 9.81 (s, 1H).

Example 1.42

(RS)—N-(benzylcarbamoyl)-S-(4-{[4-{[(R)-2-hydroxy-1-methylethyl]amino}-5-(2-thienyl)pyrimidine-2-yl]amino}phenyl)-S-methylsulfoximide

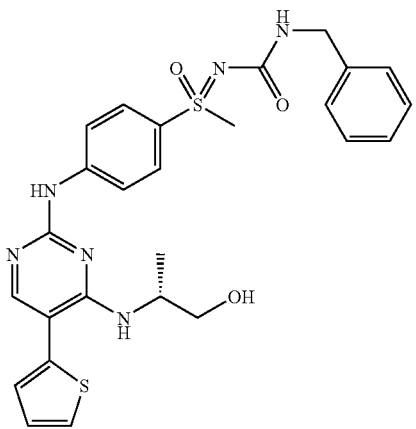

In the reaction of (R)-2-(2-chloro-5-(2-thienyl)pyrimidine-4-ylamino)propan-1-ol (175 mg, 0.65 mmol) with (RS)—S-(4-aminophenyl)-N-(benzylcarbamoyl)-S-methylsulphoximide (179 mg, 0.59 mmol) according to procedure 5c, the desired product is obtained in 26% yield (82 mg) after chromatographic purification (silica gel, dichloromethane/ethanol (0%-20% ethanol)).

$^1$H-NMR (400 MHz, DMSO-D6): δ 1.21 (d, 3H), 3.37 (s, 3H), 3.51 (t, 2H), 4.15 (d, 2H), 4.29 (m, 1H), 4.89 (t, 1H), 6.21 (d, 1H), 7.20 (dd, 1H), 7.23 (d, 3H), 7.30 (t, 2H), 7.45 (t, 1H), 7.62 (d, 1H), 7.81 (d, 2H), 7.98 (s, 1H), 8.04 (d, 2H), 9.82 (s, 1H).

Example 1.43

(RS)—N-(p-tolylcarbamoyl)-S-(4-{[4-{[(R)-2-hydroxy-1-methylethyl]amino}-5-(2-thienyl)pyrimidine-2-yl]amino}phenyl)-S-methylsulfoximide

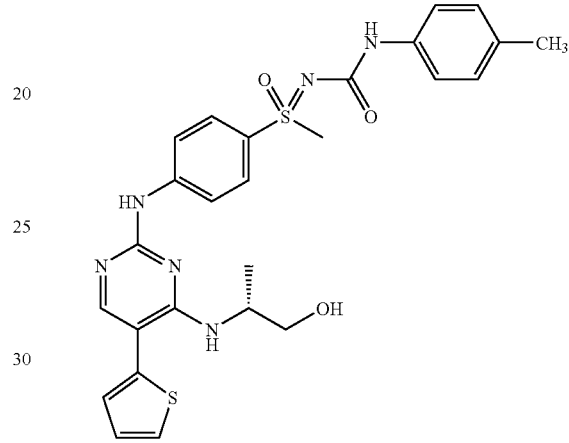

In the reaction of (R)-2-(2-chloro-5-(2-thienyl)pyrimidine-4-ylamino)propan-1-ol (39.1 mg, 0.15 mmol) with (RS)—S-(4-aminophenyl)-N-(p-tolylcarbamoyl)-S-methylsulphoximide (40 mg, 0.13 mmol) according to procedure 5c, the desired product is obtained in 21% yield (15 mg) after chromatographic purification (silica gel, dichloromethane/ethanol (0%-20% ethanol)).

$^1$H-NMR (400 MHz, DMSO-D6): δ 1.21 (d, 3H), 2.20 (s, 3H), 3.45 (s, 3H), 3.51 (t, 2H), 4.29 (m, 1H), 4.91 (t, 1H), 6.23 (d, 1H), 7.00 (d, 2H), 7.20 (dd, 1H), 7.23 (d, 1H), 7.39 (d, 2H), 7.62 (d, 1H), 7.86 (d, 2H), 7.98 (s, 1H), 8.06 (d, 2H), 9.87 (s, 1H)

Example 1.44

(RS)—N-(4-chloro-phenylcarbamoyl)-S-(4-{[4-{[(R)-2-hydroxy-1-methylethyl]amino}-5-(2-thienyl)pyrimidine-2-yl]amino}phenyl)-S-methylsulfoximide

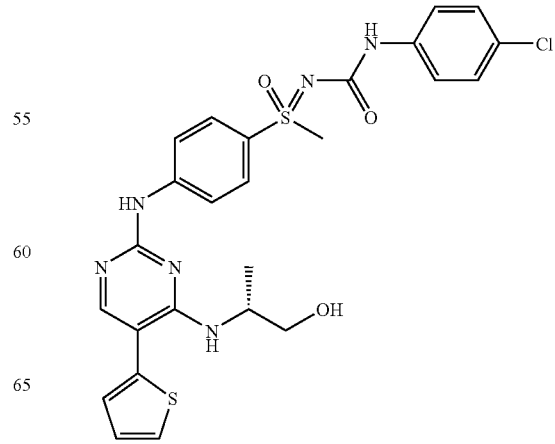

In the reaction of (R)-2-(2-chloro-5-(2-thienyl)pyrimidine-4-ylamino)propan-1-ol (164 mg, 0.61 mmol) with (RS)—S-(4-aminophenyl)-N-(4-chloro-phenylcarbamoyl)-S-methylsulphoximide (179 mg, 0.55 mmol) according to procedure 5c, the desired product is obtained in 35% yield (109 mg) after chromatographic purification (silica gel, dichloromethane/ethanol (0%-20% ethanol)).

$^1$H-NMR (400 MHz, DMSO-D6): δ 1.21 (d, 3H), 3.47 (s, 3H), 3.51 (t, 2H), 4.28 (m, 1H), 4.90 (t, 1H), 6.23 (d, 1H), 7.20 (dd, 1H), 7.23 (d, 1H), 7.25 (d, 2H), 7.53 (d, 2H), 7.63 (d, 1H), 7.86 (d, 2H), 7.98 (s, 1H), 8.07 (d, 2H), 9.88 (s, 1H)

Example 1.45

(RS)—N-(3-chloro-phenylcarbamoyl)-S-(4-{[4-{[(R)-2-hydroxy-1-methylethyl]amino}-5-(2-thienyl)pyrimidine-2-yl]amino}phenyl)-S-methylsulfoximide

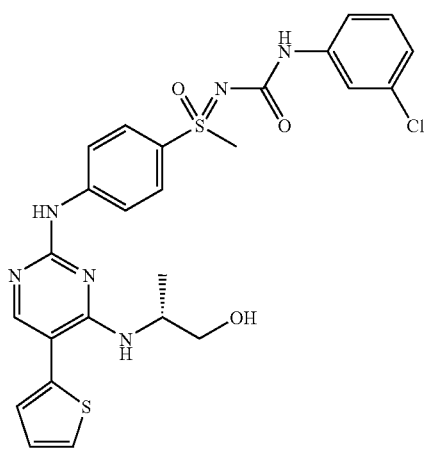

In the reaction of (R)-2-(2-chloro-5-(2-thienyl)pyrimidine-4-ylamino)propan-1-ol (115.5 mg, 0.43 mmol) with (RS)—S-(4-aminophenyl)-N-(3-chloro-phenylcarbamoyl)-S-methylsulphoximide (126 mg, 0.39 mmol) according to procedure 5c, the desired product is obtained in 26% yield (56 mg) after chromatographic purification (silica gel, dichloromethane/ethanol (0%-20% ethanol)).

$^1$H-NMR (400 MHz, DMSO-D6): δ 1.21 (d, 3H), 3.48 (s, 3H), 3.51 (t, 2H), 4.28 (m, 1H), 4.91 (t, 1H), 6.23 (d, 1H), 6.94 (d, 1H), 7.20 (dd, 1H), 7.23 (m, 2H), 7.38 (d, 1H), 7.63 (d, 1H), 7.70 (m, 1H), 7.86 (d, 2H), 7.98 (s, 1H), 8.07 (d, 2H), 9.89 (s, 1H)

Example 1.46

(RS)—N-(4-methoxy-phenylcarbamoyl)-S-(4-{[4-{[(R)-2-hydroxy-1-methylethyl]amino}-5-(2-thienyl)pyrimidine-2-yl]amino}phenyl)-S-methylsulfoximide

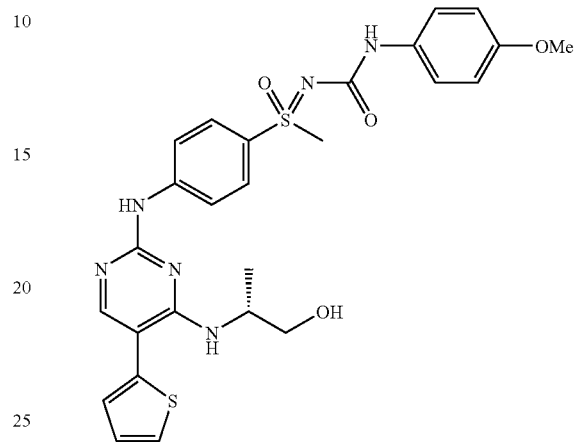

In the reaction of (R)-2-(2-chloro-5-(2-thienyl)pyrimidine-4-ylamino)propan-1-ol (200 mg, 0.74 mmol) with (RS)—S-(4-aminophenyl)-N-(4-methoxy-phenylcarbamoyl)-S-methylsulphoximide (214 mg, 0.67 mmol) according to procedure 5c, the desired product is obtained in 30% yield (110 mg) after chromatographic purification (silica gel, dichloromethane/ethanol (0%-20% ethanol)).

$^1$H-NMR (400 MHz, DMSO-D6): δ 1.21 (d, 3H), 3.45 (s, 3H), 3.51 (t, 2H), 3.68 (s, 3H), 4.29 (m, 1H), 4.89 (t, 1H), 6.21 (d, 1H), 6.79 (d, 2H), 7.19 (dd, 1H), 7.23 (d, 1H), 7.41 (d, 2H), 7.62 (d, 1H), 7.86 (d, 2H), 7.98 (s, 1H), 8.07 (d, 2H), 9.85 (s, 1H)

Example 1.47

(RS)—N-(4-dimethylamino-phenylcarbamoyl)-S-(4-{[4-{[(R)-2-hydroxy-1-methylethyl]amino}-5-(2-thienyl)pyrimidine-2-yl]amino}phenyl)-S-methylsulfoximide

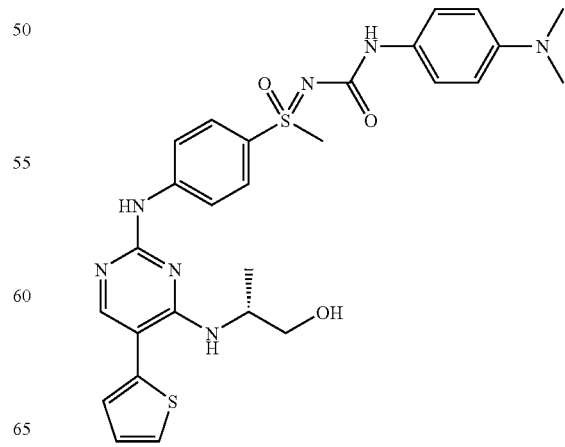

In the reaction of (R)-2-(2-chloro-5-(2-thienyl)pyrimidine-4-ylamino)propan-1-ol (146.4 mg, 0.54 mmol) with (RS)—S-(4-aminophenyl)-N-(4-dimethylamino-phenylcarbamoyl)-S-methylsulphoximide (164 mg, 0.49 mmol) according to procedure 5c, the desired product is obtained in 21% yield (59 mg) after chromatographic purification (silica gel, dichloromethane/ethanol (0%-20% ethanol)).

$^1$H-NMR (400 MHz, DMSO-D6): δ 1.21 (d, 3H), 2.79 (s, 6H), 3.44 (s, 3H), 3.51 (t, 2H), 4.29 (m, 1H), 4.91 (t, 1H), 6.23 (d, 1H), 6.62 (d, 2H), 7.20 (dd, 1H), 7.23 (d, 1H), 7.32 (d, 2H), 7.63 (d, 1H), 7.85 (d, 2H), 7.98 (s, 1H), 8.06 (d, 2H), 9.87 (s, 1H)

Example 1.48

(RS)—N-(pyridin-3-ylcarbamoyl)-S-(4-{[4-{[(R)-2-hydroxy-1-methylethyl]amino}-5-(2-thienyl)pyrimidine-2-yl]amino}phenyl)-S-methylsulfoximide

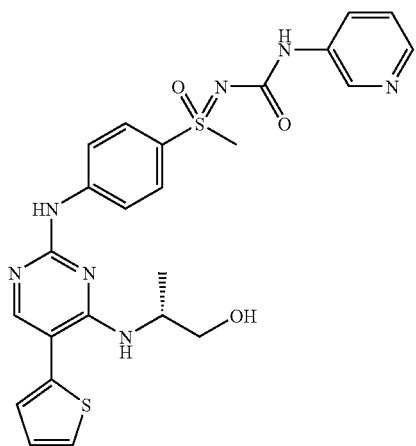

In the reaction of (R)-2-(2-chloro-5-(2-thienyl)pyrimidine-4-ylamino)propan-1-ol (30.7 mg, 0.11 mmol) with (RS)—S-(4-aminophenyl)-N-(pyridin-3-ylcarbamoyl)-S-methylsulphoximide (30 mg, 0.1 mmol) according to procedure 5c, the desired product is obtained in 4% yield (2.3 mg) after chromatographic purification (silica gel, dichloromethane/ethanol (0%-20% ethanol) and HPLC).

HPLC-MS: column: BEH C18 1.7 50×2.1
solvent: 1-99% ACN/0.1% NH$_3$
retention: 1.11 min
MS ES+: 524 (MH+, 100%), 262 (50%)

Example 1.49

(RS)—N-(2-methoxy-ethyl)-S-(4-{[4-{[(R)-2-hydroxy-1-methylethyl]amino}-5-(2-thienyl)pyrimidine-2-yl]amino}phenyl)-S-methylsulfoximide

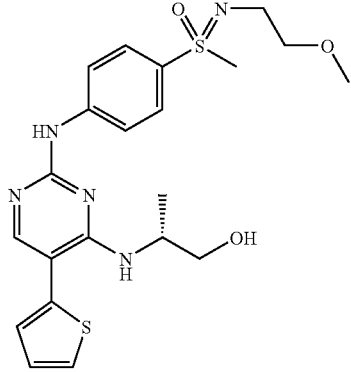

In the reaction of (R)-2-(2-chloro-5-(2-thienyl)pyrimidine-4-ylamino)propan-1-ol (248.2 mg, 0.92 mmol) with (RS)—S-(4-aminophenyl)-N-(2-methoxy-ethyl)-S-methylsulphoximide (191 mg, 0.84 mmol) according to procedure 5c, the desired product is obtained in 3% yield (10 mg) after chromatographic purification (silica gel, dichloromethane/ethanol (0%-20% ethanol) and HPLC).

$^1$H-NMR (400 MHz, DMSO-D6): δ 1.20 (d, 3H), 2.84 (m, 1H), 2.91 (m, 1H), 3.07 (s, 3H), 3.20 (s, 3H), 3.35 (t, 2H), 3.51 (t, 2H), 4.28 (m, 1H), 4.89 (t, 1H), 6.19 (d, 1H), 7.20 (dd, 1H), 7.23 (dd, 1H), 7.62 (dd, 1H), 7.71 (d, 2H), 7.97 (s, 1H), 8.02 (d, 2H), 9.78 (s, 1H).

Example 1.50

(RS)—N-(morpholine-4-carbonyl)-S-(4-{[4-{[(R)-2-hydroxy-1-methylethyl]amino}-5-(2-thienyl)pyrimidine-2-yl]amino}phenyl)-S-methylsulfoximide

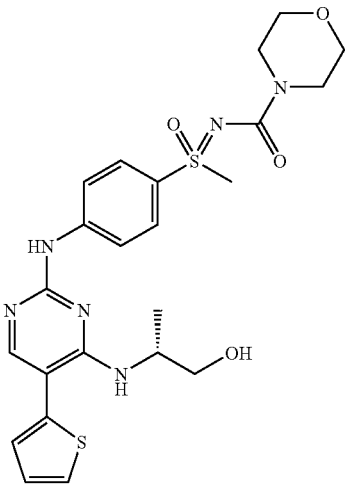

In the reaction of (R)-2-(2-chloro-5-(2-thienyl)pyrimidine-4-ylamino)propan-1-ol (49.2 mg, 0.18 mmol) with (RS)—S-(4-aminophenyl)-N-(morpholine-4-carbonyl)-S-methylsulphoximide (47 mg, 0.17 mmol) according to procedure 5c, the desired product is obtained in 7% yield (6 mg) after chromatographic purification (silica gel, dichloromethane/ethanol (0%-20% ethanol) and HPLC).

$^1$H-NMR (400 MHz, DMSO-D6): δ 1.20 (d, 3H), 3.37 (m, 4H), 3.40 (s, 3H), 3.51 (t, 2H), 3.54 (m, 4H), 4.29 (m, 1H), 6.28 (s br, 1H), 7.20 (dd, 1H), 7.23 (dd, 1H), 7.63 (dd, 1H), 7.81 (d, 2H), 7.98 (s, 1H), 8.03 (d, 2H), 9.87 (s, 1H)

Example 1.51

(RS)—N-(isopropylcarbamoyl)-S-(4-{4-(3-morpholin-4-yl-propylamino)-5-(2H-pyrazol-3-yl)-pyrimidin-2-ylamino}phenyl)-S-methylsulfoximide

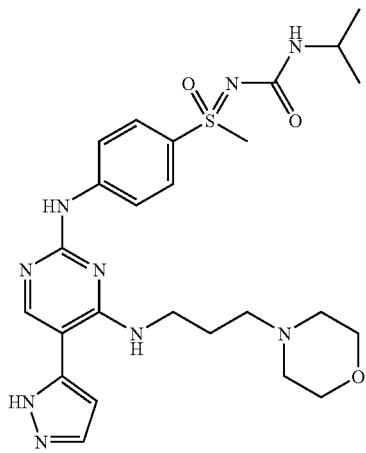

In the reaction of [2-chloro-5-(2H-pyrazol-3-yl)-pyrimidin-4-yl]-(3-morpholin-4-yl-propyl)-amine (212.8 mg, 0.66 mmol) with (RS)—S-(4-aminophenyl)-N-(isopropylcarbamoyl)-S-methylsulphoximide (153 mg, 0.6 mmol) according to procedure 5c, the desired product is obtained in 34% yield (109 mg) after chromatographic purification (silica gel, dichloromethane/ethanol (0%-20% ethanol)).

$^1$H-NMR (400 MHz, DMSO-D6): δ 1.02 (m, 6H), 1.82 (m, 2H), 2.36 (m, 6H), 3.35 (s, 3H), 3.55 (m, 6H), 3.61 (m, 1H), 6.73 (d, 1H), 6.83 (s, 1H), 7.79 (d, 2H), 7.85 (s, 1H), 8.07 (d, 2H), 8.49 (s, 1H), 8.78 (t, 1H), 9.74 (s, 1H), 12.99 (s, 1H).

Example 1.52

N-{-(2-thienyl)-2-[(4-{(RS)—S-[ethoxycarbonyl]-S-methyl-sulfoximide}-phenyl)amino]pyrimidin-4-yl}-3-amino-propionic-acid and N-{5-(2-thienyl)-2-[(4-{(RS)—S-[ethoxycarbonyl]-S-methyl-sulfoximide}-phenyl)amino]pyrimidin-4-yl}-3-amino-propionamide

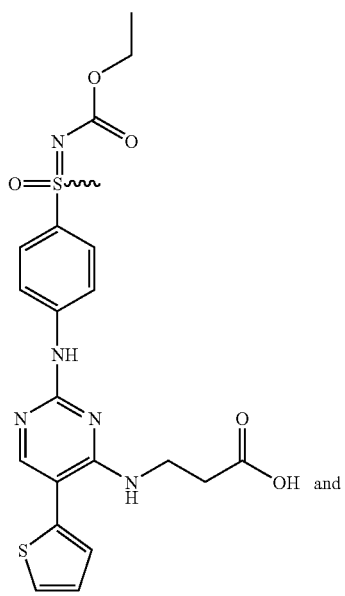

and

-continued

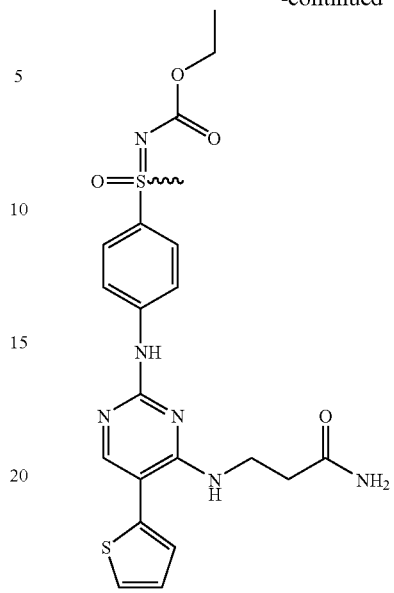

Preparation by Procedure 5b. The acid and the amide are formed, which can be separated by HPLC.

Acid:
$^1$H-NMR (300 MHz, DMSO-D$_6$): δ 1.07 (t, 3H), 2.57 (t, 2H), 3.37 (s, 3H), 3.63 (m, 2H), 3.88 (m, 2H), 6.83 (m, 1H), 7.16 (m, 2H), 7.57 (m, 1H), 7.76 (d, 2H), 7.93 (s, 1H), 8.03 (d, 2H), 9.87 (s, 1H), 12.4 (bs, 1H).

MS: 490 (MH+).

Amide:
$^1$H-NMR (300 MHz, DMSO-D$_6$): δ 1.07 (t, 3H), 2.42 (t, 2H), 3.37 (s, 3H), 3.63 (q, 2H), 3.89 (m, 2H), 6.84 (t, 1H), 6.89 (bs, 1H), 7.16 (m, 2H), 7.35 (bs, 1H), 7.57 (m, 1H), 7.77 (d, 2H), 7.93 (s, 1H), 8.04 (d, 2H), 9.87 (s, 1H).

MS: 489 (MH+).

Example 1.53

(RS)—N(ethoxycarbonyl)-(4-{[4-{propoxy}-5-(thiophen-2-yl)-pyrimidin-2-yl]amino}phenyl)-S-methylsulfoximide

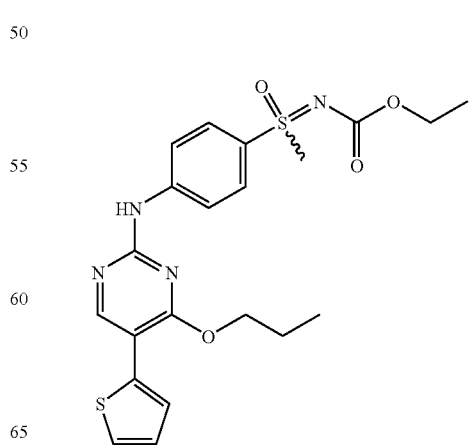

Preparation by Procedure 5b.
¹H-NMR (400 MHz, DMSO-D₆): δ 1.05 (m, 6H), 1.84 (m, 2H), 3.39 (s, 3H), 3.89 (m, 2H), 4.46 (t, 2H), 7.11 (dd, 1H), 7.54 (dd, 1H), 7.58 (dd, 1H), 7.83 (d, 2H), 8.02 (d, 2H), 8.73 (s, 1H), 10.27 (s, 1H).
MS: 461 (MH+).

Example 1.54

(RS)—N(ethoxycarbonyl)-(4-{[4-{2-N-morpholin-ethoxy}-5-(thiophen-2-yl)-pyrimidin-2-yl]amino}phenyl)-S-methylsulfoximide

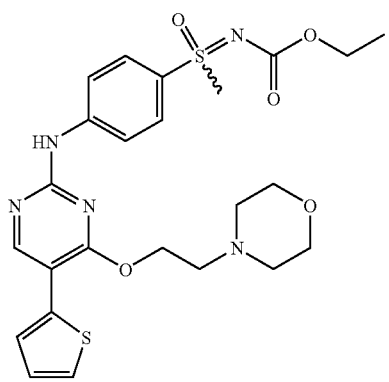

Preparation by Procedure 5b.
¹H-NMR (300 MHz, DMSO-D₆): δ 1.07 (t, 3H), 2.51 (m, 4H), 2.79 (t, 2H), 3.39 (s, 3H), 3.53 (t, 4H), 3.89 (m, 2H), 4.61 (t, 2H), 7.10 (dd, 1H), 7.53 (dd, 1H), 7.61 (d, 1H), 7.83 (d, 2H), 8.01 (d, 2H), 8.70 (s, 1H), 10.25 (s, 1H).

Example 1.55

(RS)—N(ethoxycarbonyl)-(4-{[4-{(RS)-2-methyl-3-hydroxy-propoxy}-5-(thiophen-2-yl)-pyrimidin-2-yl]amino}phenyl)-S-methylsulfoximide

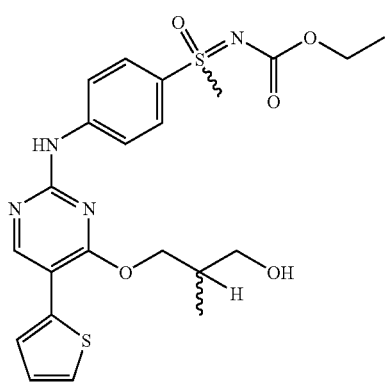

Preparation by Procedure 5b.
¹H-NMR (300 MHz, DMSO-D₆): δ 1.05 (m, 6H), 2.10 (m, 1H), 3.39 (s, 3H), 3.48 (m, 2H), 3.88 (m, 2H), 4.38 (m, 1H), 4.49 (m, 1H), 4.63 (bs, 1H), 7.11 (dd, 1H), 7.55 (dd, 1H), 7.57 (dd, 1H), 7.83 (d, 2H), 8.03 (d, 2H), 8.74 (s, 1H), 10.26 (s, 1H).

Example 1.56

(RS)—N(ethoxycarbonyl)-(4-{[4-{4-hydroxy-butoxy}-5-(thiophen-2-yl)-pyrimidin-2-yl]amino}phenyl)-S-methylsulfoximide

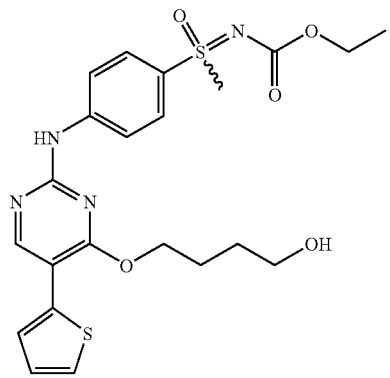

Preparation by Procedure 5b.
¹H-NMR (300 MHz, DMSO-D₆): δ 1.07 (t, 3H), 1.62 (m, 2H), 1.86 (m, 2H), 3.39 (s, 3H), 3.45 (t, 2H), 3.89 (m, 2H), 4.51 (t, 2H), 7.10 (dd, 1H), 7.53 (dd, 1H), 7.57 (dd, 1H), 7.83 (d, 2H), 8.02 (d, 2H), 8.73 (s, 1H), 10.26 (s, 1H).
MS: 491 (MH+).

Example 1.57

(RS)—N(ethoxycarbonyl)-(4-{[4-{2-hydroxy-ethoxy}-5-(thiophen-2-yl)-pyrimidin-2-yl]amino}phenyl)-S-methylsulfoximide

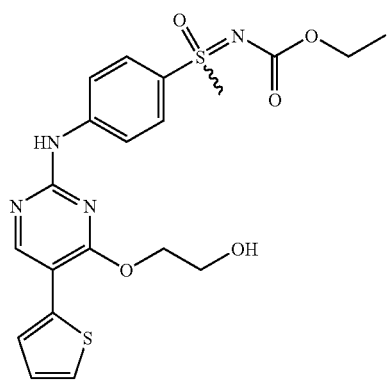

Preparation by Procedure 5b.
¹H-NMR (300 MHz, DMSO-D₆): δ 1.07 (t, 3H), 3.39 (s, 3H), 3.82 (m, 4H), 4.52 (t, 2H), 7.10 (dd, 1H), 7.53 (dd, 1H), 7.60 (dd, 1H), 7.83 (d, 2H), 8.01 (d, 2H), 8.69 (s, 1H), 10.27 (s, 1H).
MS: 463 (MH+).

Example 1.58

(RS)—N(ethoxycarbonyl)-(4-{[4-{2-methoxy-ethoxy}-5-(thiophen-2-yl)-pyrimidin-2-yl]amino}phenyl)-S-methylsulfoximide

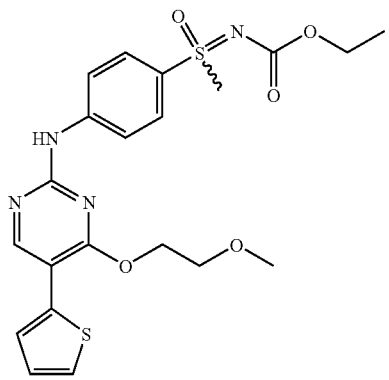

Preparation by Procedure 5b.

¹H-NMR (300 MHz, DMSO-D$_6$): δ 1.07 (t, 3H), 3.31 (s, 3H), 3.39 (s, 3H), 3.77 (m, 2H), 3.89 (m, 2H), 4.61 (m, 2H), 7.11 (dd, 1H), 7.54 (dd, 1H), 7.58 (dd, 1H), 7.84 (d, 2H), 8.01 (d, 2H), 8.71 (s, 1H), 10.28 (s, 1H).

MS: 477 (MH+).

Example 1.59

(RS)—N(ethoxycarbonyl)-(4-{[4-{(tetrahydro-furan-2-yl)methoxy}-5-(thiophen-2-yl)-pyrimidin-2-yl]amino}phenyl)-S-methylsulfoximide

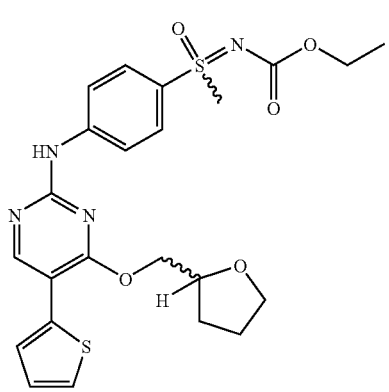

Preparation by Procedure 5b.

¹H-NMR (300 MHz, DMSO-D$_6$): δ 1.07 (t, 3H), 1.82 (m, 3H), 2.03 (m, 1H), 3.39 (s, 3H), 3.77 (m, 2H), 3.89 (m, 2H), 4.26 (m, 1H), 4.48 (m, 2H), 7.11 (dd, 1H), 7.54 (dd, 1H), 7.57 (dd, 1H), 7.83 (d, 2H), 8.01 (d, 2H), 8.71 (s, 1H), 10.27 (s, 1H).

MS: 503 (MH+).

Example 1.60

3-[N-{5-(2-thienyl)-2-[(4-{(RS)—S-[ethoxycarbonyl]-S-methyl-sulfoximide}-phenyl)amino]pyrimidin-4-yloxy}]-propionic acid tert-butylester and 3-[N-{5-(2-thienyl)-2-[(4-{(RS)—S-[ethoxycarbonyl]-S-methyl-sulfoximide}-phenyl)amino]pyrimidin-4-yloxy}]-propionic acid

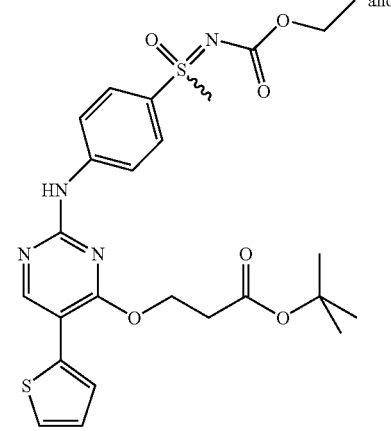

Preparation by Procedure 5b.

tert-butyl-ester:

¹H-NMR (300 MHz, CDCl$_3$): δ 1.25 (t, 3H), 1.45 (s, 9H), 2.83 (t, 2H), 3.32 (s, 3H), 4.12 (m, 2H), 4.74 (t, 2H), 7.09 (dd, 1H), 7.32 (dd, 1H), 7.43 (dd, 1H), 7.55 (bs, 1H), 7.89 (d, 2H), 7.95 (d, 2H), 8.54 (s, 1H).

MS: 547 (MH+).

Acid:

¹H-NMR (300 MHz, DMSO-D$_6$): δ 1.12 (t, 3H), 2.86 (t, 2H), 3.44 (s, 3H), 3.94 (m, 2H), 4.73 (t, 2H), 7.14 (dd, 1H), 7.57 (dd, 1H), 7.60 (dd, 1H), 7.87 (d, 2H), 8.08 (d, 2H), 8.76 (s, 1H), 10.34 (s, 1H), 12.40 (bs, 1H).

MS: 491 (MH+).

According to Process Variation 1 (see also Scheme 1) the following compounds can be prepared:

| Structure | Name |
|---|---|
| 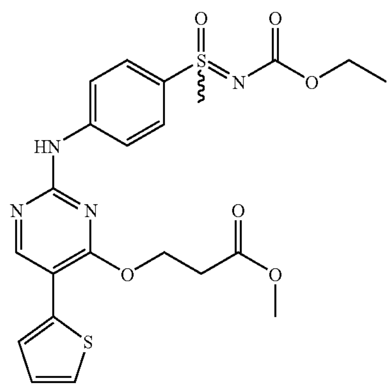 | 3-[N-{5-(2-thienyl)-2-[(4-{(RS)-S-[ethoxycarbonyl]-S-methyl-sulfoximide}-phenyl)amino]pyrimidin-4-yloxy}]-propionic acid methyl ester |
| 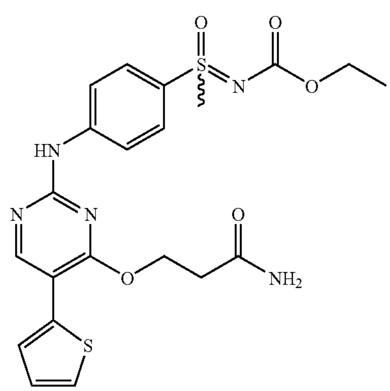 | 3-[N-{5-(2-thienyl)-2-[(4-{(RS)-S-[ethoxycarbonyl]-S-methyl-sulfoximide}-phenyl)amino]pyrimidin-4-yloxy}]-propionamide |
| 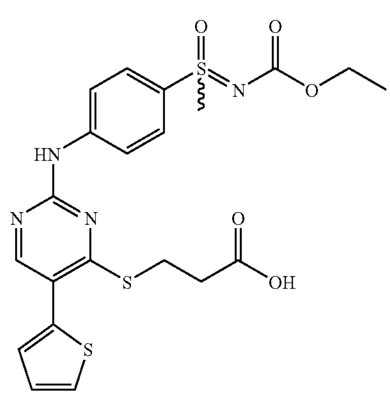 | 3-{5-(2-thienyl)-2-[(4-{(RS)-S-[ethoxycarbonyl]-S-methyl-sulfoximide}-phenyl)amino]pyrimidin-4-yl-sulfanyl} propionic acid |

-continued

| Structure | Name |
|---|---|
| 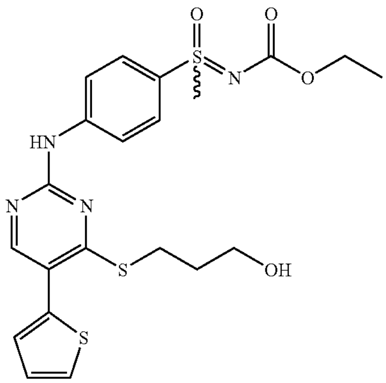 | (RS)-N-(Ethoxycarbonyl)-S-(4-{[4-{3-hydroxy-propyl-sulfanyl}-5-(2-thienyl)pyrimidin-2-yl]amino}phenyl)-S-methylsulfoximide |
| 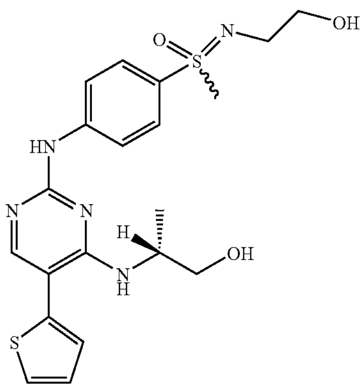 | (RS)-N-(2-hydroxy-ethyl)-S-(4-{[4-{[(R)-2-hydroxy-1-methylethyl]amino}-5-(2-thienyl)pyrimidine-2-yl]amino}phenyl)-S-methylsulfoximide |
| 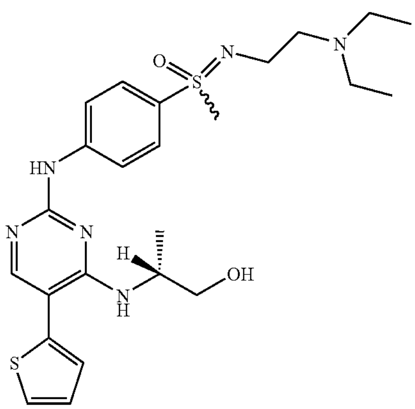 | (RS)-N-(2-di-ethylamino-ethyl)-S-(4-{[4-{[(R)-2-hydroxy-1-methylethyl]amino}-5-(2-thienyl)pyrimidine-2-yl]amino}phenyl)-S-methylsulfoximide |
| 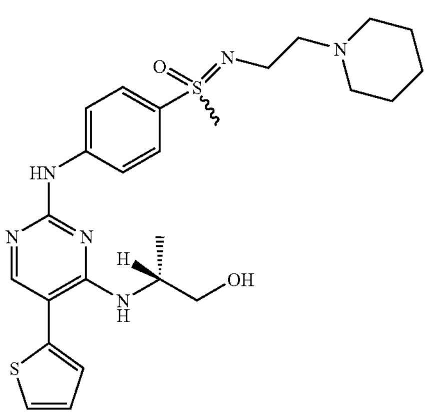 | (RS)-N-(2-piperidin-1-yl-ethyl)-S-(4-{[4-{[(R)-2-hydroxy-1-methylethyl]amino}-5-(2-thienyl)pyrimidine-2-yl]amino}phenyl)-S-methylsulfoximide |

-continued

| Structure | Name |
|---|---|
| 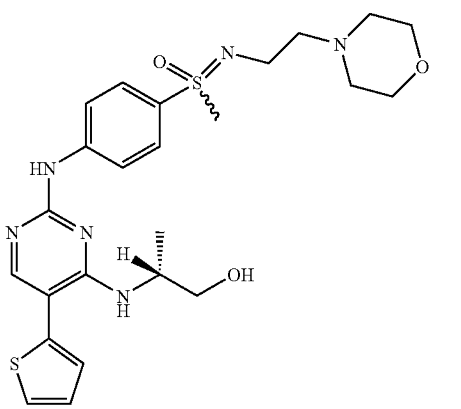 | (RS)-N-(2-morphlin-4-yl-ethyl)-S-(4-{[4-{[(R)-2-hydroxy-1-methylethyl]amino}-5-(2-thienyl)pyrimidine-2-yl]amino}phenyl)-S-methylsulfoximide |
| 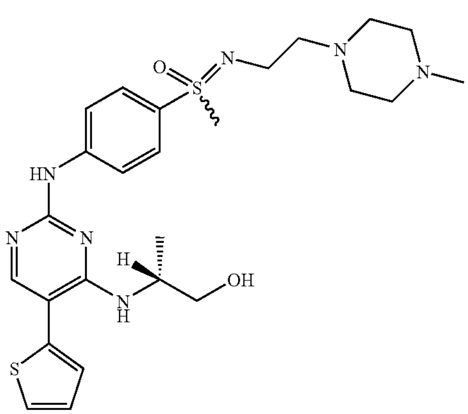 | (RS)-N-(2-[4-methyl-piperazine-1yl]-ethyl)-S-(4-{[4-{[(R)-2-hydroxy-1-methylethyl]amino}-5-(2-thienyl)pyrimidine-2-yl]amino}phenyl)-S-methylsulfoximide |
| 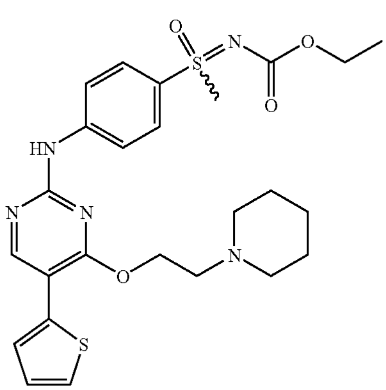 | (RS)-N-(Ethoxycarbonyl)-S-(4-{[4-{2-piperdin-1yl-ethoxy}-5-(2-thienyl)pyrimidin-2-yl]amino}phenyl)-S-methylsulfoximide |

3. Process Variation 2 (See Also Scheme 4)

General Procedures

Procedure 6—Preparation of 2,4-dichloro-pyrimidine-5-carbonyl chloride

A mixture of 30.0 g (192 mmol) 5-carboxyuracil, 44.8 ml (480 mmol) phosphorus oxychloride and 132.0 g (634 mmol) phosphorus pentachloride is stirred under argon for 6 hours at 115° C. The mixture is then stirred overnight at room temperature. The mixture is filtered and the filter cake then washed with toluene. The filtrate is first concentrated on the rotary evaporator. The residue obtained is then purified by vacuum distillation (80-90° C. at 0.15 mbar). 26.0 g (123 mmol; corresponding to 64% of theory) of the product is obtained.

Preparation of 2,4-dichloro-pyrimidine-5-tert-butylcarboxamide (VI)

A solution of 13.7 ml (129 mmol) tert.-butylamine and 17.9 ml (129 mmol) triethylamine in 163 ml THF is added dropwise under argon over a period of 70 minutes to a solution of 26.0 g (123 mmol) 2,4-dichloro-pyrimidine-5-carbonyl chloride at −7° C. to −3° C. The mixture is kept at this temperature for 4 hours and then slowly warmed to room temperature. The precipitate that forms is filtered off and the filtrate concentrated to dryness. 32.6 g of the product, which is used without further purification, is obtained.

$^1$H-NMR (DMSO): 8.79 (s, 1H), 8.29 (s, 1H), 1.32 (s, 9H).

Procedure 7—Introduction of Amines in the 4 Position of the Pyrimidine

A solution of compound VI (1.0 equiv.) in THF (17.6 equiv.) is treated with a solution of triethylamine (1.0 equiv.) and the amine component (1.0 equiv.) in THF (24.5 equiv.) with water-cooling. The mixture is stirred overnight at room temperature and then poured into dilute NaCl solution. It is extracted with ethyl acetate (3×). The combined organic phases are dried (Na$_2$SO$_4$), filtered and concentrated. The resulting crude product is purified by chromatography if necessary.

Procedure 8—Conversion to the 5-nitrile Derivative (VII)

The educt (1.0 equiv.) is stirred for 72 hours at 80° C. in thionyl chloride (85.0 equiv.). The mixture is rotary-evaporated to dryness. It is treated with toluene/water and again rotary-evaporated to dryness. The resulting crude product is purified by chromatography if necessary.

Procedure 9—Introduction of Anilines of the Type III in the 4 Position of the Pyrimidine VII Compound VII (1.2 equiv.) and the aniline III (1.0 equiv.) in acetonitrile (68 equiv.) are treated with a 4N solution of hydrogen chloride in dioxan (1.2 equiv.) and stirred for 24 hours at 60° C. After cooling, the mixture is poured into a mixture of NaHCO$_3$ solution and NaCl solution. It is extracted with ethyl acetate (3×) and the combined organic phases are dried over sodium sulphate. This is filtered and the solvent removed, and the resulting residue is chromatographically purified.

Procedure 10—Conversion to the 5-tetrazole Derivative

A suspension of compound VIII (1.0 equiv.), sodium azide (2.0 equiv.) and ammonium chloride (2.2 equiv.) in DMF (108 equiv.) is stirred for 24 hours at 120° C. Aqueous work-up and if necessary chromatographic purification yields the product IX.

Compounds which were Produced by Process Variation 2

Example 2.1

(RS)—S-(4-{[4-(cyclohexylamino)-5-(2H-tetrazol-5-yl)pyrimidine-2-yl]amino}-phenyl)-N-(ethoxycarbonyl)-S-methylsulfoximide

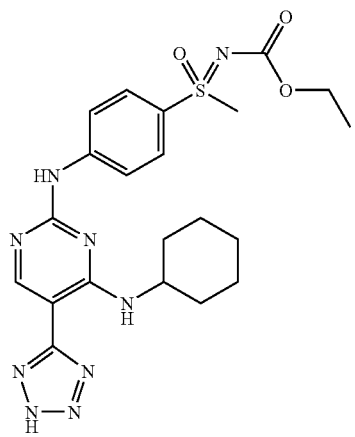

a) Production of 2-chloro-4-cyclohexylamino-pyrimidine-5-tert-butyl-carboxamide

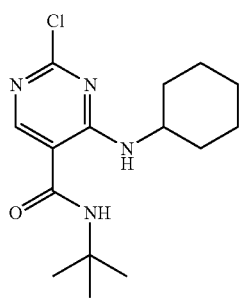

In the reaction of 2.0 g (8.1 mmol) 2,4-dichloro-pyrimidine-5-tert-butyl-carboxamide with 0.92 ml (8.1 mmol) cyclohexylamine according to procedure 7, 2.3 g (7.3 mmol; corresponding to 91% of theory) of the desired product is obtained.

$^1$H-NMR (DMSO): 8.88 (d, 1H), 8.45 (s, 1H), 7.93 (s, 1H), 3.89 (m, 1H), 1.85 (m, 2H), 1.60 (m, 3H), 1.30 (m, 14H).

b) Preparation of 2-chloro-4-cyclohexylamino-pyrimidine-5-carbonitrile

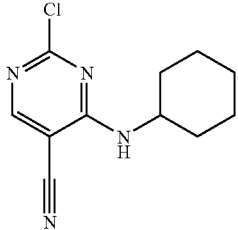

In the reaction of 1.75 g (5.6 mmol) 2-chloro-4-cyclohexylamino-pyrimidine-5-tert-butylcarboxamide in 35 ml (479 mmol) thionyl chloride according to procedure 8, 1.8 g of the desired crude product, which is used without further purification, is obtained.

$^1$H-NMR (DMSO): 8.49 (s, 1H), 8.30 (d, 1H), 3.88 (m, 1H), 1.72 (m, 4H), 1.56 (m, 1H), 1.29 (m, 4H), 1.05 (m, 1H).

c) (RS)-5-(4-{[5-cyano-4-(cyclohexylamino)pyrimidine-2-yl]amino}phenyl)-N-(ethoxycarbonyl)-S-methylsulfoximide

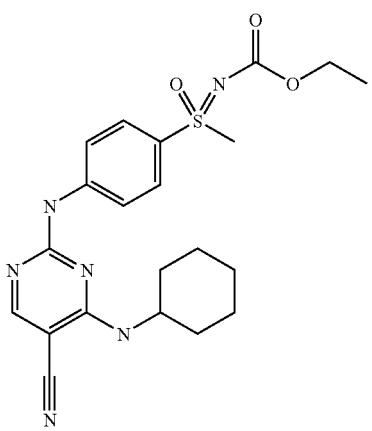

In the reaction of 1.33 g (5.6 mmol) 2-chloro-4-cyclohexylamin-pyrimidine-5-carbonitril and 1.14 g (4.7 mmol) (RS)—S-(4-aminophenyl)-N-(ethoxycarbonyl)-S-methylsulfoximide according to procedure 9, the desired product is obtained in 53% yield (1.09 g) after chromatographic purification (silica gel, DCM/EtOH (0-15% EtOH)).

$^1$H-NMR (DMSO): 10.25 (s, 1H), 8.37 (s, 1H), 7.99 (m, 2H), 7.79 (m, 2H), 7.65 (d, 1H), 3.95 (br, 1H), 3.86 (q, 2H), 3.39 (s, 3H), 1.87 (m, 2H), 1.75 (m, 2H), 1.63 (m, 1H), 1.38 (m, 5H), 1.05 (tr, 3H).

d) (RS)—S-(4-{[4-(cyclohexylamino)-5-(2H-tetrazol-5-yl)pyrimidine-2-yl]amino}phenyl)-N-(ethoxycarbonyl)-S-methylsulfoximide

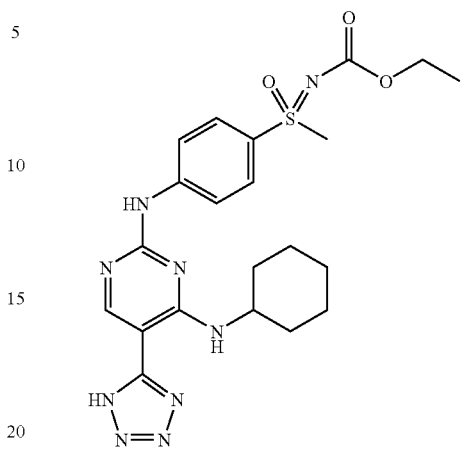

In accordance with procedure 10, 990 mg (2.24 mmol) (RS)—S-(4-{[5-cyano-4-(cyclohexylamino)pyrimidine-2-yl]amino}phenyl)-N-(ethoxycarbonyl)-S-methyl-sulfoximide, 291 mg (4.47 mmol) sodium azide and 263 mg (4.92 mmol) ammonium chloride in 19 ml DMF are stirred for 24 hours at 120° C. After cooling, the mixture is added dropwise to 200 ml. A gel-like precipitate is filtered off at the pump and then washed with water. After drying, the product is obtained in 53% yield (571 mg).

$^1$H-NMR (DMSO): 10.12 (s, 1H), 8.68 (s, 1H), 8.47 (d, 1H), 8.06 (m, 2H), 7.78 (m, 2H), 4.08 (br, 1H), 3.87 (q, 2H), 3.39 (s, 3H), 2.02 (m, 2H), 1.73 (m, 2H), 1.61 (m, 1H), 1.39 (m, 5H), 1.05 (tr, 3H).

MS: 486 (ES+).

4. Process Variation 3 (See Also Scheme 5)

Compounds which were Produced by Process Variation 3

Example 3.1

(RS)—S-(4-{[4-(cyclohexylamino)-5-(2-methyl-2H-tetrazol-5-yl)pyrimidine-2-yl]amino}phenyl)-N-(ethoxycarbonyl)-S-methylsulfoximide)

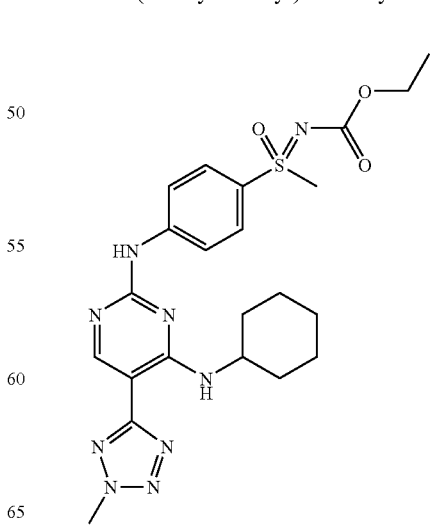

60 mg (0.12 mmol) (RS)—S-(4-{[4-(cyclohexylamino)-5-(2H-tetrazol-5-yl)-pyrimidine-2-yl]amino}phenyl)-N-(ethoxycarbonyl)-S-methylsulfoximide, 23 µl (0.37 mmol) methyl iodide and 22 mg (0.16 mmol) potassium carbonate are stirred overnight at 80° C. in 3 ml acetonitrile. After cooling, the mixture is poured into saturated NaCl solution and extracted with ethyl acetate. The combined organic phases are dried ($Na_2SO_4$), filtered and concentrated. The resulting crude product is purified by preparative TLC (DCM/EtOH 95:5). 11 mg (0.02 mmol; corresponding to 18% of theory) of the product 3.1 and 11 mg (0.02 mmol; corresponding to 18% of theory) of the product 3.2 are obtained.

$^1$H-NMR (DMSO): 10.11 (s, 1H), 8.72 (s, 1H), 8.06 (m, 2H), 7.76 (m, 3H), 4.39 (s, 3H), 4.04 (m, 1H), 3.88 (q, 2H), 3.40 (s, 3H), 2.03 (m, 2H), 1.73 (m, 2H), 1.62 (m, 2H), 1.35 (m, 4H), 1.04 (tr, 3H).

MS: 500 (ES+)

Example 3.2

(RS)—S-(4-{[4-(cyclohexylamino)-5-(1-methyl-1H-tetrazol-5-yl)pyrimidine-2-yl]amino}phenyl)-N-(ethoxycarbonyl)-S-methylsulfoximide

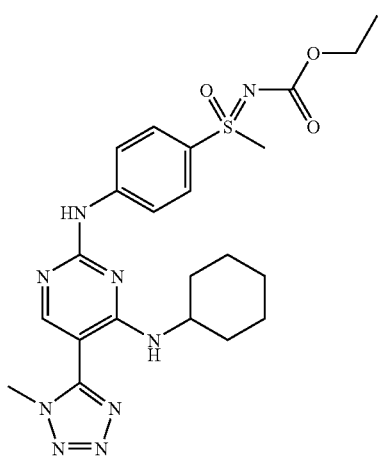

$^1$H-NMR (DMSO): 10.10 (s, 1H), 8.32 (s, 1H), 8.06 (m, 2H), 7.78 (m, 2H), 7.51 (d, 1H), 4.12 (s, 3H), 4.02 (m, 1H), 3.88 (q, 2H), 3.40 (s, 3H), 2.03 (m, 2H), 1.73 (m, 2H), 1.62 (m, 2H), 1.35 (m, 4H), 1.04 (tr, 3H).

MS: 500 (ES+).

Example 3.3

(RS)—S-(4-{[5-(2-benzyl-2H-tetrazol-5-yl)-4-(cyclohexylamino)pyrimidine-2-yl]amino}phenyl)-N-(ethoxycarbonyl)-S-methylsulfoximide

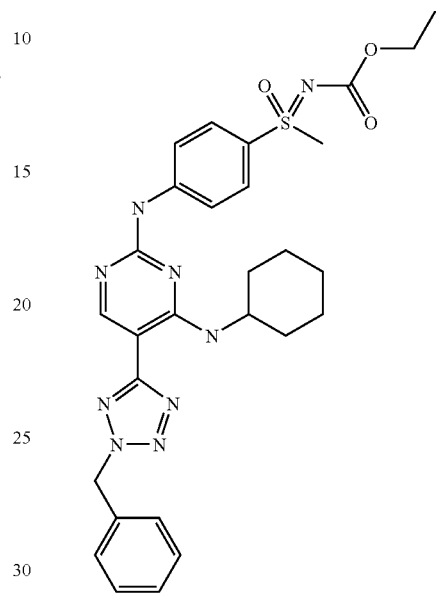

50 mg (0.1 mmol) (RS)—S-(4-{[4-(cyclohexylamino)-5-(2H-tetrazol-5-yl)-pyrimidine-2-yl]amino}phenyl)-N-(ethoxycarbonyl)-S-methylsulfoximide, 18 mg (0.1 mmol) benzyl bromide, 71 mg (0.51 mmol) potassium carbonate and 17 mg (0.1 mmol) potassium iodide in 1.6 ml 2-butanone are stirred for 6 hours at 80° C. After cooling, the mixture is absorbed onto silica gel and purified chromatographically (DCM/EtOH 95:5). 43 mg (0.07 mmol; corresponding to 73% of theory) of the product is obtained.

$^1$H-NMR (DMSO): 10.15 (s, 1H), 8.71 (s, 1H), 8.03 (m, 2H), 7.78 (m, 3H), 7.39 (m, 5H), 5.98 (s, 2H), 4.08 (m, 1H), 3.88 (q, 2H), 3.41 (s, 3H), 2.02 (m, 2H), 1.70 (m, 2H), 1.62 (m, 1H), 1.38 (m, 5H), 1.07 (tr, 3H).

MS: 576 (ESI)

5. Process Variation 4 (See Also Scheme 6)

General Procedures

Procedure 11a—Suzuki Coupling in the 5 Position of the Pyrimidine

Compounds XI (1.0 equiv.), the corresponding $R^1$-boronic acid derivative (1.4 equiv), toluene (97.0 equiv.), ethanol (178 equiv.), palladium tetrakistriphenylphosphine (0.06 equiv.) and sodium carbonate (1.93 equiv.) are filled into a microwave tube and reacted for 15 min at 120° C. For the work-up, the reaction mixture is poured into dilute sodium carbonate solution and extracted with ethyl acetate (3x). The combined organic phases are washed with brine, dried over sodium sulphate and concentrated under vacuum. After chromatographic purification, the desired product I is obtained.

Procedure 11b—Suzuki Coupling in the 5 Position of the Pyrimidine

The 5-halo-pyrimidine (1.0 equiv.), the corresponding boronic acid or pinacol ester (1.0 equiv.) and trifurylphosphine (4.0 equiv.) are mixed in DME (10 ml per mmol), then the mixture is deoxygenated by 10 min argon purge, then aq. Na$_2$CO$_3$ (1.6 eq, 1 M) is added, followed by palladium tetrakistriphenylphosphine (0.05 equiv.). This mixture is stirred at 80 OC under argon for 28 h. Then the mixture is poured in 5% aq. NaHCO$_3$, extracted twice with dichloromethane, the extracts are washed with water, dried and evaporated. After chromatographic purification, the desired product I is obtained.

Procedure 12—Stille Coupling in the 5 Position of the Pyrimidine

The 5-halo-pyrimidine (1.0 equiv.) and bis(triphenylphosphin)-palladium (II)-dichlorid (0.04 equiv.) are dissolved in DMF (4 ml per mmol) in a microwave vial and stirred for 15 min. Then the tributylstannyl compound (1.4 equiv.) is added and the reaction mixture is deoxygenated by nitrogen purge. This mixture is stirred at 80° C. for 16 h. For work-up, the reaction mixture is poured into NaHCO$_3$ solution and extracted with ethyl acetate. The organic phase is dried over sodium sulphate and concentrated under vacuum. After chromatographic purification, the desired product I is obtained.

Procedure 13—Buchwald-Hartwig Coupling in the 5 Position of the Pyrimidine

The halo-pyrimidine (1.0 equiv.) is treated with potassium carbonate (2.0 equiv.), copper(I) iodide (0.5 equiv.), L-proline (1.0 equiv.) and the NH-containing aromatic heterocycle (5.0 equiv.) and heated in DMSO (10 ml per mmol) in a microwave tube under nitrogen for 40 h at 75° C.

For the work-up, the reaction mixture is diluted with ethyl acetate, poured into sodium hydrogen carbonate solution and extracted 3× with ethyl acetate. The collected organic phases are washed with saturated sodium chloride solution, dried over sodium sulphate and concentrated under vacuum. After chromatographic purification, the desired product I is obtained.

Compounds which were Produced by Process Variation 4

Example 4.1

(RS)—N-(ethoxycarbonyl)-S-(4-{[4-{[(R)-2-(hydroxy-1-methylethyl]amino}-5-(4-benzonitrilo)pyrimindin-2-yl]amino}phenyl)-S-methylsulfoximide

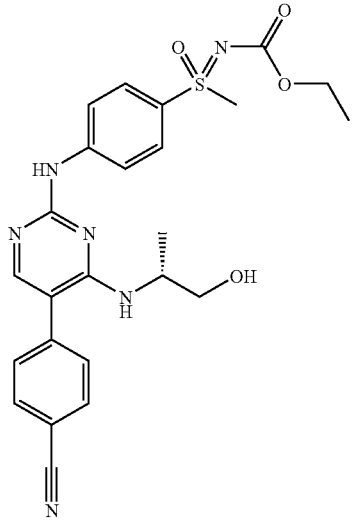

a) (RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide

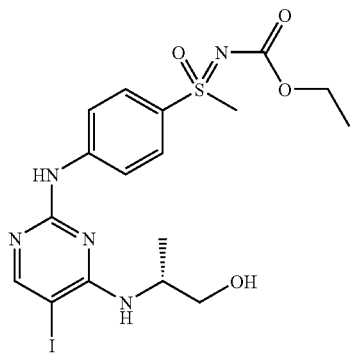

In the reaction of (R)-2-(2-chloro-5-iodopyrimidine-4-ylamino)propan-1-ol (772 mg, 2.4 mmol) with (RS)—S-(4-aminophenyl)-N-(ethoxycarbonyl)-S-methyl-sulfoximide (484 mg, 2 mmol) according to procedure 5b, the desired product is obtained in 31% yield (320 mg) after chromatographic purification.

$^1$H-NMR (400 MHz, DMSO-D6): δ 1.11 (t, 3H), 1.22 (2's, 3H), 3.42 (s, 3H), 3.53 (m, 2H), 2.30 (m, 2H), 4.24 (m, 1H), 4.97 (d, 1H), 6.08 (d, 1H), 7.81 (m, 2H), 8.00 (m, 2H), 8.24 (s, 1H), 9.84 (s, 1H).

b) (RS)—N-(ethoxycarbonyl)-S-(4-{[4-{[(R)-2-(hydroxy-1-methylethyl]amino}-5-(4 benzonitrilo)pyrimindin-2-yl]amino}phenyl)-S-methylsulfoximide

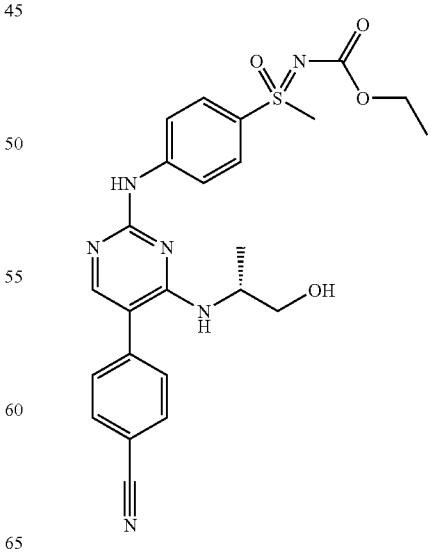

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (71 mg, 0.14 mmol), 4-cyanophenylboronic acid (28.5 mg, 0.19 mmol), toluene (1.4 ml), ethanol (1.4 ml), palladium tetrakistriphenylphosphine (9.48 mg, 0.01 mmol) and sodium carbonate (0.26 ml, 1 M) are filled into a microwave tube and reacted under nitrogen for 15 mins at 120° C. For the work-up, the reaction mixture is poured into dilute sodium carbonate solution and extracted with ethyl acetate (3×). The is combined organic phases are washed with brine, dried over sodium sulphate and concentrated under vacuum. After chromatographic purification, 57 mg (84%) of the desired product are obtained.

$^1$H-NMR (400 MHz, DMSO-D6): δ 1.07 (t, 3H), 1.12 (2×s, 3H), 3.38 (s, 3H), 3.44 (m, 2H), 3.89 (m, 2H), 4.29 (m, 1H), 4.75 (t, 1H), 6.29 (d, 1H), 7.61 (m, 2H), 7.78 (m, 2H), 7.89 (m, 3H), 8.03 (m, 2H), 9.85 (s, 1H).

Example 4.2

(RS)—N-(ethoxycarbonyl)-S-(4-{[4-{[(R)-2-(hydroxy-1-methylethyl]amino}-5-(2-trifluormethylphenyl)pyrimindin-2-yl]amino}phenyl)-S-methylsulfoximide

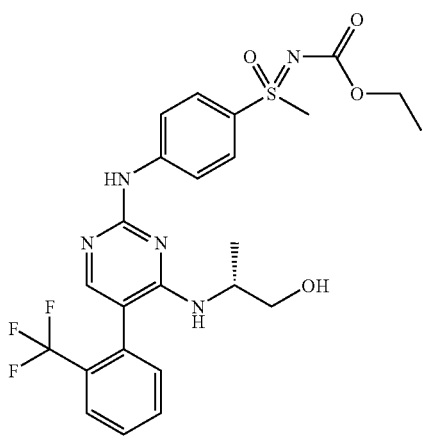

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (80 mg, 0.15 mmol), 2-tri-fluorophenylboronic acid (41.6 mg, 0.22 mmol), toluene (1.6 ml), ethanol (1.6 ml), palladium tetrakistriphenylphosphine (10.7 mg, 0.01 mmol) and sodium carbonate (0.3 ml, 1 M) are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 34 mg (41%) of the desired product are obtained.

$^1$H-NMR (DMSO): 9.76 (bs, 1H), 8.03 (d, 2H), 7.83 (d, 1H), 7.77 (d, 2H), 7.72 (t, 1H), 7.62 (m, 2H), 7.39 (t, 1H), 5.62 (dd, 1H), 4.66 (q, 1H), 4.25 (m, 2H), 3.88 (m, 2H), 3.38 (s, 3H), 3.28 (m, 2H), 1.06 (m, 6H).

MS: 538 (MH+).

Example 4.3

(RS)—N-(ethoxycarbonyl)-S-(4-{[4-{[(R)-2-(hydroxy-1-methylethyl]amino}-5-(2-methoxy-phenyl)pyrimindin-2-yl]amino}phenyl)-S-methylsulfoximide

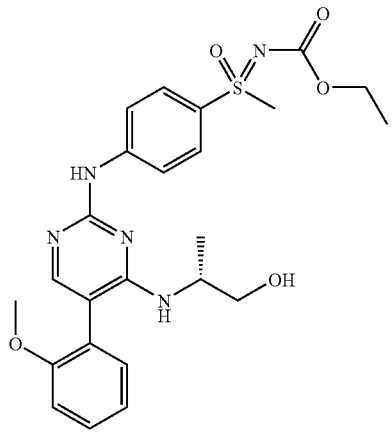

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (80 mg, 0.15 mmol), 2-methoxy-phenylboronic acid (33.3 mg, 0.22 mmol), toluene (1.6 ml), ethanol (1.6 ml), palladium tetrakistriphenylphosphine (10.7 mg, 0.01 mmol) and sodium carbonate (0.3 ml, 1 M) are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 55 mg (71%) of the desired product are obtained.

$^1$H-NMR (DMSO): 9.71 (s, 1H), 8.04 (d, 2H), 7.76 (d, 2H), 7.71 (s, 1H), 7.37 (m, 1H), 7.19 (dd, 1H), 7.09 (d, 1H), 7.01 (t, 1H), 5.54 (d, 1H), 4.75 (t, 1H), 4.25 (m, 1H), 3.89 (m, 2H), 3.74 (s, 3H), 3.38 (m, 5H), 1.13 (2s, 3H), 1.07 (t, 3H).

MS: 500 (MH+).

Example 4.4

(RS)—N-(ethoxycarbonyl)-S-(4-{[4-{[(R)-2-(hydroxy-1-methylethyl]amino}-5-(5-pyrazol)pyrimindin-2-yl]amino}phenyl)-S-methylsulfoximide

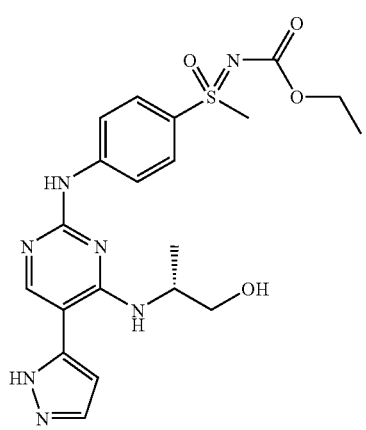

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (80 mg, 0.15 mmol), 1H-pyrazol-5-yl-boronic acid (24.5 mg, 0.22 mmol), toluene (1.6 ml), ethanol (1.6 ml), palladium tetrakistriphenylphosphine (10.7 mg, 0.01 mmol) and sodium carbonate (0.3 ml, 1 M). are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 30 mg (42%) of the desired product are obtained.

¹H-NMR (DMSO): 12.99 (s, 1H), 9.76 (s, 1H), 8.78 (d, 1H), 8.47 (s, 1H), 8.05 (d, 2H), 7.78 (m, 3H), 6.79 (m, 1H), 4.89 (t, 1H), 4.31 (m, 1H), 3.89 (m, 2H), 3.52 (m, 2H), 3.38 (s, 3H), 1.24 (2s, 3H), 1.07 (t, 3H).

MS: 460 (MH+).

Example 4.5

(RS)—N-(ethoxycarbonyl)-S-(4-{[4-{[(R)-2-(hydroxy-1-methylethyl]amino}-5-(2-methyl-phenyl)pyrimindin-2-yl]amino}phenyl)-S-methylsulfoximide

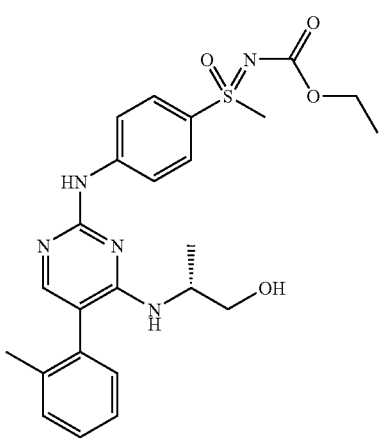

(RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide (80 mg, 0.15 mmol), 2-methylphenyl-boronic acid (29.8 mg, 0.22 mmol), toluene (1.6 ml), ethanol (1.6 ml), palladium tetrakistriphenylphosphine (10.7 mg, 0.01 mmol) and sodium carbonate (0.3 ml, 1 M). are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 19 mg (25%) of the desired product are obtained.

¹H-NMR (DMSO): 10.36 (bs, 1H), 7.96 (d, 2H), 7.88 (d, 2H), 7.72 (m, 1H), 7.31 (m, 3H), 7.19 (t, 1H), 4.30 (m, 1H), 3.89 (m, 2H), 3.42 (m, 5H), 2.14 (d, 3H), 1.07 (m, 6H).

MS: 484 (MH+).

Example 4.6

(RS)—N-(ethoxycarbonyl)-S-(4-{[4-{[(R)-2-(hydroxy-1-methylethyl]amino}-5-(4-methyl-2-thienyl)pyrimindin-2-yl]amino}phenyl)-S-methylsulfoximide

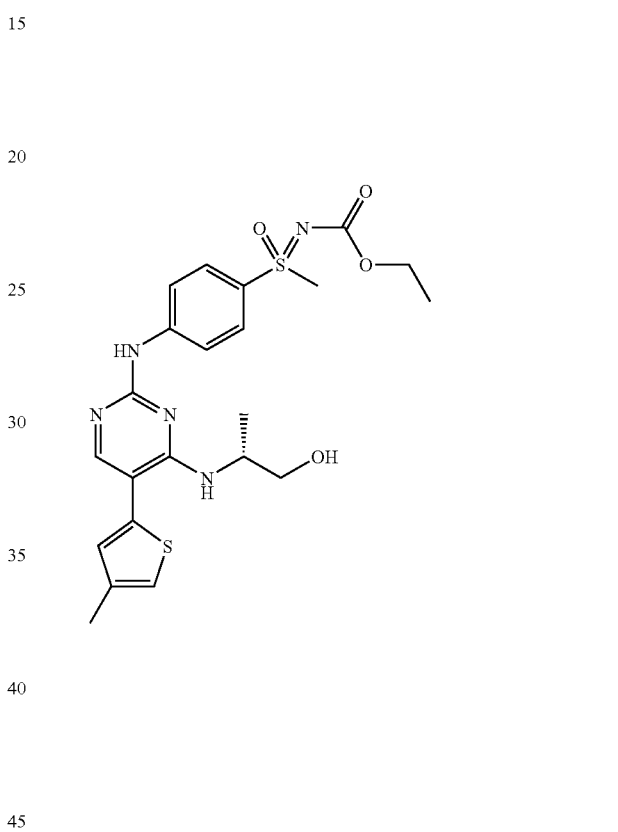

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (47 mg, 0.09 mmol), 4-methyl-2-thienyl-boronic acid (18.3 mg, 0.13 mmol), toluene (1 ml), ethanol (1 ml), palladium tetrakistriphenylphosphine (6.3 mg, 0.005 mmol) and sodium carbonate (0.2 ml, 1 M). are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 7 mg (16%) of the desired product are obtained.

¹H-NMR (DMSO): 10.07 (bs, 1H), 7.98 (d, 2H), 7.91 (s, 1H), 7.82 (d, 2H), 7.19 (s, 1H), 7.93 (s, 1H), 6.64 (bs, 1H), 4.26 (m, 1H), 3.89 (m, 2H), 3.49 (m, 2H), 3.40 (s, 3H), 2.23 (s, 3H), 1.17 (2s, 3H), 1.07 (t, 3H).

MS: 490 (MH+).

Example 4.7

(RS)—N-(ethoxycarbonyl)-S-(4-{[4-{[(R)-2-(hydroxy-1-methylethyl]amino}-5-(1-methyl-5-imidazolyl)pyrimindin-2-yl]amino}phenyl)-S-methylsulfoximide

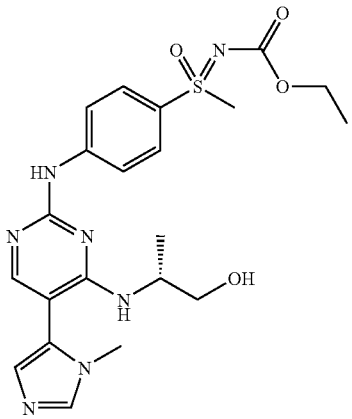

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (104 mg, 0.2 mmol) is treated with bis(triphenylphosphine)-palladium(II) dichloride (5 mg, 0.007 mmol) and stirred for 15 mins in 0.8 ml DMF in a microwave tube. Then the reaction solution is treated with 1-methyl-5-tributyl-stannanyl-1H-imidazole (107 mg, 0.29 mmol), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 74 mg (78%) of the desired product is obtained.

$^1$H-NMR (DMSO): 9.81 (s, 1H), 8.02 (d, 2H), 7.78 (m, 4H), 6.91 (s, 1H), 6.11 (d, 1H), 4.74 (t, 1H), 4.27 (m, 1H), 3.88 (m, 2H), 3.40 (m, 8H), 1.10 (m, 6H).

MS: 474 (MH+).

Example 4.8

(RS)—N-(ethoxycarbonyl)-S-(4-{[4-{[(R)-2-(hydroxy-1-methylethyl]amino}-5-(3-methoxy-6-fluorphenyl)pyrimindin-2-yl]amino}phenyl)-S-methylsulfoximide

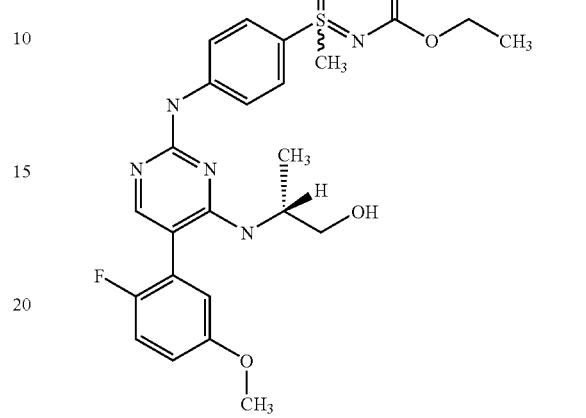

(RS)—N-(ethoxycarbonyl)-S-(4-{[4-{[(R)-2-(hydroxy-1-methylethyl]amino}5-iodo-pyrimindin-2-yl]amino}phenyl)-S-methylsulfoximide (80 mg, 0.15 mmol) and 2-fluoro-5-methoxyphenylboronic acid (34 mg, 0.2 mmol) in DMF (0.5 ml) are placed in a pressure vessel. Then 0.15 g caesium carbonate and 1,3-bis(2,6-diisopropylphenyl) imidazolium chloride (10 mg, CAS139143-09-2) in 0.25 ml water are added. After this, bis(dibenzylidenacetone)palladium (6 mg, CAS32005-36-0) dissolved in 2 ml THF is added, and the mixture heated to 80° C. for 3 hrs. Then 1 ml water and 3 ml ethyl acetate are added and the ethyl acetate phase is decanted off. After concentration of the ethyl acetate phase, the crude product is purified by preparative HPLC, see Table 1 for analytical data 1.

Analogously to the synthesis of Example 4.8, the compounds from Table 1 (Example 4.9-4.25) were prepared.

TABLE 1

| Ex. No. | Boronic acid used | Structure | | Calc. Mol. Wt. | Found Mass (ESI)* | Found Retention time* |
|---|---|---|---|---|---|---|
| 4.8 | 2-fluoro-5-methoxy-phenylboronic acid | 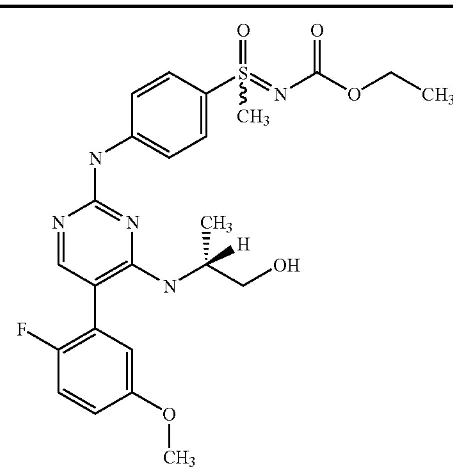 | Chiral | 517.58 | 518.1 | 6.40 |

TABLE 1-continued

| Ex. No. | Boronic acid used | Structure | | Calc. Mol. Wt. | Found Mass (ESI)* | Found Retention time* |
|---|---|---|---|---|---|---|
| 4.9 | 3-fluoro-4-methoxy-phenylboronic acid | 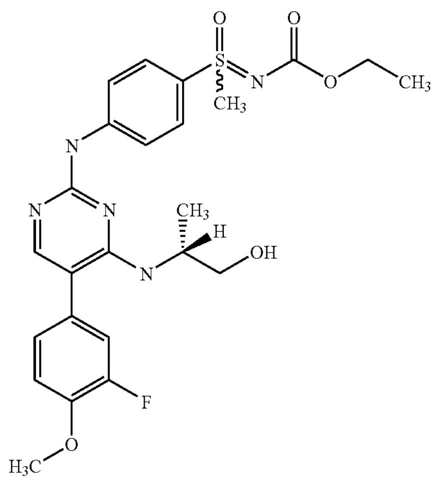 | Chiral | 517.58 | 518.0 | 6.30 |
| 4.10 | 5-chloro-2-thiophenboronic acid | 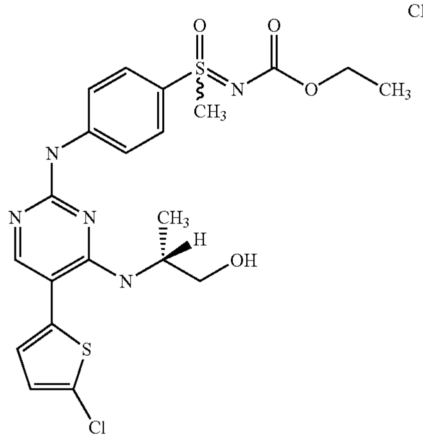 | Chiral | 510.04 | 509.9 | 6.63 |
| 4.11 | 4-pyridylboronic acid | 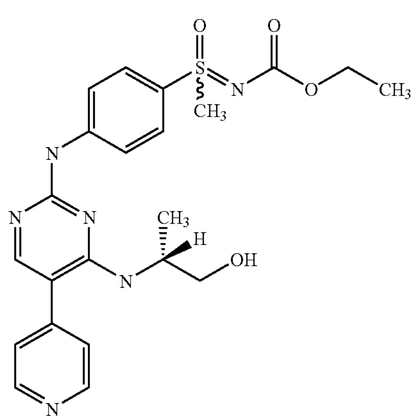 | Chiral | 470.55 | 471.0 | 4.75 |

TABLE 1-continued

| Ex. No. | Boronic acid used | Structure | | Calc. Mol. Wt. | Found Mass (ESI)* | Found Retention time* |
|---|---|---|---|---|---|---|
| 4.12 | 3-pyridiylboronic acid | 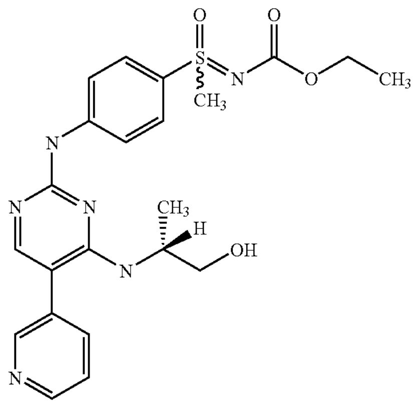 | Chiral | 470.55 | 471.0 | 4.95 |
| 4.13 | 3,4-methylene-dioxyphenyl-boronic acid | 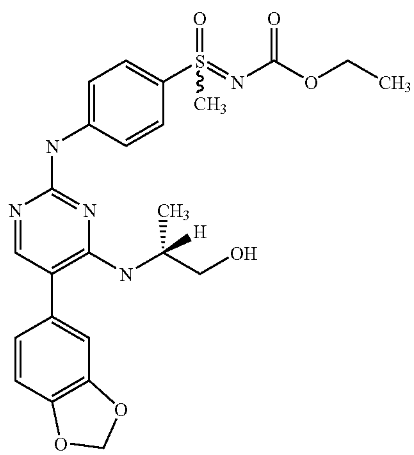 | Chiral | 513.57 | 514.0 | 6.16 |
| 4.14 | pyrimidine-5-boronic acid | 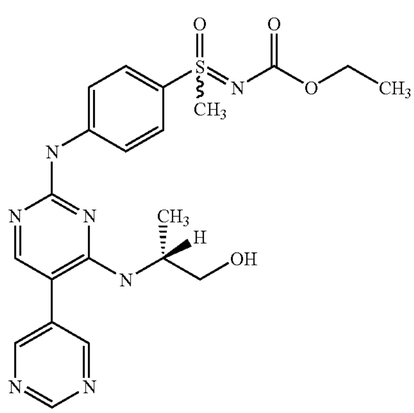 | Chiral | 471.54 | 472.0 | 5.11 |

TABLE 1-continued

| Ex. No. | Boronic acid used | Structure | | Calc. Mol. Wt. | Found Mass (ESI)* | Found Retention time* |
|---|---|---|---|---|---|---|
| 4.15 | 5-methyl-thiophen-3-boronic acid | 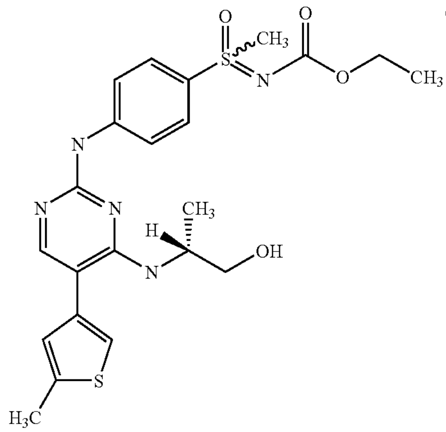 | Chiral | 489.62 | 490 | 6.45 |
| 4.16 | 3-methylthiophen-2-boronic acid | 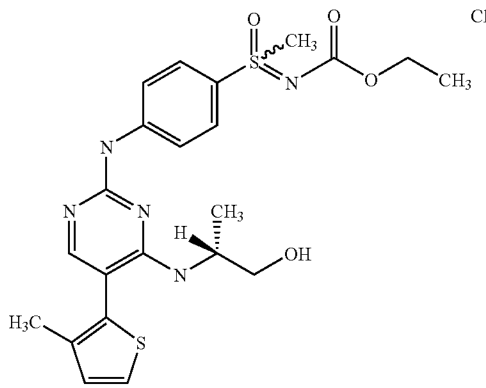 | Chiral | 489.62 | 490.6 | 6.50 |
| 4.17 | 4-(3-Butylureido)phenyl-boronsäure pinacol ester CAS 850567-59-8 | 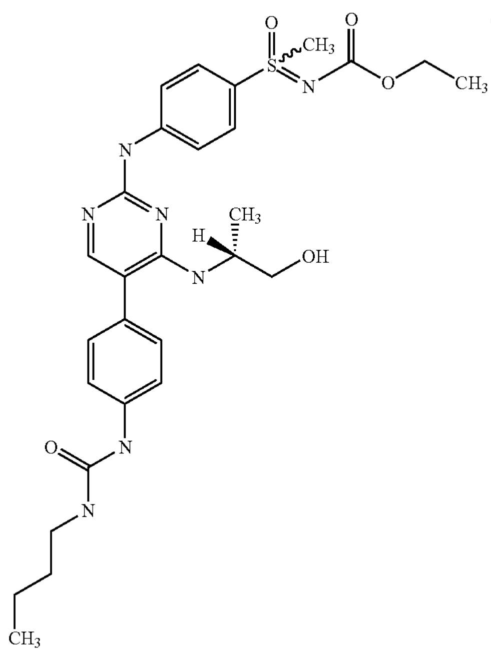 | Chiral | 583.71 | 584.7 | 6.76 |

TABLE 1-continued

| Ex. No. | Boronic acid used | Structure | Calc. Mol. Wt. | Found Mass (ESI)* | Found Retention time* |
|---|---|---|---|---|---|
| 4.18 | 2,4-dimethyl-5-(4,4,5,5-tetramethyl-1,3,2-dioxoborolane-2-yl)-1,3-thiazole | Chiral | 504.63 | 505.6 | 7.75 |
| 4.19 | [3-(2-methoxycarbonylethyl)-phenyl]boronic acid | Chiral | 555.65 | 556.7 | 6.72 |
| 4.20 | phenylboronic acid | Chiral | 469.56 | 470.7 | 8.35 |

TABLE 1-continued

| Ex. No. | Boronic acid used | Structure | | Calc. Mol. Wt. | Found Mass (ESI)* | Found Retention time* |
|---|---|---|---|---|---|---|
| 4.21 | 3-(trifluoro-methyl)-benzene-boronic acid | 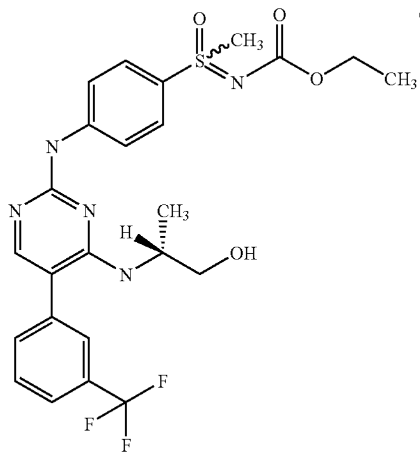 | Chiral | 537.56 | 538.7 | 7.03 |
| 4.22 | 3-acetamido-benzeneboronic acid | 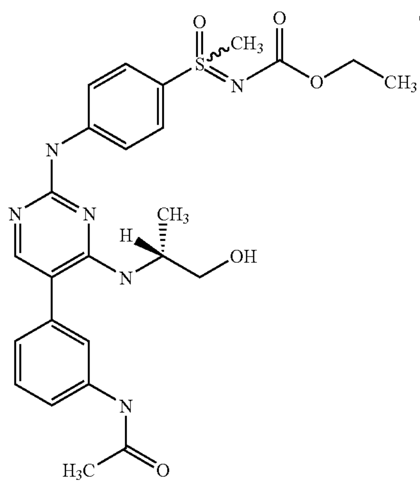 | Chiral | 526.62 | 527.7 | 5.93 |
| 4.23 | 1-methyl-5-(4,4,5,5-tetra-methyl-1,3,2-dioxaborolane-2-yl)-1-H-pyrazole | 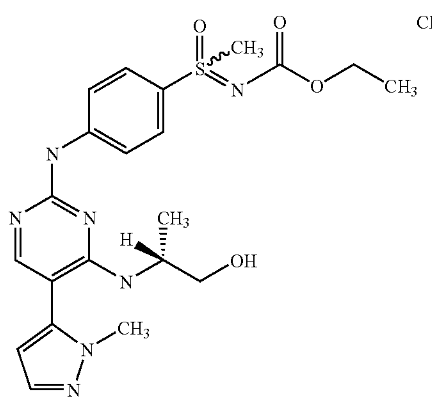 | Chiral | 473.56 | 474.7 | 5.58 |

TABLE 1-continued
| Ex. No. | Boronic acid used | Structure | | Calc. Mol. Wt. | Found Mass (ESI)* | Found Retention time* |
|---|---|---|---|---|---|---|
| 4.24 | 3-acetylboronic acid | 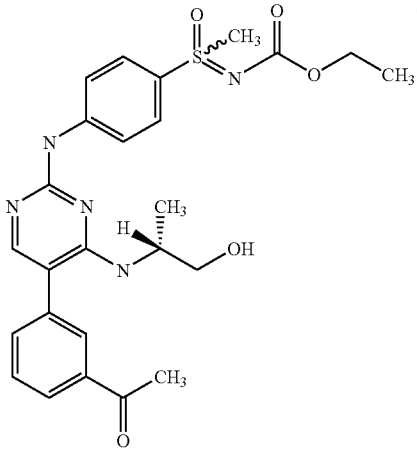 | Chiral | 511.60 | 512.7 | 8.28 |
| 4.25 | [3-(pyrrolidin-1-yl)phenylboronic acid | 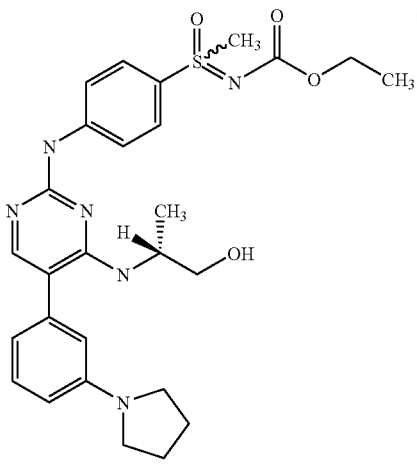 | Chiral | 538.67 | 539.8 | 7.00 |
*taken from the analytical HPLC diagrams.

Analytical conditions: HPLC Pump 2525 Binary Gradient Module (Waters), Detector Micromass ZQ (Waters), UV Lamp MUX UV 2488 Detector (Waters), Column LiChroCart Purospher 125×4.5 mm RP 18e 5 μm, Gradient used (acetonitrile and water each with 0.1% added trifluoroacetic acid): Acetonitrile 5%, water 95% after acetonitrile 95%, water 5% within 15 mins, Flow rate 1 ml/min Example 4.26

(RS)—N-(ethoxycarbonyl)-S-(4-{[4-{[(R)-2-(hydroxy-1-methylethyl]amino}-5-(5-cyano-2-thienyl)pyrimindin-2-yl]amino}phenyl)-S-methylsulfoximide

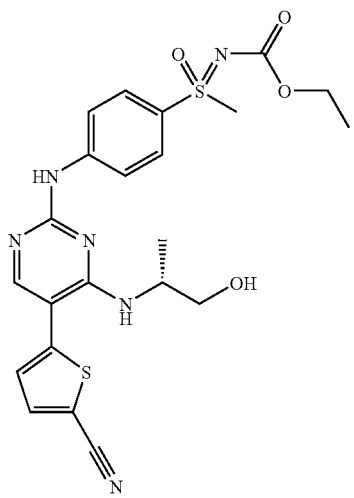

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (104 mg, 0.2 mmol), 5-cyano-2-thienyl-boronic acid (43 mg, 0.28 mmol), toluene (2.1 ml), ethanol (2.1 ml), palladium tetrakistriphenylphosphine (13.9 mg, 0.012 mmol) and sodium carbonate (0.4 ml, 1 M). are filled into a microwave tube and reacted under nitrogen for 15 mins at 120° C. For the work-up, the reaction mixture is poured into dilute sodium carbonate solution and extracted with ethyl acetate (3×). The combined organic phases are washed with brine, dried over sodium sulphate and concentrated under vacuum. After chromatographic purification, 28 mg (28%) of the desired product are obtained.

$^1$H-NMR (300 MHz, DMSO): δ 9.98 (s, 1H), 8.00 (m, 4H), 7.79 (d, 2H), 7.34 (d, 1H), 6.53 (d, 1H), 4.80 (bs, 1H), 4.27 (m, 1H), 3.88 (m, 2H), 3.45 (m, 2H), 3.38 (s, 3H), 1.14 (m, 3H), 1.07 (t, 3H).

MS: 501 (MH+).

Example 4.27

(RS)—N-(ethoxycarbonyl)-S-(4-{[4-{[(R)-2-(hydroxy-1-methylethyl]amino}-5-(2-oxazolyl)pyrimindin-2-yl]amino}phenyl)-S-methylsulfoximide

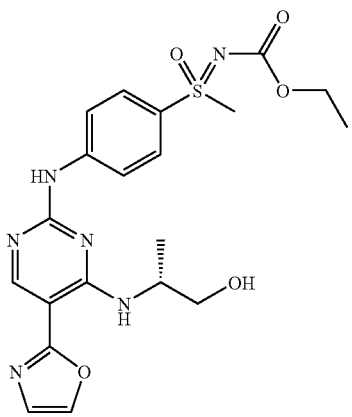

(RS)—N-(ethoxycarbonyl)-S-(4-{[4-{[(R)-2-(hydroxy-1-methylethyl]amino}-5-iodo-pyrimindin-2-yl] amino}phenyl)-S-methylsulfoximide (130 mg, 0.25 mmol) is treated with bis(triphenylphosphine)-palladium(II) dichloride (6.3 mg, 0.009 mmol) and stirred for 15 mins in 1 ml DMF in a microwave tube. Then the reaction solution is treated with 2-(tri-N-butylstannyl)oxazole (129 mg, 0.36 mmol), flushed with nitrogen, sealed and reacted at 80° C. 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 14 mg (12%) of the desired product is obtained

| HPLC/MS: | Column: | XBrigde C18 3.5μ 100 × 4.6 mm |
|---|---|---|
| | Solvent: | A: H2O B: acetonitrile |
| | Buffer: | A/0, 1% TFA |
| | Gradient: | 95% A + 5% B_5 –> 95% B(7') |
| | Flow: | 1.0 mL/min |
| | Solution: | 1 mg/mL ACN |
| | Injection Volume: | 20 μl |
| | Detection: | DAD (200-500 nm) TAC; MS-ESI + (120-1000 m/z) TIC |
| | Temperature: | RT |
| | Retention Time: | 4.32 |
| | Mass found: | 460.2 |

Example 4.28

(RS)—N-(ethoxycarbonyl)-S-(4-{[4-{[(R)-2-(hydroxy-1-methylethyl]amino}-5-(2-thiazolyl)pyrimindin-2-yl]amino}phenyl)-S-methylsulfoximide

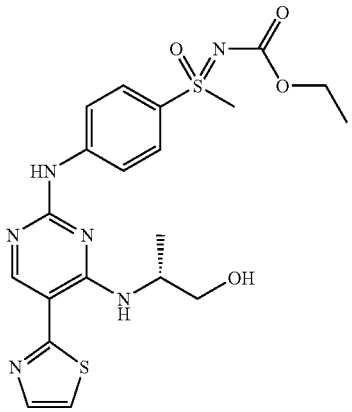

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (130 mg, 0.25 mmol) is treated with bis(triphenylphosphine)-palladium(II) dichloride (6.3 mg, 0.009 mmol) and stirred for 15 mins in 1 ml DMF in a microwave tube. Then the reaction solution is treated with 2-(tri-N-butylstannyl)thiazole (135 mg, 0.36 mmol), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification and HPLC, 2.6 and 1.8 mg (4%) of the desired product separated into diastereomers are obtained.

| HPLC/MS: | Column: | XBrigde C18 3.5µ 100 × 4.6 mm |
|---|---|---|
| | Solvent: | A: H2O B: acetonitrile |
| | Buffer: | A/0.1% TFA |
| | Gradient: | 95% A + 5% B_5−> 95% B(7') |
| | Flow: | 1.0 mL/min |
| | Solution: | 1 mg/mL ACN |
| | Injection Volume: | 20 µl |
| | Detection: | DAD (200-500 nm) TAC; MS-ESI + (120-1000 m/z) TIC |
| | Temperature: | RT |
| | Retention Time: | 3.87, 4.50 |
| | Mass found: | 476.1, 476.1 |

Example 4.29

(RS)—N-(ethoxycarbonyl)-S-(4-{[4-{[(R)-2-(hydroxy-1-methylethyl]amino}-5-(1-methyl-2-pyrolyl)pyrimindin-2-yl]amino}phenyl)-S-methylsulfoximide

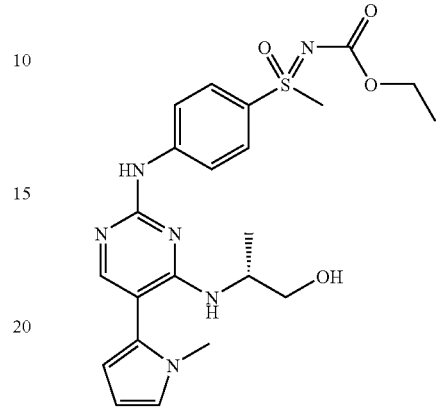

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (104 mg, 0.2 mmol) is treated with bis(triphenylphosphine)-palladium(II) dichloride (5 mg, 0.007 mmol) and stirred for 15 mins in 1 ml DMF in a microwave tube. Then the reaction solution is treated with 1-methyl-2-(tributylstannyl)-1H-pyrrole (107 mg, 0.29 mmol), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 38 mg (40%) of the desired product is obtained.

$^1$H-NMR (300 MHz, DMSO): δ 9.76 (s, 1H), 8.03 (d, 2H), 7.77 (m, 3H), 6.86 (m, 1H), 6.06 (m, 2H), 5.78 (d, 1H), 4.80 (t, 1H), 4.23 (m, 1H), 3.89 (m, 2H), 3.42 (m, 5H), 3.38 (s, 3H), 1.13 (2×s, 3H), 1.07 (t, 3H).

MS: 473 (MH+).

Example 4.30

(RS)—N-(ethoxycarbonyl)-S-(4-{[4-{[(R)-2-(hydroxy-1-methylethyl]amino}-5-(1-pyrolyl)pyrimindin-2-yl]amino}phenyl)-S-methylsulfoximide

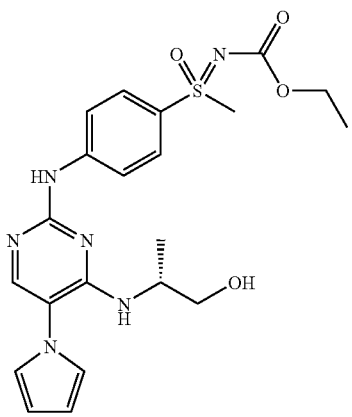

(RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide (156 mg, 0.3 mmol) are treated with potassium carbonate (83 mg, 0.6 mmol), copper(I) iodide (29 mg, 0.15 mmol), L-proline (35 mg, 0.3 mmol) and pyrrole (101 mg, 1.5 mmol), and heated in 3 ml DMSO in a microwave tube under nitrogen for 40 hrs at 75° C. For the work-up, the reaction mixture is diluted with ethyl acetate, poured into sodium hydrogen carbonate solution and extracted 3× with ethyl acetate. The collected organic phases are washed with saturated sodium chloride solution, dried over sodium sulphate and concentrated under vacuum. After HPLC purification, 15 mg (11%) of the desired product are obtained.

$^1$H-NMR (DMSO): 9.98 (bs, 1H), 8.00 (d, 2H), 7.89 (s, 1H), 7.80 (d, 2H), 6.87 (m, 2H), 6.24 (m, 2H), 5.96 (bs, 1H), 4.21 (m, 1H), 3.89 (m, 2H), 3.44 (m, 2H), 3.39 (s, 3H), 1.12 (2s, 3H), 1.07 (t, 3H).

MS: 459 (MH+).

Example 4.31

(RS)—N-(ethoxycarbonyl)-S-(4-{[4-{[(R)-2-(hydroxy-1-methylethyl]amino}-5-(2-pyrazinyl)pyrimindin-2-yl]amino}phenyl)-S-methylsulfoximide

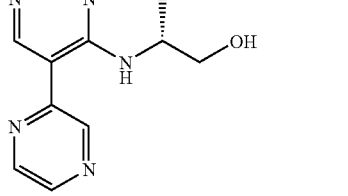

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (104 mg, 0.2 mmol) is treated with bis(triphenylphosphine)-palladium(II) dichloride (5 mg, 0.007 mmol) and stirred for 15 mins in 1 ml DMF in a microwave tube. Then the reaction solution is treated with 2-tributylstannyl-pyrazine (107 mg, 0.29 mmol), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 20 mg (21%) of the desired product is obtained.

$^1$H-NMR (DMSO): 10.22 (s, 1H), 9.74 (bd, 1H), 9.35 (m, 1H), 8.91 (s, 1H), 8.62 (m, 1H), 8.54 (d, 1H), 8.09 (d, 2H), 7.88 (d, 2H), 4.36 (m, 1H), 3.94 (m, 2H), 3.59 (m, 2H), 3.24 (s, 3H), 1.30 (2×s, 3H), 1.12 (t, 3H).

MS: 472.1 (MH+).

Example 4.32

(RS)—N-(ethoxycarbonyl)-S-(4-{[4-{[(R)-2-(hydroxy-1-methylethyl]amino}-5-(1-imidazolyl)pyrimindin-2-yl]amino}phenyl)-S-methylsulfoximide

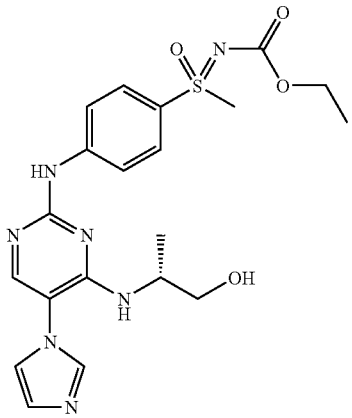

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (156 mg, 0.3 mmol) are treated with potassium carbonate (104 mg, 0.75 mmol), copper(I) iodide (6 mg, 0.03 mmol), L-proline (7 mg, 0.06 mmol) and imidazole (24 mg, 0.36 mmol), and heated in 0.6 ml DMSO in a microwave tube under nitrogen for 40 hrs at 75° C. For the work-up, the reaction mixture is diluted with ethyl acetate, poured into sodium hydrogen carbonate solution and extracted 3× with ethyl acetate. The collected organic phases are washed with saturated sodium chloride solution, dried over sodium sulphate and concentrated under vacuum. After HPLC purification, 48 mg (35%) of the desired product is obtained.

| HPLC/MS: | | |
|---|---|---|
| | Column: | XBrigde C18 3.5µ 100 × 4.6 mm |
| | Solvent: | A: H2O B: acetonitrile |
| | Buffer: | A/0.2% NH3 |
| | Gradient: | 95% A + 5% B_5 –> 95% B(7') |
| | Flow: | 1.0 mL/min |
| | Solution: | 1 mg/mL ACN |
| | Injection Volume: | 20 µl |
| | Detection: | DAD (200-500 nm) TAC; MS-ESI + (120-1000 m/z) TIC |
| | Temperature: | RT |
| | Retention Time: | 4.29 |
| | Mass found: | 459 |

Example 4.33

(RS)—N-(ethoxycarbonyl)-S-(4-{[4-{[(R)-2-(hydroxy-1-methylethyl]amino}-5-(4-thiazolyl)pyrimidin-2-yl]amino}phenyl)-S-methylsulfoximide

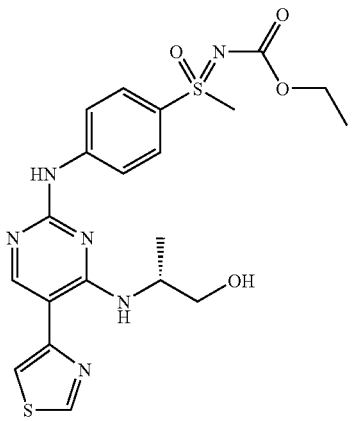

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (105 mg, 0.2 mmol) is treated with bis(triphenylphosphine)-palladium(II) dichloride (5 mg, 0.007 mmol) and stirred for 15 min in 1 ml DMF in a microwave tube. Then the reaction solution is treated with 4-(tri-N-butylstannyl)thiazole (109 mg, 0.29 mmol, prepared according to Synthesis 1986, 757), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 82 mg (85%) of the desired product is obtained.

$^1$H-NMR (DMSO): 9.85 (s, 1H), 9.28 (d, 1H), 8.69 (bs, 1H), 8.54 (s, 1H), 8.10 (d, 1H), 8.05 (d, 2H), 7.78 (d, 2H), 4.89 (m, 1H), 4.28 (m, 1H), 3.89 (m, 2H), 3.52 (m, 2H), 3.38 (s, 3H), 1.23 (2×s, 3H), 1.07 (t, 3H).

MS: 477 (MH+).

Example 4.34

(RS)—N-(ethoxycarbonyl)-S-(4-{[4-{[(R)-2-(hydroxy-1-methylethyl]amino}-5-(5-thiazolyl)pyrimidin-2-yl]amino}phenyl)-S-methylsulfoximide

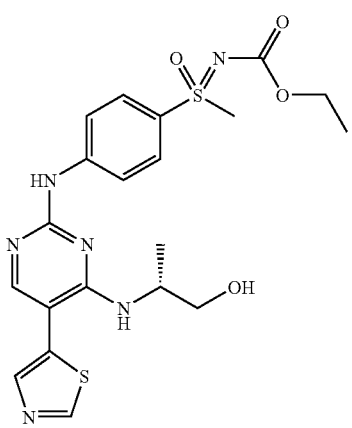

(RS)—N-(ethoxycarbonyl)-S-(4-{[4-{[(R)-2-(hydroxy-1-methylethyl]amino}-5-iodo-pyrimindin-2-yl]amino}phenyl)-S-methylsulfoximide (151 mg, 0.29 mmol) is treated with bis(triphenylphosphine)-palladium(II) dichloride (7 mg, 0.01 mmol) and stirred for 15 mins in 1 ml DMF in a microwave tube. Then the reaction solution is treated with 5-(tri-N-butylstannyl)thiazole (156 mg, 0.42 mmol, prepared according to Synthesis 1986, 757), flushed with nitrogen, sealed and reacted at 80° C. for 16 hrs.

For the work-up, the reaction mixture is diluted with ethyl acetate, poured into sodium hydrogen carbonate solution and extracted. The organic phase is dried over sodium sulphate and concentrated under vacuum. After chromatographic purification, 118 mg (85%) of the desired product is obtained.

$^1$H-NMR (DMSO): 9.89 (s, 1H), 9.15 (s, 1H), 8.02 (d, 2H), 7.96 (s, 2H), 7.78 (d, 2H), 6.30 (d, 1H), 4.80 (t, 1H), 4.26 (m, 1H), 3.89 (m, 2H), 3.46 (m, 2H), 3.38 (s, 3H), 1.15 (2×s, 3H), 1.07 (t, 3H).

MS: 477 (MH+).

Example 4.35

(RS)—N-(ethoxycarbonyl)-S-(4-{[4-{[tetrahydropyran-4-yl]amino}-5-(2-thienyl)pyrimindin-2-yl]amino}phenyl)-S-methylsulfoximide

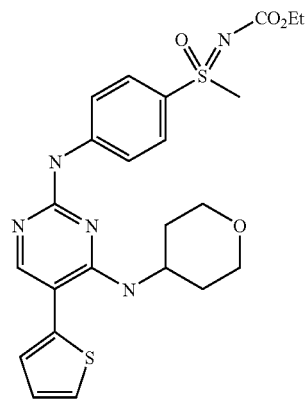

a) (RS)—N-(ethoxycarbonyl)-S-(4-{[4-{[tetrahydropyran-4-yl]amino}-5-bromopyrimindin-2-yl]amino}phenyl)-S-methylsulfoximide

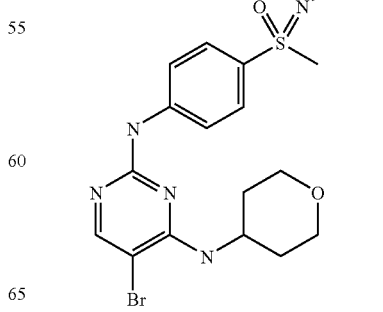

In the reaction of (5-bromo-2-chloro-pyrimidine-4-yl)-(tetrahydro-pyran-4-yl)-amine (160 mg, 0.55 mmol) and (RS)—S-(4-aminophenyl)-N-(ethoxycarbonyl)-S-methyl-sulfoximide (110 mg, 0.46 mmol) according to procedure 5b, the desired product is obtained in 26% yield (70 mg) after chromatographic purification (silica gel, ethyl acetate/hexane with ethyl acetate: 0-100%, then methylene chloride).

$^1$HNMR (400 MHz, DMSO-D6): δ 1.06 (t, 3H), 1.60-1.80 (m, 4H), 3.38-3.45 (m, 5H), 3.85-3.91 (m, 4H), 4.10-4.20 (m, 1H), 6.81 (d, 1H), 7.77 (d, 2H), 7.94 (d, 2H), 8.09 (s, 1H), 9.83 (s, 1H).

b) (RS)—N-(ethoxycarbonyl)-S-(4-{[4-{[tetrahydro-pyran-4-yl]amino}-5-(2-thienyl)pyrimidin-2-yl]amino}phenyl)-S-methylsulfoximide

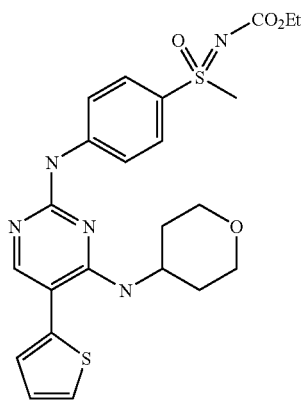

Preparation by Procedure 11a.

| HPLC/MS: | Column: | ODSII 1.5μ 33 × 4.6 mm |
|---|---|---|
| | Solvent: | A: H$_2$O B: acetonitrile |
| | Buffer: | 0.01% HCO$_2$H each |
| | Gradient: | 90% A + 10% B__10 -> 90% B(4.5') |
| | Flow: | 0.8 mL/min |
| | Solution: | 1 mg/mL MeOH |
| | Injection Volume: | 2 μl |
| | Detection: | DAD (200-350 nm) TAC; MS-ESI + (160-800 m/z) TIC |
| | Temperature: | Room temperature |
| | Retention Time: | 2.02 min |
| | Mass found: | 501 m/z |

Example 4.36

(RS)—N-(Ethoxycarbonyl)-S-(3-{[4-{methyl-sulfanyl}-5-(4-ethoxy-phenyl)-pyrimidin-2-yl]amino}phenyl)-S-methylsulfoximide

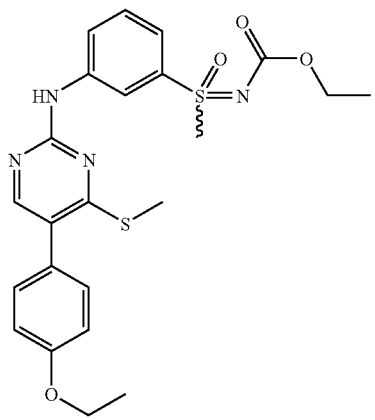

a) (RS)—N-(Ethoxycarbonyl)-S-(3-{[5-bromo-4-(methylsulfanyl)pyrimindin-2-yl]amino}phenyl)-S-methylsulfoximide

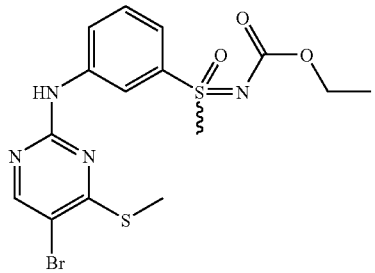

(RS)—N-(Ethoxycarbonyl)-S-(3-{[5-bromo-4-(methylsulfanyl)pyrimindin-2-yl]amino}phenyl)-S-methylsulfoximide is prepared in analogy to procedure 5b by reaction of 2.15 g of 5-Bromo-2-chloro-4-methylsulfanyl-pyrimidine (4.5 mmol, 1 eq.) and 1.09 g of (RS)—S-(3-aminophenyl)-N-(ethoxycarbonyl)-S-methylsulfoximide (4.5 mmol, 1 eq.) to yield (after crystallisation from acetonitrile) 1.2 g of (RS)—N-(Ethoxycarbonyl)-S-(3-{[5-bromo-4-(methylsulfanyl)pyrimindin-2-yl]amino}phenyl)-S-methylsulfoximide (60% yield).

$^1$H-NMR (300 MHz, DMSO); 10.25 (s, 1H); 8.60 (s, 1H); 8.40 (s, 1H); 7.90 (d, 1H); 7.58 (t, 1H); 7.50 (d, 1H); 3.84-3.96 (m, 2H); 3.40 (s, 3H); 2.55 (s, 3 H); 1.10 (t, 3H).

b) (RS)—N-(Ethoxycarbonyl)-S-(3-{[4-{methyl-sulfanyl}-5-(4-ethoxy-phenyl)-pyrimidin-2-yl]amino}phenyl)-S-methylsulfoximide

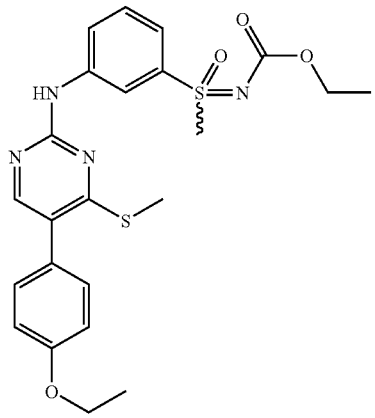

(RS)—N-(Ethoxycarbonyl)-S-(3-{[5-bromo-4-(methylsulfanyl)pyrimindin-2-yl]amino}phenyl)-S-methylsulfoximide (0.90 g (2.0 mmol), 4-ethoxyphenylboronic acid (0.35 g, 2.1 mmol), tri(2-furyl)phosphine (200 mg, 0.80 mmol), and 20 mL of dry DME are mixed in 50-mL flask and purged with argon. Then, aqueous 1M NaCO$_3$ (3.2 mL) is added, the flask is purged with argon again and then Pd(PPh$_3$)$_4$ (100 mg, 0.10 mmol) is added and the mixture is stirred under argon at 80° C. for 20 h. Subsequently, the mixture is poured into aqueous NaHCO$_3$ (200 mL), extracted with DCM, dried (Na$_2$SO$_4$) and evaporated. The product is isolated by HPLC to give the desired compound (650 mg, 66% yield). Larger batches can be readily crystallised from acetonitrile.

¹H-NMR (300 MHz, DMSO): 10.15 (s, 1H); 8.72 (s, 1H); 8.11 (s, 1H); 7.80-8.02 (m, 1H); 7.42-7.67 (m, 2H); 7.34 (d, 2H); 7.01 (d, 1H); 3.82-4.16 (m, 4 H); 3.38 (s, 3H); 2.56 (s, 3H); 1.20-1.44 (m, 3H); 0.99-1.14 (m, 3H).

MS (ESI): [M+H]⁺=487.

Example 4.37

(RS)—N-(Ethoxycarbonyl)-S-(3-{[4-{[(R)-2-hydroxy-1-methylethyl]amino}-5-(4-ethoxy-phenyl)-pyrimidin-2-yl]amino}phenyl)-S-methylsulfoximide

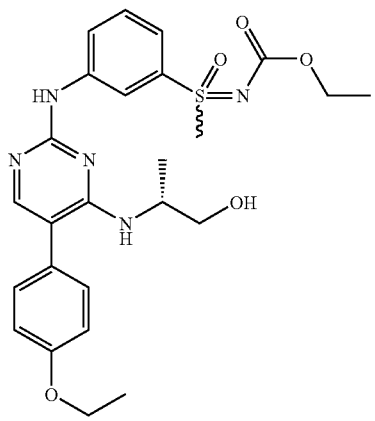

a) (RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide

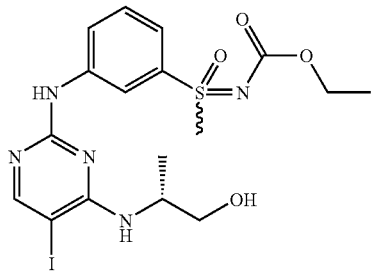

(RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide is prepared in analogy to procedure 5b by reaction of 25 g of (R)-2-(2-chloro-5-iodopyrimidine-4-ylamino)propan-1-ol and 20 g of (RS)—S-(3-aminophenyl)-N-(ethoxycarbonyl)-S-methylsulfoximide to yield (after preparative HPLC purification) 12 g of (RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide (29% yield).

¹H-NMR (300 MHz, DMSO); 9.75 (s, 1H); 8.62 (s, 1H); 8.20 (s, 1H); 7.87 (d, 1H); 7.54 (t, 1H); 7.43 (d, 1H); 6.03 (d, 1H); 4.90-4.95 (m, 1H); 4.25-4.35 (m, 1H); 3.85-3.95 (m, 2H); 3.45-3.55 (m, 2H); 3.30 (s, 3H); 1.15 (d, 3H); 1.08 (t, 3H).

b) (RS)—N-(Ethoxycarbonyl)-S-(3-{[4-{[(R)-2-hydroxy-1-methylethyl]amino}-5-(4-ethoxy-phenyl)-pyrimidin-2-yl]amino}phenyl)-S-methylsulfoximide

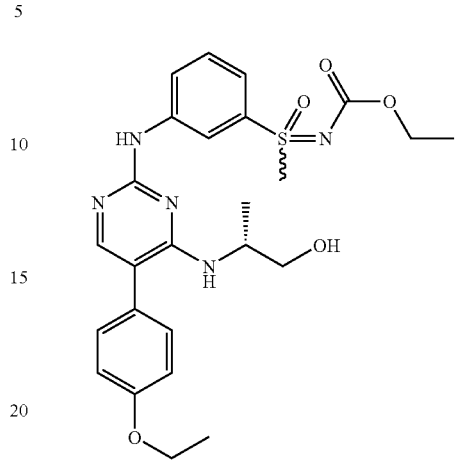

(RS)—N-(Ethoxycarbonyl)-S-(3-{[4-{[(R)-2-hydroxy-1-methylethyl]amino}-5-(4-ethoxy-phenyl)-pyrimidin-2-yl]amino}phenyl)-S-methylsulfoximide is prepared according to procedure 11a from (RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide (208 mg, 0.40 mmol) and 4-ethoxyphenyl boronic acid (94 mg, 0.57 mmol). The reaction mixture is worked up as described in procedure 11a and the crude product is purified by flash column chromatography to give the target compound in 76% yield.

¹H-NMR (300 MHz, DMSO); 9.61 (s, 1H); 8.65 (s, 1H); 7.90 (d br, 1H); 7.72 (s, 1H); 7.51 (t, 1H); 7.39 (d br, 1H); 7.29 (d, 2H); 7.00 (d, 2H); 5.77-5.88 (m, 1 H); 4.72 (s br, 1H); 4.22-4.36 (m, 1H); 4.03 (q, 2H); 3.80-3.94 (m, 2H); 3.33-3.49 (m, 5H); 1.32 (t, 3H); 1.11 (d, 3H); 1.05 (t, 3H).

MS (ESI): [M+H]⁺=514.

Example 4.38

(RS)—N-(Ethoxycarbonyl)-S-(3-{[4-{[(R)-2-hydroxy-1-methylethyl]amino}-5-(4-methoxy-phenyl)-pyrimidin-2-yl]amino}phenyl)-S-methylsulfoximide

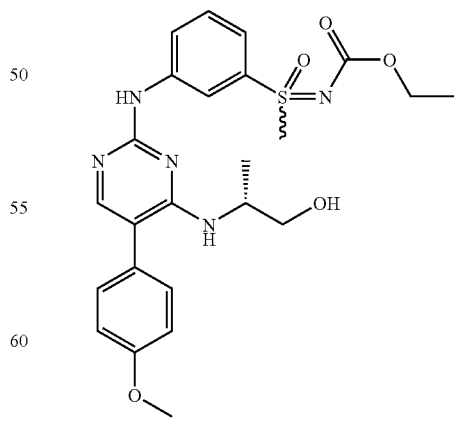

(RS)—N-(Ethoxycarbonyl)-S-(3-{[4-{[(R)-2-hydroxy-1-methylethyl]amino}-5-(4-methoxy-phenyl)-pyrimidin-2-yl]amino}phenyl)-S-methylsulfoximide is prepared according to procedure 11a from (RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide (208 mg, 0.40 mmol) and 4-methoxyphenyl boronic acid (86 mg, 0.57 mmol). The reaction mixture is worked up as described in procedure 11a and the crude product is purified by flash column chromatography, followed by trituration with diisopropyl ether containing a trace of acetonitrile to give the target compound in 20% yield.

$^1$H-NMR (300 MHz, DMSO); 9.58 (s, 1H); 8.68 (s, 1H); 7.90 (d br, 1H); 7.74 (s, 1H); 7.50 (t, 1H); 7.38 (d br, 1H); 7.30 (d, 2H); 7.02 (d, 2H); 5.75-5.84 (m, 1 H); 4.68-4.78 (m, 1H); 4.22-4.38 (m, 1H); 3.81-3.95 (m, 2H); 3.77 (s, 3 H); 3.33-3.50 (m, 5H); 1.10 (d, 3H); 1.02 (t, 3H).

MS (ESI): [M+H]$^+$=500.

Example 4.39

(RS)—N-(Ethoxycarbonyl)-S-(3-{[4-{[(R)-2-hydroxy-1-methylethyl]amino}-5-(4-ethyl-phenyl)-pyrimidin-2-yl]amino}phenyl)-S-methylsulfoximide

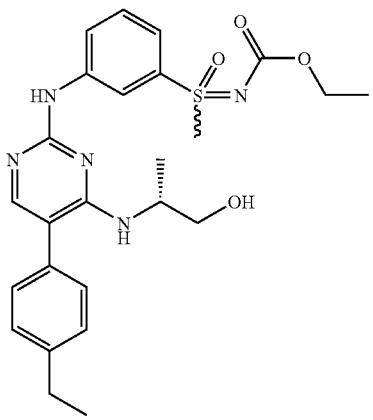

(RS)—N-(Ethoxycarbonyl)-S-(3-{[4-{[(R)-2-hydroxy-1-methylethyl]amino}-5-(4-ethyl-phenyl)-pyrimidin-2-yl]amino}phenyl)-S-methylsulfoximide is prepared according to procedure 11a from (RS)—N-(Ethoxycarbonyl)-S-(3-{[4-{[(R)-2-(hydroxy-1-methylethyl]amino}-5-iodopyrimidin-2-yl]amino}phenyl)-S-methylsulfoximide (208 mg, 0.40 mmol) and 4-ethylphenyl boronic acid (85 mg, 0.57 mmol). The reaction mixture is worked up as described in procedure 11a and the crude product is purified by flash column chromatography, followed by trituration with diisopropyl ether containing a trace of acetonitrile to give the target compound in 25% yield.

$^1$H-NMR (300 MHz, DMSO): 9.62 (s, 1H); 8.66 (s, 1H); 7.91 (d br, 1H); 7.77 (s, 1H); 7.50 (t, 1H); 7.38 (d br, 1H); 7.30 (s, 4H); 5.82-5.90 (m, 1H); 4.69-4.77 (m, 1H); 4.20-4.38 (m, 1H); 3.80-3.94 (m, 2H); 3.33-3.48 (m, 5H); 2.62 (q, 2 H); 1.18 (t, 3H); 1.12 (d, 3H); 1.05 (t, 3H).

MS (ESI): [M+H]$^+$=498.

Example 4.40

(RS)—N-(Ethoxycarbonyl)-S-(4-{[4-{[(R)-2-hydroxy-1-methylethyl]amino}-5-(4-ethoxy-phenyl)-pyrimidin-2-yl]amino}phenyl)-S-methylsulfoximide

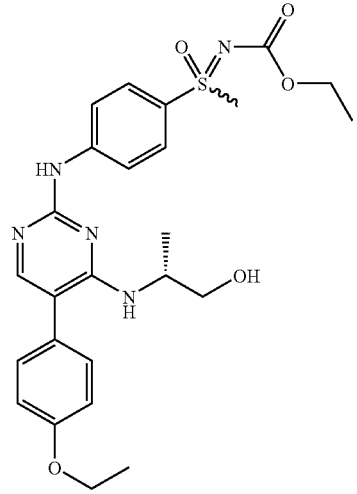

(RS)—N-(Ethoxycarbonyl)-S-(4-{[4-{[(R)-2-hydroxy-1-methylethyl]amino}-5-(4-ethoxy-phenyl)-pyrimidin-2-yl]amino}phenyl)-S-methylsulfoximide is prepared according to procedure 11a from (RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide (260 mg, 0.5 mmol) and 4-ethoxyphenyl boronic acid (118 mg, 0.71 mmol). The reaction mixture is worked up as described in procedure 11a and the crude product is purified by flash column chromatography followed by trituration with diisopropyl ether to give the target compound in 23% yield.

$^1$H-NMR (400 MHz, DMSO); 9.71 (s, 1H); 8.03 (d, 2H); 7.76 (d, 2H); 7.76 (s, 1H); 7.29 (d, 2H); 6.99 (d, 2H); 5.84 (d, 1H); 4.78 (t, 1H); 4.21-4.27 (m, 1H); 4.03 (q, 2H); 3.85-3.93 (m, 2H); 3.43 (t, 2H); 3.38 (s, 3H); 1.32 (t, 3 H); 1.13 (d, 3H); 1.07 (t, 3H).

MS (ESI): [M+H]$^+$=514.

Example 4.41

(RS)—N-(Ethoxycarbonyl)-S-(4-{[4-{[(R)-2-hydroxy-1-methylethyl]amino}-5-(4-methoxy-phenyl)-pyrimidin-2-yl]amino}phenyl)-S-methylsulfoximide

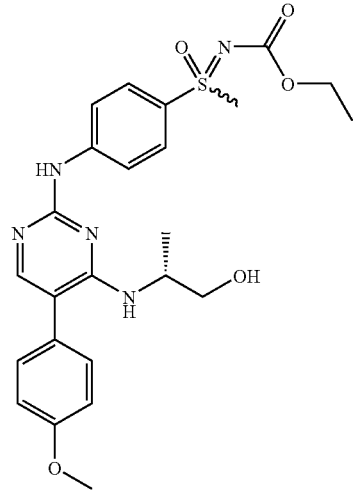

(RS)—N-(Ethoxycarbonyl)-S-(4-{[4-{[(R)-2-hydroxy-1-methylethyl]amino}-5-(4-methoxy-phenyl)-pyrimidin-2-yl]amino}phenyl)-S-methylsulfoximide is prepared according to procedure 11a from (RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide (260 mg, 0.5 mmol) and 4-methoxyphenyl boronic acid (108 mg, 0.71 mmol). The reaction mixture is worked up as described in procedure 11a and the crude product is purified by flash column chromatography followed by preparative HPLC purification to give the target compound in 23% yield.

$^1$H-NMR (400 MHz, DMSO): 9.72 (s, 1H); 8.03 (d, 2H); 7.76 (d, 2H); 7.76 (s, 1 H); 7.31 (d, 2H); 7.01 (d, 2H); 5.85 (d, 1H); 4.78 (t, 1H); 4.21-4.29 (m, 1H); 3.85-3.93 (m, 2H); 3.76 (s, 3H); 3.43 (t, 2H); 3.38 (s, 3H); 1.13 (d, 3 H); 1.07 (t, 3H).

MS (ESI): [M+H]$^+$=500.

Example 4.42

(RS)—N-(Ethoxycarbonyl)-S-(4-{[4-{[(R)-2-hydroxy-1-methylethyl]amino}-5-(4-ethyl-phenyl)-pyrimidin-2-yl]amino}phenyl)-S-methylsulfoximide

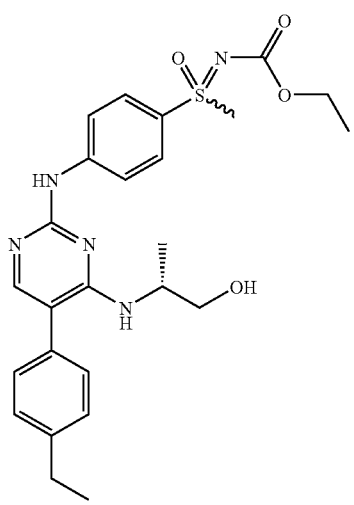

(RS)—N-(Ethoxycarbonyl)-S-(4-{[4-{[(R)-2-hydroxy-1-methylethyl]amino}-5-(4-ethyl-phenyl)-pyrimidin-2-yl]amino}phenyl)-S-methylsulfoximide is prepared according to procedure 11a from (RS)—N-(ethoxycarbonyl)-S-(4-{[4-{[(R)-2-(hydroxy-1-methylethyl]amino}-5-iodopyrimindin-2-yl]amino}phenyl)-S-methylsulfoximide (260 mg, 0.5 mmol) and 4-ethylphenyl boronic acid (107 mg, 0.71 mmol). The reaction mixture is worked up as described in procedure 11a and the crude product is purified by flash column chromatography followed by trituration with diisopropyl ether to give the target compound in 40% yield.

$^1$H-NMR (400 MHz, DMSO): 9.73 (s, 1H); 8.03 (d, 2H); 7.78 (s, 1H); 7.77 (d, 2H); 7.30 (m, 4H); 5.91 (d, 1H); 4.78 (t, 1H); 4.21-4.29 (m, 1H); 3.85-3.93 (m, 2H); 3.44 (t, 2H); 3.38 (s, 3H); 2.62 (q, 2H); 1.19 (t, 3H); 1.14 (d, 3H); 1.07 (t, 3H).

MS (ESI): [M+H]$^+$=498.

Example 4.43

(RS)—N(ethoxycarbonyl)-(4-{[4-{[(R)-2-hydroxy-1-methylethyl]amino}-5-(indol-2-yl)-pyrimidin-2-yl]amino}phenyl)-S-methylsulfoximide

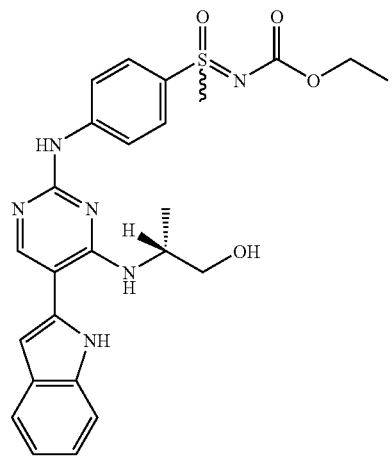

Preparation by Procedure 11a with N-tert.-butyloxycarbonyl-2-indolyl-boronic-acid. To the resulting coupling product (62 mg, 0.1 mmol) HCl/dioxane (1 ml, 4 M) is added. The reaction mixture is stirred for 3 h at RT and 3 h at 40° C. Then HCl/dioxane (0.5 ml, 4 M) is added the reaction mixture is stirred for 22 h at 50° C. For workup the mixture is poured into saturated NaHCO$_3$ solution and extracted with ethyl acetate. The organic phase is washed with brine, dried over NaSO$_4$ and is evaporated in vacuum. The crude product was purified by HPLC: 18.9 mg (36%).

$^1$H-NMR (300 MHz, DMSO-D$_6$): δ 1.12 (t, 3H), 1.24, 1.26 (2×s, 3H); 3.46 (s, 3H), 3.56 (m, 2H), 3.95 (m, 2H), 4.36 (m, 1H), 6.68 (s, 1H), 7.01 (bs, 1H), 7.05 (t, 1H), 7.15 (t, 1H), 7.43 (d, 1H), 7.59 (d, 1H), 7.90 (d, 2H), 8.05 (d, 2H), 8.16 (s, 1H), 10.26 (bs, 1H); 11.43 (bs, 1H).

MS: 509 (MH+).

Example 4.44

(RS)—N(ethoxycarbonyl)-(4-{[4-{methylsulfanyl}-5-(thiophen-2-yl)-pyrimidin-2-yl]amino}phenyl)-S-methylsulfoximide

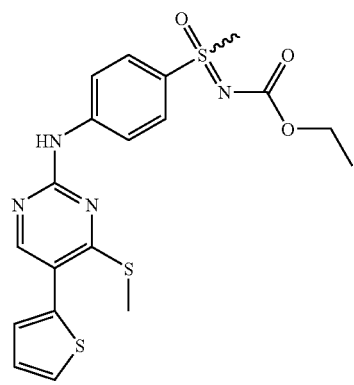

a) 5-Bromo-2-chloro-4-methylsulfanyl-pyrimidine

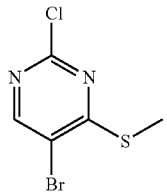

MeSNa (2 g, 28.5 mmol; 1 eq.) and 5-bromo-2,4-dichloropyrimidine (6.5 g, 28.5 mmol, 1 eq.) are stirred in dry acetonitrile (50 mL) at rt for 24 h. Then the mixture is poured into water, extracted with DCM, dried (Na$_2$SO$_4$) and evaporated to dryness. The product crystallised from hexane to yield 4.0 g of Intermediate 10 (70% yield).

$^1$H-NMR (400 MHz, CDCl$_3$): δ 8.31 (s, 1H); 2.59 (s, 3H).

b) (RS)—N(ethoxycarbonyl)-(4-{[4-{methylsulfanyl}-5-bromo-pyrimidin-2-yl]amino}phenyl)-S-methylsulfoximide

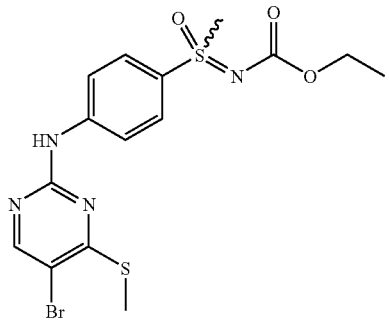

(RS)—S-(4-aminophenyl)-N-(ethoxycarbonyl)-S-methylsulfoximide (10 g, 42 mmol), 5-Bromo-2-chloro-4-methylsulfanyl-pyrimidine (10 g, 42 mmol) and 5M HCl (8 mL) in dioxane is stirred at 60° C. in 90% acetonitrile-water (250 mL) for 36 h. TLC indicates almost complete consumption of starting sulfoximine. The reaction mixture is poured into 800 mL of aq. NaHCO$_3$, the pasty precipitate filtered, washed with 70 mL of EtOAc, then crude material (7.5 g) is recrystallized from boiling EtOH (200 mL) to yield 6 g (35%).

$^1$H-NMR (300 MHz, DMSO-D$_6$): δ 1.10 (t, 3H), 2.60 (s, 3H), 3.42 (s, 3H), 3.90 (m, 2H), 7.95 (d, 2H), 7.85 (d, 2H), 8.40 (s, 1H), 10.35 (s, 1H).

c) (RS)—N(ethoxycarbonyl)-(4-{[4-{methylsulfanyl}-5-(thiophen-2-yl)-pyrimidin-2-yl]amino}phenyl)-S-methylsulfoximide

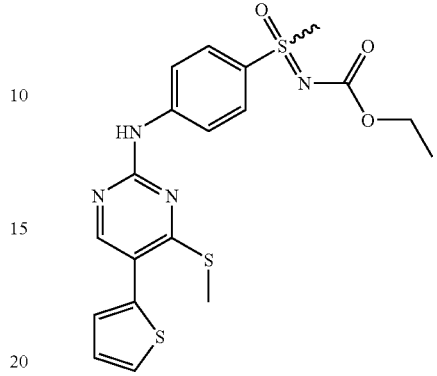

Preparation by Procedure 11b.

$^1$H-NMR (300 MHz, DMSO-D$_6$): δ 1.10 (t, 3H), 2.61 (s, 3H), 3.43 (s, 3H), 3.93 (q, 2H), 7.20 (dd, 1H), 7.36 (d, 1H), 7.70 (d, 1H), 7.88 (d, 2H), 8.06 (d, 2H), 8.34 (s, 1H), 10.32 (s, 1H).

Example 4.45

(RS)—N(ethoxycarbonyl)-(4-{[4-{[(R)-2-hydroxy-1-methylethyl]amino}-5-(2-methoxy-thiazol-4-yl)-pyrimidin-2-yl]amino}phenyl)-S-methylsulfoximide

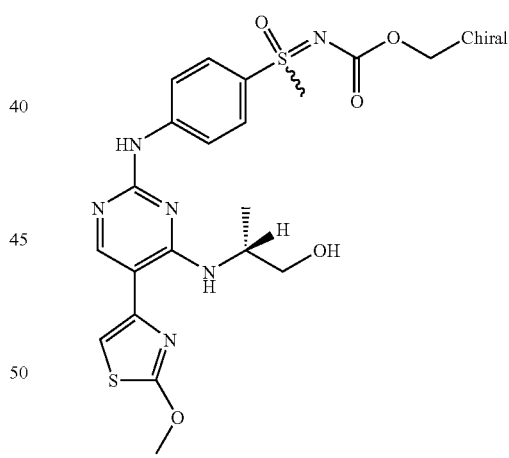

Preparation by Procedure 12.

$^1$H-NMR (300 MHz, DMSO-D$_6$): δ 1.07 (t, 3H), 1.23 (d, 3H), 3.38 (s, 3H), 3.53 (m, 2H), 3.89 (m, 2H), 4.09 (s, 3H), 4.21 (m, 1H), 4.93 (m, 1H), 7.32 (s, 1H), 7.78 (d, 2H), 8.04 (d, 2H), 8.40 (s, 1H), 8.50 (d, 1H), 9.83 (s, 1H).

MS: 507 (MH+).

Example 4.46-4.54

Preparation Analogously to the Synthesis of Example 4.8 Affords the Compounds Given in Table 2 (Example 4.46-4.54).

TABLE 2

| Ex. No. | boronic acid used | Product structure | Calc. Mol. Wt. | Found Mass (ESI)* | Found Retention time* |
|---|---|---|---|---|---|
| 4.46 | (3-methoxyphenyl)boronic acid | | 499.6 | 500.2 | 2.75 |
| 4.47 | (3-methylphenyl)boronic acid | | 483.6 | 484.2 | 2.85 |
| 4.48 | (3-methanesulfonamidophenyl)boronic acid | | 562.7 | 563.1 | 2.59 |

TABLE 2-continued

| Ex. No. | boronic acid used | Product structure | Calc. Mol. Wt. | Found Mass (ESI)* | Found Retention time* |
|---|---|---|---|---|---|
| 4.49 | | | 494.6 | 495.1 | 2.64 |
| 4.50 | | | 540.6 | 541.2 | 2.45 |
| 4.51 | | | 594.7 | 595.2 | 2.45 |

TABLE 2-continued

| Ex. No. | boronic acid used | Product structure | Calc. Mol. Wt. | Found Mass (ESI)* | Found Retention time* |
|---|---|---|---|---|---|
| 4.52 | (3-ethylcarbamoylphenyl)boronic acid | | 540.6 | 541.2 | 2.54 |
| 4.53 | (3-(morpholine-4-carbonyl)phenyl)boronic acid | | 582.7 | 583.2 | 2.47 |
| 4.54 | (3-(methoxymethyl)phenyl)boronic acid | | 513.6 | 514.1 | 2.68 |

*taken from the analytical HPLC diagrams.

Analytical conditions: HPLG Pump 2525 Binary Gradient Module (Waters), Detector Micromass ZQ (Waters), UV Lamp MUX UV 2488 Detector (Waters), Column XBridge C18 3.5 μm, 4.6×50 mm Gradient used (CH$_3$CN (A) and water (B) each with 0.1% added trifluoroacetic acid):

A 1%/B 99%->A 99%/B 1% within 5 min; flow rate 2 ml/min

According to Process Variation 4 (see also Scheme 6) the following compounds can be prepared:

| Structure | Name |
|---|---|
| 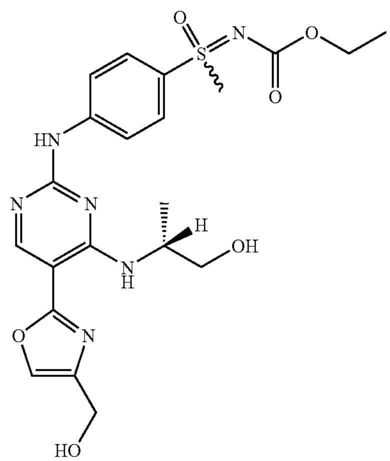 | (RS)-N-(Ethoxycarbonyl)-S-(4-{[4-{[(R)-2-hydroxy-1-methylethyl]amino}-5-(4-hydroxymethyl-oxazol-2-yl)pyrimidin-2-yl]amino}phenyl)-S-methylsulfoximide |
| 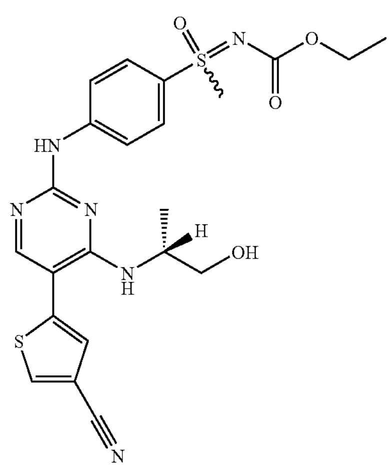 | (RS)-N-(Ethoxycarbonyl)-S-(4-{[4-{[(R)-2-hydroxy-1-methylethyl]amino}-5-(4-cyano-thien-2-yl)pyrimidin-2-yl]amino}phenyl)-S-methylsulfoximide |
| 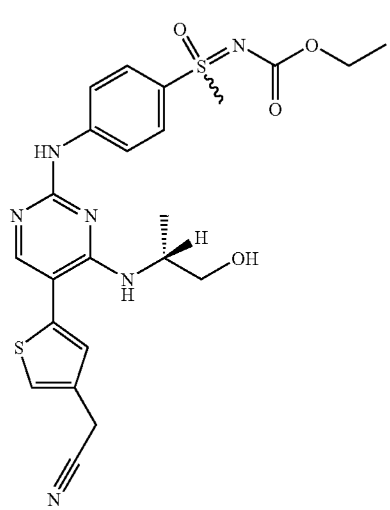 | (RS)-N-(Ethoxycarbonyl)-S-(4-{[4-{[(R)-2-hydroxy-1-methylethyl]amino}-5-(4-cyanomethyl-thien-2-yl)pyrimidin-2-yl]amino}phenyl)-S-methylsulfoximide |

| Structure | Name |
|---|---|
| 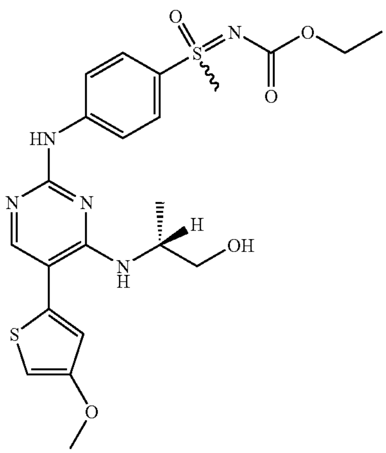 | (RS)-N-(Ethoxycarbonyl)-S-(4-{[4-{[(R)-2-hydroxy-1-methylethyl]amino}-5-(4-methoxy-thien-2-yl)pyrimidin-2-yl]amino}phenyl)-S-methylsulfoximide |
| 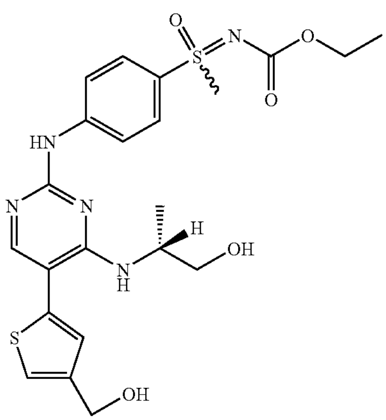 | (RS)-N-(Ethoxycarbonyl)-S-(4-{[4-{[(R)-2-hydroxy-1-methylethyl]amino}-5-(4-hydroxymethyl-thien-2-yl)pyrimidin-2-yl]amino}phenyl)-S-methylsulfoximide |

6. Process Variation 5 (See Also Scheme 7)

General Procedures

Procedure 14a—Cleavage of Ethoxycarbonyl Group (Method A)

The respective N-ethoxycarbonyl sulfoximine (1 eq.) is dissolved in EtOH (8-16 mL per mmol sulfoximine) and treated with 3-4 eq. of NaOEt solution (20% in EtOH). The resulting mixture is stirred at reflux until TLC indicated complete turnover (usually after 4-6 hours). The reaction mixture is concentrated, the residue dissolved in DCM and quenched with water. The aqueous layer is extracted with DCM, the combined organic layers are washed with brine, dried and concentrated in vacuo. Flash column chromatography optionally followed by trituration or preparative HPLC purification yield the analytically pure target compounds.

Procedure 14b—Cleavage of Ethoxycarbonyl Group (Method B)

The respective N-ethoxycarbonyl sulfoximine (1 eq.) is dissolved in EtOH (8-16 mL per mmol sulfoximine) and treated with 3-4 eq. of NaOEt solution (20% in EtOH). The resulting mixture is then subjected to focussed microwave irradiation (Biotage Initiator 2.0) to maintain a reaction temperature of 100° C. until the reaction is complete (typically between 15 and 30 minutes). The reaction mixture is concentrated and the residue is triturated with water. The precipitated solid is isolated by filtration and dried in vacuo and subsequently purified by flash column chromatography, optionally followed by trituration or preparative HPLC purification, to give the analytically pure target compounds.

Compounds which were Prepared by Process Variation 5

Example 5.1

(RS)—S-(4-{[4-{[(R)-2-hydroxy-1-methylethyl]amino}-5-(2-thienyl)pyrimidine-2-yl]amino}phenyl)-S-methylsulfoximide

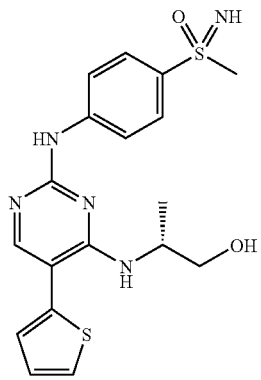

In the reaction of (RS)—N-(ethoxycarbonyl)-S-(4-{[4-{[(R)-2-hydroxy-1-methyl-ethyl]-amino}-5-(2-thienyl)pyrimidine-2-yl]amino}phenyl)-S-methylsulfoximide (94 mg, 0.2 mmol) with sodium ethylate (49 mg, 0.7 mmol) according to procedure 14, the desired product is obtained in 44% yield (35 mg) after chromatographic purification (silica gel, dichloromethane/methanol (9/1)).

$^1$H-NMR (300 MHz, DMSO-D6): δ 1.15 (d, 3H), 2.97 (s, 3H), 3.45 (t, 2H), 3.92 (s, 1H), 4.18-4.30 (m, 1H), 4.82 (t, 1H), 6.12 (d, 1H), 7.12-7.20 (m, 2H), 7.58 (dd, 1H), 7.75 (d, 2H), 7.92-8.00 (m, 3H), 9.70 (s, 1H).

Example 5.2

(RS)—S-(4-{[4-{[(S)-1-(hydroxymethyl)-3-methylbutyl]amino}-5-(3-thienyl)-pyrimidine-2-yl]amino}phenyl)-S-methylsulfoximide

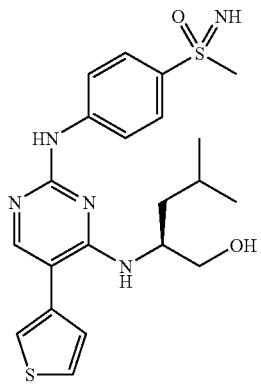

In the reaction of (RS)—N-(ethoxycarbonyl)-S-(4-{[4-{[(S)-1-(hydroxymethyl)-3-methylbutyl]amino}-5-(3-thienyl)pyrimidine-2-yl]amino}phenyl)-S-methyl-sulfoximide (135 mg, 0.26 mmol) with sodium ethylate (70 mg, 1.0 mmol) according to procedure 14, the desired product is obtained in 36% yield (42 mg) after chromatographic purification (silica gel, dichloromethane/methanol (9/1)).

$^1$H-NMR (300 MHz, DMSO-D6): δ 0.88 (m, 6H), 1.43 (m, 2H), 1.61 (m, 1H), 2.95 (s, 3H), 3.43 (m, 2H), 3.93 (s, 1H), 4.38 (m, 1H), 4.73 (t, 1H), 5.82 (d, 1H), 7.21 (m, 1H), 7.53 (m, 1H), 7.71 (m, 3H), 7.89 (s, 1H), 7.96 (m, 2H), 9.57 (s, 1H).
MS: 446 (ES+)

Example 5.3

(RS)—S-ethyl-S-(4-{[4-{[(S)-1-(hydroxymethyl)-3-methylbutyl]amino}-5-(3-thienyl)pyrimidine-2-yl]amino}phenyl)sulfoximide

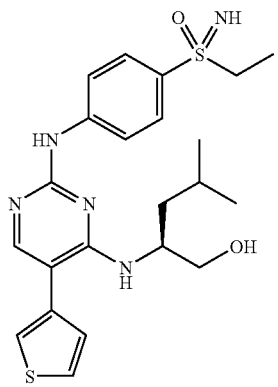

In the reaction of (RS)—N-(ethoxycarbonyl)-S-ethyl-S-(4-{[4-{[(S)-1-(hydroxy-methyl)-3-methylbutyl]amino}-5-(3-thienyl)pyrimidine-2-yl]amino}phenyl)-sulfoximide (265 mg, 0.50 mmol) with sodium ethylate (70 mg, 1.0 mmol) according to procedure 14, the desired product is obtained in 34% yield (77 mg) after chromatographic purification (silica gel, dichloromethane/methanol (9/1)).

$^1$H-NMR (300 MHz, DMSO-D6): δ 0.83 (m, 6H), 1.02 (t, 3H), 1.40 (m, 2H), 1.61 (m, 1H), 3.01 (q, 2H), 3.45 (m, 2H), 3.87 (s, 1H), 4.35 (m, 1H), 4.74 (t, 1H), 5.81 (d, 1H), 7.21 (m, 1H), 7.55 (m, 1H), 7.68 (m, 3H), 7.89 (s, 1H), 7.95 (m, 2H), 9.57 (s, 1H).
MS: 460 (ES+)

Example 5.4

(RS)—S-{2-bromo-4-[(4-{[(R)-1-(hydroxymethyl)propyl]amino}-5-(3-thienyl)-pyrimidine-2-yl)amino]phenyl}-S-methylsulfoximide

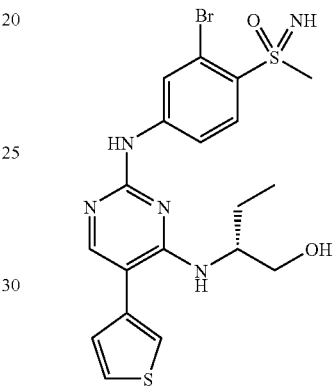

In the reaction of (RS)—S-{2-bromo-4-[4-{[(R)-1-(hydroxymethyl)propyl]amino}-5-(3-thienyl)pyrimidine-2-yl)amino]phenyl}-N-(ethoxycarbonyl)-S-methyl-sulfoximide (126 mg, 0.22 mmol) with sodium ethylate (22 mg, 0.31 mmol) according to procedure 14, the desired product is obtained in 74% yield (82 mg) after chromatographic purification (silica gel, dichloromethane/ethanol (9/1)).

$^1$H-NMR (DMSO): 9.85 (s, 1H), 8.40 (m, 1H), 7.95 (m, 2H), 7.84 (m, 1H), 7.67 (m, 1H), 7.58 (m, 1H), 7.23 (m, 1H), 5.91 (d, 1H), 4.78 (tr, 1H), 4.28 (s, 1H), 4.12 (m, 1H), 3.50 (m, 2H), 3.12 (s, 3H), 1.60 (m, 2H), 0.90 (tr, 3H).
MS: 496 (ES+).

Example 5.5

(RS)—S-{2-bromo-4-[(4-{[(R)-1-(hydroxymethyl)propyl]amino}-5-(2-thienyl)-pyrimidine-2-yl)amino]phenyl}-S-methylsulfoximide

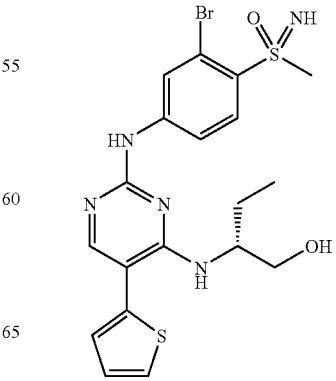

In the reaction of (RS)—S-{2-bromo-4-[(4-{[(R)-1-(hydroxymethyl)propyl]amino}-5-(2-thienyl)pyrimidine-2-yl)amino]phenyl}-N-(ethoxycarbonyl)-S-methyl-sulfoximide (130 mg, 0.23 mmol) with sodium ethylate (22 mg, 0.31 mmol) according to procedure 14, the desired product is obtained in 64% yield (73 mg) after chromatographic purification (silica gel, dichloromethane/ethanol (9/1)).

¹H-NMR (DMSO): 9.81 (s, 1H), 8.39 (m, 1H), 7.94 (m, 2H), 7.83 (m, 1H), 7.58 (m, 1H), 7.17 (m, 2H), 6.12 (d, 1H), 4.79 (tr, 1H), 4.28 (s, 1H), 4.11 (m, 1H), 3.51 (m, 2H), 3.12 (m, 3H), 1.60 (m, 2H), 0.89 (tr, 3H).

MS: 496 (ES+).

Example 5.6

(R)—S-(4-{[4-{[(R)-2-hydroxy-1-methylethyl]amino}-5-(2-thienyl)pyrimidine-2-yl]amino}phenyl)-S-cyclopropylsulfoximide

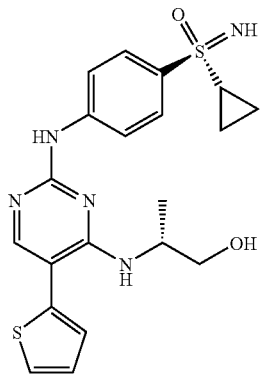

In the reaction of (R)—N-(ethoxycarbonyl)-S-(4-{[4-{[(R)-2-hydroxy-1-methyl-ethyl]amino}-5-(2-thienyl)pyrimidine-2-yl]amino}phenyl)-S-cyclopropyl-sulfoximide with sodium ethylate according to procedure 14, the desired product is obtained in 82% yield after chromatographic purification (silica gel, dichloromethane/ethanol (0-10% ethanol)).

¹H-NMR (400 MHz, DMSO-D6): δ 0.78-1.00 (m, 3H), 1.07 (m, 1H), 1.20 (d, 3H), 2.59 (m, 1H), 3.51 (t, 2H), 3.94 (s, 1H), 4.28 (m, 1H), 4.88 (t, 1H), 6.18 (d, 1H), 7.20 (m, 2H), 7.62 (d, 1H), 7.74 (d, 2H), 7.97 (s, 1H), 7.98 (d, 2H), 9.73 (s, 1H).

Example 5.7

(S)—S-(4-{[4-{[(R)-2-hydroxy-1-methylethyl]amino}-5-(2-thienyl)pyrimidine-2-yl]amino}phenyl)-S-cyclopropylsulfoximide

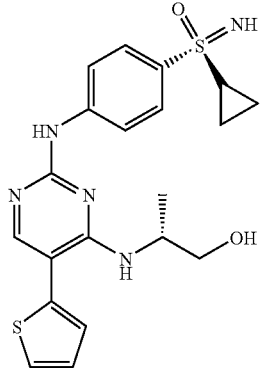

In the reaction of (S)—N-(ethoxycarbonyl)-S-(4-{[4-{[(R)-2-hydroxy-1-methylethyl]-amino}-5-(2-thienyl)pyrimidine-2-yl]amino}phenyl)-S-cyclopropylsulfoximide with sodium ethylate according to procedure 14, the desired product is obtained in 63% yield after chromatographic purification (silica gel, dichloromethane/ethanol (0-10% ethanol)).

1H-NMR (400 MHz, DMSO-D6): δ 0.81-0.97 (m, 3H), 1.07 (m, 1H), 1.20 (d, 3H), 2.59 (m, 1H), 3.50 (t, 2H), 3.95 (s, 1H), 4.28 (m, 1H), 4.89 (t, 1H), 6.18 (d, 1H), 7.20 (m, 2H), 7.62 (d, 1H), 7.74 (d, 2H), 7.97 (s, 1H), 7.98 (d, 2H), 9.73 (s, 1H).

Example 5.8

(R)—S-(4-{[4-{[(R)-1-(hydroxymethyl)propyl]amino}-5-(2-thienyl)pyrimidine-2-yl]amino}phenyl)-S-cyclopropylsulfoximide

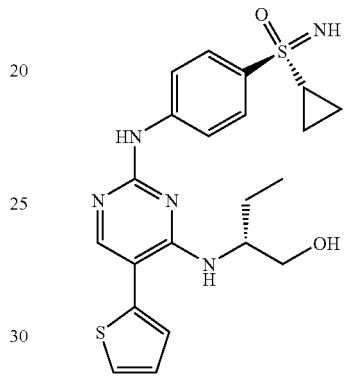

In the reaction of (R)—N-(ethoxycarbonyl)-S-(4-{[4-{[(R)-1-(hydroxymethyl)propyl]-amino}-5-(2-thienyl)pyrimidine-2-yl]amino}phenyl)-S-cyclopropylsulfoximide with sodium ethylate according to procedure 14, the desired product is obtained in 81% yield after chromatographic purification (silica gel, dichloromethane/ethanol (0-10% ethanol)).

¹H-NMR (400 MHz, DMSO-D6): δ 0.81-1.00 (m, 3H), 0.93 (t, 3H), 1.07 (m, 1H), 1.52-1.73 (m, 2H), 2.60 (m, 1H), 3.44-3.63 (m, 2H), 3.96 (s, 1H), 4.13 (m, 1H), 4.83 (t, 1H), 6.13 (d, 1H), 7.21 (m, 2H), 7.63 (d, 1H), 7.74 (d, 2H), 7.97 (s, 1H), 7.98 (d, 2H), 9.72 (s, 1H).

Example 5.9

(S)—S-(4-{[4-{[(R)-1-(hydroxymethyl)propyl]amino}-5-(2-thienyl)pyrimidine-2-yl]amino}phenyl)-S-cyclopropylsulfoximide

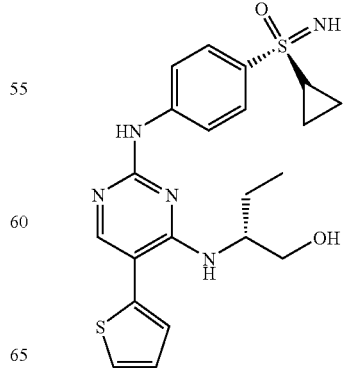

In the reaction of (S)—N-(ethoxycarbonyl)-S-(4-{[4-{[(R)-1-(hydroxymethyl)propyl]-amino}-5-(2-thienyl)pyrimidine-2-yl]amino}phenyl)-S-cyclopropylsulfoximide with sodium ethylate according to procedure 14, the desired product is obtained in 81% yield after chromatographic purification (silica gel, dichloromethane/ethanol (0-10% ethanol)).

$^1$H-NMR (400 MHz, DMSO-D6): δ 0.81-1.00 (m, 3H), 0.93 (t, 3H), 1.06 (m, 1H), 1.52-1.73 (m, 2H), 2.59 (m, 1H), 3.44-3.63 (m, 2H), 3.96 (s, 1H), 4.12 (m, 1H), 4.83 (t, 1H), 6.13 (d, 1H), 7.20 (m, 2H), 7.62 (d, 1H), 7.74 (d, 2H), 7.96 (s, 1H), 7.97 (d, 2H), 9.73 (s, 1H).

Example 5.10

(RS)—S-(4-{[4-{[(R)-2-hydroxy-1-methylethyl]amino}-5-(2-thienyl)pyrimidine-2-yl]amino}phenyl)-S-phenylsulfoximide

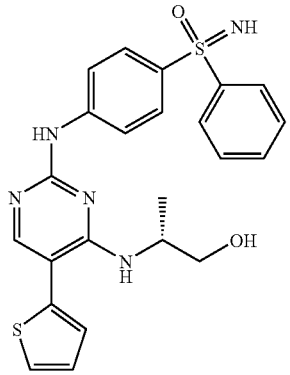

In the reaction of (RS)—N-(ethoxycarbonyl)-S-(4-{[4-{[(R)-2-hydroxy-1-methyl-ethyl]amino}-5-(2-thienyl)pyrimidine-2-yl]amino}phenyl)-S-phenylsulfoximide with sodium ethylate according to procedure 14, the desired product is obtained in 40% yield after chromatographic purification (silica gel, dichloromethane/ethanol (0-10% ethanol)).

$^1$H-NMR (400 MHz, DMSO-D6): δ 1.18 (d, 3H), 3.49 (t, 2H), 4.25 (m, 1H), 4.72 (s, 1H), 4.88 (t, 1H), 6.18 (d, 1H), 7.20 (m, 2H), 7.49-7.58 (m, 3H), 7.61 (d, 1H), 7.82 (d, 2H), 7.91-7.98 (m, 4H), 7.94 (s, 1H), 9.73 (s, 1H)

Example 5.11

(RS)—S-(4-{[4-{[(R)-1-(hydroxymethyl)propyl]amino}-5-(2-thienyl)pyrimidine-2-yl]amino}phenyl)-S-phenylsulfoximide

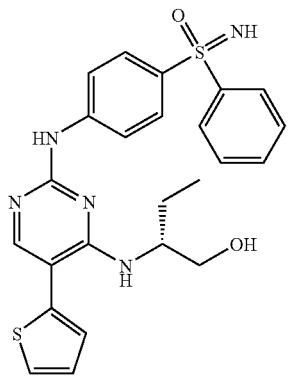

In the reaction of (RS)—N-(ethoxycarbonyl)-S-(4-{[4-{[(R)-1-(hydroxymethyl)-propyl]amino}-5-(2-thienyl)pyrimidine-2-yl]amino}phenyl)-S-phenylsulfoximide with sodium ethylate according to procedure 14, the desired product is obtained in 35% yield after chromatographic purification (silica gel, dichloromethane/ethanol (0-10% ethanol)).

$^1$H-NMR (400 MHz, DMSO-D6): δ 0.91 (t, 3H), 1.48-1.74 (m, 2H), 3.44-3.60 (m, 2H), 4.10 (m, 1H), 4.72 (s, 1H), 4.82 (t, 1H), 6.12 (d, 1H), 7.19 (m, 2H), 7.49-7.59 (m, 3H), 7.62 (m, 1H), 7.82 (d, 2H), 7.91-7.97 (m, 4H), 7.94 (s, 1H), 9.72 (s, 1H)

Example 5.12

(RS)—S-(4-{[4-{[(R)-2-(hydroxy-1-methylethyl]amino}-5-(5-pyrazolyl)pyrimindin-2-yl]amino}phenyl)-S-methylsulfoximide

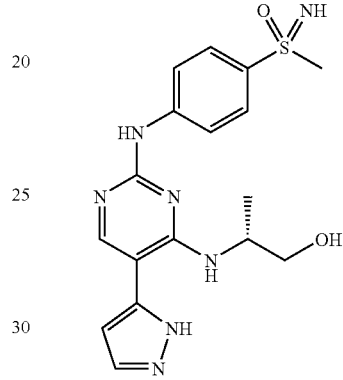

In the reaction of (RS)—N-(ethoxycarbonyl)-S-(4-{[4-{[(R)-2-(hydroxy-1-methyl-ethyl]amino}-5-(5-pyrazolyl)pyrimindin-2-yl]amino}phenyl)-S-methylsulfoximide with sodium ethylate according to procedure 14, the desired product is obtained in 49% yield after chromatographic purification.

$^1$H-NMR (400 MHz, DMSO-D6): δ 1.30 (2s, 3H), 3.59 (d, 2H), 3.72 (s, 3H), 4.36 (m, 1H), 6.90 (d, 1H), 7.91 (d, 1H), 8.02 (d, 2H), 8.15 (d, 2H), 8.56 (s, 1H), 9.31 (bs, 1H), 10.42 (bs, 1H).

MS: 388 (MH+)

Example 5.13

(RS)—S-(4-{[4-(cyclohexylamino)-5-(2-methyl-2H-tetrazol-5-yl)pyrimidine-2-yl]amino}phenyl)-S-methylsulfoximide

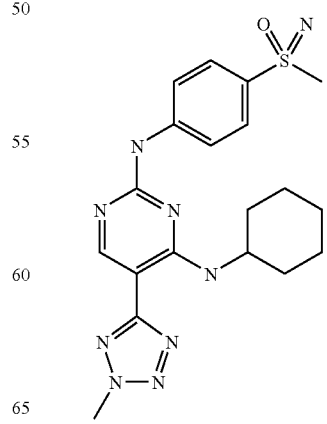

117 mg (0.23 mmol) (RS)—S-(4-{[4-(cyclohexylamino)-5-(2-methyl-2H-tetrazol-5-yl)pyrimidine-2-yl]amino}phenyl)-N-(ethoxycarbonyl)-S-methylsulfoximide) (Ex. 3.1) in 1.7 ml ethanol are treated with 0.4 mL (0.61 mmol) of a freshly prepared 1.53 molar sodium ethanolate solution and stirred for 7 hours at 60° C. The mixture is diluted with 2 mL ethanol and then treated with a further 1.0 ml (1.53 mmol) of the 1.53 molar sodium ethanolate solution. After 24 hours at 60° C., the mixture is heated to 70° C. and stirred for a further 20 hours. The mixture is treated with saturated NaCl solution and extracted with THF. The combined organic phases are dried ($Na_2SO_4$), filtered and concentrated. The resulting residue is chromatographically (DCM/EtOH 95:5) purified. 76 mg (0.18 mmol, corresponding to 76% of theor.) of the product is obtained.

$^1$H-NMR (DMSO): 9.99 (s, 1H), 8.72 (s, 1H), 7.99 (m, 2H), 7.75 (m, 3H), 4.41 (s, 3H), 4.08 (m, 1H), 3.99 (s, 1H), 3.01 (s, 3H), 2.05 (m, 2H), 1.75 (m, 2H), 1.63 (m, 1H), 1.39 (m, 5H).

MS: 428 (ES+)

Ex. 5.14

(RS)—S-(4-{[4-(cyclohexylamino)-5-(1-methyl-1H-tetrazol-5-yl)pyrimidine-2-yl]-amino}phenyl)-S-methylsulfoximide

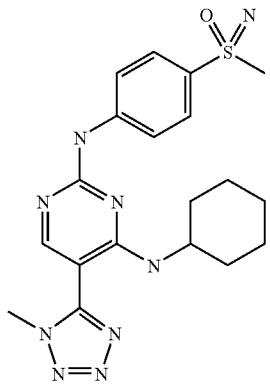

12 mg (0.024 mmol) (RS)—S-(4-{[4-(cyclohexylamino)-5-(1-methyl-1H-tetrazol-5-yl)pyrimidine-2-yl]amino}phenyl)-N-(ethoxycarbonyl)-S-methylsulfoximide (Ex. 3.2) in 1.2 ml ethanol are treated with 0.12 mL (0.18 mmol) of a freshly prepared 1.53 molar sodium ethanolate solution and stirred for 18 hrs at 70° C. The mixture is treated with saturated NaCl solution and extracted with THF. The combined organic phases are dried ($Na_2SO_4$), filtered and concentrated. The resulting residue is digested with MTB ether. 9 mg (0.021 mmol, corresponding to 86% of theor.) of the product is obtained.

$^1$H-NMR (DMSO): 10.00 (s, 1H), 8.71 (s, 1H), 7.99 (m, 2H), 7.76 (m, 2H), 7.61 (d, 1H), 4.11 (s, 3H), 4.00 (m, 2H), 3.01 (s, 3H), 1.97 (m, 2H), 1.75 (m, 2H), 1.62 (m, 1H), 1.39 (m, 5H).

Example 5.15

(RS)—S-(4-{[4-(cyclohexylamino)-5-(2H-tetrazol-5-yl)pyrimidine-2-yl]amino}phenyl)-S-methylsulfoximide

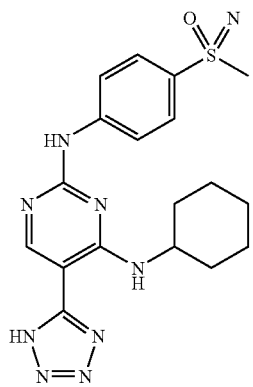

80 mg (0.16 mmol) (RS)—S-(4-{[4-(cyclohexylamino)-5-(2H-tetrazol-5-yl)-pyrimidine-2-yl]amino}phenyl)-N-(ethoxycarbonyl)-S-methylsulfoximide (Example 2.1) in 1.2 ml ethanol are treated with 0.43 mL (0.66 mmol) of a freshly prepared 1.53 molar sodium ethanolate solution and stirred for 7 hours at 60° C. Next, a further 1.0 ml (1.53 mmol) of the 1.53 molar sodium ethanolate solution is added and the mixture stirred for a further 7 hours at 70° C. The mixture is treated with saturated NaCl solution and extracted with THF. The combined organic phases are dried ($Na_2SO_4$), filtered and concentrated. The resulting residue is purified by HPLC, and 58 mg (0.14 mmol, corresponding to 85% of theor.) of the product is obtained.

Column: Purospher Star C18 5μ 125×25 mm
Eluents: A: H2O B: acetonitrile
Buffer: A/0.1% TFA
Gradient: 76% A+24% B(1')_24->38% B(10')->95% B(0.5')
Flow rate: 25.0 mL/min
Detection: PDA; MS-ESI+
Temperature: RT $^1$H-NMR (DMSO): 10.38 (s, 1H), 8.73 (s, 1H), 8.42 (d, 1H), 8.17 (m, 2H), 7.95 (m, 2H), 4.14 (br, 1H), 3.03 (s, 3H), 2.12 (m, 2H), 1.78 (m, 2H), 1.66 (m, 1H), 1.35 (m, 5H).

MS: 414 (ES+)

Example 5.16

(RS)—S-(4-{[5-(2-benzyl-2H-tetrazol-5-yl)-4-(cyclohexylamino)pyrimidine-2-yl]-amino}phenyl)-S-methylsulfoximide

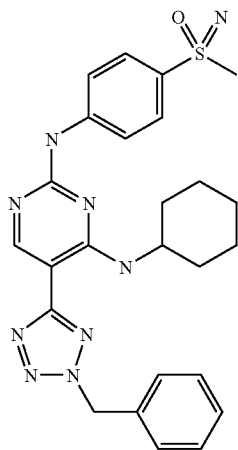

28 mg (0.048 mmol) (RS)—S-(4-{[5-(2-benzyl-2H-tetrazol-5-yl)-4-(cyclohexyl-amino)pyrimidine-2-yl]amino}phenyl)-N-(ethoxycarbonyl)-S-methylsulfoximide in 0.4 ml ethanol are treated with 78 µL (0.119 mmol) of a freshly prepared 1.53 molar sodium ethanolate solution and stirred for 22 hours at 60° C. Next, a further 0.15 ml (0.229 mmol) of the 1.53 molar sodium ethanolate solution is added, and the mixture stirred for a further 22 hours at 60° C. The mixture is treated with saturated NaCl solution and extracted with ethyl acetate. The combined organic phases are dried (Na$_2$SO$_4$), filtered and concentrated. 24 mg (0.048 mmol, corresponding to 100% of theor.) of the product is obtained.

$^1$H-NMR (DMSO): 10.05 (s, 1H), 8.71 (s, 1H), 7.98 (m, 2H), 7.75 (m, 3H), 7.39 (m, 5H), 5.98 (s, 2H), 4.03 (m, 2H), 3.01 (s, 3H), 2.01 (m, 2H), 1.70 (m, 2H), 1.61 (m, 1H), 1.25 (m, 5H).

MS: 504 (ESI)

Example 5.17

(RS)—S-(3-{[4-{[(R)-2-Hydroxy-1-methylethyl]amino}-5-(4-ethoxyphenyl)pyrimidin-2-yl]amino}phenyl)-S-methylsulfoximide (RS)—S-(3-{[4-{[(R)-2-Hydroxy-1-methylethyl]amino}-5-(4-ethoxyphenyl)pyrimidin-2-yl]amino}phenyl)-S-methylsulfoximide is prepared according to procedure 14a from (RS)—N-(Ethoxycarbonyl)-S-(3-{[4-{[(R)-2-hydroxy-1-methylethyl]amino}-5-(4-ethoxy-phenyl)-pyrimidin-2-yl]amino}phenyl)-S-methylsulfoximide (133 mg, 0.26 mmol). The reaction mixture is worked up as described in procedure 14a and the crude product is purified by flash column chromatography to give the target compound in 32% yield.

$^1$H-NMR (400 MHz, DMSO): 9.47 (s, 1H); 8.66-8.71 (m, 1H); 7.73-7.81 (m, 1H); 7.71 (s, 1H); 7.34-7.46 (m, 2H); 7.28 (d, 2H); 6.98 (d, 2H); 5.77 (t, 1 H); 4.74-4.90 (m, 1H); 4.26-4.38 (m, 1H); 4.13 (s br, 1H); 4.03 (q, 2 H); 3.32-3.48 (m, 2H); 1.32 (t, 3H); 1.12 (d, 3H).

MS (ESI): [M+H]$^+$=442.

The following example compounds were prepared according to procedure 14a or 14b (vide infra) from the respective N-ethoxycarbonyl sulfoximines (such as (RS)—N-(Ethoxycarbonyl)-S-(3-{[4-{methyl-sulfanyl}-5-(4-ethoxy-phenyl)-pyrimidin-2-yl]amino}phenyl)-S-methylsulfoximide or (RS)N-(Ethoxycarbonyl)-S-(4-{[4-{[(R)-2-hydroxy-1-methylethyl]amino}-5-(4-ethoxy-phenyl)-pyrimidin-2-yl]amino}phenyl)-S-methylsulfoximide) and sodium ethoxide in ethanol:

TABLE 3

| Example | procedure | Structure | Name | Analytical date |
|---|---|---|---|---|
| 5.18 | 14b | 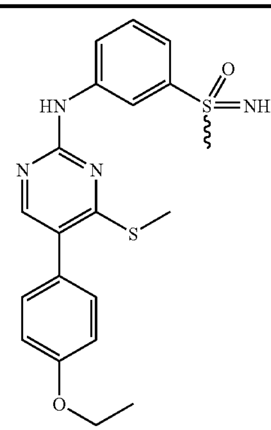 | (RS)-S-(3-{[4-{methylsulfanyl}-5-(4-ethoxyphenyl)-pyrimidin-2-yl]amino}phenyl)-S-methylsulfoximide | $^1$H-NMR (DMSO, 400 MHz): 9.98 (s, 1 H); 8.61 (s, 1 H); 8.04 (s, 1 H); 7.75-7.83 (m, 1 H); 7.44-7.52 (m, 2 H); 7.34 (d, 2 H); 6.97 (d, 2 H); 4.10 (s, 1 H); 4.02 (q, 2 H); 3.00 (s, 3 H); 2.53 (s, 3 H); 1.31 (t, 3 H). MS (ESI): [M + H]$^+$ = 415. |

TABLE 3-continued

| Example | procedure | Structure | Name | Analytical date |
|---|---|---|---|---|
| 5.19 | 14a | 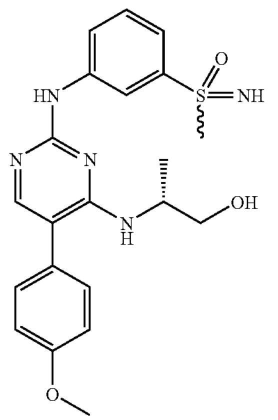 | (RS)-S-(3-{[4-{[(R)-2-Hydroxy-1-methylethyl]amino}-5-(4-methoxyphenyl)-pyrimidin-2-yl]amino}phenyl)-S-methylsulfoximide | $^1$H-NMR (DMSO, 400 MHz): 9.48 (s, 1 H); 8.66-8.72 (m, 1 H); 7.73-7.81 (m, 1 H); 7.71 (s, 1 H); 7.35-7.45 (m, 2 H); 7.31 (d, 2 H); 7.00 (d, 2 H); 5.78 (t, 1 H); 4.74-4.88 (m, 1 H); 4.28-4.39 (m, 1 H); 4.14 (s br, 1 H); 3.76 (s, 3 H); 3.32- 3.48 (m, 2 H); 2.98 (s, 3 H); 1.12 (d, 3 H). MS (ESI): [M + H]$^+$ = 428. |
| 5.20 | 14a | 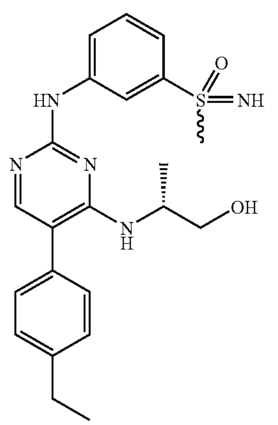 | (RS)-S-(3-{[4-{[(R)-2-Hydroxy-1-methylethyl]amino}-5-(4-ethyl-phenyl)pyrimidin-2-yl]amino}phenyl)-S-methylsulfoximide | $^1$H-NMR (DMSO, 300 MHz): 9.49 (s, 1 H); 8.66-8.72 (m, 1 H); 7.71-7.83 (m, 2 H); 7.36-7.48 (m 2 H); 7.28 (s, 4 H); 5.84 (t, 1 H); 4.76-4.88 (m, 1 H); 4.26-4.42 (m, 1 H); 4.10 (s br, 1 H); 3.33-3.51 (m, 2 H); 3.00 (s, 3 H); 2.62 (q, 2 H); 1.18 (t, 3 H); 1.12 (d, 3 H). MS (ESI):. [M + H]$^+$ = 426. |
| 5.21 | 14a | 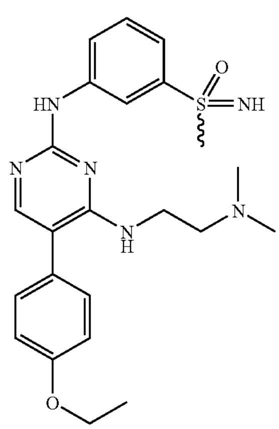 | (RS)-S-(3-{[4-{[2-dimethylamino-ethyl]amino}-5-(4-ethoxyphenyl)-pyrimidin-2-yl]amino}phenyl)-S-methylsulfoximide | $^1$H-NMR (DMSO, 400 MHz): 9.54 (s, 1 H); 8.69 (s, 1 H); 7.89 (d br, 1 H); 7.72 (s, 1 H); 7.33-7.46 (m, 2 H); 7.27 (d, 2 H); 6.98 (d, 2 H); 6.21 (t br, 1 H); 4.12 (s br, 1 H); 4.03 (q, 2 H); 3.42-3.54 (m, 2 H); 2.98 (s, 3 H); 2.33-2.48 (m, 2 H); 2.12 (s, 6 H); 1.32 (t, 3 H). MS (ESI): [M + H]$^+$ = 455 |

TABLE 3-continued

| Example | procedure | Structure | Name | Analytical date |
|---------|-----------|-----------|------|-----------------|
| 5.22 | 14a | 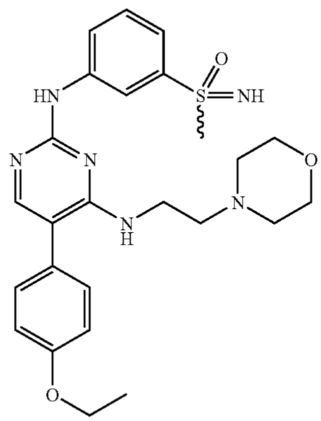 | (RS)-S-(3-{[4-{[2-N-morpholine-ethyl]amino}-5-(4-ethoxyphenyl)-pyrimidin-2-yl]amino}phenyl)-S-methylsulfoximide | $^1$H-NMR (CDCl$_3$, 400 MHz): 8.77 (s, 1 H); 7.82 (s, 1 H); 7.52-7.65 (m, 3 H); 7.44 (t, 1 H); 7.28 (d, 2 H); 6.99 (d, 2 H); 5.97 (t br, 1 H); 4.08 (q, 2 H); 3.53-3.70 (m, 6 H); 3.12 (s, 3 H); 2.52-2.66 (m, 2 H); 2.37-2.49 (m, 4 H); 1.48 (t, 3 H). MS (ESI): [M + H]$^+$ = 497. |
| 5.23 | 14a | 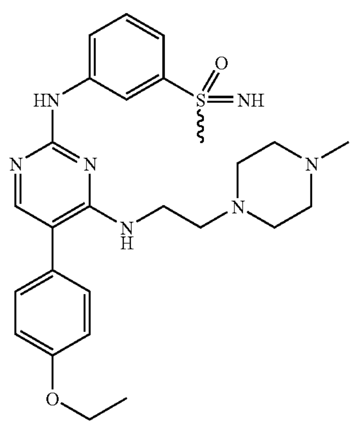 | (RS)-S-(3-{[4-{[2-N-(4-mehyl-piperazine)-ethyl]amino}-5-(4-ethoxyphenyl)-pyrimidin-2-yl]amino}phenyl)-S-methylsulfoximide | $^1$H-NMR (DMSO, 400 MHz): 9.46 (s, 1 H); 8.62 (s, 1 H); 7.82-7.89 (m, 1 H); 7.73 (s, 1 H); 7.34-7.43 (m, 2 H); 7.28 (d, 2 H); 6.98 (d, 2 H); 6.25 (t br, 1 H); 3.97-4.11 (m, 3 H); 3.42-3.55 (m, 2 H); 2.98 (s, 3 H); 2.08 (s, 3 H); 2.05-2.57 (m, 10 H); 1.31 (t, 3 H). MS (ESI): [M + H]$^+$ = 510. |
| 5.24 | 14b | 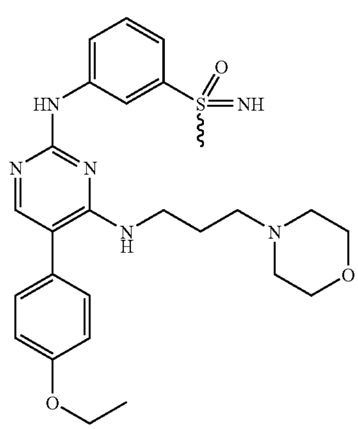 | (RS)-S-(3-{[4-{[3-N-morpholine-propyl]amino}-5-(4-ethoxyphenyl)-pyrimidin-2-yl]amino}phenyl)-S-methylsulfoximide | $^1$H-NMR (DMSO, 400 MHz): 9.43 (s, 1 H); 8.63 (s, 1 H); 7.85 (d br, 1 H); 7.68 (s, 1 H); 7.35-7.44 (m, 2 H); 7.26 (d, 2 H); 6.97 (d, 2 H); 6.46 (t br, 1 H); 3.98-4.07 (m, 3 H); 3.41-3.53 (m, 2 H); 3.31-3.38 (m, 4 H); 2.98 (s, 3 H); 2.28 (t, 2 H); 2.24 (s br, 4 H); 1.62-1.73 (m, 2 H); 1.31 (t, 3 H). MS (ESI): [M + H]$^+$ = 511. |

TABLE 3-continued

| Example | procedure | Structure | Name | Analytical date |
|---|---|---|---|---|
| 5.25 | 14a | 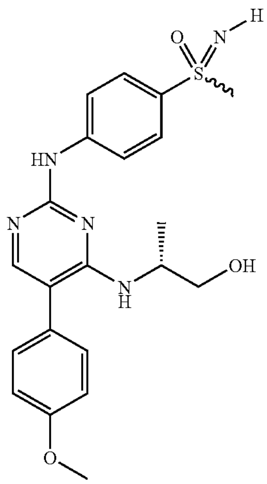 | (RS)-S-(4-{[4-{[(R)-2-Hydroxy-1-methylethyl]amino}-5-(4-methoxyphenyl)-pyrimidin-2-yl]amino}phenyl)-S-methylsulfoximide | $^1$H-NMR (DMSO, 400 MHz): 9.57 (s, 1 H); 7.96 (d, 2 H); 7.75 (s, 1 H); 7.74 (d, 2 H); 7.30 (d, 2 H); 7.01 (d, 2 H); 5.81 (d, 1 H); 4.78 (br. s, 1 H); 4.20-4.29 (m, 1 H); 3.91 (s, 1 H); 3.76 (s, 3 H); 3.43 (m, 2 H); 2.98 (s, 3 H); 1.13 (d, 3 H). MS (ESI): [M + H]$^+$ = 428. |
| 5.26 | 14a | 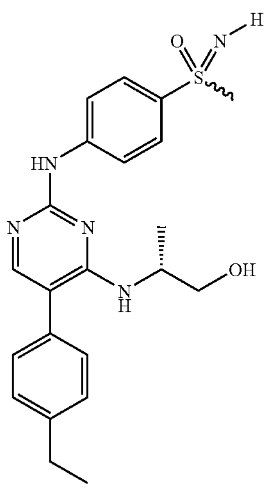 | (RS)-S-(4-{[4-{[(R)-2-Hydroxy-1-methylethyl]amino}-5-(4-ethylphenyl)-pyrimidin-2-yl]amino}phenyl)-S-methylsulfoximide | $^1$H-NMR (DMSO, 300 MHz): 9.59 (s, 1 H); 7.96 (d, 2 H); 7.77 (s, 1 H); 7.74 (d, 2 H); 7.29 (s [higher order], 4 H); 5.88 (d, 1 H); 4.79 (t, 1 H); 4.19-4.30 (m, 1 H); 3.92 (s, 1 H); 3.44 (t, 2 H); 2.98 (s, 3 H); 2.62 (q, 2 H); 1.19 (t, 3 H); 1.13 (d, 3 H). MS (ESI): [M + H]$^+$ = 426. |
| 5.27 | 14a | 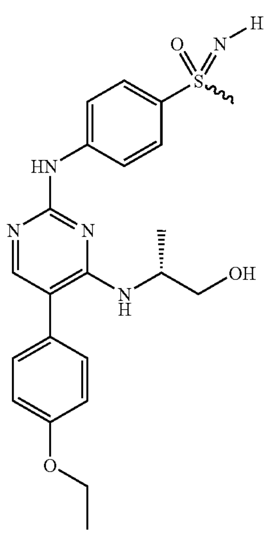 | (RS)-S-(4-{[4-{[(R)-2-Hydroxy-1-methylethyl]amino}-5-(4-ethoxyphenyl)-pyrimidin-2-yl]amino}phenyl)-S-methylsulfoximide | $^1$H-NMR (DMSO, 400 MHz): 9.57 (s, 1 H); 7.95 (d, 2 H); 7.74 (s, 1 H); 7.74 (d, 2 H); 7.28 (d, 2 H); 6.99 (d, 2 H); 5.81 (d, 1 H); 4.78 (t, 1 H); 4.18-4.28 (m, 1 H); 4.03 (q, 2 H); 3.92 (s, 1 H); 3.43 (t, 2 H); 2.98 (s, 3 H); 1.32 (t, 3H); 1.13 (d, 3 H). MS (ESI): [M + H]$^+$ = 442. |

Example 5.28

(RS)-(4-{[4-{methylsulfanyl}-5-(thiophen-2-yl)-pyrimidin-2-yl]amino}phenyl)-S-methylsulfoximine

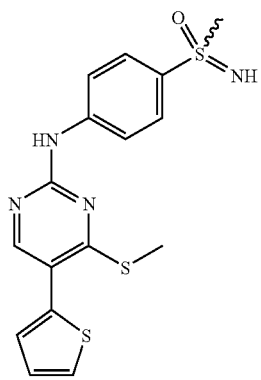

Preparation by Procedure 14b.

$^1$H-NMR (300 MHz, DMSO-D$_6$): δ 2.56 (s, 3H), 3.00 (s, 3H), 4.00 (s, 1H), 7.15 (dd, 1H), 7.31 (dd, 1H), 7.65 (dd, 1H), 7.81 (d, 2H), 7.95 (d, 2H), 8.28 (s, 1H), 10.19 (bs, 1H).

MS: 377 (MH+).

Example 5.29

(RS)-(4-{[4-{[2-acetoxy-ethyl]amino}-5-(thiophen-2-yl)-pyrimidin-2-yl]amino}phenyl)-S-methylsulfoximine

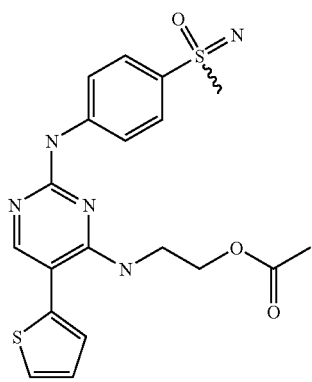

Preparation by Procedure 14a. In this case the sulfoximine is deprotected and the OH function is acetylated starting with (RS)—N-(ethoxycarbonyl)-S-[4-({4-[(2-hydroxyethyl)amino]-5-(2-thienyl)-pyrimidine-2-yl}amino)phenyl]-S-methylsulfoximide.

$^1$H-NMR (600 MHz, DMSO-D$_6$): δ 2.00 (s, 3H), 3.02 (s, 3H), 3.69 (q, 2H), 4.05 (bs, 1H), 4.24 (t, 2H), 6.87 (t, 1H), 7.18 (m, 2H), 7.61 (m, 1H), 7.80 (d, 2H), 7.96 (s, 1H), 7.98 (d, 2H), 9.76 (s, 1H).

MS: 432 (MH+).

7. Process Variation 7 (See Also Scheme 9)

General Procedure

Procedure 15—In Situ Sulfide oxidation-amine Displacement

To a solution of the respective pyrimidin-4-yl thioether (1 eq.) in N-methylpyrrolidin-2-one (0.1 M) is added meta-chlorobenzoic acid (1.1-1.5 eq.) and the mixture is stirred for 1-2 h at room temperature. Subsequently, triethylamine (2.5-5.0 eq.) and the respective nucleophile, e.g. an amine is added and the mixture is stirred at 50-90° C. The reaction is monitored by TLC and is typically completed within 3 to 6 hours. After cooling to room temperature, water is added and the mixture is extracted with ethyl acetate. The combined organic layers are washed with brine, dried, and concentrated in vacuo. The crude products are purified by flash column chromatography, optionally followed by recrystallisation from a suitable solvent, e.g. diethyl ether.

Compounds which were Prepared by Process Variation 7

Example 6.1

(RS)—N-(Ethoxycarbonyl)-S-(3-{[4-{[2-dimethyl-amino-ethyl]amino}-5-(4-ethoxy-phenyl)-pyrimidin-2-yl]amino}phenyl)-S-methylsulfoximide

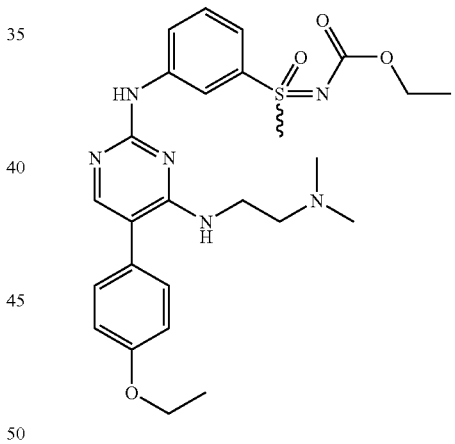

(RS)—N-(Ethoxycarbonyl)-S-(3-{[4-{[2-dimethyl-amino-ethyl]amino}-5-(4-ethoxy-phenyl)-pyrimidin-2-yl]amino}phenyl)-S-methylsulfoximide is prepared according to procedure 15 from (RS)—N-(Ethoxycarbonyl)-S-(3-{[4-{methyl-sulfanyl}-5-(4-ethoxy-phenyl)-pyrimidin-2-yl]amino}phenyl)-S-methylsulfoximide (243 mg, 0.50 mmol) and N1,N1-dimethylethan-1,2-diamine (110 µL, 1.00 mmol). The reaction mixture is worked up as described in procedure 15 and the crude product is purified by flash column chromatography to give the target compound in 68% yield.

$^1$H-NMR (400 MHz, DMSO); 9.59 (s, 1H); 8.63 (s, 1H); 7.97 (d br, 1H); 7.72 (s, 1H); 7.48 (t, 1H); 7.38 (d br, 1H); 7.27 (d, 2H); 6.98 (d, 2H); 6.24 (t br, 1H); 4.04 (q, 2H); 3.81-3.95 (m, 2H); 3.41-3.54 (m, 2H); 3.39 (s, 3H); 2.40 (t, 2H); 2.11 (s, 6H); 1.32 (t, 3H); 1.05 (t, 3H.

MS (ESI): [M+H]$^+$=527.

The following example compounds are prepared according to procedure 15 from the respective 4-thiomethyl pyrimidine analogues (such as (RS)—N-(Ethoxycarbonyl)-S-(3-{[4-{methyl-sulfanyl}-5-(4-ethoxy-phenyl)-pyrimidin-2-yl]amino}phenyl)-S-methylsulfoximide) and the respective amines:

TABLE 4

| Example | Structure | Name | Analytical date |
|---|---|---|---|
| 6.2 | 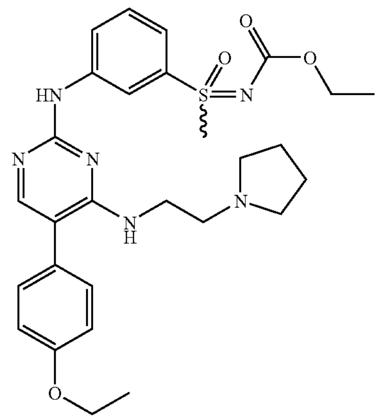 | (RS)-N-(Ethoxycarbonyl)-S-(3-{[4-{[2-N-pyrrolidine-ethyl]amino}-5-(4-ethoxy-phenyl)-pyrimidin-2-yl]amino}phenyl)-S-methylsulfoximide | $^1$H-NMR (CHCl$_3$, 300 MHz): 8.76 (s, 1 H); 7.85 (s, 1 H); 7.76 (d br, 1 H); 7.47-7.62 (m, 2 H); 7.28-7.35 (m, 3 H); 7.01 (d, 2 H); 5.93 (t br, 1 H); 4.07-4.23 (m, 4 H); 3.59-3.70 (m, 2 H); 3.36 (s, 3 H); 2.26 (t, 2 H); 2.57 (s br, 4 H); 1.72- 1.85 (m, 4 H); 1.48 (t, 3 H); 1.27 (t, 3 H). MS (ESI): [M + H]$^+$ = 553. |
| 6.3 | 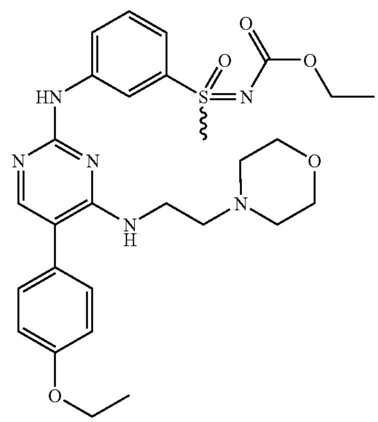 | (RS)-N-(Ethoxycarbonyl)-S-(3-{[4-{[2-N-morpholine-ethyl]amino}-5-(4-ethoxy-phenyl)-pyrimidin-2-yl]amino}phenyl)-S-methylsulfoximide | $^1$H-NMR (DMSO, 300 MHz): 9.62 (s 1 H); 8.71 (s, 1 H); 7.98 (d br, 1 H); 7.80 (s, 1 H), 7.53 (t, 1 H); 7.41 (d br, 1 H); 7.34 (d, 2 H), 7.04 (d, 2 H); 6.33 (t br, 1 H); 4.08 (q, 2 H); 3.85-4.00 (m, 2 H); 3.47-3.60 (m, 6 H); 3.41 (s, 3 H); 2.50-2.58 (m, 2 H, partly covered by DMSO); 2.39 (s br, 4 H); 1.28 (t, 3 H); 1.10 (t, 3 H). MS (ESI): [M + H]$^+$ = 569. |
| 6.4 | 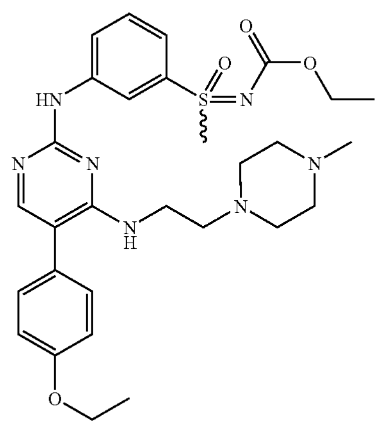 | (RS)-N-(Ethoxycarbonyl)-S-(3-{[4-{[2-N-(4-methyl-piperazine)-ethyl]amino}-5-(4-ethoxy-phenyl)-pyrimidin-2-yl]amino}phenyl)-S-methylsulfoximide | $^1$H-NMR (DMSO, 400 MHz): 9.59 (s, 1 H); 8.70 (s, 1 H); 7.93 (d br, 1 H); 7.74 (s, 1 H); 7.49 (t, 1 H); 7.38 (d br, 1 H); 7.29 (d, 2 H); 6.99 (d, 2 H); 6.29 (t br, 1 H); 4.05 (q, 2 H); 3.82-3.93 (m, 2 H); 3.42-3.50 (m, 2 H); 3.37 (s, 3 H); 2.11 (s, 3 H); 2.04-2.56 (m, 10 H); 1.32 (t, 3 H); 1.05 (t, 3 H). MS (ESI): [M + H]$^+$ = 582. |

TABLE 4-continued

| Example | Structure | Name | Analytical date |
|---|---|---|---|
| 6.5 | 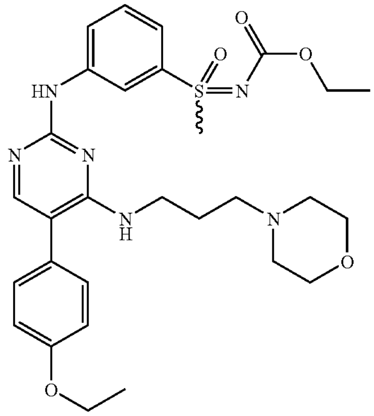 | (RS)-N-(Ethoxycarbonyl)-S-(3-{[4-{[3-N-morpholine-propyl]amino}-5-(4-ethoxy-phenyl)-pyrimidin-2-yl]amino}phenyl)-S-methylsulfoximide | $^1$H-NMR (DMSO, 400 MHz): 9.57 (s, 1 H); 8.68 (s, 1 H); 7.88-7.96 (m, 1 H); 7.70 (s, 1 H); 7.49 (t, 1 H); 7.34-7.40 (m, 1 H); 7.26 (d, 2 H); 6.98 (d, 2 H); 6.53 (t br, 1 H); 4.02 (q, 2 H); 3.81-3.93 (m, 2 H); 3.42-3.56 (m, 2 H); 3.36 (s, 3 H); 3.28-3.40 (m, 4 H); 2.28 (t, 2 H); 2.23 (s br, 4 H); 1.61-1.72 (m, 2 H); 1.31 (t, 3 H); 1.03 (t, 3 H). MS (ESI): [M + H]$^+$ = 583. |
| 6.6 | 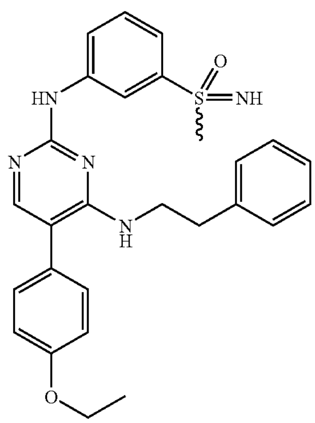 | (RS)-S-(3-{[4-{[2-phenyl-ethyl]amino}-5-(4-ethoxy-phenyl)pyrimidin-2-yl]amino}phenyl)-S-methylsulfoximide | $^1$H-NMR (DMSO, 400 MHz): 9.43 (s, 1 H); 8.48 (s, 1 H); 7.94-8.03 (m, 1 H); 7.70 (s, 1 H); 7.36-7.44 (m, 2 H); 7.21-7.29 (m, 2 H); 7.10-7.20 (m, 54 H); 6.93 (d, 2 H); 6.26 (t br, 1 H); 4.02 (m, 3 H); 3.63 (m, 2 H); 2.97 (s, 3 H); 2.84 (t, 2 H); 1.30 (t, 3 H). MS (ESI): [M + H]$^+$ = 488. |
| 6.7 | 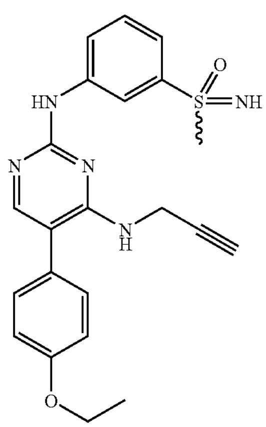 | (RS)-S-(3-{[4-{[2-propargyl]amino}-5-(4-ethoxy-phenyl)pyrimidin-2-yl]amino}phenyl)-S-methylsulfoximide | $^1$H-NMR (CDCl$_3$, 300 MHz): 8.64-8.69 (m, 1 H); 7.86 (s, 1 H); 7.73 (dd, 1 H); 7.51-7.64 (m, 2 H); 7.46 (t, 1 H); 7.26 (d, 2 H); 6.99 (d, 2 H); 5.22 (t br, 1 H); 4.27-4.37 (m, 2 H); 4.08 (q, 2 H); 3.13 (s, 3 H); 2.21 (t, 1 H); 1.43 (t, 3H). MS (ESI): [M + H]$^+$ = 422. |

Example 6.8

N-{5-(2-thienyl)-2-[(4-{(RS)—S-[ethoxycarbonyl]-S-methyl-sulfoximide}-phenyl)amino]pyrimidin-4-yl}-glycin-tert-butyl ester

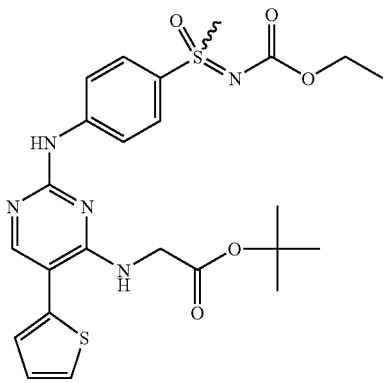

Preparation by Procedure 15.

$^1$H-NMR (400 MHz, DMSO-D$_6$): δ 1.07 (t, 3H), 1.31 (s, 9H), 3.37 (s, 3H), 3.89 (m, 2H), 4.03 (m, 2H), 7.08 (t, 1H), 7.18 (m, 2H), 7.60 (dd, 1H), 7.76 (d, 2H), 7.98 (d, 2H), 7.99 (s, 1H), 9.88 (s, 1H).

Example 6.9

(RS)—N(ethoxycarbonyl)-(4-{[4-{(3-oxo-butyl}amino)-5-(thiophen-2-yl)-pyrimidin-2-yl]amino}phenyl)-S-methylsulfoximide

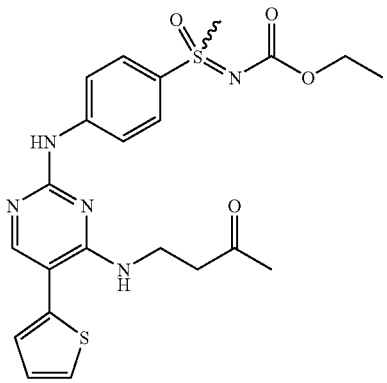

a) (RS)—N(ethoxycarbonyl)-(4-{[4-{(3-hydroxy-butyl)amino}-5-(thiophen-2-yl)-pyrimidin-2-yl]amino}phenyl)-S-methylsulfoximide

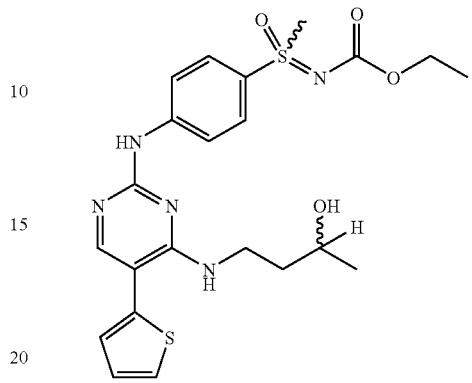

Preparation by Procedure 15.

$^1$H-NMR (300 MHz, DMSO-D$_6$): δ 1.12 (m, 6H), 1.67 (m, 2H), 3.42 (s, 3H), 3.54 (m, 2H), 3.77 (m, 1H), 3.94 (m, 2H), 4.68 (d, 1H), 6.92 (t, 1H), 7.20 (m, 2H), 7.61 (dd, 1H), 7.81 (d, 2H), 7.95 (s, 1H), 8.10 (d, 2H), 9.86 (s, 1H).

MS: 490 (MH+).

b) (RS)—N(ethoxycarbonyl)-(4-{[4-{(3-oxo-butyl)amino}-5-(thiophen-2-yl)-pyrimidin-2-yl]amino}phenyl)-S-methylsulfoximide

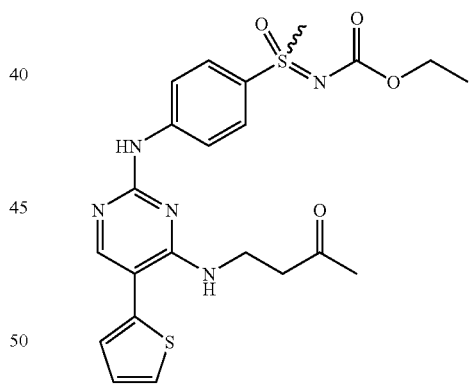

(RS)—N(ethoxycarbonyl)-(4-{[4-{(3-hydroxybutyl)amino}-5-(thiophen-2-yl)-pyrimidin-2-yl]amino}phenyl)-S-methylsulfoximide (169 mg, 0.35 mmol) is dissolved in dichloromethane (15 ml) and N-methylmorpholin-N-oxid (123 mg, 1.05 mmol) and molecular sieve (4 A, 496 mg) is added. The mixture is stirred for 15 min at RT. Then tetrapropylammoniumperruthenat (6.3 mg, 0.018 mmol) is added, the reaction mixture is stirred for 24 h at RT. Additional tetrapropylammoniumperruthenat (10.4 mg, 0.03 mmol) is added and the reaction mixture is stirred for 24 h at RT. For workup the mixture is filtered through celite and washed with dichlo romethane. The solvent is evaporated resulting in the crude product which is purified by column chromatography: 39 mg, 23%.

$^1$H-NMR (300 MHz, DMSO-D$_6$): δ 1.07 (t, 3H), 2.08 (s, 3H), 2.80 (t, 2H), 3.37 (s, 3H), 3.60 (q, 2H), 3.89 (m, 2H), 6.72 (t, 1H), 7.14 (m, 2H), 7.58 (dd, 1H), 7.75 (d, 2H), 7.92 (s, 1H), 8.02 (d, 2H), 9.84 (s, 1H).

MS: 488 (MH+).

Example 6.10-6.33

(RS)—N(ethoxycarbonyl)-(4-{[4-{methylsulfanyl}-5-(thiophen-2-yl)-pyrimidin-2-yl]amino}phenyl)-S-methyl-sulfoximide (example 4.44) is transformed with the amines given in table 5 according to procedure 15 (after addition of the amines the reactions are heated to 100° C.) using a Chemspeed synthesis robot and HPLC-purification of the products.

TABLE 5

| Ex. No. | Amine used | Structure | Calc. Mol. Wt. | Found Mass (ESI)* | Found Retention time* |
|---|---|---|---|---|---|
| 6.10 | 4-(2-AMINOETHYL)-MORPHOLINE | 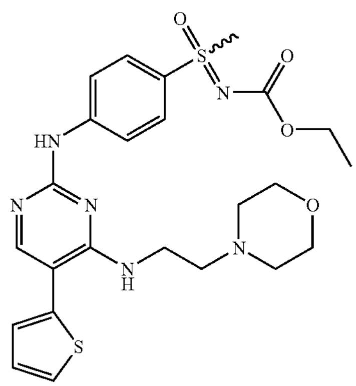 | 530.7 | 531.2 | 4.78 |
| 6.11 | N,N-DIMETHYL-1,3-PROPANEDIAMINE | 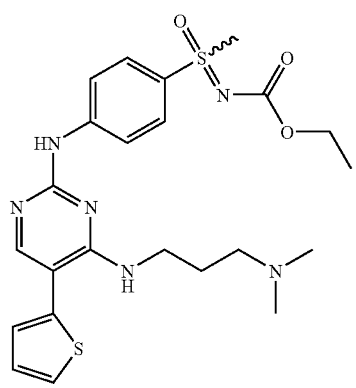 | 502.7 | 503.2 | 4.98 |
| 6.12 | TRYPTAMINE | 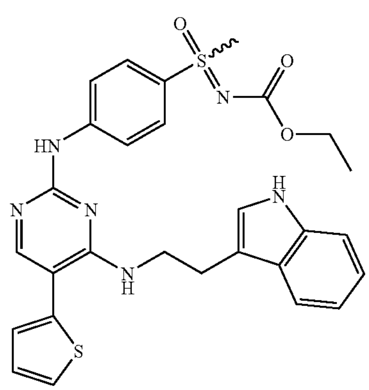 | 560.7 | 561.2 | 7.26 |

TABLE 5-continued

| Ex. No. | Amine used | Structure | Calc. Mol. Wt. | Found Mass (ESI)* | Found Retention time* |
|---|---|---|---|---|---|
| 6.13 | (R)-METHYLBENZYL-AMINE | 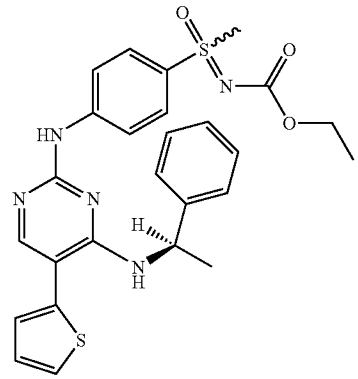 | 521.7 | 522.2 | 7.2 |
| 6.14 | 2-METHOXYISO-PROPYLAMINE | 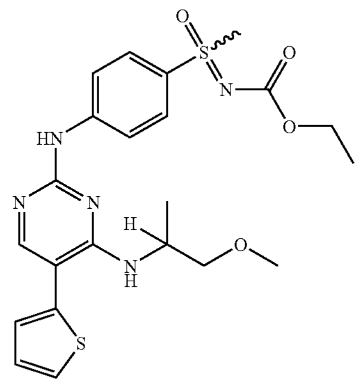 | 489.6 | 490.2 | 6.52 |
| 6.15 | 2-(AMINOMETH-YL)PYRIDINE | 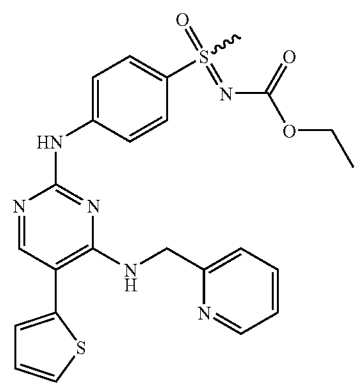 | 508.6 | 509.2 | 5.38 |
| 6.16 | 3-(AMINOMETH-YL)PYRIDINE | 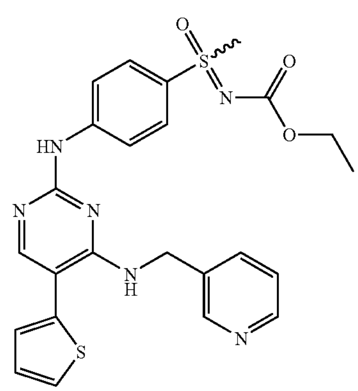 | 508.6 | 509.2 | 5.08 |

TABLE 5-continued

| Ex. No. | Amine used | Structure | Calc. Mol. Wt. | Found Mass (ESI)* | Found Retention time* |
|---|---|---|---|---|---|
| 6.17 | 4-(AMINOMETH-YL)PYRIDINE | 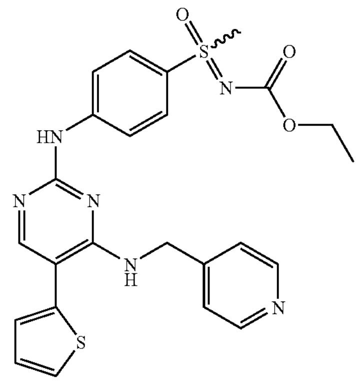 | 508.6 | 509.2 | 5.3 |
| 6.18 | CYCLOPENT-YLAMINE | 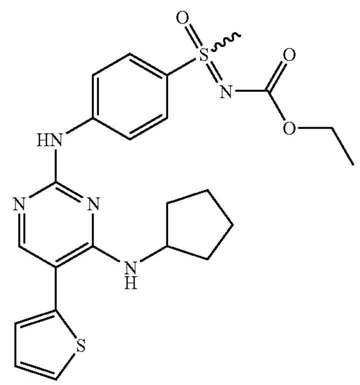 | 485.6 | 486.2 | 7.33 |
| 6.19 | (S)-3-AMINO-AZEPAN-2-ONE | 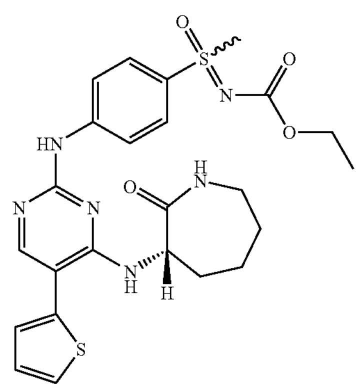 | 528.7 | 529.2 | 6.13 |
| 6.20 | TYRAMINE | 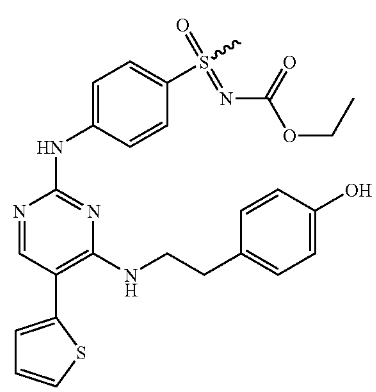 | 537.7 | 538.2 | 6.47 |

TABLE 5-continued

| Ex. No. | Amine used | Structure | | Calc. Mol. Wt. | Found Mass (ESI)* | Found Retention time* |
|---|---|---|---|---|---|---|
| 6.21 | C-BIPHENYL-2-YL-METHYLAMINE | 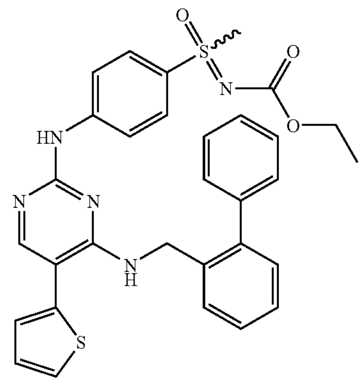 | | 583.7 | 584.2 | 7.84 |
| 6.22 | (S)-(+)-1-AMINO-2-PROPANOL | 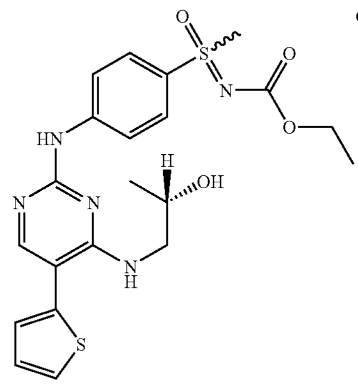 | Chiral | 475.6 | 476.2 | 5.67 |
| 6.23 | 3-AMINO-2,2-DIMETHYL-1-PROPANOL | 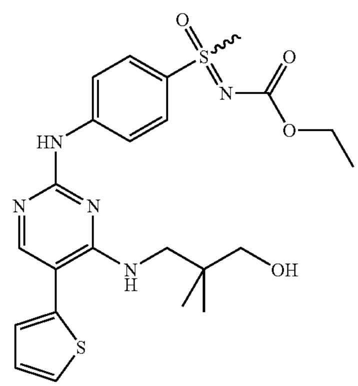 | | 503.6 | 504.2 | 6.34 |
| 6.24 | TETRAHYDRO-FURFURYL AMINE | 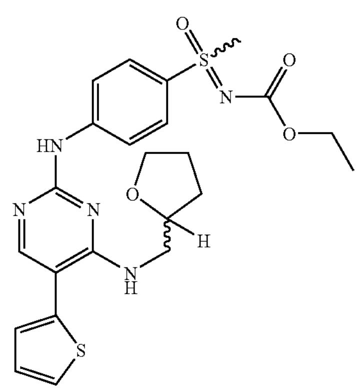 | | 501.6 | 502.2 | 6.28 |

TABLE 5-continued
| Ex. No. | Amine used | Structure | Calc. Mol. Wt. | Found Mass (ESI)* | Found Retention time* |
|---|---|---|---|---|---|
| 6.25 | AMINODIPHENYL-METHANE | 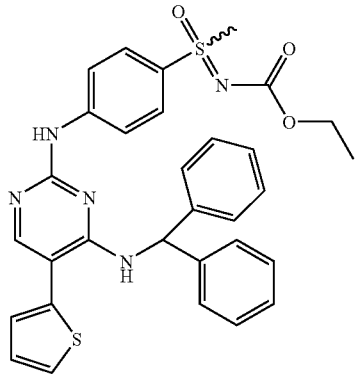 | 583.7 | 584.2 | 8.07 |
| 6.26 | 4-METHYL-BENZYLAMINE | 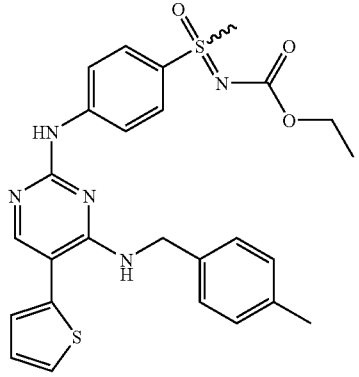 | 521.7 | 522.2 | 7.38 |
| 6.27 | 2-(AMINOMETH-YL)-1-ETHYL-PYRROLIDINE | 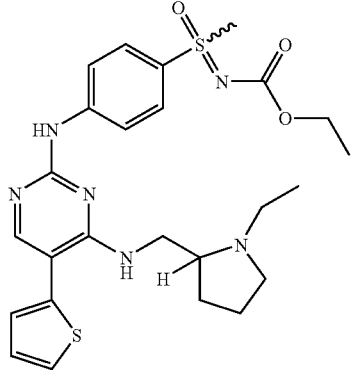 | 528.7 | 529.2 | 5.03 |
| 6.28 | D-PHENYL-ALANINOL | 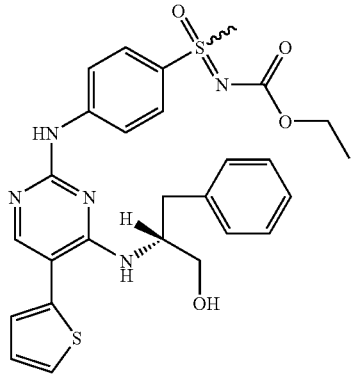 | 551.7 | 552.2 | 6.73 |

TABLE 5-continued

| Ex. No. | Amine used | Structure | | Calc. Mol. Wt. | Found Mass (ESI)* | Found Retention time* |
|---|---|---|---|---|---|---|
| 6.29 | 4-AMINO-1-BUTANOL | 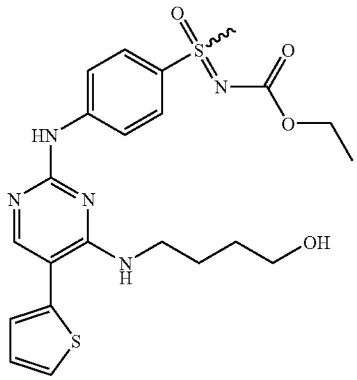 | | 489.6 | 490.2 | 5.81 |
| 6.30 | 2-AMINO-PENTANOL | 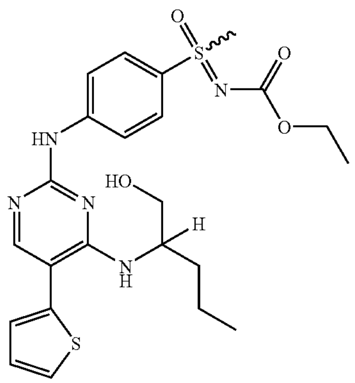 | | 503.6 | 504.2 | 6.48 |
| 6.31 | D-LEUCINOL | 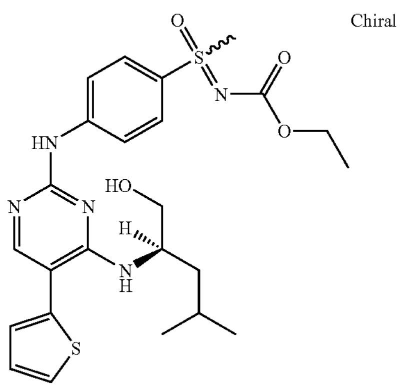 | Chiral | 517.7 | 518.2 | 6.58 |
| 6.32 | 2-PHENOXY-ETHYLAMINE | 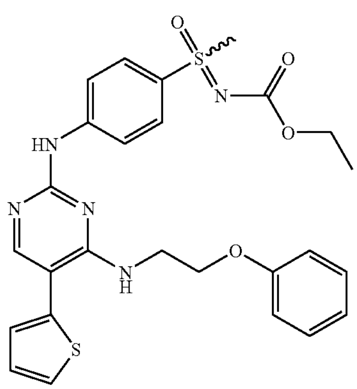 | | 537.7 | 538.2 | 7.49 |

TABLE 5-continued

| Ex. No. | Amine used | Structure | Calc. Mol. Wt. | Found Mass (ESI)* | Found Retention time* |
|---|---|---|---|---|---|
| 6.33 | N-(2-AMINOETHYL)-N-ETHYL-M-TOLUIDINE | 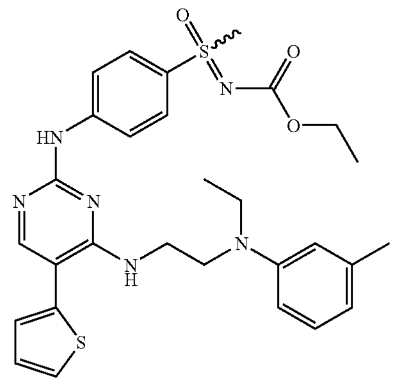 | 578.8 | 579.3 | 6.51 |

*taken from the analytical HPLC diagrams.

Analytical conditions: HPLC Pump 2525 Binary Gradient Module (Waters),
Detector Micromass ZQ (Waters), UV Lamp MUX UV 2488 Detector (Waters),
Column LiChroCart Purospher 125×4.5 mm RP 18e 5 μm,
Gradient used (CH$_3$CN and water each with 0.1% added trifluoroacetic acid):
Gradient: CH$_3$CN 5%/water 95% to CH$_3$CN 95%/water 5% within 15 mins,
Flow rate 1 ml/min
According to Process Variation 7 (see also Scheme 9) the following compounds can be prepared:

| Structure | Name |
|---|---|
| 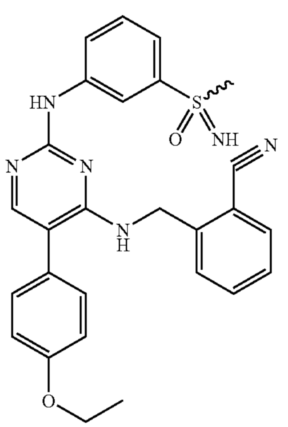 | (RS)-S-(3-{[4-{[(2-cyano-benzyl]amino}-5-(4-ethoxy-phenyl)pyrimidin-2-yl]amino}phenyl)-S-methylsulfoximide |

-continued

| Structure | Name |
|---|---|
| 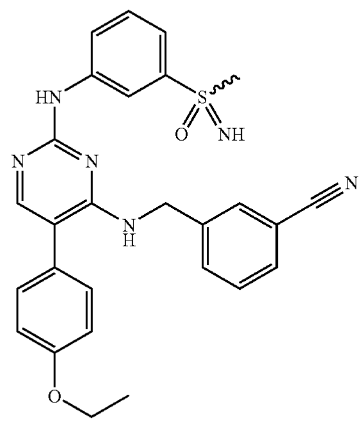 | (RS)-S-(3-{[4-{[(3-cyano-benzyl]amino}-5-(4-ethoxy-phenyl)pyrimidin-2-yl]amino}phenyl)-S-methylsulfoximide |
| 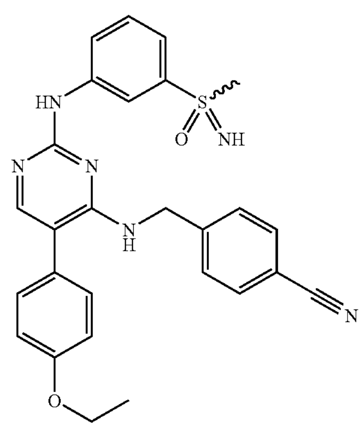 | (RS)-S-(3-{[4-{[4-cyano-benzyl]amino}-5-(4-ethoxy-phenyl)pyrimidin-2-yl]amino}phenyl)-S-methylsulfoximide |
| 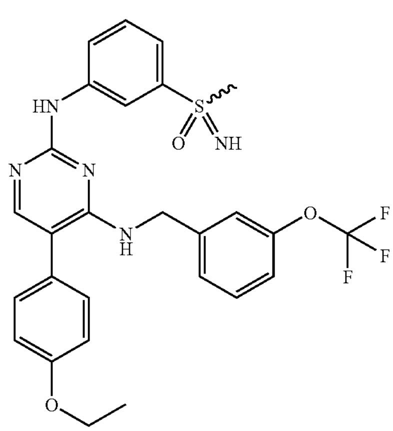 | (RS)-S-(3-{[4-{[3-trifluormethoxy-benzyl]amino}-5-(4-ethoxy-phenyl)pyrimidin-2-yl]amino}phenyl)-S-methylsulfoximide |

-continued

| Structure | Name |
|---|---|
| 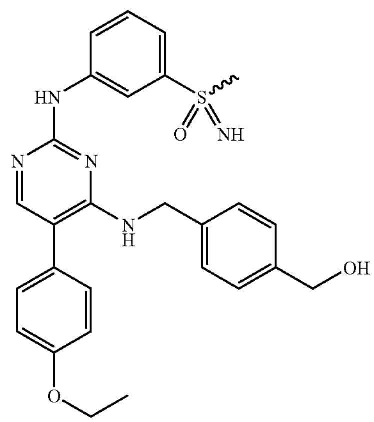 | (RS)-S-(3-{[4-{[4-hydroxymethyl-benzyl]amino}-5-(4-ethoxy-phenyl)pyrimidin-2-yl]amino}phenyl)-S-methylsulfoximide |
| 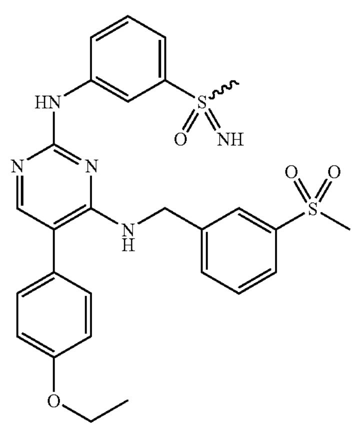 | (RS)-S-(3-{[4-{[3-methanesulfonyl-benzyl]amino}-5-(4-ethoxy-phenyl)pyrimidin-2-yl]amino}phenyl)-S-methylsulfoximide |
| 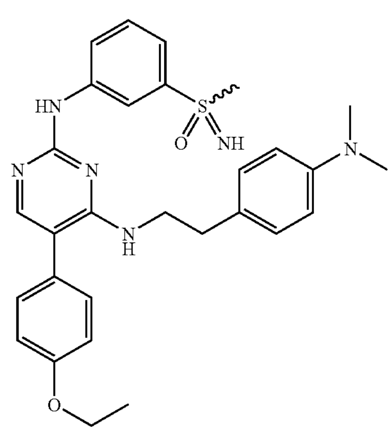 | (RS)-S-(3-{[4-{[2-(4-dimethylamino-phenyl)ethyl]amino}-5-(4-ethoxy-phenyl)pyrimidin-2-yl]amino}phenyl)-S-methylsulfoximide |

| Structure | Name |
|---|---|
| 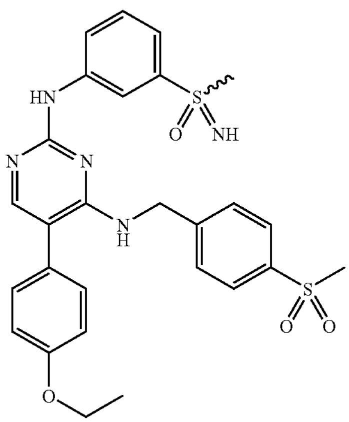 | (RS)-S-(3-{[4-{[4-methanesulfonyl-benzyl]amino}-5-(4-ethoxy-phenyl)pyrimidin-2-yl]amino}phenyl)-S-methylsulfoximide |
| 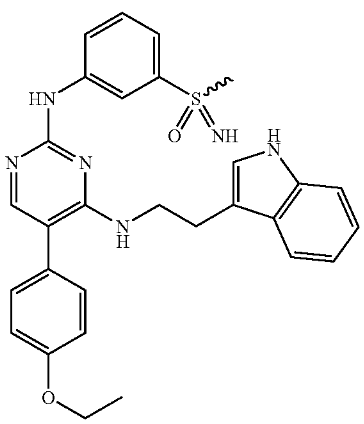 | (RS)-S-(3-{[4-{[2-(indol-3-yl)ethyl]amino}-5-(4-ethoxy-phenyl)pyrimidin-2-yl]amino}phenyl)-S-methylsulfoximide |
| 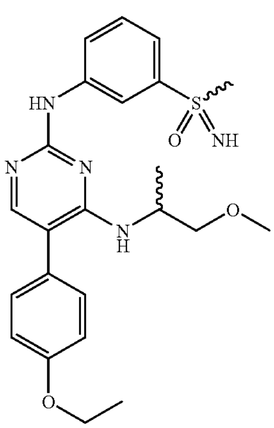 | (RS)-S-(3-{[4-{[(RS)-2-methoxy-1methyl-ethyl]amino}-5-(4-ethoxy-phenyl)pyrimidin-2-yl]amino}phenyl)-S-methylsulfoximide |

-continued

| Structure | Name |
|---|---|
| 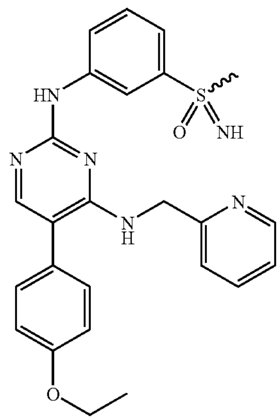 | (RS)-S-(3-{[4-{[(2-pyridyl)methyl]amino}-5-(4-ethoxy-phenyl)pyrimidin-2-yl]amino}phenyl)-S-methylsulfoximide |
| 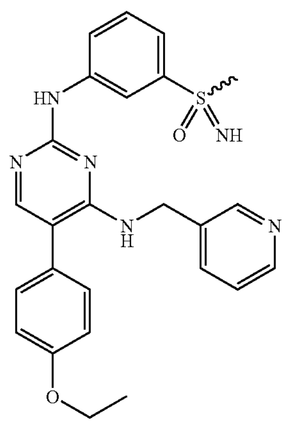 | (RS)-S-(3-{[4-{[(3-pyridyl)methyl]amino}-5-(4-ethoxy-phenyl)pyrimidin-2-yl]amino}phenyl)-S-methylsulfoximide |
| 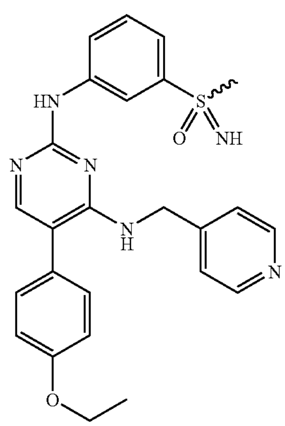 | (RS)-S-(3-{[4-{[(4-pyridyl)methyl]amino}-5-(4-ethoxy-phenyl)pyrimidin-2-yl]amino}phenyl)-S-methylsulfoximide |

| Structure | Name |
|---|---|
| 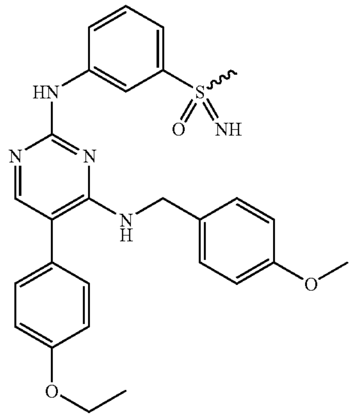 | (RS)-S-(3-{[4-{[4-methoxy-benzyl]amino}-5-(4-ethoxy-phenyl)pyrimidin-2-yl]amino}phenyl)-S-methylsulfoximide |
| 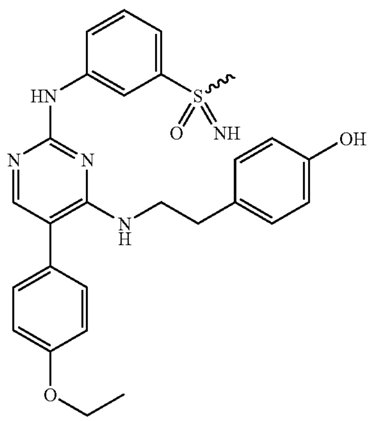 | (RS)-S-(3-{[4-{[2-(4-hydroxy-phenyl)ethyl]amino}-5-(4-ethoxy-phenyl)pyrimidin-2-yl]amino}phenyl)-S-methylsulfoximide |
| 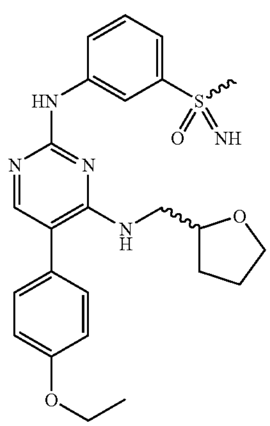 | (RS)-S-(3-{[4-{[tetrahydro-furan-2-ylmethyl]amino}-5-(4-ethoxy-phenyl)pyrimidin-2-yl]amino}phenyl)-S-methylsulfoximide |

-continued

| Structure | Name |
|---|---|
| 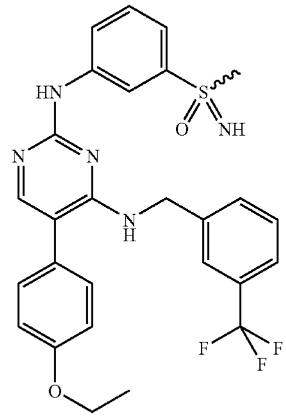 | (RS)-S-(3-{[4-{[3-trifluormethyl-benzyl]amino}-5-(4-ethoxy-phenyl)pyrimidin-2-yl]amino}phenyl)-S-methylsulfoximide |
| 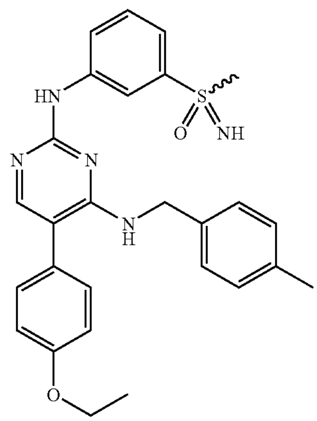 | (RS)-S-(3-{[4-{[4-methyl-benzyl]amino}-5-(4-ethoxy-phenyl)pyrimidin-2-yl]amino}phenyl)-S-methylsulfoximide |
| 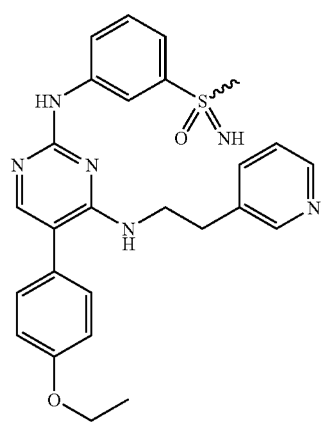 | (RS)-S-(3-{[4-{[2-(pyridin-3-yl)ethyl]amino}-5-(4-ethoxy-phenyl)pyrimidin-2-yl]amino}phenyl)-S-methylsulfoximide |

-continued

| Structure | Name |
|---|---|
| 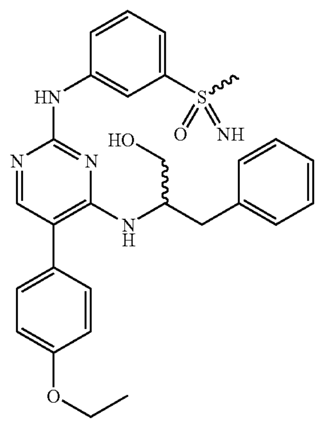 | (RS)-S-(3-{[4-{[(RS)-1-hydroxymethyl-2-phenyl-ethyl]amino}-5-(4-ethoxy-phenyl)pyrimidin-2-yl]amino}phenyl)-S-methylsulfoximide |
| 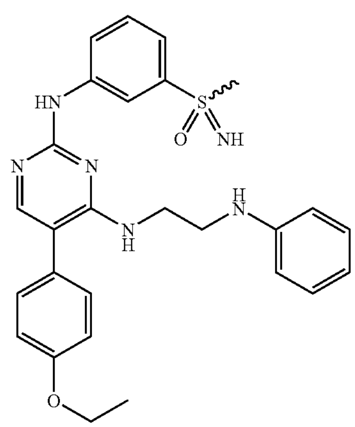 | (RS)-S-(3-{[4-{[2-phenylamino-ethyl]amino}-5-(4-ethoxy-phenyl)pyrimidin-2-yl]amino}phenyl)-S-methylsulfoximide |
| 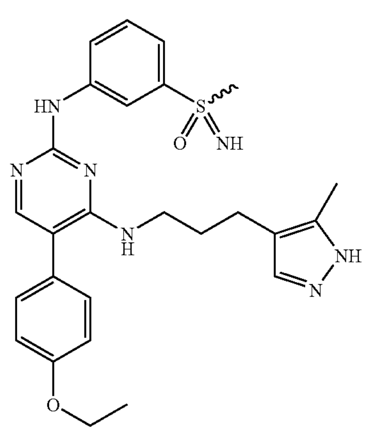 | (RS)-S-(3-{[4-{[3-(5-methyl-pyrazol-4-yl)-propyl]amino}-5-(4-ethoxy-phenyl)pyrimidin-2-yl]amino}phenyl)-S-methylsulfoximide |

| Structure | Name |
|---|---|
| 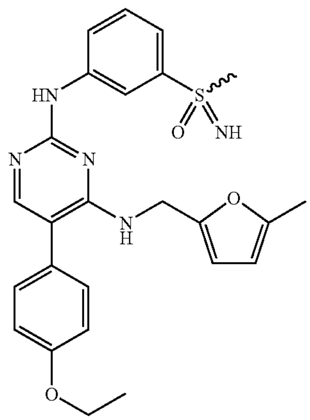 | (RS)-S-(3-{[4-{[(5-methyl-furan-2-yl)methyl]amino}-5-(4-ethoxy-phenyl)pyrimidin-2-yl]amino}phenyl)-S-methylsulfoximide |
| 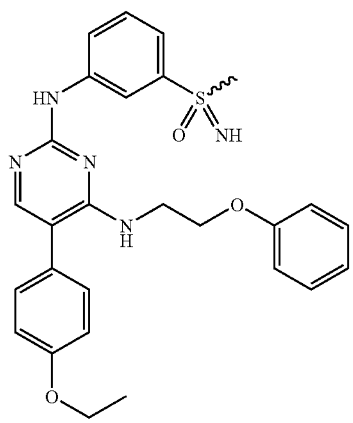 | (RS)-S-(3-{[4-{[2-phenyloxy-ethyl]amino}-5-(4-ethoxy-phenyl)pyrimidin-2-yl]amino}phenyl)-S-methylsulfoximide |
| 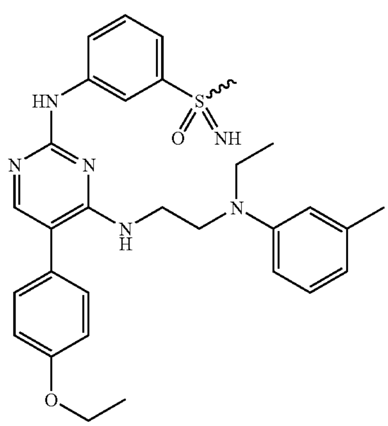 | (RS)-S-(3-{[4-{[2-(ethyl-m-tolyl-amino-ethyl]amino}-5-(4-ethoxy-phenyl)pyrimidin-2-yl]amino}phenyl)-S-methylsulfoximide |

-continued

| Structure | Name |
|---|---|
| 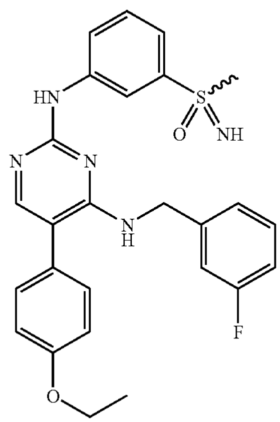 | (RS)-S-(3-{[4-{[3-fluoro-benzyl]amino}-5-(4-ethoxy-phenyl)pyrimidin-2-yl]amino}phenyl)-S-methylsulfoximide |
| 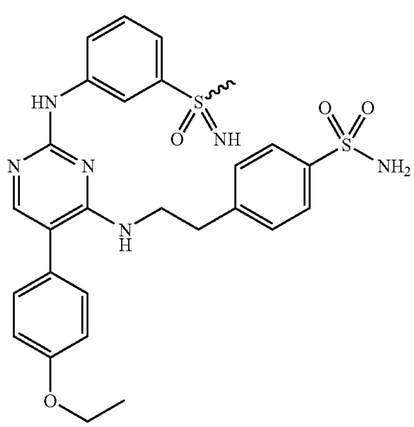 | (RS)-S-(3-{[4-{[2-(4-sulfamoylphenyl)-ethyl]amino}-5-(4-ethoxy-phenyl)pyrimidin-2-yl]amino}phenyl)-S-methylsulfoximide |
| 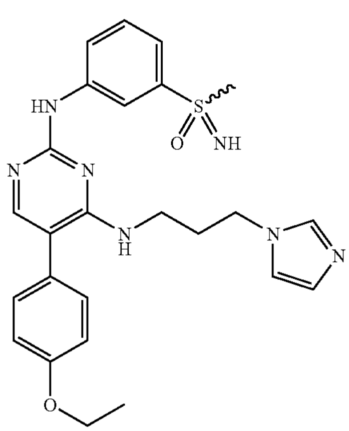 | (RS)-S-(3-{[4-{[3-(imidazol-1-yl)-propyl]amino}-5-(4-ethoxy-phenyl)pyrimidin-2-yl]amino}phenyl)-S-methylsulfoximide |

| Structure | Name |
|---|---|
| 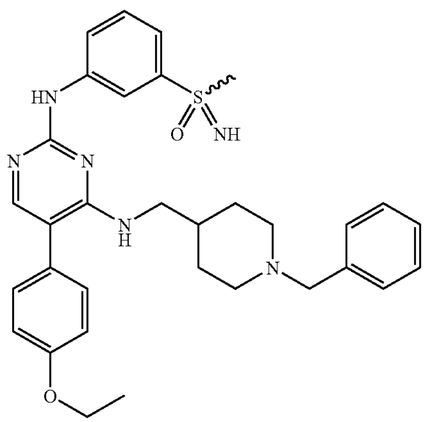 | (RS)-S-(3-{[4-{[1-Benzyl-piperidin-4-yl-methyl]amino}-5-(4-ethoxy-phenyl)pyrimidin-2-yl]amino}phenyl)-S-methylsulfoximide |
| 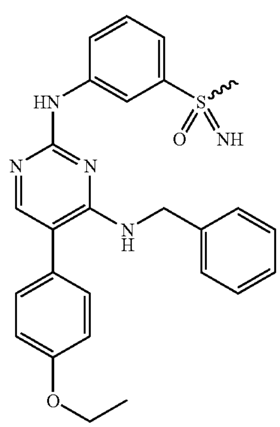 | (RS)-S-(3-{[4-{benzylamino}-5-(4-ethoxy-phenyl)pyrimidin-2-yl]amino}phenyl)-S-methylsulfoximide |
| 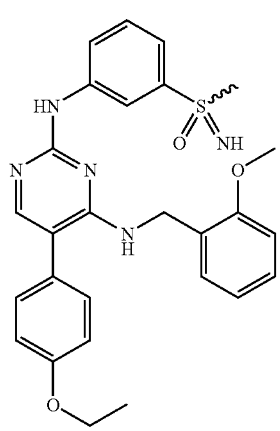 | (RS)-S-(3-{[4-{2-methoxy-benzylamino}-5-(4-ethoxy-phenyl)pyrimidin-2-yl]amino}phenyl)-S-methylsulfoximide |

-continued

| Structure | Name |
|---|---|
| 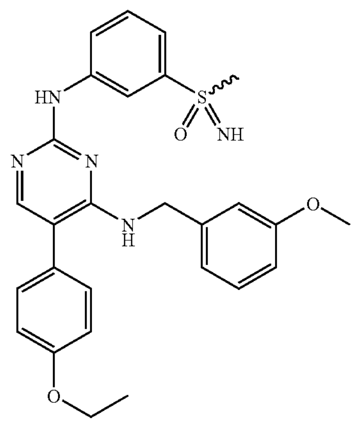 | (RS)-S-(3-{[4-{3-methoxy-benzylamino}-5-(4-ethoxy-phenyl)pyrimidin-2-yl]amino}phenyl)-S-methylsulfoximide |
| 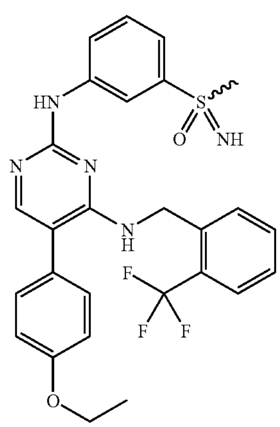 | (RS)-S-(3-{[4-{2-trifluormethyl-benzylamino}-5-(4-ethoxy-phenyl)pyrimidin-2-yl]amino}phenyl)-S-methylsulfoximide |
| 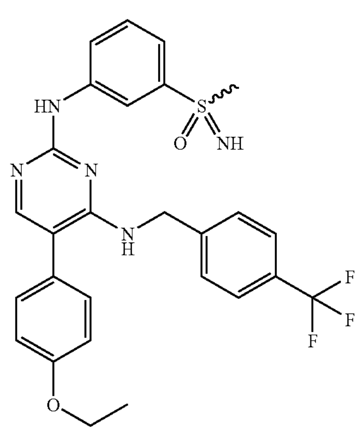 | (RS)-S-(3-{[4-{4-trifluormethyl-benzylamino}-5-(4-ethoxy-phenyl)pyrimidin-2-yl]amino}phenyl)-S-methylsulfoximide |

| Structure | Name |
|---|---|
| 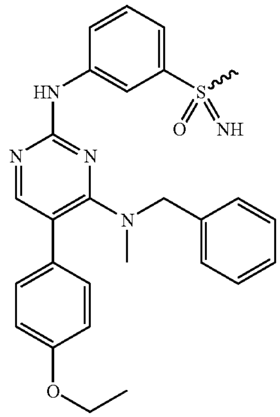 | (RS)-S-(3-{[4-{methyl-benzyl-amino}-5-(4-ethoxy-phenyl)pyrimidin-2-yl]amino}phenyl)-S-methylsulfoximide |
| 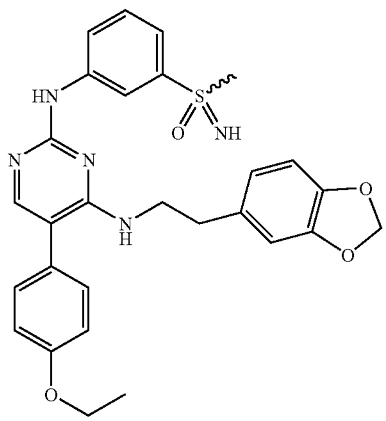 | (RS)-S-(3-{[4-{2-Benzo[1,3]dioxol-5-yl-ethyl-amino}-5-(4-ethoxy-phenyl)pyrimidin-2-yl]amino}phenyl)-S-methylsulfoximide |
| 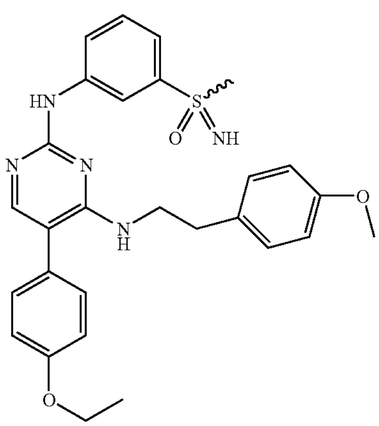 | (RS)-S-(3-{[4-{2-(4-methoxyphenyl)ethyl-amino}-5-(4-ethoxy-phenyl)pyrimidin-2-yl]amino}phenyl)-S-methylsulfoximide |

-continued

| Structure | Name |
|---|---|
| 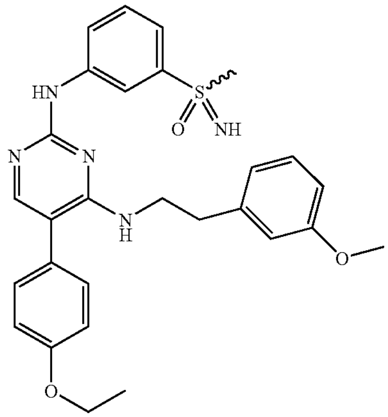 | (RS)-S-(3-{[4-{2-(3-methoxyphenyl)ethyl-amino}-5-(4-ethoxy-phenyl)pyrimidin-2-yl]amino}phenyl)-S-methylsulfoximide |
| 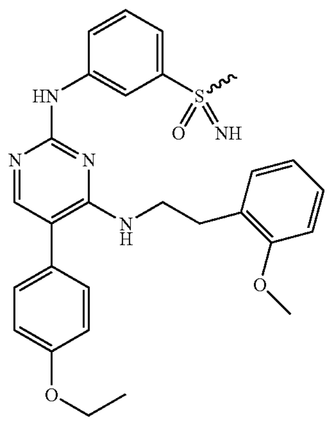 | (RS)-S-(3-{[4-{2-(2-methoxyphenyl)ethyl-amino}-5-(4-ethoxy-phenyl)pyrimidin-2-yl]amino}phenyl)-S-methylsulfoximide |
| 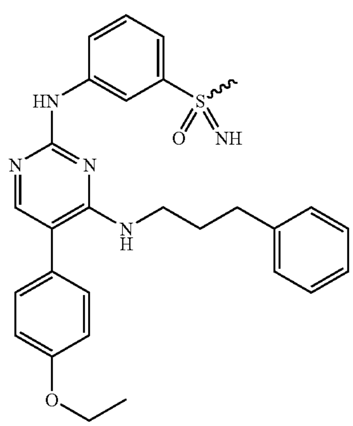 | (RS)-S-(3-{[4-{3-phenyl-propyl-amino}-5-(4-ethoxy-phenyl)pyrimidin-2-yl]amino}phenyl)-S-methylsulfoximide |

-continued

| Structure | Name |
|---|---|
| 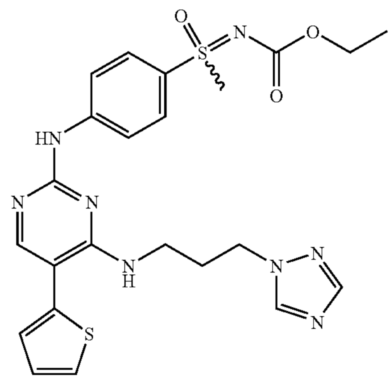 | (RS)-N-(ethoxycarbonyl)-S-(4-{[4-{[3-([1,2,4]triazol-1-yl-)propyl]amino}-5-(2-thienyl)pyrimidin-2-yl]amino}phenyl) S-methylsulfoximide |
| 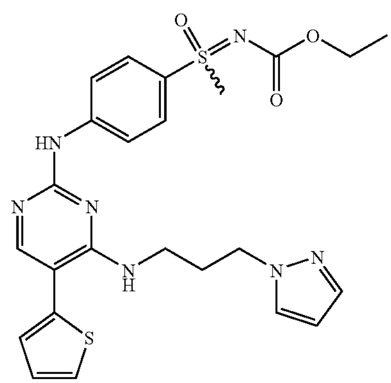 | (RS)-N-(ethoxycarbonyl)-S-(4-{[4-{[3-(pyrazol-1-yl-)propyl]amino}-5-(2-thienyl)pyrimidin-2-yl]amino}phenyl) S-methylsulfoximide |
| 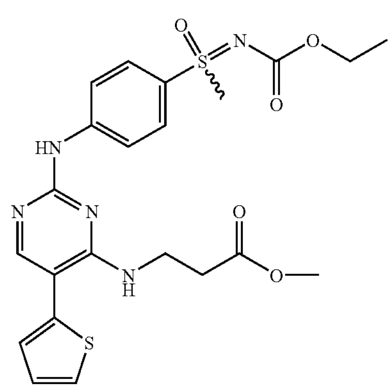 | N-{5-(2-thienyl)-2-[(4-{(RS)-S-[ethoxycarbonyl]-S-methyl-sulfoximide}-phenyl)amino]pyrimidin-4-yl}-3-amino-propionic acid-methyl ester |
| 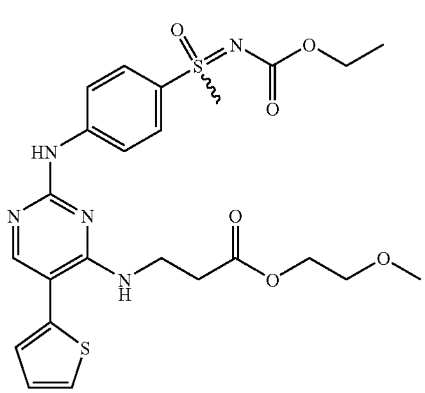 | N-{5-(2-thienyl)-2-[(4-{(RS)-S-[ethoxycarbonyl]-S-methyl-sulfoximide}-phenyl)amino]pyrimidin-4-yl}-3-amino-propionic acid-(2-methoxy-ethyl)- ester |

-continued

| Structure | Name |
|---|---|
| 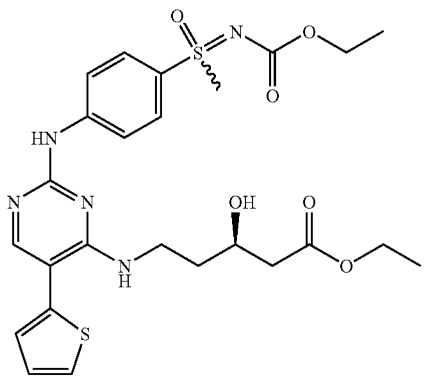 | N-{5-(2-thienyl)-2-[(4-{(RS)-S-[ethoxycarbonyl]-S-methyl-sulfoximide}-phenyl)amino]pyrimidin-4-yl}-5-amino-3-hydroxy-pentanoic acid-ethyl ester |
| 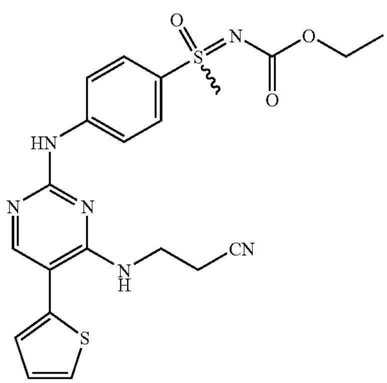 | (RS)-N-(ethoxycarbonyl)-S-(4-{[4-{[2-cyano-ethyl]amino}-5-(2-thienyl)pyrimidin-2-yl]amino}phenyl) S-methylsulfoximide |
| 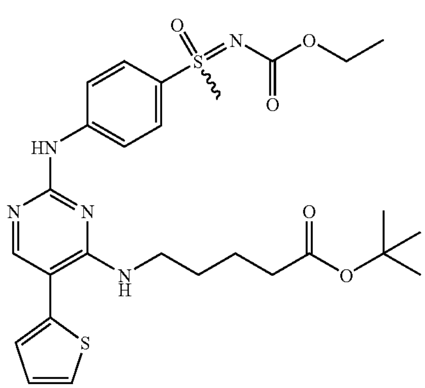 | N-{5-(2-thienyl)-2-[(4-{(RS)-S-[ethoxycarbonyl]-S-methyl-sulfoximide}-phenyl)amino]pyrimidin-4-yl}-3-amino-pentanoic acid-tert-butyl ester |
| 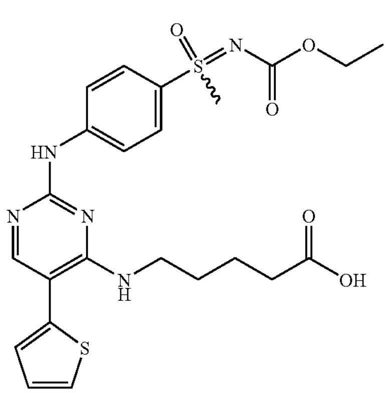 | N-{5-(2-thienyl)-2-[(4-{(RS)-S-[ethoxycarbonyl]-S-methyl-sulfoximide}-phenyl)amino]pyrimidin-4-yl}-3-amino-pentanoic acid |

-continued

| Structure | Name |
|---|---|
| 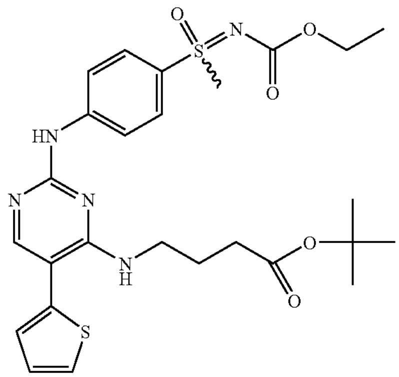 | N-{5-(2-thienyl)-2-[(4-{(RS)-S-[ethoxycarbonyl]-S-methyl-sulfoximide}-phenyl)amino]pyrimidin-4-yl}-3-amino-butyric acid-tert-butyl ester |
| 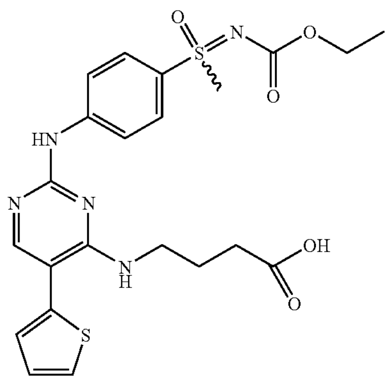 | N-{5-(2-thienyl)-2-[(4-{(RS)-S-[ethoxycarbonyl]-S-methyl-sulfoximide}-phenyl)amino]pyrimidin-4-yl}-3-amino-butyric acid |
| 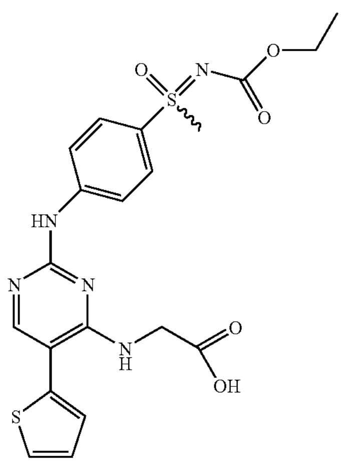 | N-{5-(2-thienyl)-2-[(4-{(RS)-S-[ethoxycarbonyl]-S-methyl-sulfoximide}-phenyl)amino]pyrimidin-4-yl}-glycine |

| Structure | Name |
|---|---|
| 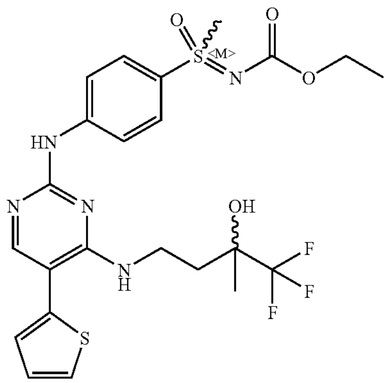 | (RS)-N(ethoxycarbonyl)-(4-{[4-{(3-trifluormethyl-3-hydroxy-butyl)amino}-5-(thiophen-2-yl)-pyrimidin-2-yl]amino}phenyl)-S-methylsulfoximide |
| 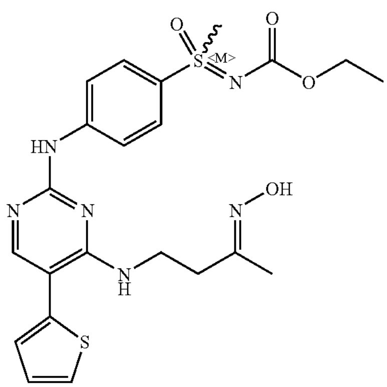 | (RS)-N(ethoxycarbonyl)-(4-{[4-{([(EZ)hydroxyimino]-butyl)amino}-5-(thiophen-2-yl)-pyrimidin-2-yl]amino}phenyl)-S-methylsulfoximide |

The activity of the compounds according to the invention can be determined by the following assays:

Assay I

CDK2/CycE Kinase Assay

Recombinant CDK2- and CycE-GST fusion proteins, purified from Baculovirus-infected insect cells (Sf9), were purchased from ProQinase GmbH, Freiburg. Histone IIIS, which was used as the kinase substrate, was purchased from the Sigma Co.

CDK2/CycE (50 ng/data point) was incubated for 10 mins at 22° C. in the presence of different concentrations of test substances (0 µM, and within the range 0.01-100 µM) in assay buffer [50 mM tris/HCl pH8.0, 10 mM $MgCl_2$, 0.1 mM Na orthovanadate, 1.0 mM dithiothreitol, 0.5 µM ATP, 10 µg/data point Histone IIIS, 0.2 µCi/data point $^{33}$P-gamma ATP, 0.05% NP40, 1.25% dimethylsulfoxide]. The reaction was stopped by addition of EDTA solution (250 mM, pH8.0, 15 µl/data point).

15 µl of each reaction mixture was applied onto P30 filter strips (Wallac Co.), and non-incorporated $^{33}$P-ATP was removed by washing the filter strips three times, for 10 mins each time, in 0.5% phosphoric acid. After drying of the filter strips for 1 hour at 70° C., the filter strips were covered with scintillator strips (MeltiLex™ A, Wallac Co.) and baked for 1 hour at 90° C. The quantity of incorporated $^{33}$P (substrate phosphorylation) was determined by scintillation measurement in a gamma radiation meter (Wallac).

For example, the $IC_{50}$ from Example (5.3) is: 3 µM.

Assay II

Aurora-C Kinase Assay

Recombinant Aurora-C Protein was expressed in transiently transfected HEK293 cells and then purified. As the kinase substrate, the biotinylated peptide with the amino acid sequence biotin-FMRLRRLSTKYRT, which was purchased from the company Jerini AG in Berlin, was used.

Aurora-C [5 nM in the test mixture, test volume 5 µl] was incubated for 90 mins at 22° C. in the presence of different concentrations of test substances (0 µM, and 10 data points within the range 0.001-20 µM in duplicate values) in assay buffer [25 mM HEPES pH 7.4, 0.5 mM $MnCl_2$, 0.1 mM Na orthovanadate, 2.0 mM dithiothreitol, 0.05% bovine serum albumin (BSA), 0.01% Triton X-100, 3 µM adenosine trisphosphate (ATP), 0.67 nCi/µl gama-P33-ATP, 2.0 µM substrate peptide biotin-FMRLRRLSTKYRT, 1.0% dimethylsulfoxide]. The reaction was stopped by addition of 12.5 µl of an EDTA/detection solution [16 mM EDTA, 40 mM ATP, 0.08% Triton X-100, 4 mg/ml PVT-streptavidin-SPA beads (Amersham Co.)]. After 10 minutes' incubation, the SPA beads were pelleted by 10-minute centrifugation at 1000×G. The measurement was performed in a Topcount scintillation meter from the Perkin Elmer company. The measurement data were normalised to 0% inhibition (enzyme reaction with no inhibitor) and 100% inhibition (enzyme reaction in presence of 0.1 µM stauro-sporin (Sigma Co.)). The IC50 values were determined by a 4-parameter fit using in-house software. For example, the $IC_{50}$ from Ex. (1.1)=2 µM Assay III Aurora-A Kinase Assay Recombinant Aurora-A Protein, expressed in Sf21 insect cells, purchased from the company Upstate. As the kinase substrate, the biotinylated peptide with the amino acid sequence biotin-LNYNRRLSLGPMF, which was purchased from the company Jerini AG in Berlin, was used.

Aurora-A [15 nM in the test mixture, test volume 5 µl] was incubated for 90 mins at 22° C. in the presence of different concentrations of test substances (0 µM, and 10 data points within the range 0.001-20 µM in duplicate values) in assay buffer [25 mM HEPES pH7.4, 3 mM MnCl$_2$, 5 mM MnCl$_2$, 0.1 mM Na orthovanadate, 2.0 mM dithiothreitol, 0.05% bovine serum albumin (BSA), 0.01% Triton X-100, 8 µM ATP, 4 nCi/µl gama-P33-ATP, 5.0 µM substrate peptide biotin-LNYNRRLSLGPMF, 1.0% dimethylsulfoxide]. The reaction was stopped by addition of 12.5 µl of an EDTA/ detection solution [16 mM EDTA, 40 mM ATP, 0.08% Triton X-100, 4 mg/ml PVT-Streptavidin-SPA beads (Amersham Co.)]. After 10 minutes' incubation, the SPA beads were pelleted by 10-minute centrifugation at 1000×G. The measurement was performed in a Topcount scintillation meter from the Perkin Elmer company.

The measurement data were normalised to 0% inhibition (enzyme reaction with no inhibitor) and 100% inhibition (enzyme reaction in presence of 0.1 µM stauro-sporin (Sigma Co.)). The IC50 values were determined by a 4-parameter fit using in-house software.

Assay IV

Tie-2 Kinase Assay a): Tie-2 Kinase Assay without Prior Activation of the Kinase For the kinase assay, a recombinant fusion protein expressed in insect cells (Hi-5) and purified by glutathione-sepharose affinity chromatography, consisting of GST and the intracellular domain of Tie-2, was used. Alternatively, commercially available GST-Tie2 fusion protein (Upstate Biotechnology, Dundee, Scotland) can be used. As the substrate for the kinase reaction, the biotinylated peptide biotin-Ahx-EPKDDAYPLYSDFG (C-terminus in amide form), which can be acquired e.g. from the company Biosyntan GmbH (Berlin-Buch, Germany) was used.

Tie-2 (3.5 ng/data point) was incubated for 60 mins at 22° C. in the presence of 10 µM adenosine triphosphate (ATP) and 1 µM substrate peptide (Biotin-Ahx-EPKDDAYPLYSDFG-NH$_2$) with different concentrations of the test compounds (0 µM and concentrations in the range from 0.001-20 µM) in a volume of 5 µl of assay buffer [50 mM Hepes/NaOH pH 7, 10 mM MgCl$_2$, 0.5 mM MnCl$_2$, 1.0 mM dithiothreitol, 0.01% NP40, protease inhibitor mixture ("Complete without EDTA" from Roche, 1 tablet per 2.5 ml), 1% (v/v) dimethylsulfoxide]. The reaction was stopped by addition of 5 µl of an aqueous buffer (25 mM Hepes/NaOH pH 7.5, 0.28% (w/v) bovine serum albumin), which contained EDTA (90 mM) and the HTRF (Homogeneous Time Resolved Fluorescence) detection reagents streptavidin-XLent (0.2 µM, from Cis Biointernational, Marcoule, France) and PT66-Eu chelate (0.3 ng/µl; an anti-phosphotyrosine antibody labelled with europium chelate, from Perkin Elmer).

The resulting mixture was incubated for 1 hr at 22° C. in order to allow the binding of the biotinylated phosphorylated peptide to the streptavidin-XLent and the PT66-Eu-chelate. After this, the quantity of the phosphorylated substrate peptide was determined by measurement of the resonance energy transfer from the PT66-Eu chelate to the streptavidin-XLent. For this purpose, the fluorescence emission at 620 nm and 665 nm after excitation at 350 nm was measured in a HTRF meter, e.g. Rubystar (BMG Labtechnologies, Offenburg, Germany) or Viewlux (Perkin-Elmer). The ratio of the emissions at 665 nm and at 622 nm was used as a measure of the quantity of the phosphorylated substrate peptide. The data were normalised (enzyme reaction without inhibitor=0% inhibition, all other assay components but no enzyme=100% Inhibition), and IC$_{50}$ values were calculated by a 4 parameter fit using in-house software. For example, for Example 5.5 an IC$_{50}$=3 µM was found.

Tie-2 Kinase Assay b): Tie-2 Kinase Assay with Prior Activation of the Kinase

For the kinase assay, a purified recombinant fusion protein expressed in insect cells (Hi-5) and purified by glutathione-sepharose affinity chromatography, consisting of GST and the intracellular domain of Tie-2, was used. As the substrate for the kinase reaction the biotinylated peptide biotin-Ahx-EPKDDAYPLYSDFG (C-terminus in amide form), which can for example be acquired from the company Biosyntan GmbH (Berlin-Buch, Germany) was used. For the activation, Tie-2 at a concentration of 12.5 ng/µl was incubated for 20 mins at 22° C. in the presence of 250 µM adenosine triphosphate (ATP) in assay buffer [50 mM Hepes/NaOH pH 7, 10 mM MgCl$_2$, 0.5 mM MnCl$_2$, 1.0 mM dithiothreitol, 0.01% NP40, protease inhibitor mixture ("Complete without EDTA" from Roche, 1 tablet per 2.5 ml)].

For the subsequent kinase reaction, activated Tie-2 (0.5 ng/data point) was incubated for 20 min at 22° C. in the presence of 10 µM adenosine triphosphate (ATP) and 1 µM substrate peptide (Biotin-Ahx-EPKDDAYPLYSDFG-NH$_2$) with different concentrations of the test compounds (0 µM and concentrations in the range from 0.001-20 µM) in a volume of 5 µl in assay buffer [50 mM Hepes/NaOH pH 7.10 mM MgCl$_2$, 0.5 mM MnCl$_2$, 0.1 mM sodium-orthovanadate, 1.0 mM dithiothreitol, 0.01% NP40, protease inhibitor mixture ("Complete without EDTA" from Roche, 1 tablet per 2.5 ml), 1% (v/v) dimethylsulfoxide]. The reaction was stopped by addition of 5 µl of an aqueous buffer (25 mM Hepes/NaOH pH 7.5, 0.28% (w/v) bovine serum albumin), which contained EDTA (90 mM) and the HTRF (Homogeneous Time Resolved Fluorescence) detection reagents streptavidin-XLent (0.2 µM, von Cis Biointernational, Marcoule, France) and PT66-Eu chelate (0.3 ng/µl; an anti-phosphotyrosine antibody labelled with europium chelate from Perkin Elmer).

The resulting mixture was incubated for 1 hr at 22° C. in order to allow the binding of the biotinylated phosphorylated peptide to the streptavidin-XLent and the PT66-Eu-chelate. After this, the quantity of the phosphorylated substrate peptide was determined by measurement of the resonance energy transfer from the PT66-Eu chelate to the streptavidin-XLent. For this purpose, the fluorescence emission at 620 nm and 665 nm after excitation at 350 nm was measured in a HTRF meter, e.g. Rubystar (BMG Labtechnologies, Offenburg, Germany) or Viewlux (Perkin-Elmer). The ratio of the emissions at 665 nm and at 622 nm was used as a measure of the quantity of the phosphorylated substrate peptide. The data were normalised (enzyme reaction without inhibitor=0% inhibition, all other assay components but no enzyme=100% Inhibition), and IC$_{50}$ values were calculated by a 4 parameter fit with in-house software.

Assay V a) ITK Kinase Assay

For the determination of the kinase activity of ITK, the phosphorylation of polyGT is measured. In the kinase reaction, 106 pM ITK, 1.3 µM ATP and 20 nM polyGT are used.

The reaction runs for 20 mins at RT and is then stopped by addition of EDTA (final concentration 60 mM).

The reaction buffer contains 50 mM TrisCL pH7.5, 10 mM MnCl2, 10% glycerine, 1 mM DTT, 0.1% Tween-20 and 0.1 mM Na3V04 and a protease inhibitor cocktail ("complete", Roche diagnostics)

The measurement of the enzyme activity is effected by the determination of the phosphorylated substrates. The poly GT substrate used is biotinylated. The measurement is performed in a FRET-based assay, wherein an anti-phospho-tyrosine antibody recognises and binds the phosphorylated substrate poly GT.

The bound antibody is now in the spatial vicinity of a streptavidin-coupled fluorescence dye, which was bound to polyGt by biotin-streptavidin interaction. On excitation of the europium chelate on the phosphotyrosine antibody with 337 nM UV light, light of the wavelength 620 nm is emitted, which in turn excites the dye XLent, which then emits light of longer wavelength (665 nm).

The detection reagents are added in 50 mM Hepes pH 7.0 with 0.1% BSA. 4 ng PT66 chelate and 20 nM SA-XLent are used.

After addition of the detection reagents, the samples stand overnight at 4 degrees Celsius, in order to form the FRET-creating complexes. For example, an $IC_{50}$=4 µM was measured for Example 1.7.

b) ITK Kinase Assay

Itk inhibitory activity of compounds of the present invention was quantified employing the Itk HTRF assay as described in the following paragraphs.

N-terminal 6His-tagged recombinant kinase domain of the human Itk (amino acids 352-617) expressed in baculovirus infected SF21 cells and purified using $Ni^{2+}$/NTA agarose was purchased form Upstate (Dundee, UK) and used as kinase. As substrate for the kinase reaction the biotinylated myelin basic protein was used which can be purchased form GE Healthcare (Freiburg i. Br., Germany).

Itk was incubated for 15 min at 22° C. in the presence of different concentrations of test compounds in 5 µl assay buffer [8 mM MOPS/NaOH pH 7.0, 10 mM $Mg(OAc)_2$, 0.2 mM EDTA, 1.0 mM dithiothreitol, 0.1 mM sodium orthovanadate, 10 µM adenosine-tri-phosphate (ATP), 0.5 µM substrate, 0.07% (v/v) Tween20 (Sigma), 1% (v/v) dimethylsulfoxide]. The concentration of Itk was adjusted depending of the activity of the enzyme lot and was chosen appropriate to have the assay in the linear range, a typical concentration was about 40 ng/ml. The reaction was stopped by the addition of 5 µl of a solution of HTRF detection reagents (40 nM streptavidine-XLent and 2.4 nM PT66-Eu-Chelate, an europium-chelate labelled anti-phospho-tyrosine antibody from Perkin Elmer) in an aqueous EDTA-solution (100 mM EDTA, 0.2% (w/v) bovine serum albumin in 50 mM HEPES/NaOH pH 7.0).

The resulting mixture was incubated 1 h at 22° C. to allow the binding of the biotinylated phosphorylated substrate to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

For example, an $IC_{50}$=0.4 µM was measured for Example 1.7.

Assay VI

Cytokine-/Proliferation Determination in Activated Human T-Cells=HTRF-Test

PBMCs (peripheral blood mononucleated cells) isolated from human whole blood are stimulated with αCD3 monoclonal antibodies (mab) and αCD28 mab. The cytokine determination is performed by means of an ELISA-Kit. The cell isolation and the test preparation are carried out in sterile conditions under the Cleanbench.

For the cell preparation, heparinised human whole blood is used. 100 µl Liquemin (20000 I.E.) per 20 ml blood are taken per syringe. 15 ml Histopaque are placed in each Leucosep tube and by brief centrifugation are forced down through the frit. 20 ml blood is placed in the tubes thus prepared and centrifuged for 15 minutes (800×g). The PBMC together with the lower Histopaque layer are transferred to a new 50 ml tube, the contents of two Leucosep tubes always being poured into one 50 ml tube. The 50 ml tubes are then filled to 50 ml with medium. This cell suspension is now washed three times. The resulting pellet is taken up in a defined volume of medium (from now on, if appropriate with test substances). Next, the cells are adjusted to a previously defined cell count (e. g. $4 \times 10^5$ cells in 0.2 ml medium/well).

The substances are generally tested in a concentration range from $1 \times 10^{-6}$ to $1 \times 10^{-12}$ M. The preparations are incubated on CD3/CD28 mab-coated culture plates for 20 hours in the incubation cabinet at 37° C. After this incubation, the plates are briefly shaken, then centrifuged for 10 minutes at 300×g and 250 µl supernatant withdrawn and analysed, or the supernatants are frozen at −80° C.

The cytokine determination in the supernatants (e. g. IL-2 and IFN-γ) is performed with specific ELISA kits. The measured results are assessed with the use of statistical software.

In order to determine the influence of the substances on proliferation, the prepared plates are incubated for ca. 92 hours. Next, the plates are incubated with $^3$H-Thymidine (0.2 µCi/25 µl/well) for 18 hours. After completion of this time, the plates can be frozen at −20° C.

For the measurement, the plates must be thawed, transferred onto filter plates by suction with the Cell-Harvester and then assayed in the β-counter.

The compound described in Example 2 has an $IC_{50}$ value of 700 nM on purified Itk Protein in the HTRF test. The same compound inhibits the release of IL-2 in activated human T cells with an $IC_{50}$ value of 2 µM.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10/2005/062742.0, filed Dec. 22, 2005 and corresponding German application No. 10/2006/031224.4, filed Jun. 30, 2006 and, U.S. Provisional Application Ser. No.

60/757,859, filed Jan. 11, 2006 and U.S. Provisional Application Ser. No. 60/818,501, filed Jul. 6, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I,

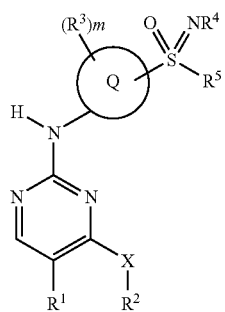

(I)

wherein
- $R^1$ means an optionally partly or fully saturated, optionally substituted mono- or bicyclic heteroaryl group or an optionally substituted aryl group,
- $R^2$ a hydrogen atom,
  a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_8$ heterocyclyl group, an aryl or heteroaryl group, which is optionally substituted one or more times, identically or differently with a group selected from halogen, hydroxy, cyano, $SO_2NR^8R^9$, $SO_2R^{10}$, $S(O)(NR^8)R^9$, $C_1$-$C_6$ alkyl, perfluoro($C_1$-$C_6$)alkyl,
  $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, —COO—($C_1$-$C_6$) alkyl-O—($C_1$-$C_6$)alkyl, $C_1$-$C_6$ alkyl(CO)O—, $C_3$-$C_{10}$ cycloalkyl, =N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)$C_1$-$C_6$ alkylene-NH—(CO)aryl, —NH(CO)(($C_1$-$C_6$)alkylene) aryl, —NH—(CH$_2$)$_n$—$C_3$-$C_{10}$ cycloalkyl, —(CH$_2$)$_n$aryl, —(CH$_2$)$_n$—O-aryl, —(CH$_2$)$_n$ heteroaryl, —(CH$_2$)$_n$—($C_3$-$C_8$) heterocyclyl,
  —$CF_3$, —$OCF_3$, —$NR^7$—C(O)—$OC_1$-$C_3$ alkyl, —$NR^7$—C(O)—$NR^8R^9$ or —$NR^7$—$SO_2$—$R^{10}$,
  wherein,
  if the $C_3$-$C_{10}$ cycloalkyl group, the (CH$_2$)$_n$—($C_3$-$C_8$) heterocyclyl group, the (CH$_2$)$_n$ aryl- or the (CH$_2$)$_n$-heteroaryl group are substituents of $R^2$,
  these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—(CH$_2$)$_o$—O—, halogen($C_1$-$C_4$) alkoxy, —(CH$_2$)$_n$aryl, $NR^8R^9$, $COOR^7$ or $SO_2NR^8R^9$, and/or the ring of any $C_3$-$C_{10}$ cycloalkyl group, $C_3$-$C_8$ heterocyclyl group and the $C_1$-$C_{10}$ alkyl group can optionally contain one or several —$NR^8$, oxygen and/or sulphur atoms and/or can optionally contain one or several —C(O)— groups in the ring and/or optionally one or several possible double bonds can be contained in the ring,
n means 0-6,
o means 1-4,
$R^3$ hydroxy, halogen, nitro, cyano, —(CO)$NR^8R^9$, —(CS)$NR^8R^9$, $CF_3$, $OCF_3$, —$R^9N(CO)NR^8R^9$, —$R^7N(CO)R^8$, —$R^7NS(O)_2R^8$, the group —$NR^8R^9$ or
  a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$,
$R^4$ a hydrogen atom, a —C(O)O—$R^{10}$, —C(O)—$R^{10}$, —C(O)—$NR^8R^9$, —C(S)—$NR^8R^9$, $NO_2$, —Si($R^{15}R^{16}R^{17}$), —$R^{18}$—Si($R^{15}R^{16}R^{17}$), —$SO_2$—$R^{18}$—Si($R^{15}R^{16}R^{17}$) group or an —$SO_2R^{10}$ group or
  a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CSR^6$, —$CF_3$, —$OCF_3$ or —$NR^8R^9$
or
  an optionally substituted —(CH$_2$)$_n$-aryl or —(CH$_2$)$_n$-heteroaryl group or
$R^3$ and $R^5$ together form a 5 to 7-membered ring,
  where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q,
$R^4$ and $R^5$ together form a 5 to 8-membered ring of the formula

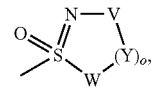

where
V, W and Y
  each independently of one another stands for a —CH$_2$ group which is optionally substituted one or more times, identically or differently with hydroxy, $C_1$-$C_{10}$ alkyl, $C_1$-$C_{10}$ alkoxy or —$NR^8R^9$,
  where
  the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$
  and/or the ring
  can be interrupted by one or several —C(O)— groups and/or
  optionally can contain one or several double bonds, and
$R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with
  hydroxy, $C_1$-$C_6$ alkoxy, $C_3$-$C_{10}$ cycloalkyl, halogen, cyano, —$CF_3$, —$OCF_3$ or the group —$NR^8R^9$, an aryl group or heteroaryl group which is optionally substituted one or more times,
identically or differently with halogen, hydroxy, $C_1$-$C_6$ alkyl, halogen-($C_1$-$C_4$) alkyl, $C_1$-$C_6$ alkoxy, halogen ($C_1$-$C_4$) alkoxy, —$COR^6$, $COOR^7$, —$NR^8R^9$, CN, $NO_2$, or $SO_2NR^8R^9$ X an oxygen atom, a sulphur atom or a —$NR^8$— group
or
X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$— group, Q $C_6$-$C_{10}$ arylene, heteroarylene with 5-10 ring atoms m 0-4

$R^6$ a hydrogen atom or a hydroxy, benzyloxy or $NR^8R^9$ group
or
a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalkyl group, $C_6$-$C_{10}$-aryl group or heteroaryl group with 5 or 6 ring atoms, which is optionally substituted one or more times, identically or differently with hydroxy,
—$NR^8R^9$, cyano, halogen, —$CF_3$, $C_1$-$C_6$ alkyl, $C_1$-$C_6$ alkoxy or —$OCF_3$ $R^7$ a hydrogen atom or a $C_1$-$C_6$ alkyl group, $R^8$, $R^9$ independently of one another mean a hydrogen atom, ($C_1$-$C_6$)alkoxy group, a ($C_1$-$C_6$)alkyl group, hydroxy($C_1$-$C_6$)alkyl group, dihydroxy($C_1$-$C_6$)alkyl group, ($C_3$-$C_7$)cycloalkyl, ($CH_2$)$_n$—$NR^{11}R^{12}$, $NR^{11}R^{12}$, —(CO)—($C_1$-$C_6$)alkyl, —(CO)-phenyl, —(CO)—($C_1$-$C_6$)alkyl-NH—(CO)aryl, —(CO)benzyl, —(CO)O($C_1$-$C_6$)alkyl,
a —($CH_2$)$_n$—($C_6$-$C_{10}$)aryl group or a heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$,
or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy,
—$NR^{11}R^{12}$, cyano, halogen, —$CF_3$, $C_1$-$C_6$ alkoxy and/or —$OCF_3$, $R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or an aryl group, which is optionally substituted one or more times, identically or differently with halogen, hydroxy, $C_1$-$C_6$ alkyl, $C_1$-$C_6$ alkoxy, cyano, —$CF_3$, —$OCF_3$, —$NR^8R^9$ or with the group —$SiR^{15}R^{16}R^{17}$, $R^{11}$, $R^{12}$ independently of one another mean a hydrogen atom, a $C_1$-$C_6$ alkyl, $C_1$-$C_6$ alkoxy-, hydroxy($C_1$-$C_6$) alkyl, dihydroxy($C_1$-$C_6$) alkyl, (CO)—($C_1$-$C_6$) alkyl, (CO)-phenyl, or a benzyl group, which is optionally substituted one or more times, identically or differently with hydroxy, cyano, halogen, —$CF_3$, $C_1$-$C_6$ alkoxy and/or —$OCF_3$,
or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group, and/or a phenyl group
and
$R^{18}$ stands for a $C_1$-$C_3$ alkylene group.

2. A compound of formula I according to claim 1, wherein
$R^1$ means an optionally partly or fully saturated mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, ($C_1$-$C_6$)alkyl, halogen($C_1$-$C_6$)alkyl, hydroxy ($C_1$-$C_6$)alkyl, cyano($C_1$-$C_6$)alkyl-,
($NR^8R^9$)($C_1$-$C_4$)alkyl, —NH(CO)($C_1$-$C_6$)alkylene-NH—(CO)aryl,
—NH(CO)($C_1$-$C_6$)alkylene-aryl, ($R^6OC$)($C_1$-$C_6$)alkyl-, [($HR^8N(OC)$)]—($C_1$-$C_6$)alkyl-, ($C_1$-$C_6$)-alkoxy, halogen($C_1$-$C_6$)alkoxy, $SO_2NR^8R^9$
or an aryl group
which is optionally substituted one or more times, identically or differently with a group selected from halogen, hydroxy, $C_1$-$C_5$alkyl, hydroxy($C_1$-$C_5$)alkyl, ($C_1$-$C_5$) alkoxy, —O-perfluoro($C_1$-$C_5$)alkyl, —($C_1$-$C_5$)-alkyl-O—($C_1$-$C_5$)-alkyl, —($C_1$-$C_5$)-alkyl-$COOR^7$, —O—($CH_2$)$_o$O—, cyano, $CF_3$, nitro, (CO)$R^6$, $NR^8R^9$, —$NR^8$—(CO)—($C_1$-$C_4$)alkyl, —$NR^8$—$SO_2$—($C_1$-$C_4$)-alkyl, —($C_1$-$C_4$)alkyl-$NR^8$—(CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), phenyl, —(CO)-morpholino, $R^2$ a hydrogen atom,
a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_8$ heterocyclyl group, an aryl or heteroaryl group, which is optionally substituted one or more times, identically or differently with a group selected from halogen, hydroxy, cyano, $SO_2NR^8R^9$, $SO_2R^{10}$, S(O)($NR^8$)$R^9$, $C_1$-$C_6$ alkyl, perfluoro($C_1$-$C_6$)alkyl,
$C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl,
=N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)$C_1$-$C_6$ alkylene-NH—(CO)aryl, —NH(CO)(($C_1$-$C_6$)alkylene)aryl, —NH—($CH_2$)$_n$—$C_3$-$C_{10}$ cycloalkyl, —($CH_2$)$_n$aryl, —($CH_2$)$_n$—O-aryl, —($CH_2$)$_n$ heteroaryl, —($CH_2$)$_n$—($C_3$-$C_8$) heterocyclyl,
—$CF_3$, —$OCF_3$, —$NR^7$—C(O)—$OC_1$-$C_3$ alkyl, —$NR^7$—C(O)—$NR^8R^9$ or —$NR^7$—$SO_2$—$R^{10}$,
wherein,
if the $C_3$-$C_{10}$ cycloalkyl group, the ($CH_2$)$_n$—($C_3$-$C_8$) heterocyclyl group, the ($CH_2$)$_n$ aryl- or the ($CH_2$)$_n$-heteroaryl group are substituents of $R^2$,
these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—($CH_2$)$_o$—O—, halogen($C_1$-$C_4$) alkoxy,
—($CH_2$)$_n$aryl, $NR^8R^9$, $COOR^7$ or $SO_2NR^8R^9$,
and/or the ring of any $C_3$-$C_{10}$ cycloalkyl group, $C_3$-$C_8$ heterocyclyl group and the $C_1$-$C_{10}$ alkyl group can optionally contain one or several —$NR^8$, oxygen and/or sulphur atoms and/or can optionally contain one or several —C(O)— groups in the ring and/or optionally one or several possible double bonds can be contained in the ring, means 0-6,
o means 1-4,
$R^3$ hydroxy, halogen, nitro, cyano, —(CO)$NR^8R^9$, —(CS)$NR^8R^9$, $CF_3$, $OCF_3$, —$R^9N(CO)NR^8R^9$, —$R^7N(CO)R^8$, —$R^7NS(O)_2R^8$, the group —$NR^8R^9$ or
a $C_1$-$C_6$ alkyl group, a $C_3$-$C_7$ cycloalkyl group or a $C_1$-$C_6$ alkoxy group, which is optionally substituted one or more times, identically or differently with halogen, hydroxy, $C_1$-$C_6$ alkoxy or the group —$NR^8R^9$, $R^4$ a hydrogen atom, a —C(O)O—$R^{10}$, —C(O)—$R^{10}$, —C(O)—$NR^8R^9$, —C(S)—$NR^8R^9$, $NO_2$, —Si($R^{15}R^{16}R^{17}$), —$R^{18}$—Si($R^{15}R^{16}R^{17}$), —$SO_2$—$R^{18}$—Si($R^{15}R^{16}R^{17}$) group or an —$SO_2R^{10}$ group
or
a $C_1$-$C_{10}$ alkyl, $C_3$-$C_{10}$ cycloalkyl, $C_2$-$C_{10}$ alkenyl, or a $C_2$-$C_{10}$ alkynyl group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, $C_2$-$C_6$ alkenyl, $C_2$-$C_6$ alkynyl, $C_1$-$C_6$ alkoxy-$C_1$-$C_6$ alkyl, $C_1$-$C_6$ alkoxy-$C_1$-$C_6$ alkoxy-$C_1$-$C_6$ alkyl, —$COR^6$, —$CSR^6$, —$CF_3$, —$OCF_3$ or —$NR^8R^9$
or
an optionally substituted —$(CH_2)_n$-aryl or —$(CH_2)_n$-heteroaryl group or $R^3$ and $R^5$ together form a 5 to 7-membered ring,
where the ring optionally can be substituted one or more times, identically or differently with hydroxy, $C_1$-$C_6$ alkyl, $C_1$-$C_6$ alkoxy, halogen or the group —$NR^8R^9$ and contain 1-2 double bonds and $R^3$ and the sulfoximine residue must be bound at neighbouring positions of Q, $R^4$ and $R^5$ together form a 5 to 8-membered ring of the formula

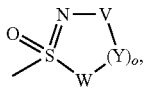

where
V, W and Y
each independently of one another stands for a —$CH_2$ group which is optionally substituted one or more times, identically or differently with hydroxy, $C_1$-$C_{10}$ alkyl, $C_1$-$C_{10}$ alkoxy or —$NR^8R^9$,
where
the $C_1$-$C_{10}$ alkyl- or $C_1$-$C_{10}$ alkoxy group likewise can be substituted one or more times, identically or differently with hydroxy, $C_1$-$C_6$ alkoxy or $NR^8R^9$
and the ring can be interrupted
by one or several —C(O)— groups
and/or
optionally can contain one or several double bonds, and $R^5$ a $C_1$-$C_6$ alkyl, $C_2$-$C_6$ alkenyl, $C_2$-$C_6$ alkynyl or $C_3$-$C_7$ cycloalkyl group which is optionally substituted one or more times, identically or differently with
hydroxy, $C_1$-$C_6$ alkoxy, $C_3$-$C_{10}$ cycloalkyl, halogen, cyano, —$CF_3$, —$OCF_3$ or the group —$NR^8R^9$,
an aryl group or heteroaryl group which is optionally substituted one or more times, identically or differently with halogen, hydroxy, $C_1$-$C_6$ alkyl, halogen-($C_1$-$C_4$) alkyl, $C_1$-$C_6$ alkoxy, halogen($C_1$-$C_4$) alkoxy, —$COR^6$, $COOR^7$, —$NR^8R^9$, CN, $NO_2$, or $SO_2NR^8R^9$ X an oxygen atom, a sulphur atom or a —$NR^8$— group
or X and $R^2$ together form a 3 to 8-membered ring, which contains one or several hetero atoms, and which is optionally substituted one or more times, identically or differently with hydroxy, $C_1$-$C_6$ alkyl, $C_1$-$C_6$ alkoxy, halogen or the group —$NR^8R^9$, if X means a —$NR^8$— group Q $C_6$-$C_{10}$ arylene, heteroarylene with 5-10 ring atoms
m 0-4

$R^6$ a hydrogen atom or a, hydroxy, benzyloxy, $NR^8R^9$
or
a $C_1$-$C_6$ alkyl group, $C_2$-$C_6$ alkenyl group, $C_2$-$C_6$ alkynyl group, $C_1$-$C_6$ alkoxy group, $C_1$-$C_6$ alkylthio group, $C_3$-$C_7$ cycloalkyl group, $C_6$-$C_{10}$-aryl group or heteroaryl group with 5 or 6 ring atoms, which is optionally substituted one or more times, identically or differently with hydroxy,
—$NR^8R^9$, cyano, halogen, —$CF_3$, $C_1$-$C_6$ alkyl, $C_1$-$C_6$ alkoxy or —$OCF_3$ $R^7$ a hydrogen atom or a $C_1$-$C_6$ alkyl group, $R^8$, $R^9$ independently of one another mean a hydrogen atom, ($C_1$-$C_6$)alkoxy group, a ($C_1$-$C_6$)alkyl group, hydroxy($C_1$-$C_6$)alkyl group, dihydroxy($C_1$-$C_6$)alkyl group, ($C_3$-$C_7$)cycloalkyl, $(CH_2)_n$—$NR^{11}R^{12}$, $NR^{11}R^{12}$, —(CO)—($C_1$-$C_6$)alkyl, —(CO)-phenyl, —(CO)—($C_1$-$C_6$)alkyl-NH—(CO)aryl, —(CO)benzyl, —(CO)O($C_1$-$C_6$)alkyl,
a —$(CH_2)_n$—($C_6$-$C_{10}$)aryl group or a heteroaryl group with 5 or 6 ring atoms, which is optionally substituted one or more times, identically or differently with hydroxy, —$NR^{11}R^{12}$, cyano, halogen, —$CF_3$, $C_1$-$C_6$ alkyl, $C_1$-$C_6$ alkoxy, or —$OCF_3$,
or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy,
—$NR^{11}R^{12}$, cyano, halogen, —$CF_3$, $C_1$-$C_6$ alkoxy and/or —$OCF_3$, $R^{10}$ a $C_1$-$C_6$ alkyl, $C_2$-$C_6$ alkenyl, $C_2$-$C_6$ alkynyl, $C_3$-$C_7$ cycloalkyl, $C_3$-$C_{10}$ heterocyclyl, heteroaryl group with 5 or 6 ring atoms or aryl group, which is optionally substituted one or more times, identically or differently with halogen, hydroxy, $C_1$-$C_6$ alkyl, $C_1$-$C_6$ alkoxy, cyano, —$CF_3$, —$OCF_3$,
—$NR^8R^9$ or with the group $SiR^{15}R^{16}R^{17}$, $R^{11}$, $R^{12}$ independently of one another mean a hydrogen atom, a $C_1$-$C_6$ alkyl group, $C_1$-$C_6$ alkoxy group, hydroxy ($C_1$-$C_6$) alkyl, dihydroxy($C_1$-$C_6$) alkyl, (CO)—($C_1$-$C_6$) alkyl, (CO)-phenyl, benzyl, which is optionally substituted one or more times, identically or differently with hydroxy, cyano, halogen, —$CF_3$, $C_1$-$C_6$ alkoxy and/or —$OCF_3$,
or $NR^{11}R^{12}$ forms a saturated or unsaturated 5-7-membered ring, in which up to two methylene groups can be replaced by —O—, —$NR^7$—, or —C(=O)—, $R^{15}$, $R^{16}$ and $R^{17}$ independently of one another can be a $C_1$-$C_6$ alkyl group and/or a phenyl group
and $R^{18}$ stands for a $C_1$-$C_3$ alkylene group.

3. A compound of formula I according to claim 1,
wherein $R^1$ means an optionally substituted mono- or bicyclic heteroaryl group or an optionally substituted aryl group.

4. A compound of formula I according to claim 1,
wherein Q means phenylene.

5. A compound of formula I according to claim 1, wherein $R^1$ means an mono- or bicyclic heteroaryl group, which is optionally substituted one or more times, identically or differently with halogen, hydroxy, $NO_2$, $NR^8R^9$, $OCF_3$, $CF_3$, cyano, —$COR^6$, ($C_1$-$C_6$)alkyl, halogen($C_1$-$C_6$)alkyl, hydroxy($C_1$-$C_6$)alkyl, cyano($C_1$-$C_6$)alkyl-, ($NR^8R^9$)($C_1$-$C_4$)alkyl, —NH(CO)($C_1$-$C_6$)alkylene-NH—(CO)phenyl, —NH(CO)($C_1$-$C_6$)alkylene-phenyl, ($R^6$OC)($C_1$-$C_6$)alkyl-, [($HR^8$N(OC)]—($C_1$-$C_6$)alkyl ($C_1$-$C_6$)-alkoxy, ($CH_2$)$_n$phenyl, halogen($C_1$-$C_6$)alkoxy, $SO_2NR^8R^9$ or a phenyl group which is optionally substituted one or more times, identically or differently with a group selected from halogen, hydroxy, $C_1$-$C_5$alkyl, hydroxy($C_1$-$C_5$)alkyl, $C_1$-$C_5$alkoxy, —O-perfluoro($C_1$-$C_5$)alkyl, —($C_1$-$C_5$)-alkyl-O—($C_1$-$C_5$)-alkyl, —($C_1$-$C_5$)-alkyl-$COOR^7$, —O—($CH_2$)$_o$O—, cyano, $CF_3$, nitro, (CO)$R^6$, $NR^8R^9$, —$NR^8$—(CO)—($C_1$-$C_4$)alkyl, —$NR^8$—$SO_2$—$C_1$-$C_4$-alkyl, —($C_1$-$C_4$)alkyl-$NR^8$ (CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), phenyl, —(CO)-morpholino, $R^2$ a hydrogen atom, a $C_1$-$C_{10}$ alkyl group, a $C_2$-$C_{10}$ alkenyl group, a $C_2$-$C_{10}$ alkynyl group, a $C_3$-$C_8$ cycloalkyl group, a $C_3$-$C_3$ heterocyclyl group, an phenyl or heteroaryl group, which is optionally substituted one or more times, identically or differently with a group selected from halogen, hydroxy, cyano, $SO_2NR^8R^9$, $SO_2R^{10}$, S(O)($NR^8$)$R^9$, $C_1$-$C_6$ alkyl, perfluoro($C_1$-$C_6$)alkyl, $C_1$-$C_6$ hydroxyalkyl, $C_2$-$C_6$ alkenyl, $C_2$-$C_6$ alkynyl, $C_1$-$C_6$ alkoxy, $C_1$-$C_6$ alkoxy-($C_1$-$C_6$) alkyl, $C_1$-$C_6$ alkoxy-($C_1$-$C_6$) alkoxy-($C_1$-$C_6$) alkyl, —$COR^6$, —$C_1$-$C_6$ alkylO(CO)$C_1$-$C_6$ alkyl, $C_1$-$C_6$ alkyl(CO)O—, $C_3$-$C_{10}$ cycloalkyl, =N—OH, —$NR^8R^9$, —NH($C_1$-$C_6$) alkyl, —N($C_1$-$C_6$ alkyl)$_2$, —NH(CO)$C_1$-$C_6$ alkyl, —N[(CO)($C_1$-$C_6$ alkyl)]$_2$, —NH(CO)$C_1$-$C_6$ alkylene-NH—(CO)phenyl, —NH(CO)(($C_1$-$C_6$)alkylene)phenyl, —NH—($CH_2$)$_n$—$C_3$-$C_{10}$ cycloalkyl, —($CH_2$)$_n$aryl, —($CH_2$)$_n$—O-phenyl, —($CH_2$)$_n$ heteroaryl, —($CH_2$)$_n$—($C_3$-$C_8$) heterocyclyl, —$CF_3$, —$OCF_3$, —$NR^7$—C(O)—$OC_1$-$C_3$ alkyl, —$NR^7$—C(O)—$NR^8R^9$ or —$NR^7$—$SO_2$—$R^{10}$, wherein, if the $C_3$-$C_{10}$ cycloalkyl group, the ($CH_2$)$_n$—($C_3$-$C_8$) heterocyclyl group, the ($CH_2$)$_n$-phenyl- or the ($CH_2$)$_n$-heteroaryl group are substituents of $R^2$, these themselves optionally can be substituted one or more times, identically or differently with halogen, hydroxy, $C_1$-$C_6$ alkyl, halogen-($C_1$-$C_4$) alkyl, $C_1$-$C_6$ alkoxy, —O—($CH_2$)$_o$—O—, halogen($C_1$-$C_4$) alkoxy, —($CH_2$)$_n$phenyl, $NR^8R^9$, $COOR^7$ or $SO_2NR^8R^9$, and/or the ring of any $C_3$-$C_{10}$ cycloalkyl group, $C_3$-$C_8$ heterocyclyl group and the $C_1$-$C_{10}$ alkyl group can optionally contain one or several —$NR^8$, oxygen and/or sulphur atoms and/or can optionally contain one or several —C(O)— groups in the ring and/or optionally one or several possible double bonds can be contained in the ring, n means 0-3,
o means 1-2,
$R^3$ halogen $R^4$ a hydrogen atom, a —C(O)O—$R^{10}$, —C(O)—$R^{10}$, —C(O)—$NR^8R^9$, —C(S)—$NR^8R^9$, or a $C_1$-$C_{10}$ alkyl, $C_3$-$C_{10}$ cycloalkyl, group, which is optionally substituted one or more times, identically or differently with hydroxy, halogen, $C_1$-$C_6$ alkoxy, $C_1$-$C_6$ alkylthio, cyano, $C_3$-$C_{10}$ cycloalkyl, $C_1$-$C_6$ hydroxyalkyl, or —$NR^8R^9$ or $R^5$ a $C_1$-$C_6$ alkyl, $C_3$-$C_7$ cycloalkyl group, a phenyl group X an oxygen atom, a sulphur atom or a —$NR^8$— group Q phenylene, m 0-1

$R^6$ a hydrogen atom or a, hydroxy, benzyloxy, $NR^8R^9$ or a $C_1$-$C_6$ alkyl group, $C_1$-$C_6$ alkoxy group, $C_1$-$C_6$ alkylthio group, $C_6$-$C_{10}$-phenyl group, $R^7$ a hydrogen atom or a $C_1$-$C_6$ alkyl group, $R^8$, $R^9$ independently of one another mean a hydrogen atom, ($C_1$-$C_6$)alkoxy group, a ($C_1$-$C_6$)alkyl group, hydroxy($C_1$-$C_6$)alkyl group, dihydroxy($C_1$-$C_6$)alkyl group, ($C_3$-$C_7$)cycloalkyl, ($CH_2$)$_n$—$NR^{11}R^{12}$, $NR^{11}R^{12}$, —(CO)—($C_1$-$C_6$)alkyl, —(CO)-phenyl, —(CO)—($C_1$-$C_6$)alkyl-NH—(CO)phenyl, —(CO)benzyl, —(CO)O($C_1$-$C_6$)alkyl, a —($CH_2$)$_n$—($C_6$-$C_{10}$)phenyl group or $R^8$ and $R^9$ together form a saturated or unsaturated 5 to 7-membered ring, which optionally can contain 1-3 further hetero atoms selected from the group oxygen, sulphur, =N— or —$NR^{11}$— and which is optionally substituted one or more times, identically or differently with hydroxy, —$NR^{11}R^{12}$, cyano, halogen, —$CF_3$, $C_1$-$C_6$ alkoxy and/or —$OCF_3$, $R^{10}$ a $C_1$-$C_6$ alkyl, $R^{11}$, $R^{12}$ independently of one another mean a hydrogen atom, a $C_1$-$C_6$ alkyl group, $C_1$-$C_6$ alkoxy group, hydroxy ($C_1$-$C_6$) alkyl, dihydroxy($C_1$-$C_6$) alkyl, (CO)—($C_1$-$C_6$) alkyl, (CO)-phenyl, benzyl, which is optionally substituted one or more times, identically or differently with hydroxy, cyano, halogen, —$CF_3$, $C_1$-$C_6$ alkoxy and/or —$OCF_3$, or $NR^{11}R^{12}$ forms a saturated or unsaturated 5-7-membered ring, in which up to two methylene groups can be replaced by —O—, —$NR^7$—, or —C(=O)—.

6. A compound according to claim 1, wherein $R^1$ means an optionally one or more times substituted phenyl group whereby its substituents are selected from the group halogen, $C_1$-$C_5$alkyl, ($C_1$-$C_5$)alkoxy, —($C_1$-$C_5$)-alkyl-O—($C_1$-$C_5$)-alkyl, —($C_1$-$C_5$)-alkyl-$COOR^7$, —O—($CH_2$)$_o$O—, cyano, $CF_3$, (CO)$R^6$, $NR^8R^9$, —$NR^8$—(CO)—($C_1$-$C_4$)alkyl, —$NR^8$—$SO_2$—$C_1$-$C_4$-alkyl, —($C_1$-$C_4$)alkyl-$NR^8$(CO)—($C_1$-$C_4$)-alkyl, —(CO)$NR^8$—($C_1$-$C_5$)alkyl, —NH(CO)NH—($C_1$-$C_5$)-alkyl, —(CO)(4-oxo-piperidinyl), —(CO)-morpholino.

7. A compound of formula I according to claim 1, wherein $R^1$ means an mono- or bicyclic heteroaryl group, which is optionally substituted one or more times, identically or differently with halogen, hydroxy, $NO_2$, $NR^8R^9$, perfluoro($C_1$-$C_3$)alkyl, cyano, —$COR^6$, $COOR^7$, ($C_1$-$C_4$)alkyl, halogen($C_1$-$C_4$) alkyl, hydroxy($C_1$-$C_4$)alkyl, cyano($C_1$-$C_4$)alkyl, ($NR^8R^9$)($C_1$-$C_4$)alkyl, ($C_1$-$C_6$)alkoxy, ($CH_2$)$_n$aryl, perfluoro($C_1$-$C_3$)alkoxy or $SO_2NR^8R^9$.

8. A compound of formula I according to claim 1, wherein means a mono- or bicyclic heteroaryl group, which is optionally substituted one or more times, identically or differently with halogen, cyano, $(C_1-C_3)$alkyl, hydroxy$(C_1-C_3)$alkyl, cyano$(C_1-C_3)$alkyl, $(C_1-C_3)$alkoxy, $(CH_2)_n$aryl, or an aryl group which is optionally substituted one or more times, identically or differently with a group selected from halogen, $(C_1-C_3)$alkyl, $(C_1-C_3)$alkoxy, —$(C_1-C_3)$-alkyl-O—$(C_1-C_3)$-alkyl, —$(CH_2)_3$—COO—$(C_1-C_3)$-alkyl, —O—$(CH_2)_o$O—, cyano, $CF_3$, —NH—(CO)$(C_1-C_3)$-alkyl, —(CO)$(C_1-C_3)$-alkyl, —$NHSO_2(C_1-C_3)$-alkyl, —$(C_1-C_3)$-alkylen-NH—(CO)$(C_1-C_3)$-alkyl, —(CO)(4-oxo-N-piperidyl), —(CO)NH—$(C_1-C_3)$-alkyl, —NH(CO)NH—$(C_1-C_5)$-alkyl, —(CO)-morpholine, $R^2$ a $C_1-C_5$ alkyl group, a $(C_3-C_8)$cycloalkyl group, a $(C_3-C_8)$heterocyclyl group, a phenyl group, which is optionally substituted one or more times, identically or differently with a group selected from halogen, hydroxy, cyano, $CF_3$, $SO_2NH_2$, $(C_2-C_4)$alkynyl, $(C_1-C_3)$alkoxy, —$COR^6$, —COO—$(C_1-C_4)$alkyl-O—$(C_1-C_3)$alkyl, $(C_1-C_3)$alkyl(CO)O—, =N—OH, —$NR^8R^9$, —NH(CO)$(C_1-C_4)$alkyl, —NH(CO)$(C_1-C_4)$alkylene-NH—(CO)phenyl, —NH(CO)(($C_1-C_6$)alkylene)aryl, —$(CH_2)_n$phenyl, —$(CH_2)_n$—O-phenyl, —$(CH_2)_n$heteroaryl, —$(CH_2)_n$—$(C_3-C_8)$heterocyclyl, wherein, if the $(C_3-C_8)$cycloalkyl group, the $(CH_2)_n$—$(C_3-C_7)$ heterocyclyl group, the $(CH_2)_n$ aryl- or the $(CH_2)_n$-heteroaryl group are substituents of $R^2$, these themselves optionally can be substituted one or more times, identically or differently with halogen, hydroxy, $(C_1-C_3)$alkyl, $(C_1-C_3)$alkoxy, —O—$(CH_2)_o$O—, hydroxy$(C_1-C_5)$alkyl, cyano, —$OCF_3$, $CF_3$, —N($C_1-C_3$ alkyl)$_2$, —$SO_2NH_2$, —$SO_2$—$(C_1-C_4)$-alkyl, phenyl and/or the ring of any $(C_3-C_8)$cycloalkyl group, $(C_3-C_8)$ heterocyclyl group and the $(C_1-C_5)$alkyl group can optionally contain one —$NR^8$, oxygen and/or sulphur atoms and/or can optionally contain one —C(O)— group can be contained in the ring, n means 0-3, o means 1-3, $R^3$ halogen $R^4$ a hydrogen atom, a —C(O)O—$R^{10}$, —C(O)—$NR^8R^9$, or a $C_1-C_6$ alkyl, which is optionally substituted one or more times, identically or differently with hydroxy, $(C_1-C_3)$alkoxy, $(C_3-C_6)$cycloalkyl, or —$NR^8R^9$ or an optionally substituted —$(CH_2)_n$-aryl group or $R^5$ a $(C_1-C_4)$alkyl or $(C_3-C_6)$cycloalkyl group or an aryl group X an oxygen atom, a sulphur atom or a —$NR^8$— group Q phenylene m 0, 1

$R^6$ a hydrogen atom or a hydroxy, or $NR^8R^9$ group or a $(C_1-C_6)$alkyl group, $(C_1-C_6)$alkoxy group $R^7$ a hydrogen atom $R^8$, $R^9$ independently of one another mean a hydrogen atom, a $(C_1-C_6)$alkyl group, $(C_3-C_7)$cycloalkyl, —(CO)O$(C_1-C_6)$alkyl, a —$(CH)_n$—$(C_6-C_{10})$aryl group, which is optionally substituted one or more times, identically or differently with hydroxy, —$NR^{11}R^{12}$, halogen $C_1-C_6$ alkyl, or $R^8$ and $R^9$ together form a saturated 5 to 7-membered ring, which optionally can contain 1-3 further hetero atoms selected from the group oxygen, or =N— or —$NR^{11}$, $R^{10}$ a $C_1-C_6$ alkyl, $R^{11}$, $R^{12}$ independently of one another mean a hydrogen atom, a $(C_1-C_3)$alkyl.

9. A compound of formula I according to claim 1 wherein $R^1$ means a heteroaryl or phenyl group, optionally independently of one another substituted with 1 to 2 groups selected from $C_1-C_3$ alkyl, benzyl, cyano, $CF_3$, $C_1-C_3$ alkoxy, halogen, —O—$CH_2$—O—, —$(CH_2)_2$(CO)O $(C_1-C_3$ alkyl), —NH(CO)($C_1-C_3$ alkyl), —(CO)($C_1-C_3$ alkyl), —$(C_3-C_3)$ heterocyclyl, $R^2$ a $C_3-C_6$ cycloalkyl group, an phenyl group or a $C_1-C_8$ alkyl group, which optionally is identically or differently substituted with a group selected from hydroxy, $(CH_2)_n$-phenyl-$SO_2NH_2$, —$(C_3-C_8)$ heterocyclyl, —$(C_5-C_8)$ heteroaryl, —NH(CO)$CH_2$—NH(CO)-phenyl, $NR^8R^9$, —$COR^6$, NH(CO)$CH_2$-phenyl or $SO_2R^8R^9$, $R^3$ a hydrogen atom or a halogen atom, $R^4$ a hydrogen atom, a $C_1-C_3$ alkyl group, a COO($C_1-C_6$) alkyl group, an phenyl group, a —$(CH_2—)_n$—$(C_3-C_6)$ cycloalkyl group $R^5$ a $C_1-C_3$ alkyl group, a $C_3-C_6$ cycloalkyl group or a phenyl group

X —NH—, —O—

Q phenylene a m 0 or 1.

10. A compound of formula I according to claim 1 wherein $R^1$ means an optionally substituted heteroaryl- or an optionally substituted phenyl group, $R^2$ a $C_1-C_6$-hydroxyalkyl group or a group $(CH_2)_2$—NH (CO)—$(C_1-C_3)$Alkyl, a $C_3-C_{10}$-cycloalkyl group $R^3$ a hydrogen atom or a halogen atom, $R^4$ a hydrogen atom, a $C_1-C_{10}$-alkyl group, a (CO)($C_1-C_{10}$)-alkyl group or a COO($C_1-C_3$)alkyl group, $R^5$ a $C_1-C_6$-alkyl group, a $C_3-C_7$-cycloalkyl-group or a phenyl group

X —NH—

Q phenylene and m means 0 or 1.

11. A compound of formula I, according to claim 1, in the form of a salt with physiologically compatible anions.

12. A method for the treatment of breast cancer, comprising administering to a host in need thereof an effective amount of a compound according to claim 1.

13. A method for the treatment of rheumatoid arthritis, comprising administering to a host in need thereof an effective amount of a compound according to claim 1.

14. A pharmaceutical composition comprising at least one compound according to claim 1 or mixtures thereof and a pharmaceutically acceptable carrier.

15. A process for the preparation of compound of formula I, according to claim 1, comprising reacting a compound of formula II

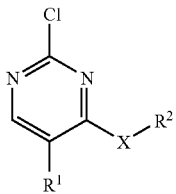

under acidic conditions with a compound of formula III

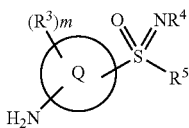

to give the compounds of formula I, wherein the residues $R^1$, $R^2$, $R^3$, $R^4$, $R^5$, and Q, X and m have the meanings stated in claim 1.

16. A process for the preparation of a compound of formula I, according to claim 1, comprising reacting a compound of formula IV

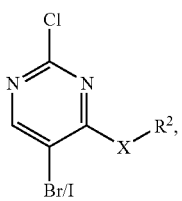

obtainable by reaction of 5-bromo-2,4-dichloropyrimidine or 5-iodo-2,4-dichloropyrimidine with $R^2$—X—H under basic conditions, with a compound of formula III under acidic conditions

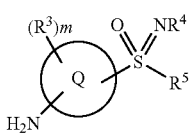

and reacting a resulting compound of formula XI

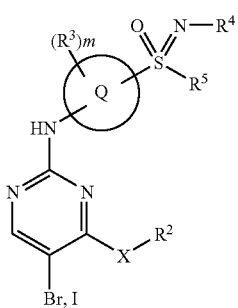

optionally with the use of a catalyst, with a compound of formula

M-$R^1$, wherein M means
B(OH)$_2$, B(OR$^{19}$)(OR$^{20}$), whereby
$R^{19}$ and $R^{20}$ mean (C$_1$-C$_6$) alkyl, or
$R^{19}$ and $R^{20}$ together can form a ring from C$_1$-C$_{10}$ alkyl,
Sn(R$^{21}$)$_3$, R$^{21}$MgR$^{22}$/Zn(R$^{22}$)$_2$ whereby
$R^{21}$ means C$_1$-C$_6$ alkyl, and
$R^{22}$ means halogen.
to give a compound of formula I, where the residues $R^1$, $R^2$, $R^3$, $R^4$, $R^5$, and Q, X and m have the meanings stated in claim 1.

17. A process for the preparation of a compound of formula I according to claim 1, comprising, for the case where $R^4$ means a —C(O)O—$R^{10}$ group, cleaving
the —C(O)O—$R^{10}$ group under basic conditions from a compound of formula XII

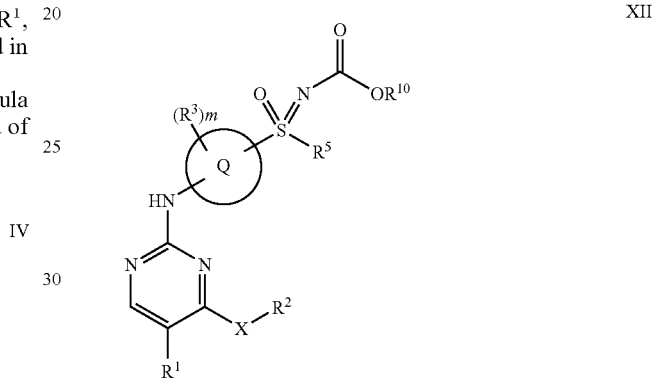

and functionalizing a sulfoximine thus obtained by
a) alkylation
b) acylation
c) arylation
d) reaction with isocyanates or isothiocyanates
e) reaction with sulphonyl chlorides
f) reaction with chloroformates, or
g) silylation.

18. A process for the preparation of a compound of formula I according to claim 1, comprising reacting a compound of formula XIV

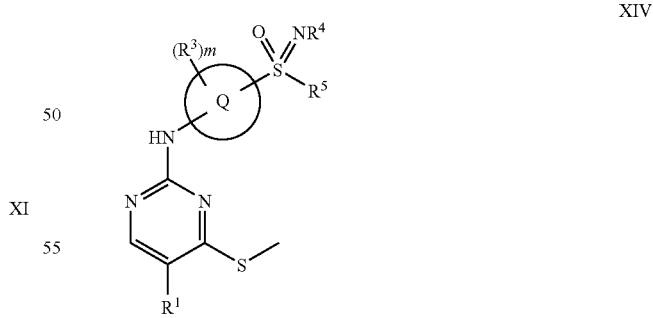

wherein $R^1$, $R^3$, m, $R^4$ and $R^5$ have the meanings as defined in claim 1
under oxidative conditions followed by substitution with

HX—$R^2$ wherein X and $R^2$ have the meaning as defined in claim 1, to result in compounds of formula I.

* * * * *